United States Patent
Chabok

(10) Patent No.: US 12,096,980 B2
(45) Date of Patent: Sep. 24, 2024

(54) MEDIATOR-FREE UNIVERSAL LASER LIGHT AMPLIFICATION WITH COAXIAL PROPAGATING FOCUSED ULTRASOUND AND SYSTEM

(71) Applicant: PHONONZ INC, San Bernardino, CA (US)

(72) Inventor: Hamid Reza Chabok, Highland, CA (US)

(73) Assignee: PHONONZ INC, San Bernardino, CA (US)

( * ) Notice: Subject to any disclaimer, the term of this patent is extended or adjusted under 35 U.S.C. 154(b) by 967 days.

(21) Appl. No.: 17/087,649

(22) Filed: Nov. 3, 2020

(65) Prior Publication Data

US 2021/0128238 A1 May 6, 2021

Related U.S. Application Data

(60) Provisional application No. 63/048,005, filed on Jul. 3, 2020, provisional application No. 62/969,309, filed
(Continued)

(51) Int. Cl.
 *A61B 18/20* (2006.01)
 *A61M 37/00* (2006.01)
 (Continued)

(52) U.S. Cl.
 CPC ....... *A61B 18/203* (2013.01); *A61M 37/0092* (2013.01); *A61N 5/0616* (2013.01); *A61N 5/067* (2021.08)

(58) Field of Classification Search
 CPC ... A61B 18/203; A61B 5/0075; A61B 5/0093; A61B 18/22; A61B 2017/0057;
(Continued)

(56) References Cited

U.S. PATENT DOCUMENTS

| 5,419,335 A | 5/1995 | Hartmann et al. |
| 9,256,009 B2 | 2/2016 | Theriault et al. |

(Continued)

FOREIGN PATENT DOCUMENTS

| WO | WO-2018014021 A2 * | 1/2018 | ......... A61B 17/2202 |
| WO | WO-2019097317 A1 * | 5/2019 | ........... A61B 5/0084 |

OTHER PUBLICATIONS

Debye, P.., et al., "On the Scattering of Light by Supersonic Waves", Proceedings of the National Academy of Sciences, vol. 18, No. 6, Jun. 1932, pp. 409-414.
(Continued)

*Primary Examiner* — Yingchuan Zhang
*Assistant Examiner* — Sebastian X Lukjan
(74) *Attorney, Agent, or Firm* — Makoui Law, PC; Ali Makoui

(57) ABSTRACT

A co/counter propagating acousto-optic modulator is provided that creates a low-intensity focused ultrasound (FUS) wave on a laser beam in a medium such as water without any auxiliary mediators or special software/hardware. The main optical effect of the FUS is the controllable focusing of the laser beam through modification of the refractive index of the medium in a time-stable and dynamic fashion. The laser beam and the FUS wave are coaxially mixed and propagated through each other. The FUS pressure field highly amplifies the power density, highly amplifies the intensity, sharpens the diameter, and reduces the full width at half maximum (FWHM) of the laser beam. The FUS pressure field keeps the laser beam's lensing power positive, with small fluctuations, as long as the ultrasound wave is coaxially propagated with the laser beam.

19 Claims, 112 Drawing Sheets

Related U.S. Application Data on Feb. 3, 2020, provisional application No. 62/930,335, filed on Nov. 4, 2019.

(51) Int. Cl.
*A61N 5/06* (2006.01)
*A61N 5/067* (2006.01)

(58) Field of Classification Search
CPC .......... A61B 2018/00684; A61B 2018/00785; A61B 2018/00994; A61B 2018/2035; A61B 2018/20359; A61B 2018/00452; A61B 2018/20353; A61M 37/0092; A61N 5/0616; A61N 5/067; A61N 5/0622; A61N 5/062

See application file for complete search history.

(56) References Cited

U.S. PATENT DOCUMENTS

| | | | |
|---|---|---|---|
| 9,594,288 B2 | 3/2017 | Arnold et al. | |
| 9,946,081 B2 | 4/2018 | Arnold | |
| 9,983,459 B2 | 5/2018 | Arnold | |
| 2005/0085725 A1* | 4/2005 | Nagar | A61B 5/14532 600/437 |
| 2013/0109950 A1* | 5/2013 | Herzog | A61B 5/14551 600/407 |
| 2014/0188145 A1 | 7/2014 | Slayton et al. | |
| 2017/0360399 A1* | 12/2017 | Rothberg | A61B 8/483 |
| 2020/0030638 A1 | 1/2020 | Chamanzar et al. | |

OTHER PUBLICATIONS

Hargrove, L.E., "Diffraction of a Gaussian Light Beam by Ultrasonic Cylindrical Standing Waves," The Journal of the Acoustical Society of America, vol. 51, No. 3, Jul. 1971, pp. 888-893.

Higginson, Keith A., et al., "Tunable optics derived from nonlinear acoustic effects," Journal of Applied Physics, vol. 95, No. 10, May 2004, pp. 5896-5904.

McGloin, D., et al., "Bessel beams: diffraction in a new light," Contemporary Physics, vol. 46, No. 1, Jan. 2005, pp. 15-28.

McLeod, Euan, et al., "Multiscale Bessel beams generated by a tunable acoustic gradient index of refraction lens," Optics Letters, vol. 31, No. 21, Nov. 2006, pp. 3155-3157.

McLeod, Euan, et al., "Optical analysis of time-averaged multiscale Bessel beams generated by a tunable acoustic gradient index of refraction lens," Applied Optics, vol. 47, No. 20, Jul. 2008, pp. 3609-3618.

Mermillod-Blondin, Alexandre, et al., "High-speed varifocal imaging with a tunable acoustic gradient index of refraction lens," Optics Letters, vol. 33, No. 18, Sep. 2008, pp. 2146-2148.

Mermillod-Blondin, Alexandre, et al., "Dynamic pulsed-beam shaping using a TAG lens in the near UV," Applied Physics A, Month unknown 2008, pp. 231-234.

Grulkowski, Ireneusz, et al., "Acousto-optic interaction with the use of cylindrical ultrasonic waves in the laser cavity," Applied Optics, vol. 48, No. 7, Mar. 2009, (C81-C85 pages).

Duocastella, M, et al., "Enhanced depth of field laser processing using an ultra-high-speed axial scanner," Applied Physics Letters, vol. 102, Month unknown 2013, (4 Pages).

Kang, SeungYeon, et al., "Variable optical elements for fast focus control," Nature Photonics, vol. 14, Sep. 2020, pp. 533-542.

Duocastella, Martí, et al., "Acousto-optic systems for advanced microscopy," Journal of Physics: Photonics, Oct. 2021, (16 pages).

Saleh, Bahaa E. A., et al., "Acousto-Optics", Fundamentals of Photonics, Chapter 20, John Wiley & Sons, Inc., Month unknown 1991, pp. 799-831.

Wang, Lihong, et al., "Continuous-wave ultrasonic modulation of scattered laser light to image objects in turbid media," Optics Letters, vol. 20, No. 6, Mar. 1995, pp. 629-631.

Yao, Gang, et al., "Theoretical and experimental studies of ultrasound-modulated optical tomography in biological tissue," Applied Optics, vol. 39, No. 4, Feb. 2000, pp. 659-664.

Li, Jun, et al., "Transmission- and side-detection configurations in ultrasound-modulated optical tomography of tick biological tissues," Applied Optics, vol. 42, No. 19, Jul. 2003, pp. 4088-4094.

Tsai, Tracy, et al., "Generating Bessel beams with a tunable acoustic gradient index of refraction lens," Optical trapping and Optical Micromanipulation III, eds. Dholakia and G. Spalding, International Society for Optical Engineering (SPIE), vol. 6326, Month unknown 2006, (8 pages).

Chabok, Hamid Reza, "Development of High Frequency Composites for Ultrasound Transducer Applications," Dissertation, University of Southern California, Dec. 2011, (191 pages).

Lai, Puxiang, et al., "Photoacoustically guided wavefront shaping for enhanced optical focusing in scattering media," Nature Photonics, Jan. 2015, pp. 1-7.

Kim, Haemin, et al., "Increased light penetration due to ultrasound-induced air bubbles in optical scattering media," Scientific Reports, Nov. 2017, pp. 1-8.

Chamanzar, Maysamreza, et al., "Ultrasonic sculpting of virtual optical waveguides in tissue," Nature Communications, Month unknown 2019, pp. 1-10.

Scopelliti, Matteo Giuseppe, et al., "Ultrasonically sculpted virtual relay lens for in situ microimaging," Light: Science & Applications, Month unknown 2019, pp. 1-15.

Li, Xuzhou, et al., "Ultrasound Modulated Droplet Lasers," ACS Photonics, Jan. 2019, pp. 531-537.

\* cited by examiner

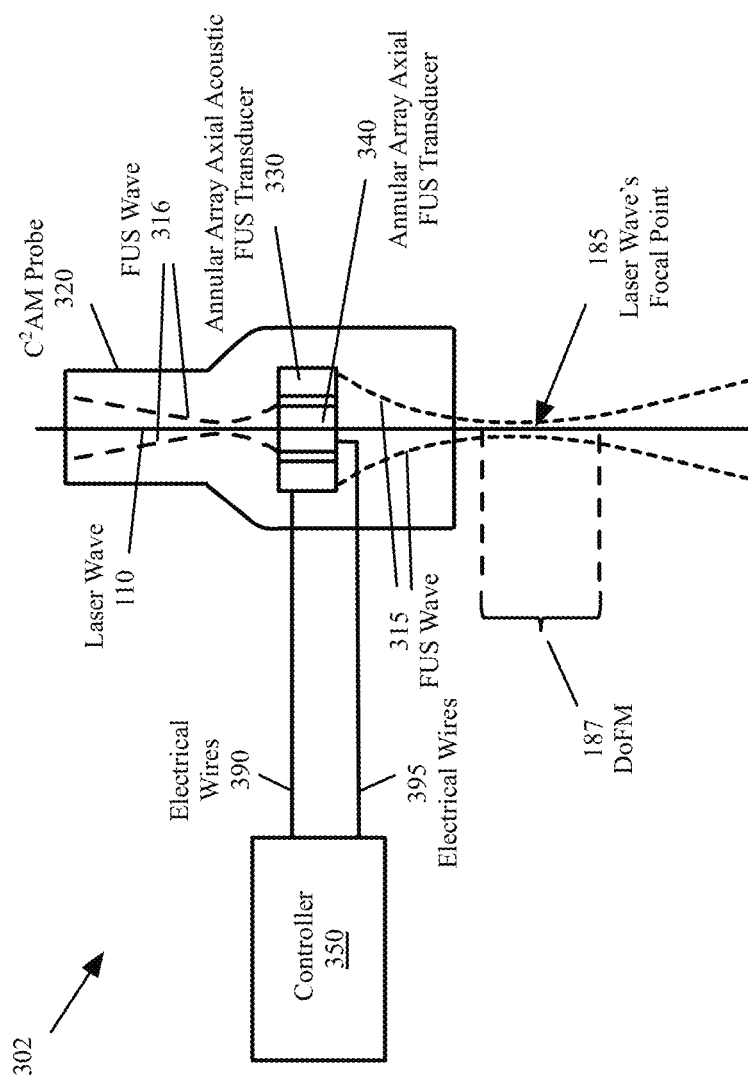

TABLE 1 - LASER INTENSITY VALUES MEASURE AT Z EQUAL TO 5 MM DISTANCE

Duty Cycle (%) 515 →

Voltage (V) 510

| | 1 | 5 | 10 | 20 | 30 |
|---|---|---|---|---|---|
| 50 | 76 | 81 | 93 | 102 | 242 |
| 75 | 83 | 135 | 211 | 201 | 254 |
| 100 | 95 | 211 | 289 | 187 | 175 |
| 125 | 130 | 235 | 269 | 194 | 181 |

TABLE 2 - LASER INTENSITY VALUES MEASURE AT Z EQUAL TO 50 MM DISTANCE

| | 1 | 5 | 10 | 20 | 30 |
|---|---|---|---|---|---|
| 50 | 86 | 84 | 100 | 151 | 251 |
| 75 | 101 | 271 | 281 | 267 | 271 |
| 100 | 261 | 326 | 310 | 208 | 191 |
| 125 | 132 | 371 | 235 | 181 | 132 |

TABLE 3 - LASER INTENSITY VALUES MEASURE AT Z EQUAL TO 100 MM DISTANCE

| | 1 | 5 | 10 | 20 | 30 |
|---|---|---|---|---|---|
| 50 | 91 | 112 | 181 | 277 | 304 |
| 75 | 104 | 281 | 291 | 292 | 271 |
| 100 | 121 | 291 | 280 | 161 | 147 |
| 125 | 271 | 256 | 192 | 149 | 163 |

TABLE 4 - LASER INTENSITY VALUES MEASURE AT Z EQUAL TO 150 MM DISTANCE

| | 1 | 5 | 10 | 20 | 30 |
|---|---|---|---|---|---|
| 50 | 58 | 61 | 91 | 172 | 252 |
| 75 | 51 | 191 | 281 | 252 | 161 |
| 100 | 92 | 261 | 139 | 128 | 91 |
| 125 | 131 | 209 | 91 | 96 | 121 |

TABLE 5 - LASER INTENSITY VALUES MEASURE AT Z EQUAL TO 200 MM DISTANCE

| | 1 | 5 | 10 | 20 | 30 |
|---|---|---|---|---|---|
| 50 | 61 | 71 | 102 | 171 | 277 |
| 75 | 66 | 127 | 256 | 265 | 151 |
| 100 | 98 | 268 | 141 | 91 | 91 |
| 125 | 162 | 212 | 99 | 71 | 72 |

FIG. 5

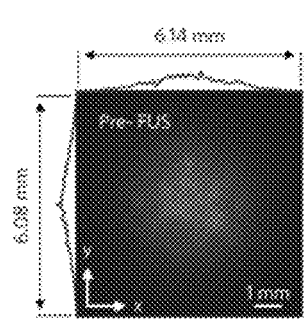 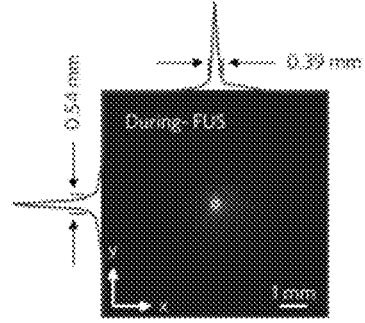 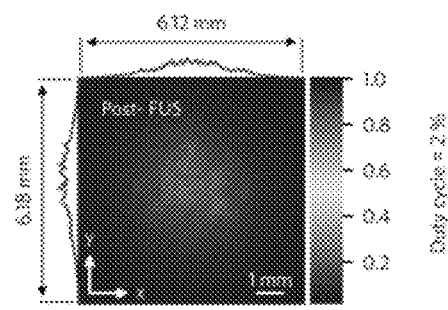
FIG. 14A  FIG. 14B  FIG. 14C
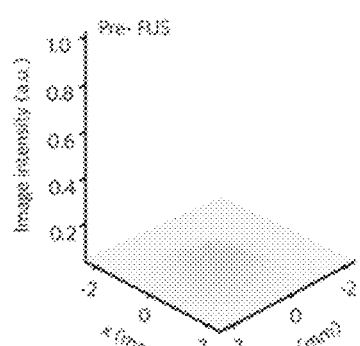 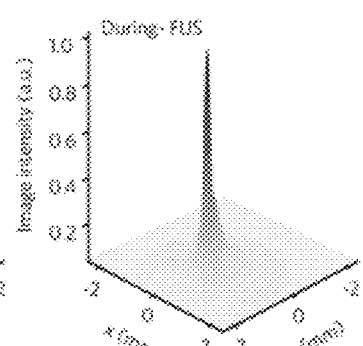 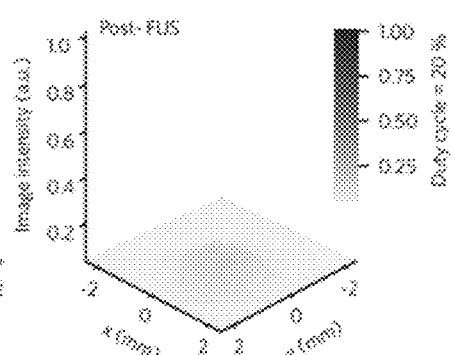
FIG. 14D  FIG. 14E  FIG. 14F
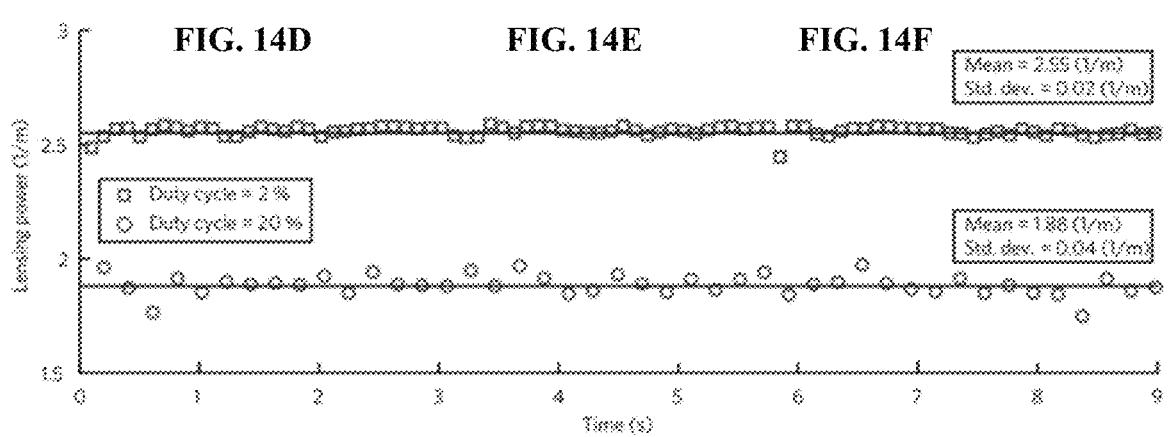
FIG. 14G

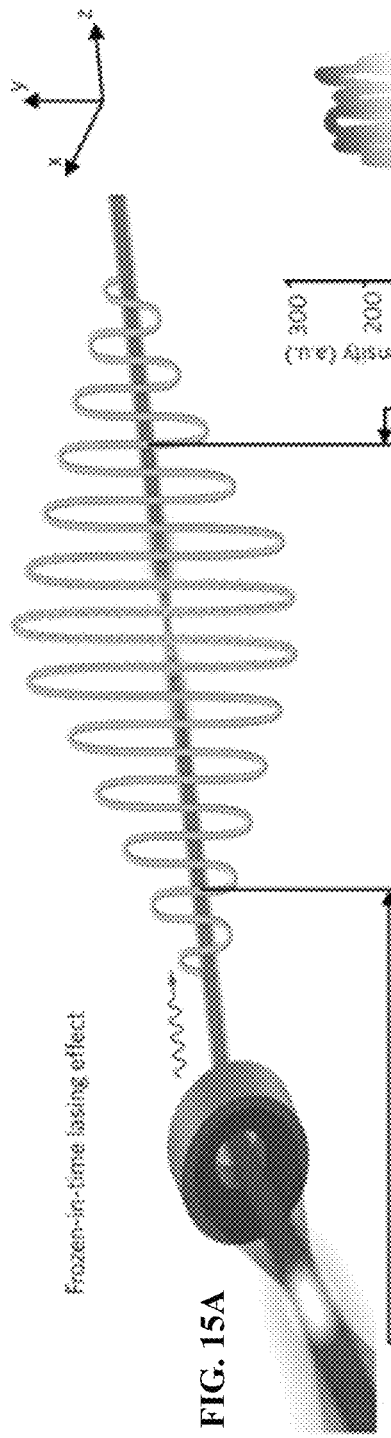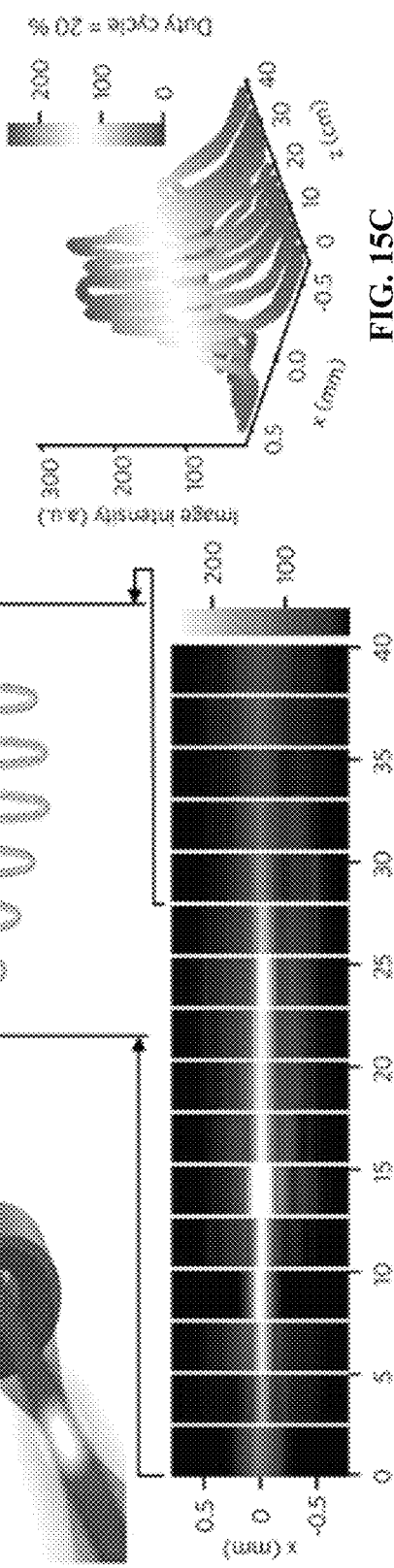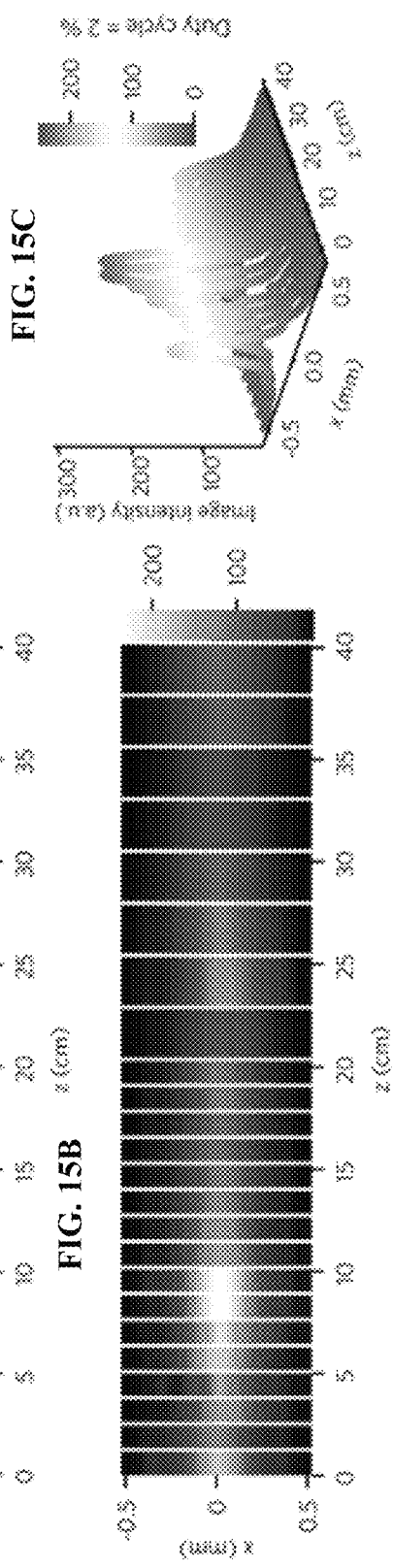
FIG. 15A
FIG. 15B
FIG. 15C
FIG. 15D
FIG. 15E

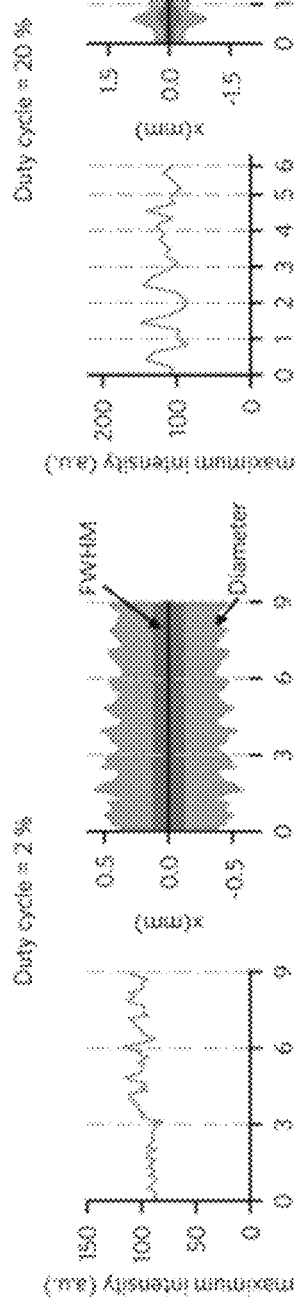
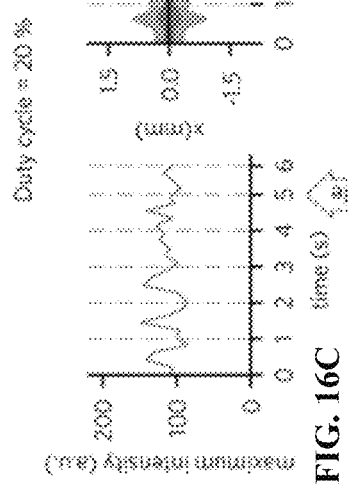
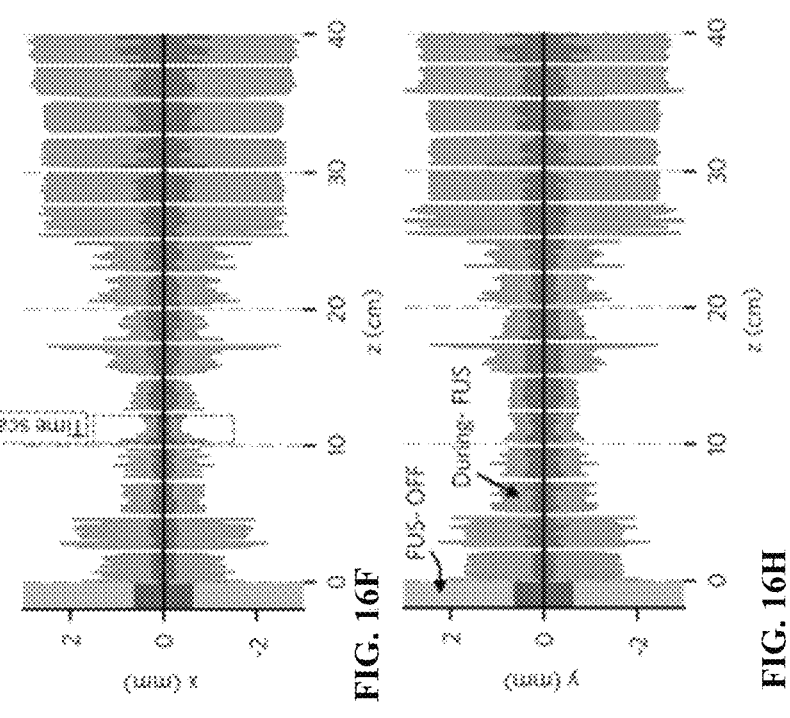
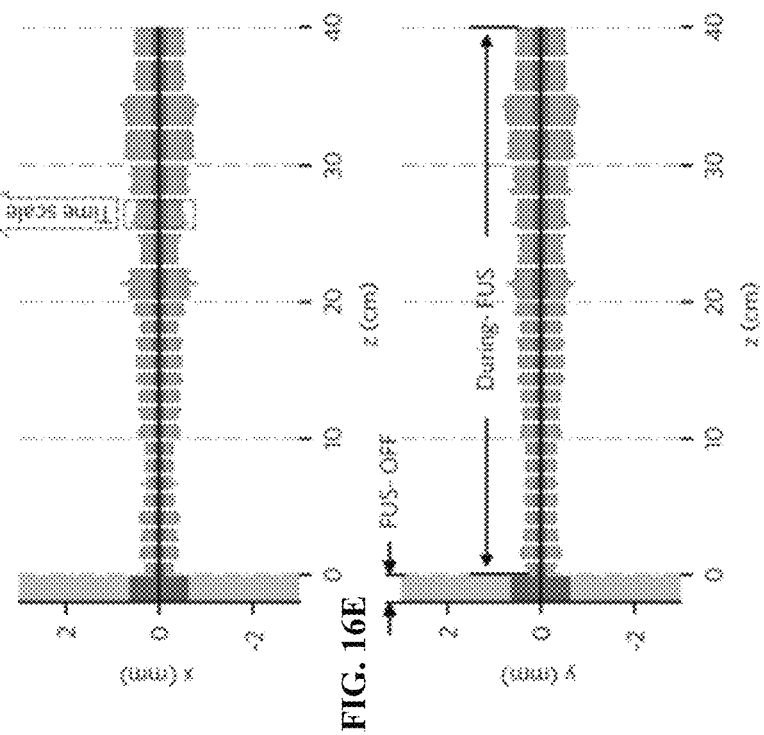
FIG. 16A FIG. 16B FIG. 16C FIG. 16D
FIG. 16E FIG. 16F
FIG. 16G FIG. 16H

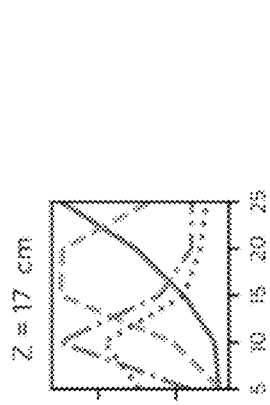 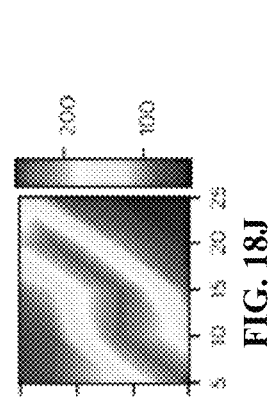 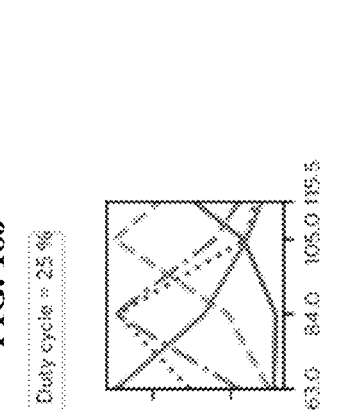
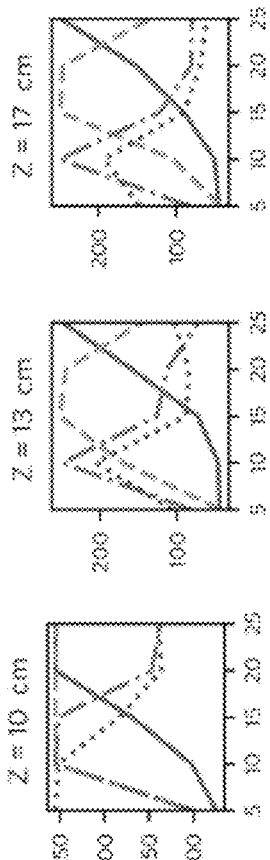
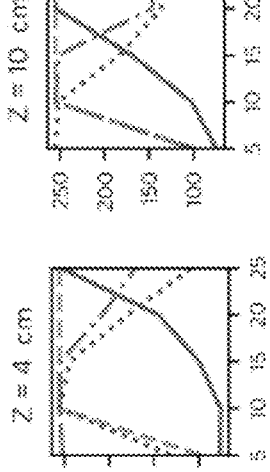 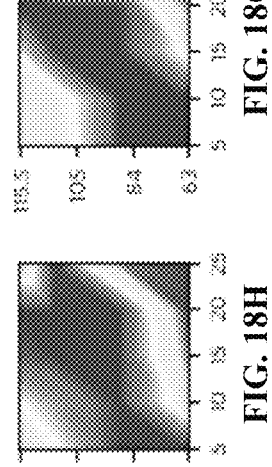 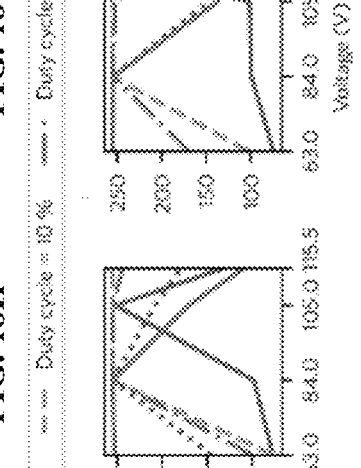
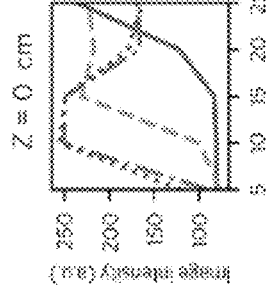
FIG. 18A  FIG. 18B  FIG. 18C  FIG. 18D  FIG. 18E
FIG. 18F  FIG. 18G  FIG. 18H  FIG. 18I  FIG. 18J
FIG. 18K  FIG. 18L  FIG. 18M  FIG. 18N  FIG. 18O

| | |
|---|---|
| $a_0 = 0.2442257733$ | $a_1 = 0.009746344476$ |
| $a_2 = -0.003732234996$ | $a_3 = 0.003732234996$ |
| $a_4 = 0.002457337988$ | $a_5 = 0.002459342259$ |
| $a_6 = 0.900070492$ | $a_7 = -0.016662619$ |
| $\lambda_{UV} = 0.2442257733$ | $\lambda_{IR} = 0.2442257733$ |
| $\bar{T} = \dfrac{273 + 25}{273} = 1.0915575091$ | $\bar{\lambda} = \dfrac{0.633}{0.589} = 1.0747702886$ |
| $a_8 = a_0 + a_2\bar{T} + a_3\bar{\lambda}^2\bar{T} + \dfrac{a_4}{\bar{\lambda}^2} + \dfrac{a_5}{\bar{\lambda}^2 - \lambda_{UV}^2} + \dfrac{a_6}{\bar{\lambda}^2 - \lambda_{IR}^2} = 0.2131119257$ | |
| $a_9 = a_1 + a_8 + a_7 = 0.2062029980$ | $a_{10} = a_1 + 2a_7 = -0.023578899$ |
| $a_{11} = a_9 + a_{10} = 0.1826224081$ | $a_{12} = a_7 + a_{10} = -0.040241520$ |
| $a_{14} = 1 + 2a_9 = 1.4124059600$ | $a_{15} = 1 - a_9 = 0.7937970190$ |

FIG. 27

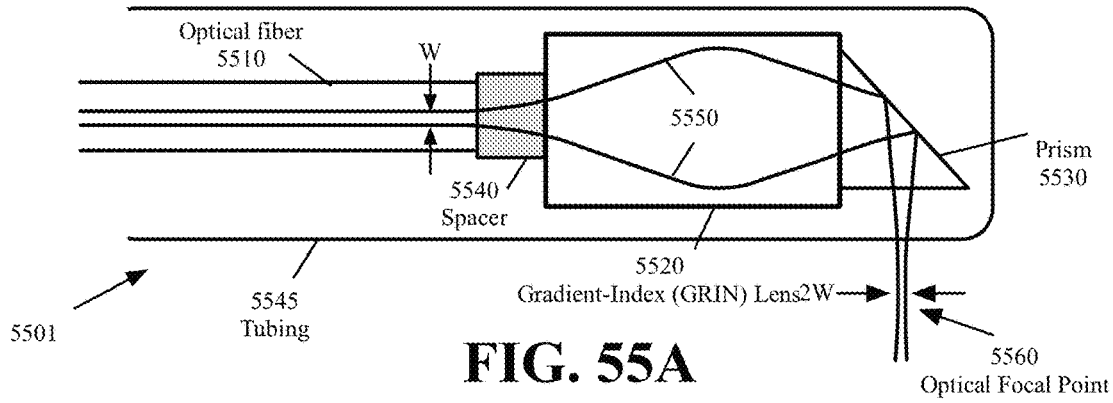
FIG. 55A
Prior Art
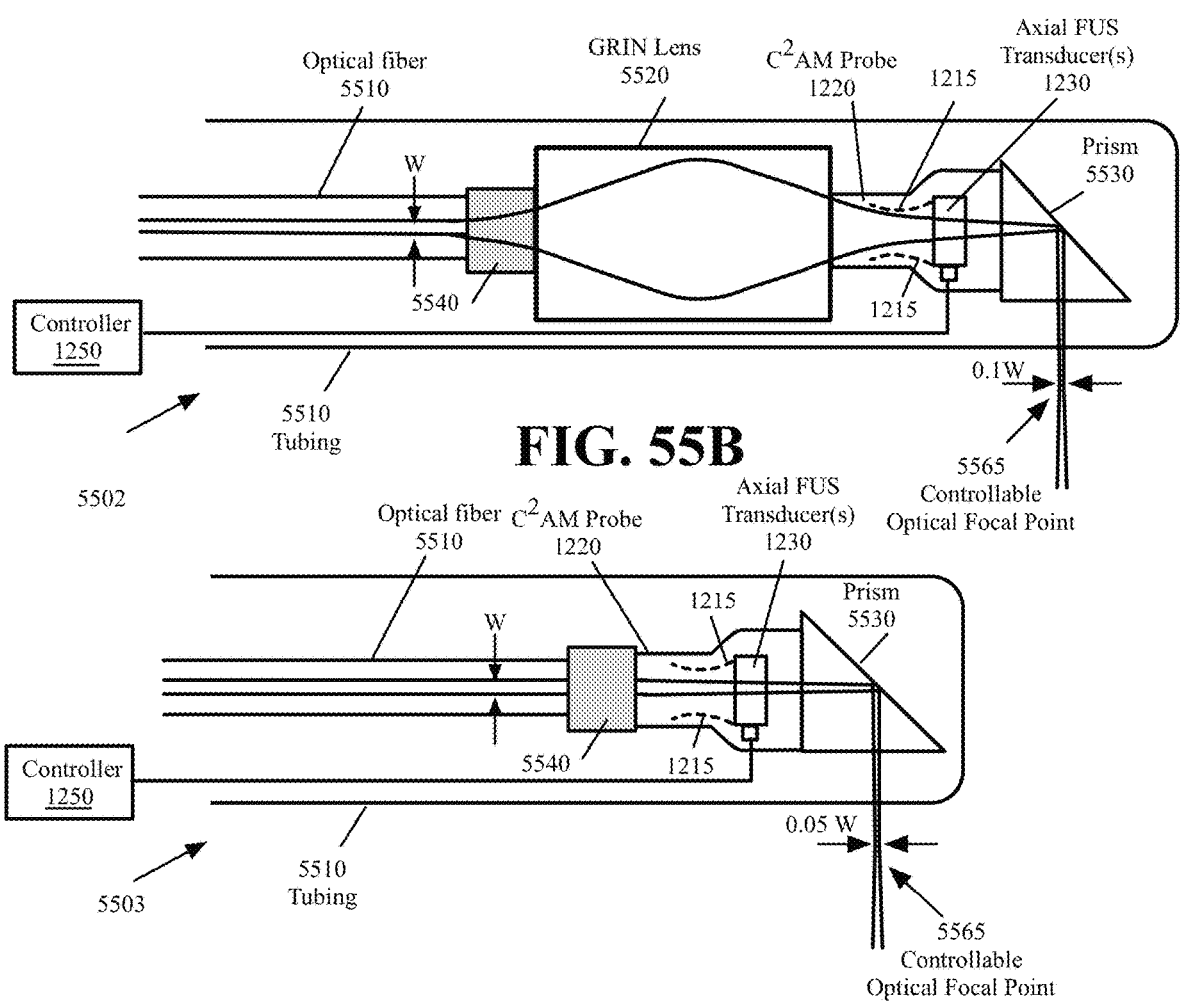
FIG. 55B
FIG. 55C

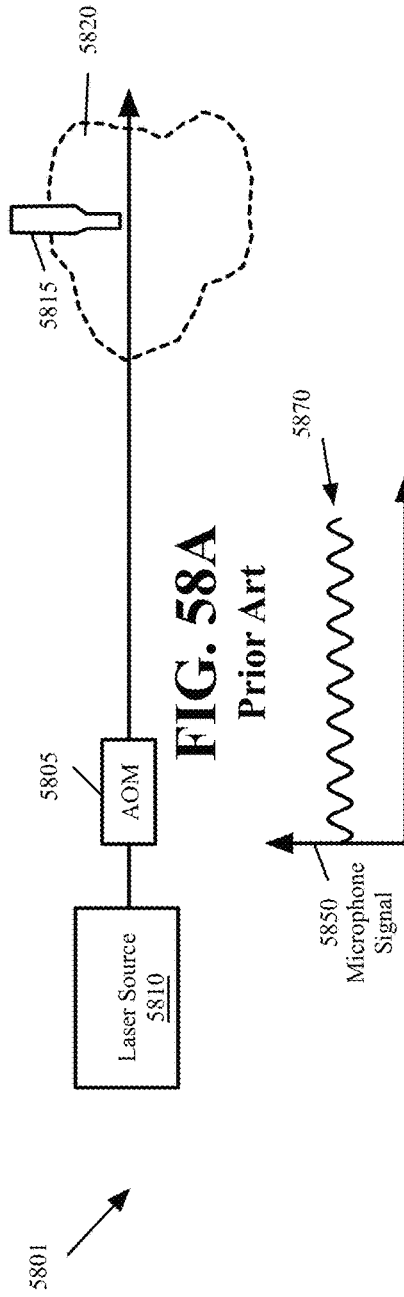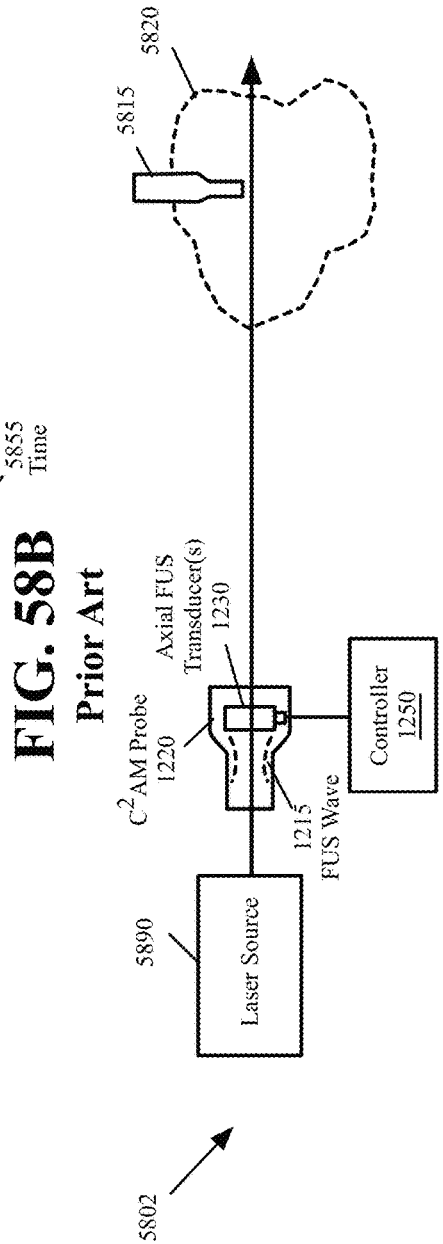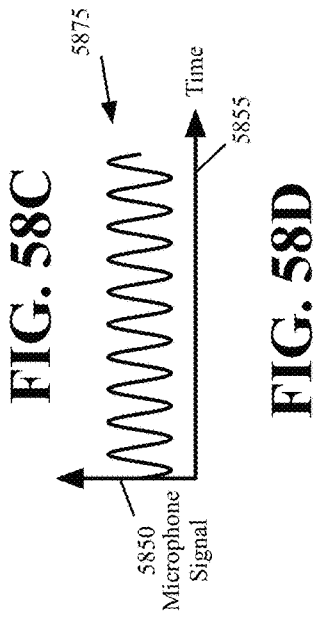

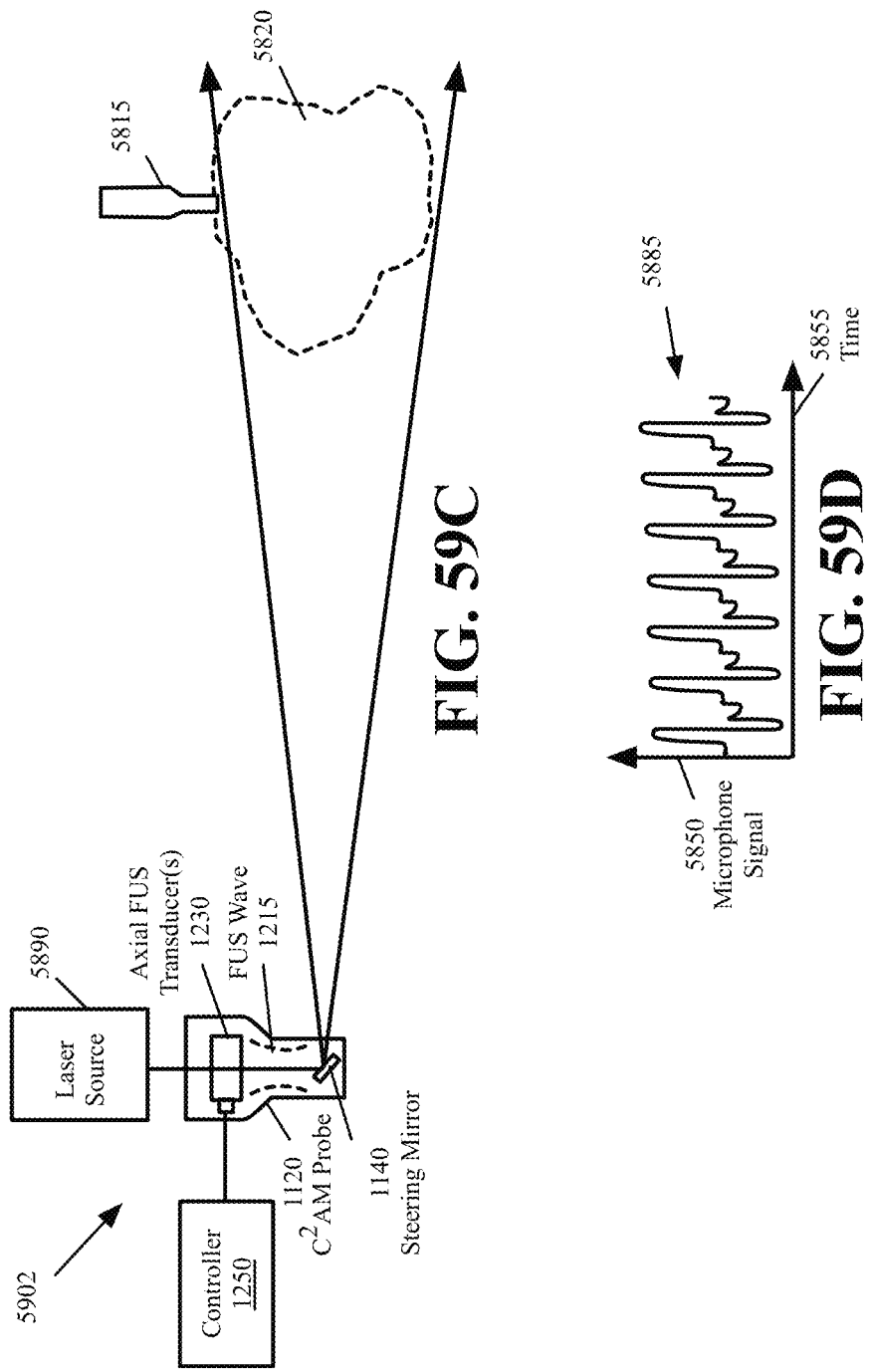

MEDIATOR-FREE UNIVERSAL LASER LIGHT AMPLIFICATION WITH COAXIAL PROPAGATING FOCUSED ULTRASOUND AND SYSTEM

CLAIM OF BENEFIT TO PRIOR APPLICATIONS

This application claims the benefit of U.S. Provisional Patent Application Ser. No. 63/048,005, filed on Jul. 3, 2020; U.S. Provisional Patent Application Ser. No. 62/969,309, filed on Feb. 3, 2020; and U.S. Provisional Patent Application Ser. No. 62/930,335, filed on Nov. 4, 2019. The contents of U.S. Provisional Patent Application 63/048,005, U.S. Provisional Patent Application 62/969,309, and Provisional Patent Application 62/930,335 are hereby incorporated by reference.

BACKGROUND

The acousto-optic interaction of narrow laser beams has gained interest since lasers became the most popular coherent light source. The phenomenon of acoustic modulation on propagation of light through scattering media by polarization modulation, optical phase conjugation, wave front shaping, binarized time-reversed adapted perturbation, speckle-contrast mechanism, and intense acoustic bursts have been investigated. For example, the generation of acoustic shear wave enhances the signal to noise ratio and resolution in ultrasound (US)-modulated optical tomography. In the above mentioned investigations, the US wave was implemented perpendicularly to the light propagation direction.

Other investigators have demonstrated that temporally US-induced air bubbles using sonification parallel to the light incident direction may be used to increase light penetration in the medium. The rationale behind this phenomenon is that the air bubbles act as a Mie scattering induced medium. Still other investigators have demonstrated the US-modulated droplet lasers, in which the enhancement of laser intensity from whispering gallery mode of oil droplets was presented. In both of these investigations, bubbles play the main role as a mediator for the effect of lasing and reducing scattered photons. In some studies on the interaction of laser and US waves, the laser and the US waves have been perpendicular to each other, which does not provide time-stable focusing. In other studies, either auxiliary media (such as air bubbles or oil droplets) have been applied or additional hardware/software have been used for focusing, which infringe the natural (or mediator-free) property of focusing in the work. Yet in other studies, the US transducer has been a passive element (instead of being an active transmitter) that merely receives the vibrations generated due to incident laser (e.g., photoacoustics).

BRIEF DESCRIPTION OF THE DRAWINGS

The various embodiments of the present mediator-free universal laser light amplification with coaxial propagating focused ultrasound and system now will be discussed in detail with an emphasis on highlighting the advantageous features. These embodiments depict the novel and non-obvious mediator-free universal laser light amplification with coaxial propagating focused ultrasound and system shown in the accompanying drawings, which are for illustrative purposes only. These drawings include the following figures, in which like numerals indicate like parts:

FIG. 3C is a functional diagram illustrating an embodiment of an acousto-optic modulator system that includes two concentric axial FUS transducers, one co-propagating transducer and one counter propagating transducer, according to various aspects of the present disclosure;

FIG. 5 illustrates the tabulation of the modulated laser intensity values measured at different distances from the coaxial acousto-optic modulator probe for different values of the duty cycle and different values of the voltage amplitude, according to various embodiments of the present disclosure;

FIGS. 14A-14C illustrate the 2D images of the light showing intensity patterns recorded by CCD in pre-, during-, and post-FUS modes, respectively, according to various aspects of the present disclosure;

FIGS. 14D-14F illustrate 3D image intensity profiles of the US-modulated light for duty cycle of 20% at 84 V in pre-, during-, and post-FUS modes, respectively, according to various aspects of the present disclosure;

FIG. 14G illustrate distribution of the measured lensing power over time for two distant duty cycles of 2% (squares) and 20% (circles), respectively, revealing time stability in lensing power with only miniscule variations over time, according to various aspects of the present disclosure;

FIG. 15A illustrates a schematic portrait of the basic principle of the intrinsic acousto-optic modulation method (CAM) in the counter-propagating configuration, according to various aspects of the present disclosure;

FIGS. 15B-15E illustrate experimental results of 2D and 3D optical intensities along the propagation axis with FUS-input duty cycle of 20% and 2%, both at 84 V, according to various aspects of the present disclosure;

FIGS. 16A-16B reveal the frozen-in-time lensing effect in measured maximum intensity, FWHM, and beam diameter over US-input duty cycles of 2%. at 84 V, according to various aspects of the present disclosure;

FIGS. 16C-16D reveal the frozen-in-time lensing effect in measured maximum intensity, FWHM, and beam diameter over US-input duty cycles of 20%. at 84 V, according to various aspects of the present disclosure;

FIGS. 16E-16H illustrate the 2D modulation of spatial resolution in propagating direction utilizing CAM, according to various aspects of the present disclosure;

FIGS. 18A-18E illustrate comprehensive experimental results of light intensity variations as a function of the US-input voltages at different locations of propagation axis (z), according to various aspects of the present disclosure;

FIGS. 18F-18J illustrate color scale 2D cross-sections of intensity variations for z=0 cm, 4 cm, 10 cm, 13 cm, and 17 cm as a reciprocal interplay of input voltages and duty cycles, collectively, according to various aspects of the present disclosure;

FIGS. 18K-18O illustrate comprehensive experimental results of light intensity variations as a function of the duty cycles at different locations of propagation axis (z), according to various aspects of the present disclosure;

FIG. 27 illustrates the coefficients for the equation expressing the relationship between pressure change and index of refraction variation in water, according to various aspects of the present disclosure;

FIG. 55A is a cross section of an OCT catheter, according to prior art;

FIG. 55B is a cross section of an OCT catheter of FIG. 55A after a coaxial acousto-optic modulator probe is added inside the catheter, according to various embodiments of the present disclosure;

FIG. 55C is a cross section of the imaging probe of FIG. 55A after the GRIN lens is replaced by a coaxial acousto-optic modulator probe, according to various embodiments of the present disclosure;

FIG. 58A is a functional diagram illustrating an apparatus used for photoacoustic communication, according to prior art;

FIG. 58B shows the sound generated in the system of FIG. 58A as recorded by a microphone, according to prior art;

FIG. 58C is a functional diagram illustrating the replacement of the acousto-optic modulator in the apparatus of FIG. 58A with a coaxial acousto-optic modulator probe, according to various aspects of the present disclosure;

FIG. 58D shows the sound generated in the system of FIG. 58C as recorded by a microphone, according to various aspects of the present disclosure;

FIG. 59C is a functional diagram illustrating the replacement of the fast steering mirror in the acousto-optic modulator in the apparatus of FIG. 59A with a coaxial acousto-optic modulator probe that includes a fast steering mirror, according to various aspects of the present disclosure;

FIG. 59D shows the sound generated in the system of FIG. 59C as recorded by a microphone, according to various aspects of the present disclosure;

DETAILED DESCRIPTION

Figures 1A, 1B:
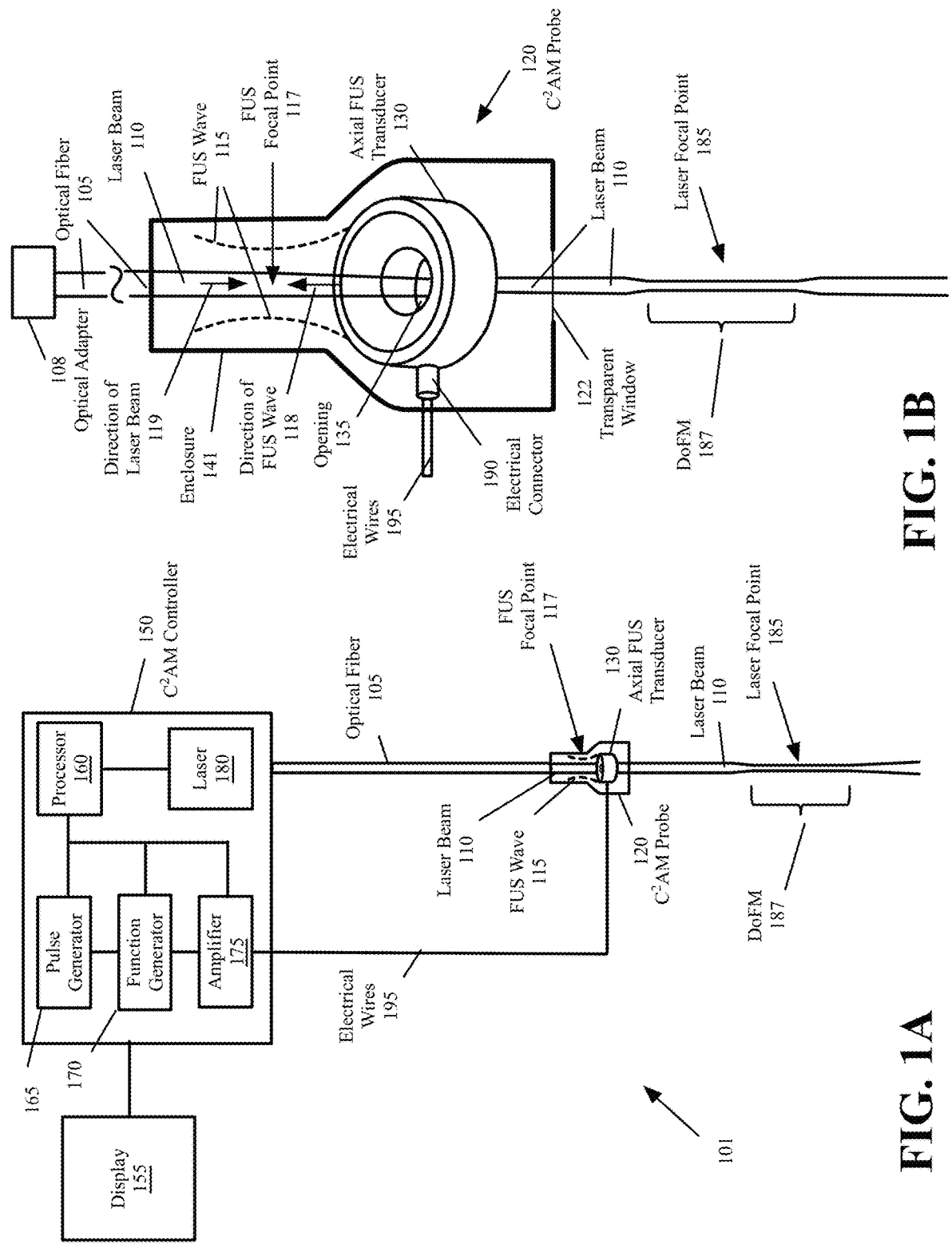
FIG. 1A is a functional diagram illustrating an embodiment of a counter propagating acousto-optic modulator system, according to various aspects of the present disclosure.
FIG. 1B is a functional diagram illustrating an embodiment of the counter propagating acousto-optic modulator probe of FIG. 1A, according to various aspects of the present disclosure.

Amplification and focusing of light, as well as the light's depth of penetration in the media, power density, and optical dynamic focusing are of paramount importance in different fields. One aspect of the present embodiments includes the realization that a major limitation in using optical methods, for example, for biological applications, is low penetration depth in the order of millimeters. To increase the penetration depth, one would use light of near-infrared to infrared regions, which has limitations in imaging resolution. Aside from changing the frequency of illumination, modulation of the media has been proposed to overcome limitations in optical imaging, such as using US in photoacoustic imaging. The phenomenon of light diffraction by a focused US (FUS) wave, has attracted attention recently. The methods used in prior art involved using mediators, such as air bubble or oil droplets, using heat, or using US in a perpendicular direction to the light, which does not provide time-stable focusing.

The present embodiments, as described in detail below, solve the above-mentioned problems by providing a co/counter propagating (co-propagating or counter propagating) acousto-optic modulator that creates a low-intensity FUS on a laser beam in a medium such as water without any auxiliary mediators or special software or hardware. With the co/counter propagating acousto-optic modulator, referred herein as $C^2AM$, the US intensity range of interest is, for example, in the range of less than 1 W/cm2, which does not cause cavitation or noted temperature increase in the medium. The main optical effect of the FUS is the controllable focusing of the laser beam through modification of the refractive index of the medium in a dynamic fashion.

The laser wave and the FUS wave are coaxially mixed and propagated through each other. The term coaxial (or co-axial) waves is referred herein as two waves (or two beams) having a common axis or coincident axes of propagation. The FUS pressure field amplifies the laser intensity and reduces the diameter and full width at half maximum (FWHM) of the laser beam. The FUS pressure field keeps the laser's lensing power positive, with small positive fluctuations, as long as the mechanical momentum is applied.

The $C^2AM$, in some embodiments, may use a low-intensity FUS and low power laser. No air bubbles or cavitation is generated at the focal point of the FUS. The effects of the FUS on the laser is reversible. As soon as the FUS is turned off, the laser beam turns back to its original shape and form with no delay.

The $C^2AM$, in some embodiments, may include a $C^2AM$ probe and a $C^2AM$ controller. The $C^2AM$ probe may include an enclosure to house one or more FUS transducers and a medium such as a gas, a liquid, or a gel to surround the FUS transducer. The FUS transducer may be a ring FUS transducer or a phased array FUS transducer. The phased array FUS transducer may be used to steer the FUS wave without physically moving the FUS transducer. The $C^2AM$ probe, in some embodiments, may include more than one FUS transducers.

The present embodiments provide the unexpected intrinsic (mediator-free) control and strong focusing of EM (laser) waves using mechanical (ultrasound) waves in a relatively boundless path of interplay owing to co- and counter propagating alignment between laser and ultrasound (US). The lab experimentation and simulation results provided below shows that the simple and unconventional architecture of the present embodiments achieves time-stable deep dynamic control of the focal length and intensity, with a depth of field of more than 28 cm, more than two orders of magnitude enhancement of power density, and a ~450-fold reduction in full width at half maximum of the beam profile. This new universal acousto-optic modality has the potential to transform optical modulation, low-loss time-stable light delivery, and spatial propagation limits. and provides an intrinsic deep dynamic control and time-stable focusing of light vis co-propagating and/or counter propagating ultrasound. This is in contrast to all previous studies, which so far have relied on either mediators or perpendicular configurations between the EM and mechanical waves, which severely limits their depth of field, modulation effectiveness, and feasibility.

The remaining detailed description describes the present embodiments with reference to the drawings. In the drawings, reference numbers label elements of the present embodiments. These reference numbers are reproduced below in connection with the discussion of the corresponding drawing features.

I. CO/COUNTER PROPAGATING ACOUSTO-OPTIC MODULATOR

Some embodiments may provide a coaxial acousto-optic modulator. The coaxial acousto-optic modulator may be a co-propagating or a counter propagating acousto-optic modulator, referred herein as co/counter propagating acousto-optic modulator (CAM). The CAM may create a low-intensity FUS on a laser beam in coaxial direction in a medium, such as, for example, a gas, a liquid, or a gel.

The intensity and frequency of the FUS wave is selected such that no cavitation is created in the medium. The only optical effect of the FUS wave is the modification of the refractive index of the medium. The refractive index of a medium is a factor by which the speed and the wavelength of the light are reduced in the medium with respect to their vacuum values.

FIG. 1A is a functional diagram illustrating an embodiment of a counter propagating acousto-optic modulator system 101, according to various aspects of the present disclosure. The system 101 may include a CAM probe 120 and a $C^2AM$ controller 150. FIG. 1B is a functional diagram illustrating an embodiment of the counter propagating acousto-optic modulator probe 120 of FIG. 1A, according to various aspects of the present disclosure.

With reference to FIGS. 1A and 1B, the $C^2AM$ probe 120 may include an axial FUS transducer 130. A FUS transducer converts electrical signals into focused US. The axial FUS transducer 130, in some embodiments, may be a single element FUS transducer (e.g., as described below with reference to FIG. 2A). The axial FUS transducer 130, in some embodiments, may be a multiple element transducer (e.g., as described below with reference to FIGS. 2B, 2D, and 2E). The $C^2AM$ probe, in some embodiments, may include more than one transducer (e.g., as described below with reference to FIGS. 3A-3C).

The axial FUS transducer 130 may receive a driving signal from the $C^2AM$ controller 150 and may generate a FUS wave 115. Sound waves, including the US waves, are mechanical waves that cause local positive and negative pressure differences in the receiving medium during propagation. The US waves are sound waves with frequencies that are much higher than human hearing range.

Although the term US is used in several examples herein, in addition to, or in lieu of the US, different embodiments may use other mechanical forces, for example, and without limitations, sound waves, air movements, etc., to generate an oscillation in the medium surrounding the transducer to transfer a mechanical momentum coaxial to the propagation axis an electromagnetic (EM) wave. The examples of the EM wave may include, for example, and without limitations, radio waves, microwaves, infrared light waves, visible light waves (e.g., white light waves, laser, which is a monochrome, directional, and coherent type of light wave), ultraviolet light waves, X rays, gamma rays, etc. Such a coaxial propagation of the mechanical momentum (e.g., the US waves) and the EM waves (e.g., laser), in the present embodiments, causes increase in the EM wave's focus, causes increase in the EM waves' intensity, and keeps the EM wave's lensing power positive (with small positive fluctuations instead of fluctuating between positive and negative values) as long as the mechanical momentum is applied.

With further reference to FIG. 1A, the controller 150 may include, for example, and without limitations, a pulse generator 165, a function generator 170, and an amplifier 175. The pulse generator 165, the function generator 170, and the amplifier 175, in some embodiments, may be separate hardware units. In other embodiments, the functionality of two or all three of them may be provided by one hardware unit.

The $C^2AM$ controller 150, in some embodiments, may include a laser (or laser device) 180. The $C^2AM$ controller 150, in some embodiments, may include a beam expander (not shown) that may expand and collimate the laser beam. The laser 180 may be a low power laser, for example, and without limitations, a laser with less than 1 milliwatt of power. The laser 180, in the depicted embodiment, is a component of the CAM controller 150. In other embodiments, the laser 180 may be a separate device that may be moved around independent of the CAM controller 150.

A laser is a device that emits light through a process of optical amplification based on the stimulated emission of electromagnetic radiation. A laser emits spatial and/or temporal coherent light. Light, including laser, travels as waves. Sunlight or light from a typical lightbulb is made up of light with many different wavelength. A laser, however, produces a narrow beam of light in which all of the light waves have very similar wavelengths. Although the terms laser wave or laser beam are used in several examples herein, the CAM probe 120 may be used with other types of light or other types of electromagnetic waves. For simplicity, several of the following examples may use either the term laser or light.

The $C^2AM$ controller 150, in some embodiments, may include a display 155. The display 155, in some embodiments, may be a separate device coupled to the $C^2AM$ controller 150. The display, in other embodiments, may be a part of the $C^2AM$ controller 150. For example, and without limitations, the display 155 may be a display panel on the external perimeter of the $C^2AM$ controller 150 enclosure. The display, in other embodiments, may be part of an electronic device, such as, for example, and without limitations, a mobile device, a server, a computing device, etc., that may be communicatively coupled to the $C^2AM$ controller 150. The $C^2AM$ controller 150, in some embodiments, may include a keyboard (not shown). and/or a keypad (not shown). In several examples described below, the display 155, the keyboard, and/or the keypad are not shown for simplicity.

The $C^2AM$ controller 150, in some embodiments, may include a processor 160. As described below, the processor 160 may control the operations of the pulse generator 165, the function generator 170, the amplifier 175, the laser 180, and/or the display 155.

As described below with reference to FIG. 4, the driving signal to the amplifier 175, may be a pulsed square wave generated through the combination of the signals from the pulse generator 165 and the function generator 170. The duty cycle of the pulsed square wave may be tuned by adjusting the pulse generator 165, while the acoustic intensity may be adjusted by changing the amplitude of the voltage generated by the function generator 170.

The specific values of the duty cycle and the voltage amplitude may be set by using a table lookup in order to control the US focal point 117 and the intensity of the US wave 115. The values of the duty cycle and the voltage amplitude may be set such that no temperature rise and no bubble or cavitation is formed in the medium surrounding the axial FUS transducer 130.

In some embodiments, the processor 160 may set the values of the duty cycle and the voltage amplitude. In other embodiments, the duty cycle and the voltage amplitude may be set manually (e.g., through a set of controls on the $C^2AM$ controller 150). Yet in other embodiments, the duty cycle and the voltage amplitude may be set by a separate electronic device such as, for example, and without limitations, a remote server, a client device (e.g., a mobile device, a tablet), etc. In some embodiments, the specific values of the duty cycle and the voltage amplitude may be calculated, for example by the processor 160, by using an algorithm.

With further reference to FIGS. 1A and 1B, the $C^2AM$ probe 120 may include a sealed enclosure 141 for retaining a medium such as liquid, gas, gel, etc. The sealed enclosure 141 may include an optical input, and an optical output. The optical input in the embodiment shown in FIGS. 1A and 1B, may be an optical fiber 105. The optical fiber 105, in some embodiments, may be connected to the $C^2AM$ probe 120 with an optical adhesive. The optical fiber 105, in some embodiments, may be connected to an optical adapter 108 for connecting the $C^2AM$ probe 120 to other devices to receive a light beam or a laser beam 110.

The optical output in the embodiment shown in FIGS. 1A and 1B, may be a transparent window 122 (FIG. 1B) that may allow the light or laser waves to exit the $C^2AM$ probe 120. Although in the embodiment of FIG. 1B, the optical input is received by the $C^2AM$ probe 120 through the optical fiber 105 and the optical output is sent out of the $C^2AM$ probe 120, in other embodiments both the input and the output may be transparent windows, both the input and the output may be optical fibers, or one of the input or the output may be optical fiber and the other may be a transparent window.

With further reference to FIGS. 1A and 1B, the axial FUS transducer 130 may receive the driving signal through a set of electrical wires 195 that may enter the sealed enclosure 141 of the $C^2AM$ probe 120. The electrical wires 195 may be connected to the axial FUS transducer 130 by an electrical connector 190.

The optical (e.g., laser) beam 110 may pass through an opening 135 in the axial FUS transducer 130. The axial FUS transducer 130 may be a low power transducer and may generate a US wave 115 with an intensity range of, for example, and without limitations, less than 350 Watt per square centimeter ($W/cm^2$).

In the counter propagating configuration of FIGS. 1A and 1B, the laser beam travels (as shown by the arrow 119 in FIG. 1B) from the optical fiber 105, through the axial FUS transducer 130, and out of the transparent window 122. The FUS wave 115 travels (as shown by the arrow 118 in FIG. 1B), on the same axis, in the opposite direction of the laser beam 110.

The FUS wave 115 may alter the refractive index of the optical medium contained in the $C^2AM$ probe 120 and may, therefore, modify the effect of the medium on the light. For example, the FUS wave may narrow the laser beam light, when coaxially aligned with laser. The $C^2AM$ probe 120 is configured such that the intensity of the US wave 115 does not cause cavitation in the medium. Therefore, the only optical effect of the US wave 115 is the modification of the refractive index of the medium. The small contrast of the refractive index on the laser beam's 110 axis constrains the laser beam 110 from scattering and confines it in the medium. The driving signal supplied by the $C^2AM$ controller 150 to the axial FUS transducer 130 may be configured such that the low intensity US wave 115 may focus the laser beam 110 only by modifying the refractive index of the medium.

The driving signal to the FUS transducer 130, in some embodiments, may be configured such that the focal point 117 of the US wave 115 may be inside the enclosure of the $C^2AM$ probe 120 and the FUS wave 115 may be attenuated such that no significant amount of the FUS wave 115 may leave the $C^2AM$ probe 120. On the other hand, the focal point 185 of the laser beam 110 may fall outside of the $C^2AM$ probe 120.

Optical depth of field of the modulated laser beam (DoFM) 187 is defined as a domain over the propagation axis (z) where the intensity of US-modulated laser remains above −3 dB intensity (half maximum) relative to the maximum intensity. Across the DoFM region, time-stable phenomena of optical beam forming, and dynamic control of the focal point intensity may be obtained.

It should be noted that the focal point of the laser beam, in some embodiments, may be a zone where the laser intensity is at maximum. As long as the FUS wave 115 is generated by the axial FUS transducer 130, the lensing power of the laser beam 110 remains constant with very miniscule fluctuations over time. The coaxial FUS wave 115 may amplify the laser intensity and may modulate the laser beam's shape to reduce the FWHM of the laser beam 110.

Figures 1C, 1D:
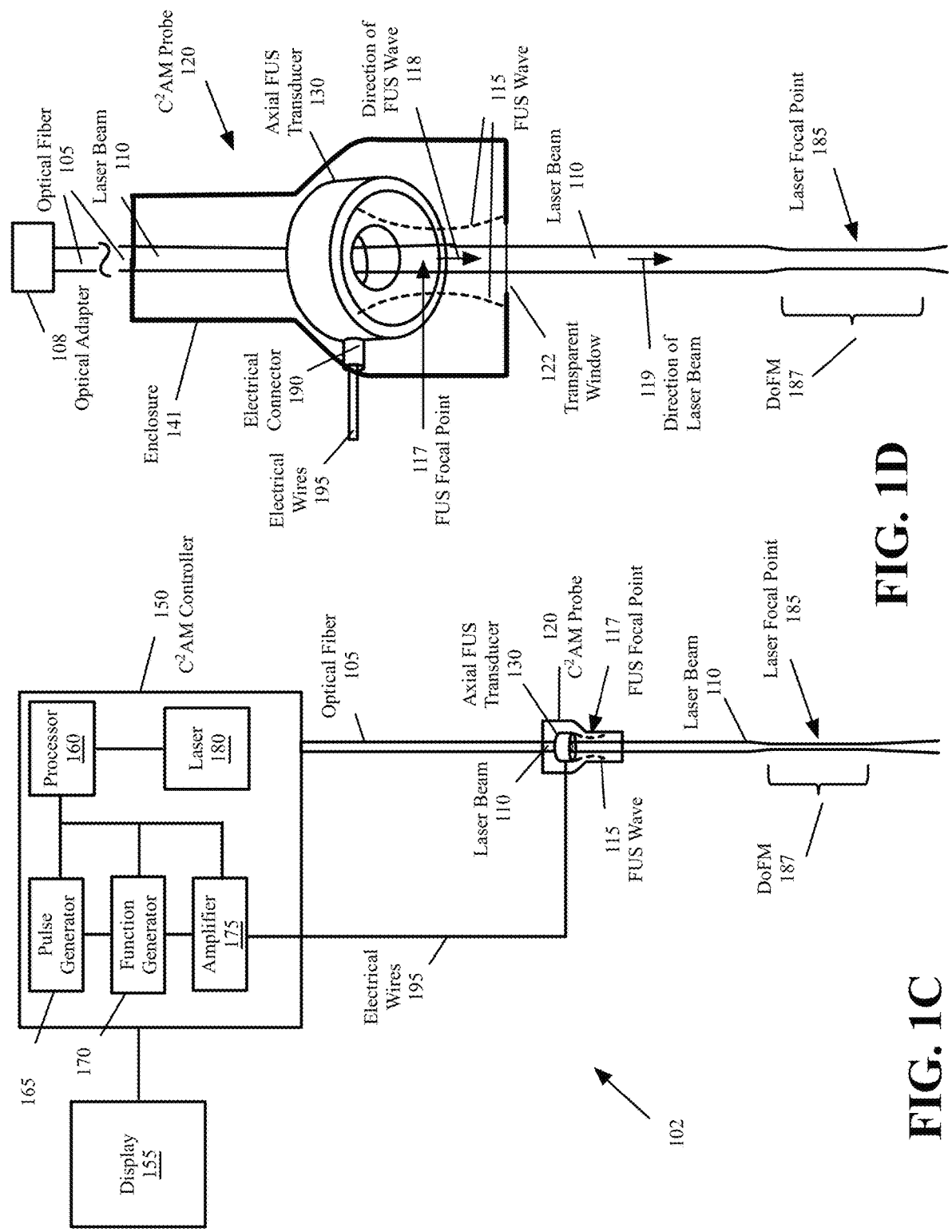
FIG. 1C is a functional diagram illustrating an embodiment of a co-propagating acousto-optic modulator system, according to various aspects of the present disclosure.
FIG. 1D is a functional diagram illustrating an embodiment of the co-propagating acousto-optic modulator probe of FIG. 1C, according to various aspects of the present disclosure.

In the example of FIGS. 1A and 1B, the FUS wave 115 coaxially travels in the opposite direction of the laser beam 110. Alternatively, the FUS wave 115 and the laser beam 110 may co-propagate. FIG. 1C is a functional diagram illustrating an embodiment of a co-propagating acousto-optic modulator system 102, according to various aspects of the present disclosure. The system 102 may include similar components as the system 101 of FIG. 1A, except the axial FUS transducer 130 in FIG. 1C may be configured such that the FUS wave 115 and the laser beam 110 propagate in the same direction.

FIG. 1D is a functional diagram illustrating an embodiment of the co-propagating acousto-optic modulator probe 120 of FIG. 1C, according to various aspects of the present disclosure. In the co-propagating configuration of FIGS. 1C and 1D, the laser beam travels (as shown by the arrow 119 in FIG. 1D) from the optical fiber 105, through the axial FUS transducer 130 and out of the transparent window 122. The US wave 115 travels (as shown by the arrow 118 in FIG. 1D) on the same axis in the same direction as the laser beam 110. When the two systems 101 (FIG. 1A) and 102 (FIG. 1C) are configured with the same components and the same parameters, the distance between the FUS focal point 117 and the laser focal point 185 on the penetration axis (z) in both systems may be close or the same.

a. Examples of Axial FUS Transducer

Different embodiments may use different types and/or different configurations of axial FUS transducers. Although the term FUS transducer is used in several examples herein, a FUS transmitter may also be used instead of a FUS transducer in the present embodiments.

Figure 2A:
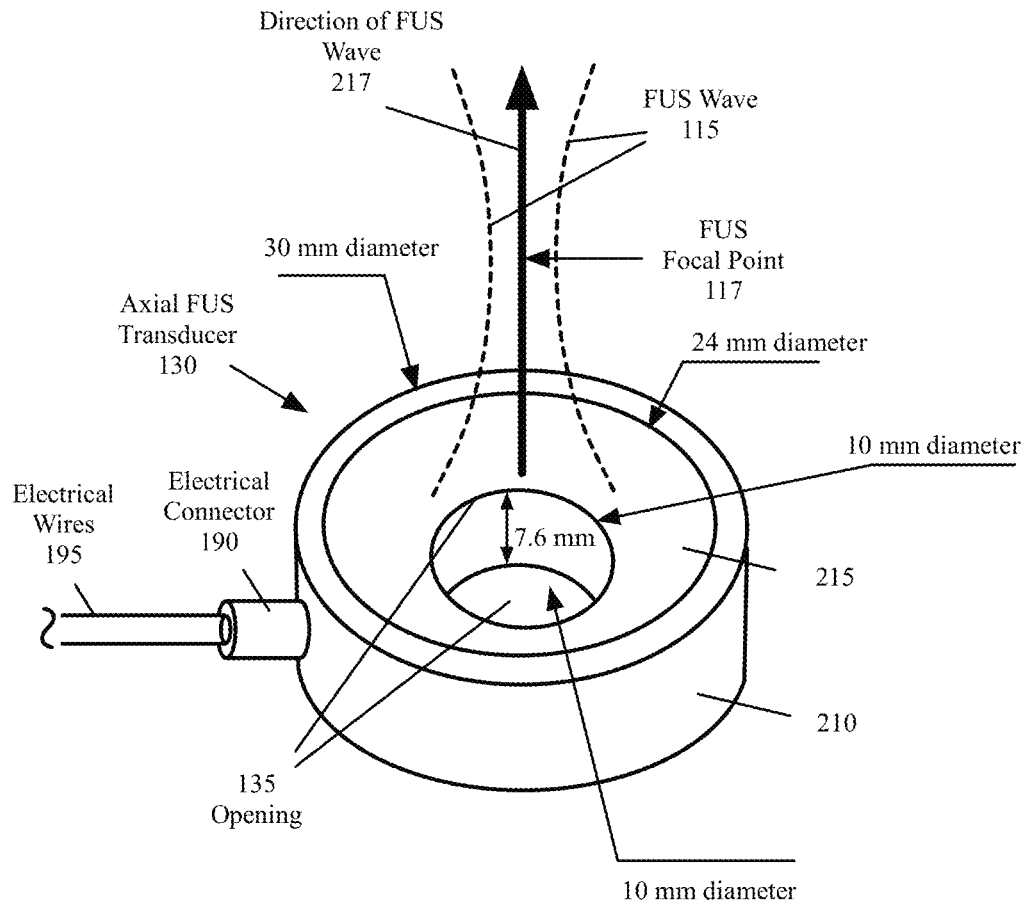
FIG. 2A is an upper front perspective illustrating an embodiment of a single element axial focused US transducer, according to various aspects of the present disclosure.

FIG. 2A is an upper front perspective illustrating an embodiment of a single element axial FUS transducer 130, according to various aspects of the present disclosure. With reference to FIG. 2A, the FUS transducer 130 is an axial, or forward looking, focused US (FUS) transducer. The figure shows a non-limiting example of the dimensions of an axial FUS transducer 130 of some embodiments. When an alternating voltage (e.g., and without limitations, a voltage pulse) is applied to the transducer 130, the transducer 130 may vibrate in the axial direction and may send US waves in the axial direction. For example, and without limitations, the ring transducer of FIG. 2A may have a center frequency of 3.3. MHz and a focal point of 23 mm, in some embodiments.

The FUS transducer 130, in some embodiments, may have a cylindrical body 210. The FUS transducer 130 may, for example, and without limitations, be at least partially composed of metal, plastic, and/or glass. In some embodiments, such as the depicted embodiment, the FUS transducer 130 may include an aperture, which may include an inner tapered or conical-shaped region 215 that may lead to a cylindrical opening 135.

The FUS transducer in other embodiments is not limited to a cylindrical shape, the depicted aperture shape, and/or the dimensions shown in FIG. 2A. The size, shape, and/or dimensions of the FUS transducer may be different and/or may be scaled up or down. The aperture of the FUS transducer may be filled, or partially filled, with a medium (such as for example a fluid or a semi-solid) to form a co/counter-propagating acousto-optic modulator that may be used and implemented in a number of different laser-bases applications, such as, for example, and without limitations, the applications illustrated and described herein. The medium deposited in the aperture may be a fluid (e.g., a liquid or gas), or may be semi-solid (e.g., a gel). For example, the medium may be a gas, a liquid such as water (e.g., and without limitations, deionized nanopure water), a liquid such as oil, or a semi-solid such as a gel. In the embodiments of FIG. 1A-1D, the medium may be contained inside the sealed enclosure 141 of the $C^2AM$ probe 120.

With further reference to FIG. 2A, the driving electrical signal may be received through the electrical wires 195 and may be applied to the axial FUS transducer 130 through the electrical connector 190. The axial FUS transducer 130, in some embodiments, may be fabricated by a piezoelectric material or a piezoelectric composite as its active element. For example, and without limitations, the axial FUS transducer 130, in some embodiments, may be fabricated by lead zirconate titanate (PZT), lithium niobite (LiNbO3), piezo polymer (e.g., Polyvinylidene fluoride (PVDF)), and/or single crystal (e.g., PMN-PT). Piezoelectric materials may change size and shape when a voltage is applied to them. Applying an alternating voltage, such as voltage pulses, makes the crystal oscillate at the same frequency and produces US waves. The US wave 115 may travel in the direction 217, which faces outward from the aperture.

In some embodiments, the FUS transducer 130 may use transduction methods other than piezoelectric conducting. For example, some embodiments may use capacitive micromachined ultrasonic transducers (CMUTs). The CMUTs are microelectromechanical (MEMS) based devices that may include a parallel-plate capacitor. One of the plates may be a fixed substrate back plate and the other plate may be supported by a flexible membrane. When an alternating voltage is applied between the membrane and the fixed plate, the membrane may vibrate and may generate US waves.

In some embodiments, the FUS transducer 130 may not have a through hole. Instead, the opening 135 may be covered by a mirror (e.g., and without limitations, a gold coated mirror) at the center, on the side that is opposite to the region 215, to reflect the laser beam.

The FUS transducer, in some embodiments, may be a phased array transducer that may include multiple elements that may be pulsed separately. The elements of a phased array FUS transducer are typically divided into several groups and each group is pulsed separately. Several examples of the phased array FUS transducers used in some embodiments are described below.

Figure 2B:
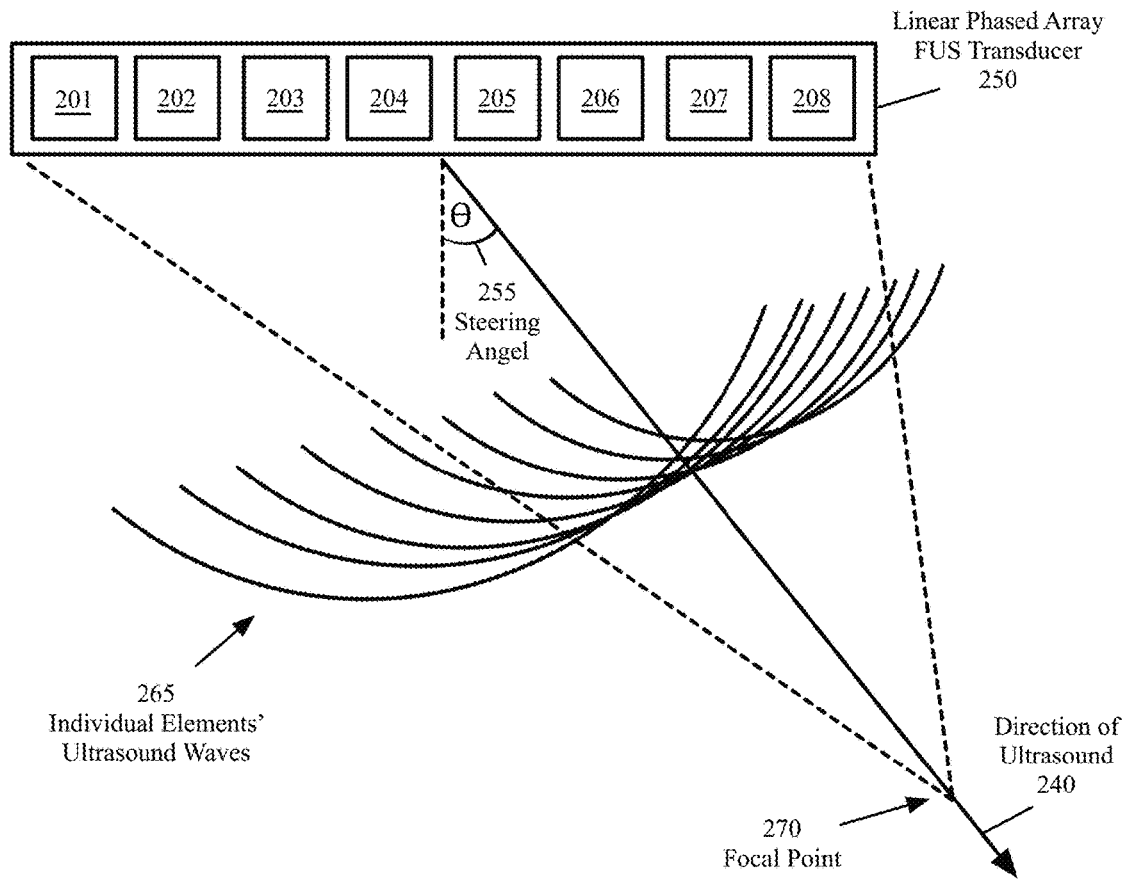
FIG. 2B is functional diagram illustrating an embodiment of a multiple element linear/phased array US transducer, according to various aspects of the present disclosure.

FIG. 2B is functional diagram illustrating an embodiment of a multiple element linear/phased array FUS transducer 250, according to various aspects of the present disclosure. With reference to FIG. 2B, the linear/phased array FUS transducer 250 may include multiple elements 201-208 arranged in a strip. Although the example of FIG. 2B shows eight elements 201-208, other embodiments many use a different number of two or more elements, for example, and without limitations, 32, 64, 256, etc. A linear phased array FUS transducer may include a smaller number of elements and may have smaller dimensions than a linear array FUS transducer. As an example, a linear phased array FUS transducer may include 32 elements where groups of 8 elements may be pulsed together, while a linear array FUS transducer may include 128 element where groups of 32 elements may be pulsed together.

The elements 201-208 may be covered by piezoelectric material (PZT, Lithium Niobate, etc.) or may use a different transduction method other than piezoelectric transducing, such as, for example, and without limitations, CMUT. Every element in a linear/phased array transducer may behave like an element in a single element transducer. However, each element 201-208 may be pulsed separately in order to steer the US beam and/or to change the focal point of the linear/phased array transducer. By varying the time between the outgoing US pulses from each element, the individual wave fronts generated by each element in the array may combine with each other to add or cancel energy in predictable ways that effectively steer and shape the overall US wave.

Figure 2C:
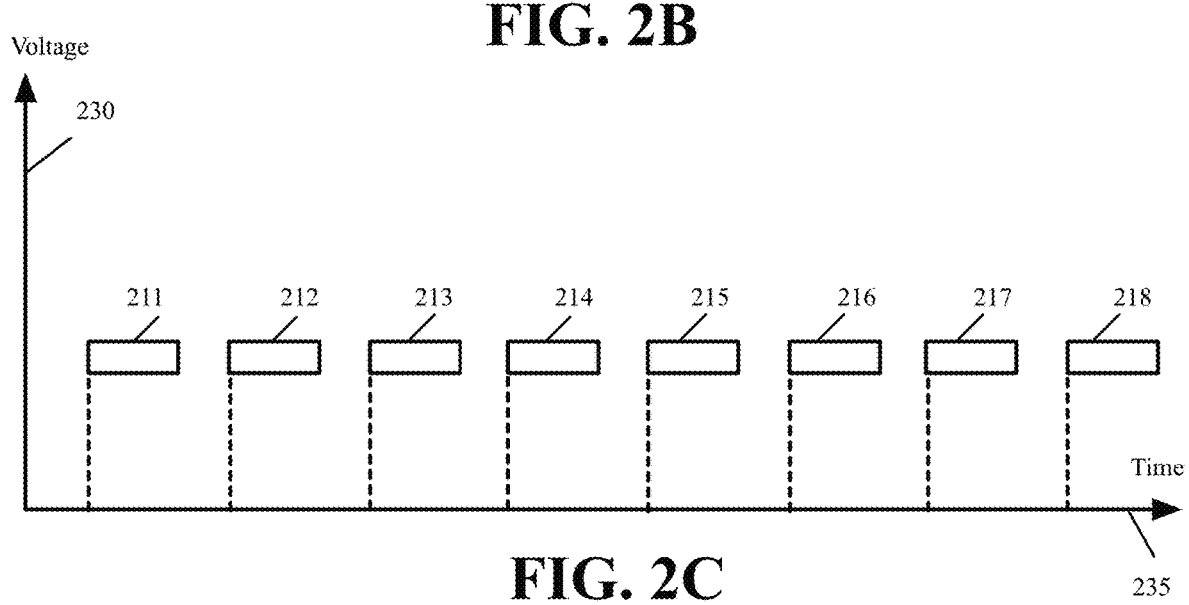
FIG. 2C illustrates an example of pluses applied to the elements of the linear/phased array transducer of FIG. 2B, according to various aspects of the present disclosure.

FIG. 2C illustrates an example of pluses that may be applied to the elements of the liner/phased array transducer of FIG. 2B, according to various aspects of the present disclosure. With reference to FIG. 2C, the voltage 230 is depicted against the time 235. As shown, the individual pulses 211-218 may be generated at slightly different times. Each pulse 211-218 may be applied to a corresponding individual element 201-208 of FIG. 2B. In some embodiments, several elements may be pulsed together as a group to improve effective sensitivity and enable sharper focusing.

In some embodiments, the processor 160 of the $C^2AM$ controller 150 (FIGS. 1A and 1C) may include software and/or hardware to pulse the individual elements (or groups of two or more elements) such that the overall US wave is steered to a particular direction and/or to focus at a particular point. As shown in the example of FIG. 2B, the individual elements' US waves 265 are combined such that the combined US wave is steered at a desired steering angel 255 and the combined US wave may travel in a desired direction 240. Furthermore, individual elements 201-208 may be pulsed such that the focal point 270 of the combined US wave may be located at a desired location.

Figure 2D:
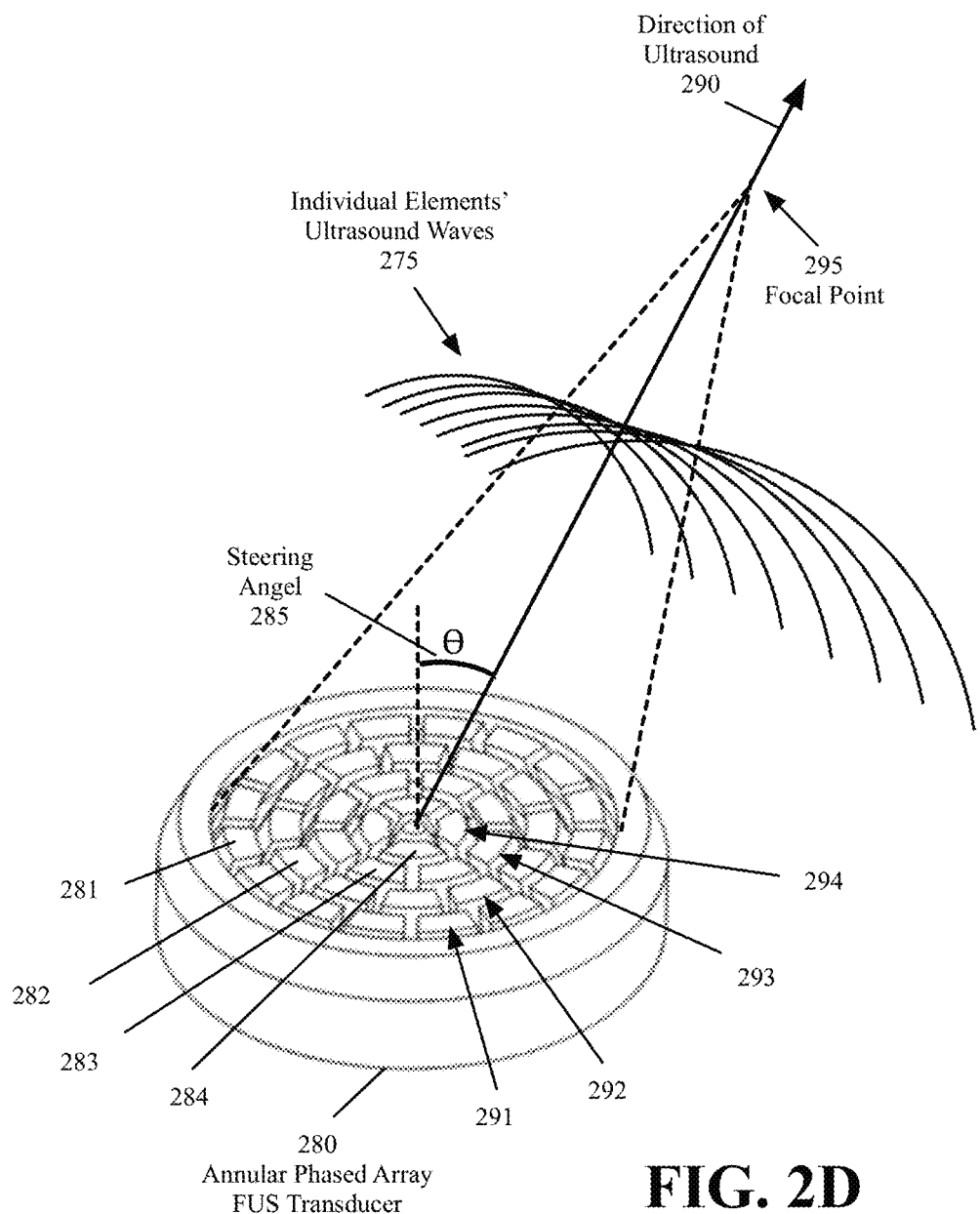
FIG. 2D is a functional diagram illustrating an embodiment of a multiple element annular phased array FUS transducer, according to various aspects of the present disclosure.

FIG. 2D is a functional diagram illustrating an embodiment of a multiple element annular phased array FUS transducer 280, according to various aspects of the present disclosure. The annular phased array transducer 280 may include concentric rings 291-294 of transducer elements. As shown, each ring 291-294 may be divided into a number of elements 281-284, respectively. Although four rings 291-294 of elements are shown in the example of FIG. 2D, any number of one or more rings may be used. An annular phased array transducer that has one ring of multiple elements may be referred to as a circular phased array transducer.

The annular phased array FUS transducer 280 may operate on similar principles as the linear/phased array FUS transducer 250 of FIG. 2A. The elements 281-283 may be covered by piezoelectric material (PZT, Lithium Niobate, etc.) or may use a different transduction method other than piezoelectric transducing, such as, for example, and without limitations, CMUT.

Every element in the phased array transducer 280 may behave like an element in a single element transducer. Each element, or each group of elements, may be pulsed separately in order to steer the US beam and/or to change the focal point of the phased array transducer 280. Alternatively, all elements may be pulsed together. By varying the time between the outgoing US pulses from each element (or each group of two or more elements), the individual wave fronts generated by each element (or each group of elements) in the array may combine with each other to add or cancel energy in predictable ways that effectively steer and shape the overall US wave.

As shown in the example of FIG. 2D, eight individual elements (or eight groups of elements) may be pulsed such that the individual US waves 275 are combined. The combined US wave may be steered at a desired steering angel 285 and the combined US wave may travel in a desired direction 290. Furthermore, individual elements 281-284 may be pulsed such that the focal point 295 of combined US wave may be located at a desired location.

Figure 2E:
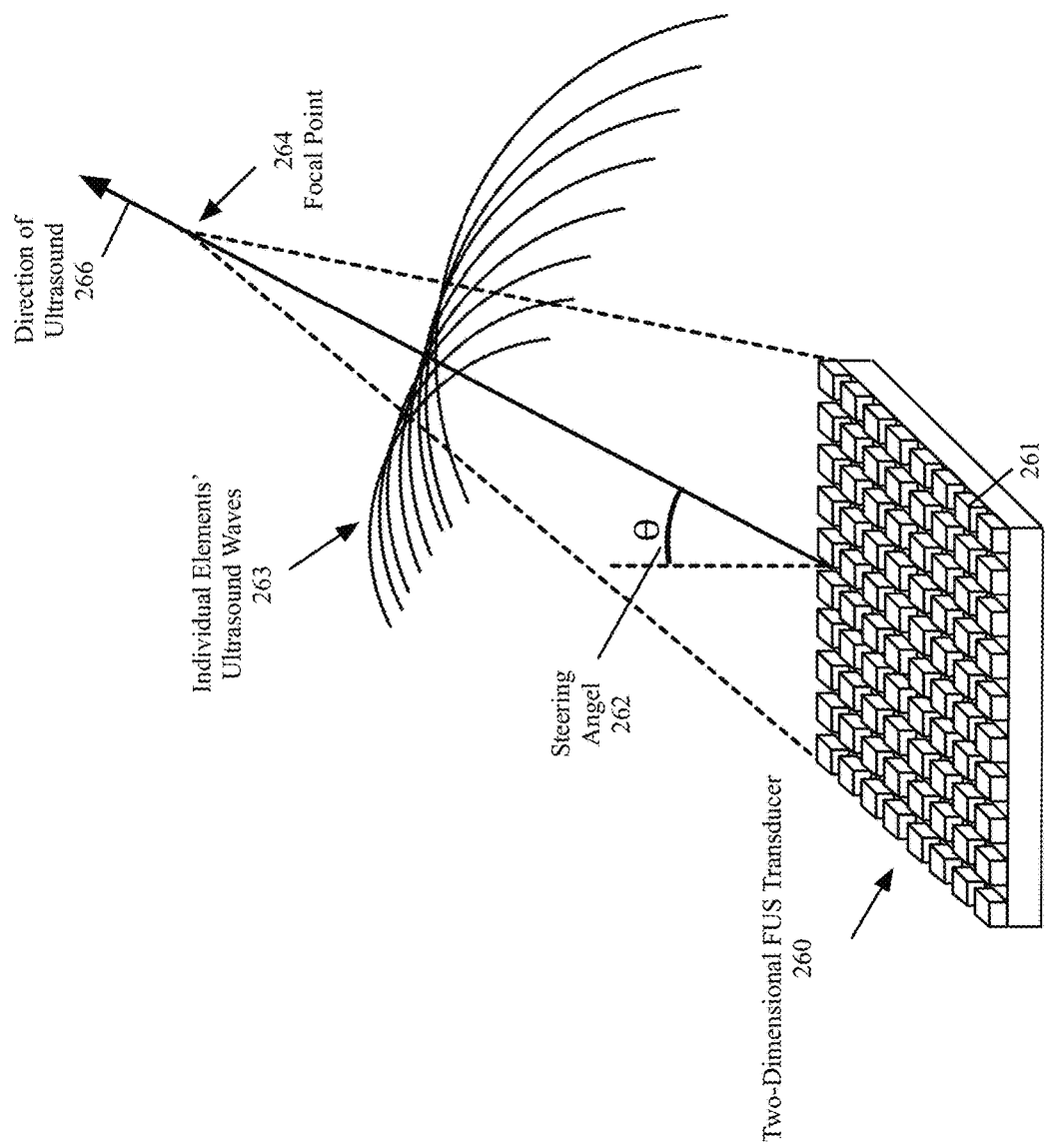
FIG. 2E is functional diagram illustrating an embodiment of a multiple element two-dimensional array FUS transducer, according to various aspects of the present disclosure.

FIG. 2E is functional diagram illustrating an embodiment of a multiple element two-dimensional array FUS transducer 260, according to various aspects of the present disclosure. The two-dimensional array transducer 260 may include an array of transducer elements 261. Although an array of 10 by 8 elements 261 are shown in the example of FIG. 2E, any number of two or more elements may be used. The two-dimensional array FUS transducer 260 may operate on similar principles as the linear/phased array FUS transducer 250 of FIG. 2A and/or the annular phased array transducer 280 of FIG. 2D.

As shown in the example of FIG. 2E, the individual elements 261 may be pulsed such that the individual elements' US waves 263 are combined. The combined US wave 263 may be steered at a desired steering angel 262 and the combined US wave may travel in a desired direction 266. Furthermore, individual elements 261 may be pulsed such that the focal point 264 of combined US wave may be located at a desired location. In the example of FIG. 2E, eight elements (or eight groups of two or more elements) are pulsed at each time.

Several example types (e.g., linear array, annular array, two-dimensional array) of phased array transducers have been described above. It should be noted that other types of phased array transducers with different arrangements of two or more elements may be used in the $C^2AM$ probes of the present embodiments.

The $C^2AM$ probe, in some embodiments, may include two FUS transducers. The coupling of the laser and acoustical waves is typically a weak coupling. Using a second axial FUS transducer may improve the coupling of the laser and acoustical waves. The interaction of US wave with laser may cause the self-phase modulation (SPM) of the laser, which may produce a change in the laser's frequency spectrum. The interaction of the US wave with the laser from the first transducer may create the SPM and may cause the laser to focus. Once the SPM is created, the US from the second transducer may have a stronger coupling with the laser.

Figure 3A:
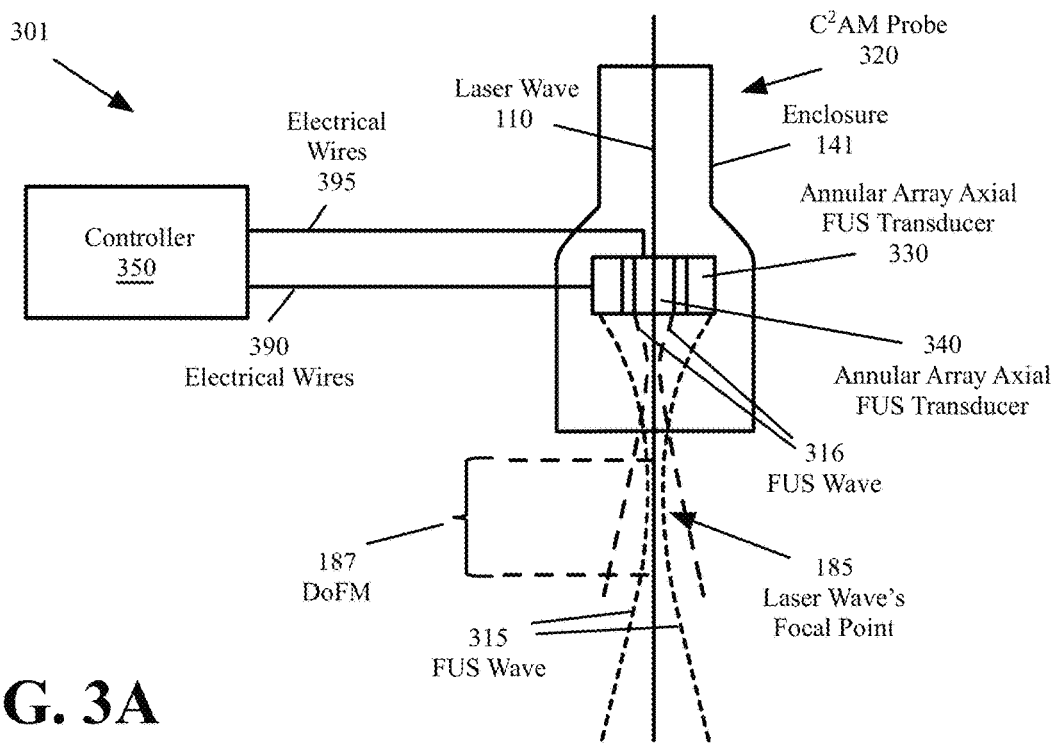
FIG. 3A is a functional diagram illustrating an embodiment of an acousto-optic modulator system that includes two concentric co-propagating axial FUS transducers, according to various aspects of the present disclosure.

FIG. 3A is a functional diagram illustrating an embodiment of an acousto-optic modulator system 301 that includes two concentric co-propagating axial FUS transducers, according to various aspects of the present disclosure. With reference to FIG. 3A, the system 301 may include similar components as the system 101 of FIGS. 1A-1B (some of which are not shown for simplicity), except that the CAM probe 320 of FIG. 3A may include two axial FUS transducers 330 and 340.

Figure 3B:
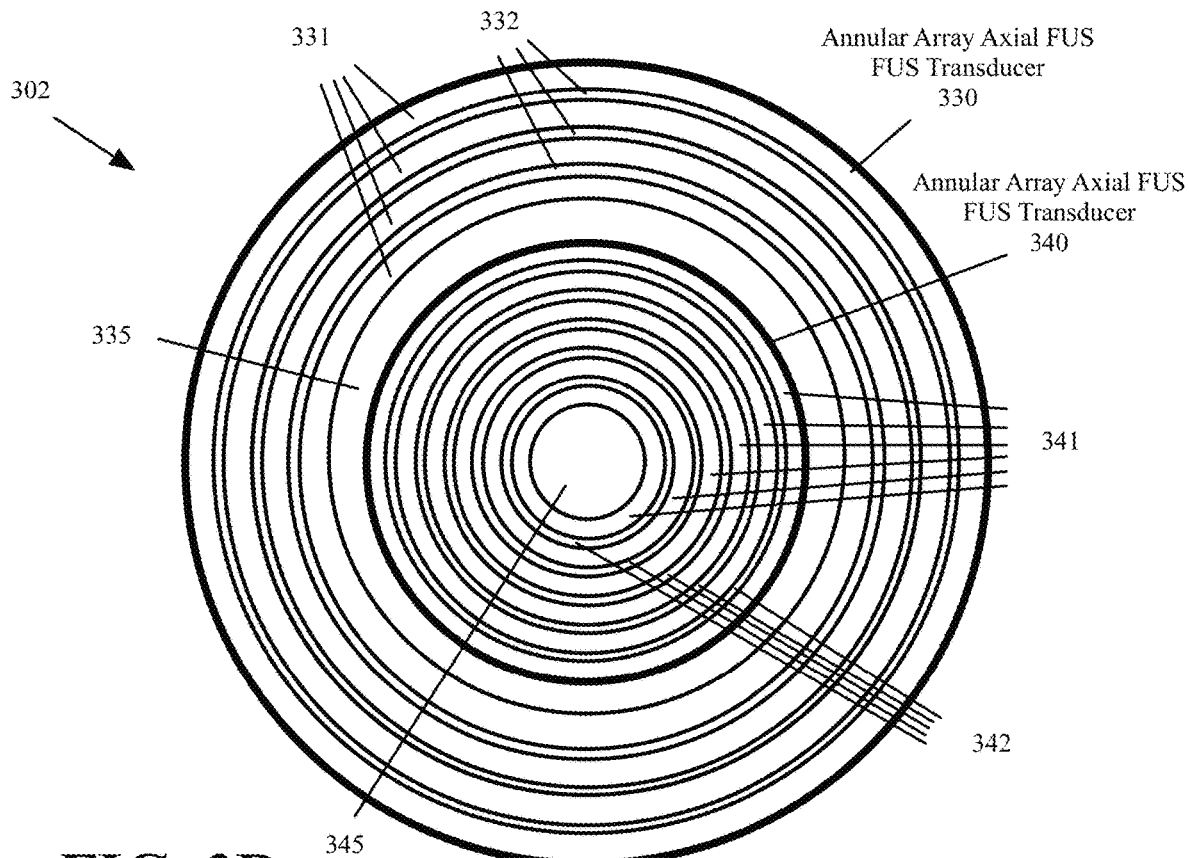
FIG. 3B is a top view of the two concentric axial FUS transducers of an acousto-optic modulator system, according to various aspects of the present disclosure.

In some embodiments, each of the axial FUS transducers 330 and 340 may be an annular array FUS transducer. FIG. 3B is a top view of the two concentric axial FUS transducers of an acousto-optic modulator system, according to various aspects of the present disclosure. As shown, the axial FUS transducer 340 may be positioned inside the axial FUS transducer 330. Each of the axial FUS transducers 330 and 340 may include a single element axial FUS transducer or several concentric transducer elements 331 and 341, respectively. The axial FUS transducers 330 and 340 may include gaps 332 and 342 between the adjacent elements, respectively. There may be a gap 335 between the two axial FUS transducers 330 and 340, and a gap 345 at the center of the axial FUS transducers 340.

Although in the example of FIG. 3B, five elements 331 are shown for the axial FUS transducer 330 and six elements 341 are shown for the axial FUS transducer 340, each of the annular array axial FUS transducers 330 and 340 may include any number of one or more elements. For example, in some embodiments, one or both of the transducers 330 and 340 may be a single element axial FUS transducer similar to the single element axial FUS transducer 130 in FIGS. 1A-1D and 2A, instead of having multiple concentric transducer elements.

In some embodiments, each of the axial FUS transducers 330 and 340 may be a phased array FUS transducer (not shown), for example, similar to the linear phased array FUS transducer 250 of FIG. 2B, the annular phased array FUS transducer 280 of FIG. 2D, and/or the two-dimensional array FUS transducer 260 of FIG. 2E. In these embodiments, the phased array FUS transducers 330 and/or 340 may operate on similar principles as the linear phased array FUS transducer 250 of FIG. 2A, the annular phased array FUS transducer 280 of FIG. 2D, and/or the two-dimensional array FUS transducer 260 of FIG. 2E.

With reference to FIG. 3A, the controller 350 may provide driving signals for the axial FUS transducers 330 and 340 through the electrical wires 390 and 395, respectively. Each element of the axial FUS transducers 330 and 340 may be controlled separately or as a group or two or more. Each axial FUS transducer 330 and 340 may have a different piezo-material (PZT, Lithium Niobate, etc.) or may use a different transduction method other than piezoelectric transducing. For example, one or both of the axial FUS transducers 330 and 340 may be a CMUT. Each axial FUS transducer 330 and 340 may have a different pressure field, a different f-number (or the ratio of focal length to the diameter of the aperture), a different thickness and thus a different operating frequency, a different aperture size, a different beam forming and dynamic focusing method, a different spatial resolution, and/or a different focal zone and depth of field. For example, and without limitations, in some embodiments, the FUS transducer 330 may have a piezoelectric coating with 400 micron thickness and may operate at 3 MHz, while the FUS transducer 340 may have a piezoelectric coating with 40 micron thickness and may operate at 30 MHz.

With reference to FIG. 3A, the annular array axial FUS transducer 330 may be configured by the controller 350 such that the focal point of the FUS wave 315, generated by the FUS transducer 330, may be outside the $C^2AM$ probe 320. The annular array axial FUS transducer 340 may be configured by the controller 350 such that the focal point of the FUS wave 316, generated by the FUS transducer 340, may be inside the $C^2AM$ probe 320. The FUS wave 315 may be configured to focus close to, or substantially at the same location as, the focal point 185 of the laser wave 110.

By changing the duty cycle and/or the voltage amplitude that is applied to each element of the axial FUS transducer 330 and 340 by the controller 350, the effect of the US waves 315 and 316 on the laser wave 110 may be changed, resulting in controlling the focal point 185 of the laser wave 110. Controlling the focal point 185 of the laser wave 110 may control the penetration depth of the laser wave 110 when the laser is incident on a target, such as a biological sample.

FIG. 3C is a functional diagram illustrating an embodiment of an acousto-optic modulator system 302 that includes two concentric axial FUS transducers, one co-propagating transducer and one counter propagating transducer, according to various aspects of the present disclosure. With reference to FIG. 3C, the system 302 may include similar components as the system 301 of FIG. 3A, except that the axial FUS transducer 340 of FIG. 3C is configured to generate a FUS wave 316 that counter propagates with respect to the laser wave 110 and the FUS wave 315. The $C^2AM$ probe 320 of FIG. 3C may have a longer enclosure than the $C^2AM$ probe 320 of FIG. 3A in order to house the two axial FUS transducers 330 and 340 that counter propagate with respect to each other.

Unless otherwise stated, the embodiments of the present disclosure that use an axial FUS transducer, may use either a single element axial FUS transducer (e.g., as described above with reference to FIGS. 1A-1D and 2A), a two element axial FUS transducer (e.g., as described above with reference to FIGS. 3A-3C) that each may or may not be a phased array axial FUS transducer, or a phased array axial FUS transducer (e.g., as described above with reference to FIGS. 2B, 2D, and 2E). Single element and two element transducers are generally smaller and less expensive. Phased array transducers may provide the advantage of allowing the US to allow the beam to be steered to a point at any three-dimensional direction in the space without moving the $C^2AM$ probe with dynamic focusing capability and changing resolution of the $C^2AM$ system.

b. $C^2AM$ Controller

With reference to FIGS. 1A, 1C, 3A, and 3C, the $C^2AM$ controller may provide a driving electrical signal to an axial FUS transducer 130, 330, 340 (or to a phased array FUS transducer described above) for generating the FUS wave 115. The driving signal may be generated by the amplifier 175. The amplifier 175, in some embodiments, may be a high voltage amplifier that may receive a pulse wave, which may be generated by a combination of a signal from the pulse generator 165 and a signal from the function generator 170. The amplifier 175 may amplify the received pulse to drive the axial FUS transducer 130, 330, 340, etc.

The duty cycle of the pulse squared wave may be adjusted by the pulse generator 165 and the amplitude of the signal may be adjusted by changing the voltage amplitude of the function generator 170. The duty cycle may determine what percentage of the driving signal to the axial FUS transducer is on and what percentage of the driving signal is off.

Figure 4:
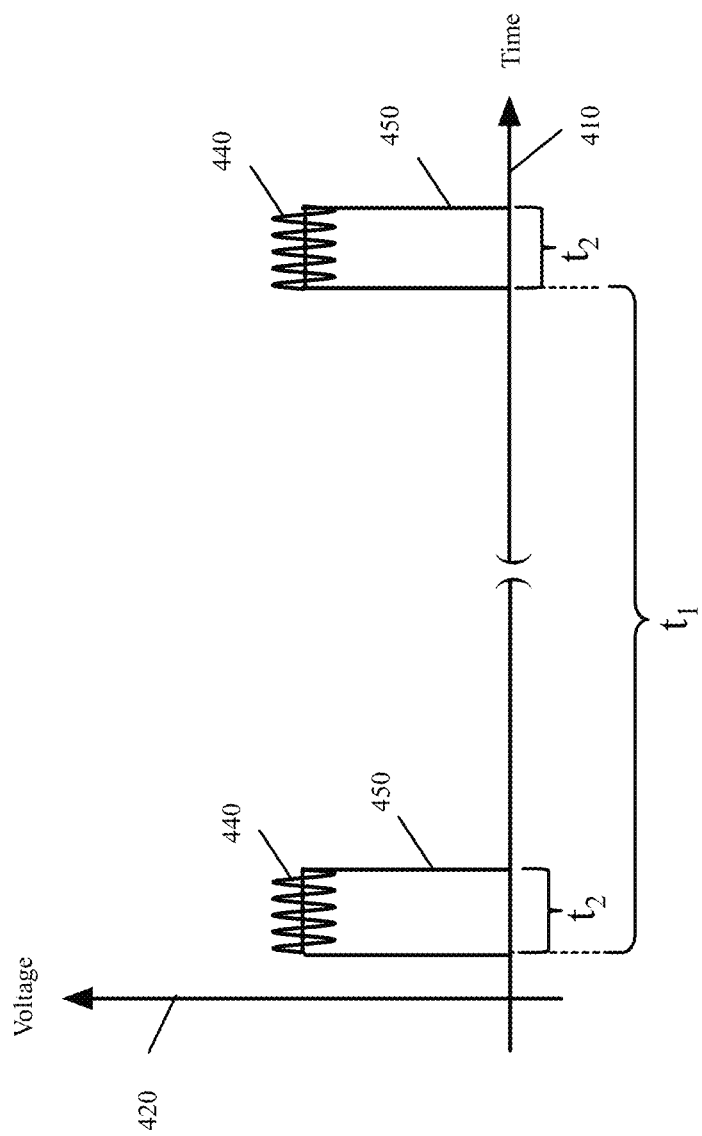
FIG. 4 is a diagram illustrating an example of the signal received by the amplifier of the acousto-optic modulator's controller, according to various embodiments of the present disclosure.
Figure 6A:
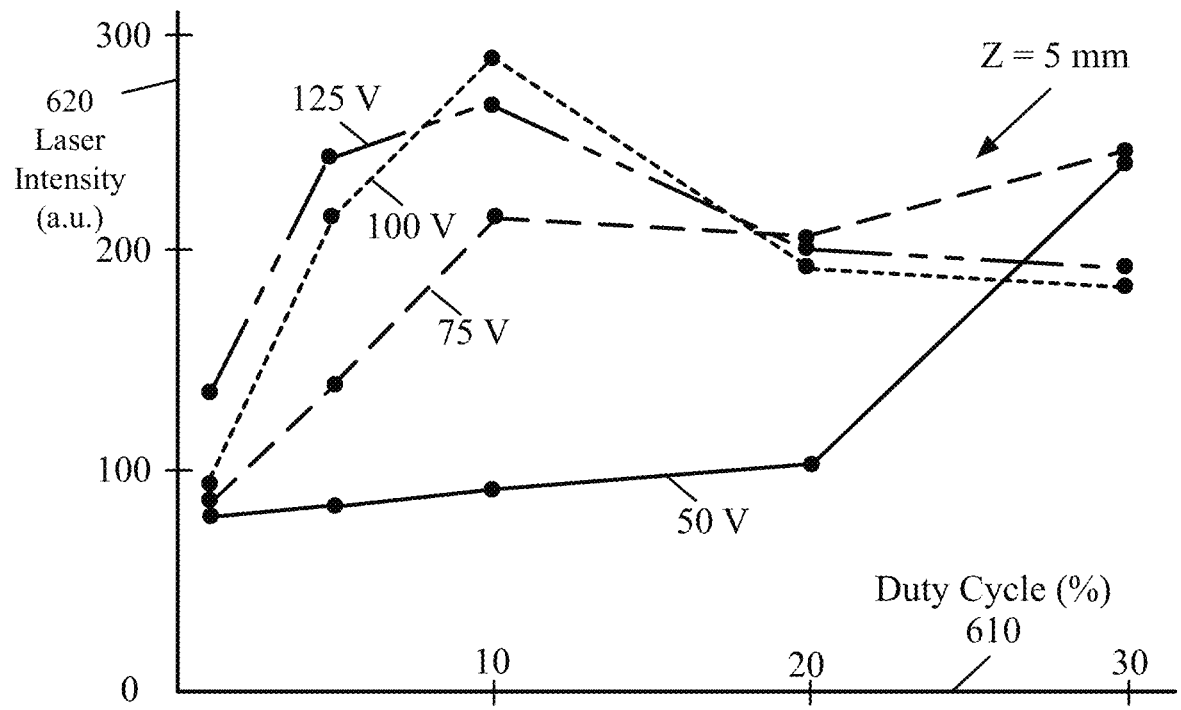
FIGS. 6A-6E are graphs depicting the modulated laser intensity values of Tables 1-5 of FIG. 5, respectively, according to various embodiments of the present disclosure.
Figure 6B:
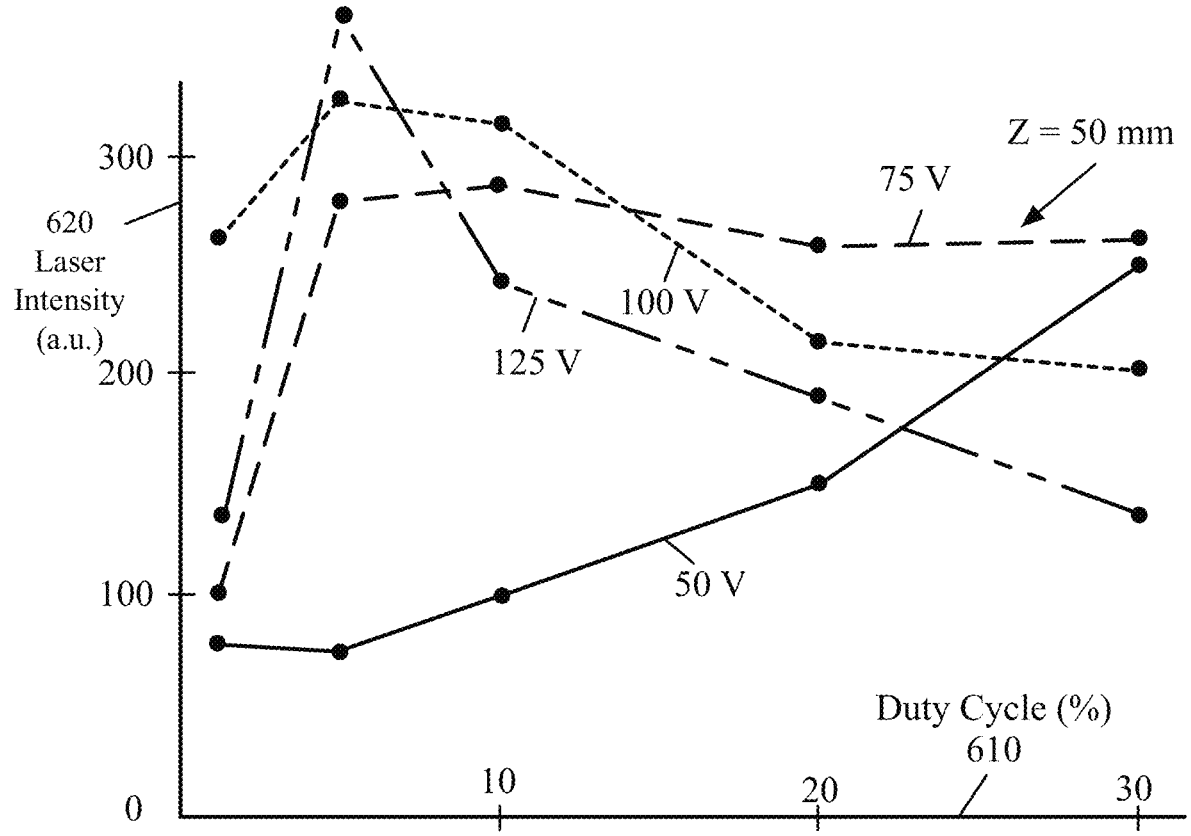
Figure 6C:
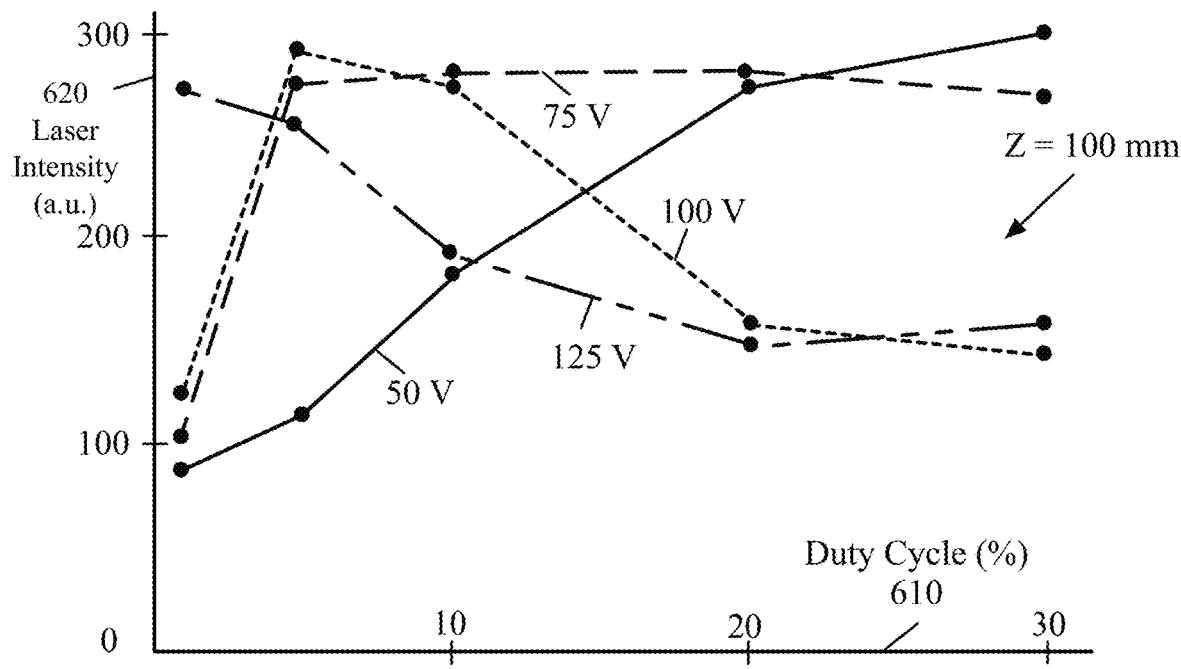
Figure 6D:
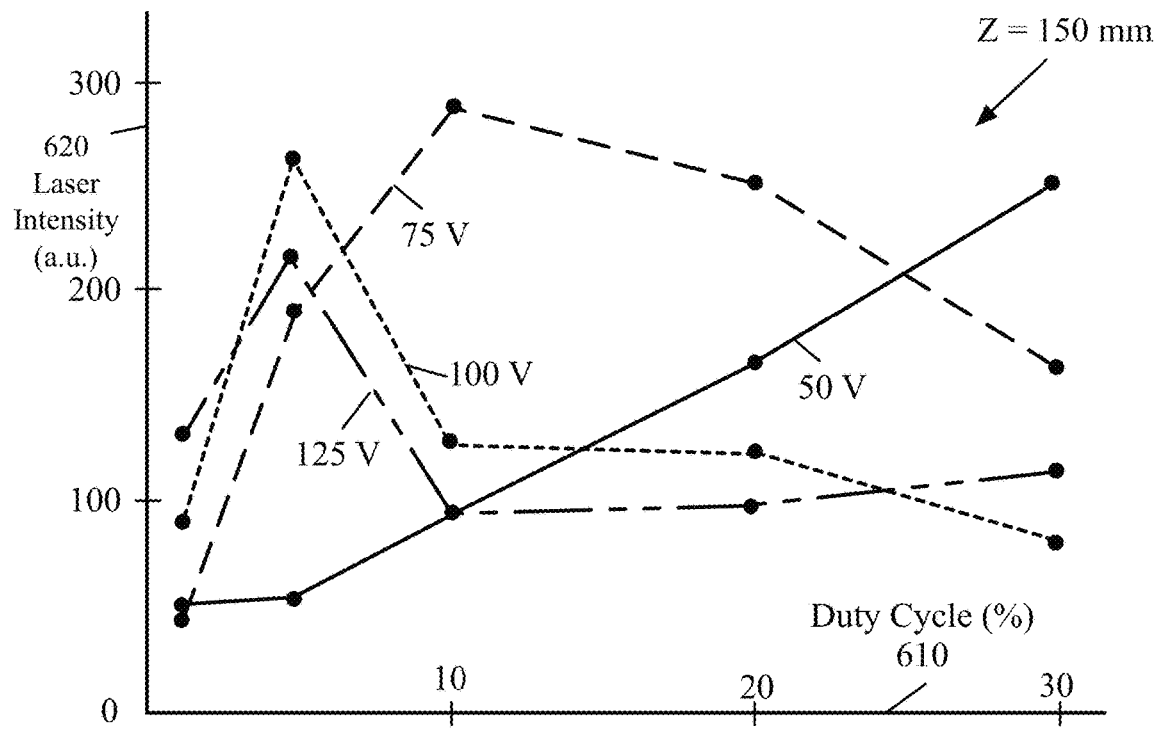
Figure 6E:
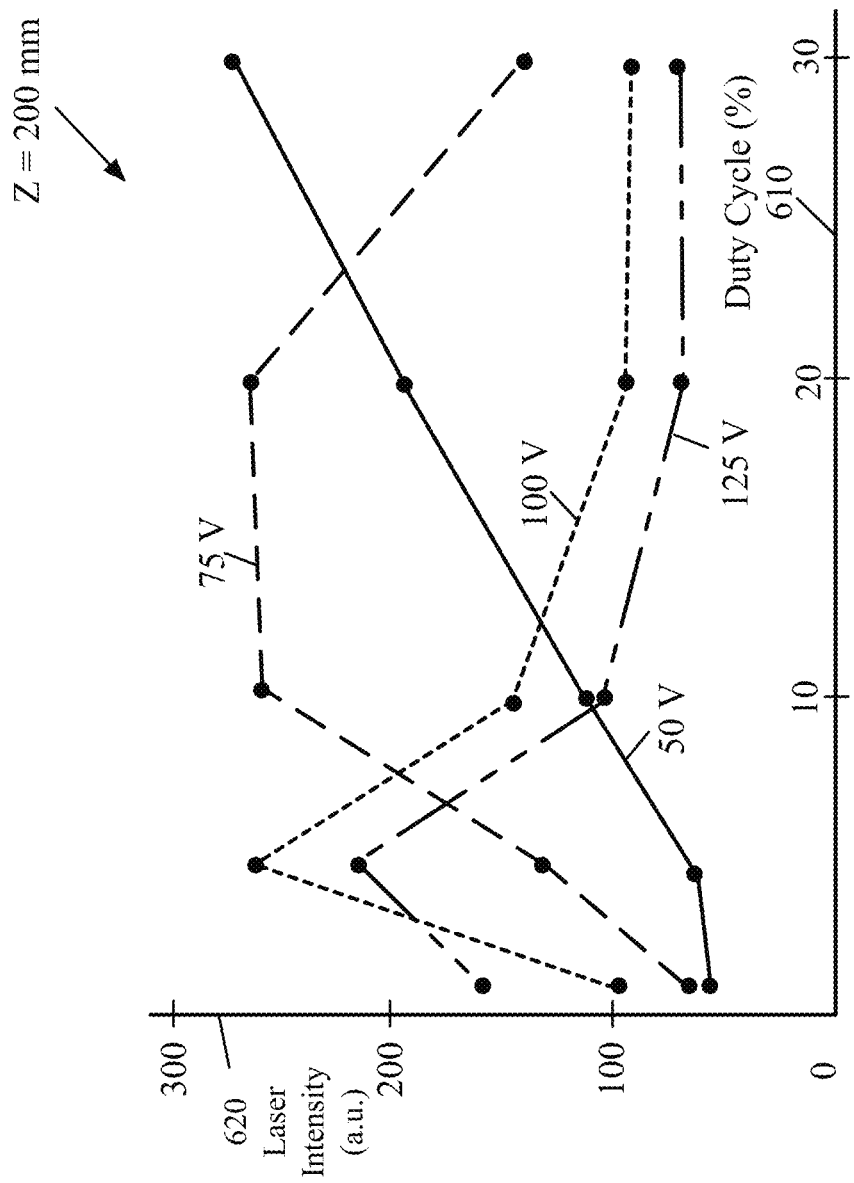

FIG. 4 is a diagram illustrating an example of the signal received by the amplifier of the $C^2AM$ controller, according to various embodiments of the present disclosure. With reference to FIG. 4, the voltage 420 is depicted against the time 410. The carrier pulse 450 may be generated by the pulse generator 165 (FIGS. 1A and 1C) and may determine the duty cycle.

For example, when the duration of each pulse 450 is $t_2$ and the pulse repeats every $t_1$ seconds, the duty cycle of the pulse 450 may be expressed as follows:

$$\text{Duty Cycle} = t_2/t_1 * 100\%$$

With further reference to FIG. 4, a high frequency signal 440 may then be added to the "on" portion of the pulse 450. The signal 440 may be generated by the function generator 170 (FIGS. 1A and 1C). The signal 440 may be, for example, and without limitation, a pulse, a sine wave, an arbitrary periodic wave, etc.

The frequency of the US wave generated by the axial FUS transducer may be substantially the same as the frequency of the signal 440 generated by the function generator 170. The acoustic intensity of the US wave may also be controlled by adjusting the voltage amplitude of the signal 440 generated by the function generator 170 and the amount of amplification provided by the amplifier 175. The acoustic (or sound) intensity may be defined as the power carried by an acoustic wave per unit area in a direction perpendicular to that area.

The combination of the two signals 450 and 440 may be received as the input at the amplifier 175. The amplifier may then amplify the input signal and send the output to the axial FUS transducer 130, 330, 340, etc. As indicated above, the functionality of the pulse generator 165, the function generator 170, and the amplifier 175, in some embodiments, may be provided by separate hardware units. In other embodiments, the functionality of two or all three of them may be provided by one hardware unit.

In order to set the duty cycle and the acoustic intensity of the US wave for each particular application, some embodiments may perform a table lookup. For example, for a particular brand of FUS transducer, a particular medium, and a particular type of laser, a series of experiments may be performed and the values of the laser intensity may be measured at different distances from the CAM probe for different values of the duty cycle and different values of the voltage amplitude of the function generator.

In some embodiments, the distance may, for example and without limitations, be the distance from the closest point of the $C^2AM$ probe enclosure 141 to the focal point of the laser. In other embodiments, the distance may be the distance from any fixed reference point in the system to the focal point of the laser. The intensity values may be measured for example, and without limitations, by placing a charge-coupled device (CCD) camera at different distances from the $C^2AM$ probe and measuring the laser intensity values by the CCD camera.

FIG. 5 illustrates the tabulation of the modulated laser intensity values measured at different distances from the $C^2AM$ probe for different values of the duty cycle and different values of the voltage amplitude, according to various embodiments of the present disclosure. With reference to FIG. 5, Tables 1 to 5 tabulate the values of laser intensity as functions of the duty cycle 515 (expressed as a percentage) and the voltage 510 (expressed as volts). The duty cycle may be generated by the pulse generator 165 and the voltage may be the voltage of a square pulse that is amplified by the amplifier 175.

Table 1 tabulate the laser intensity values measured at 5 millimeters (mm), Table 2 tabulate the laser intensity values measured at 50 mm, Table 3 tabulate the laser intensity values measured at 100 mm, Table 4 tabulate the laser intensity values measured at 150 mm, and Table 5 tabulate the laser intensity values measured at 200 mm from the reference point. The values of the laser intensities are the normalized values showing the ratio of the laser intensity to a predetermined reference intensity value and are expressed in arbitrary unit (a.u.).

FIGS. 6A-6E are graphs depicting the modulated laser intensity values of Tables 1-5 of FIG. 5, respectively, according to various embodiments of the present disclosure. The horizontal axis 610 is duty cycle in percentage and the vertical axis 620 is laser intensity in a.u.

Some embodiments may use tables similar to the Tables 1-5 of FIG. 5 to select the duty cycle for the pulse generator 165 and the voltage amplitude for the function generator 170 and/or the voltage amplifier 175 in order to have a required laser intensity at a given distance. For intensity values and/or distances for which an exact match may not be found in the tables, interpolation or extrapolation may be performed to determine the values of the duty cycle and/or the voltage amplitude. Although in the example of FIGS. 5A-5E only five tables are generated, in other embodiments, fewer or more tables with fewer or more data point may be generated. Furthermore, some embodiments may generate different tables for different types of medium and/or different type of laser sources used.

Figure 7:
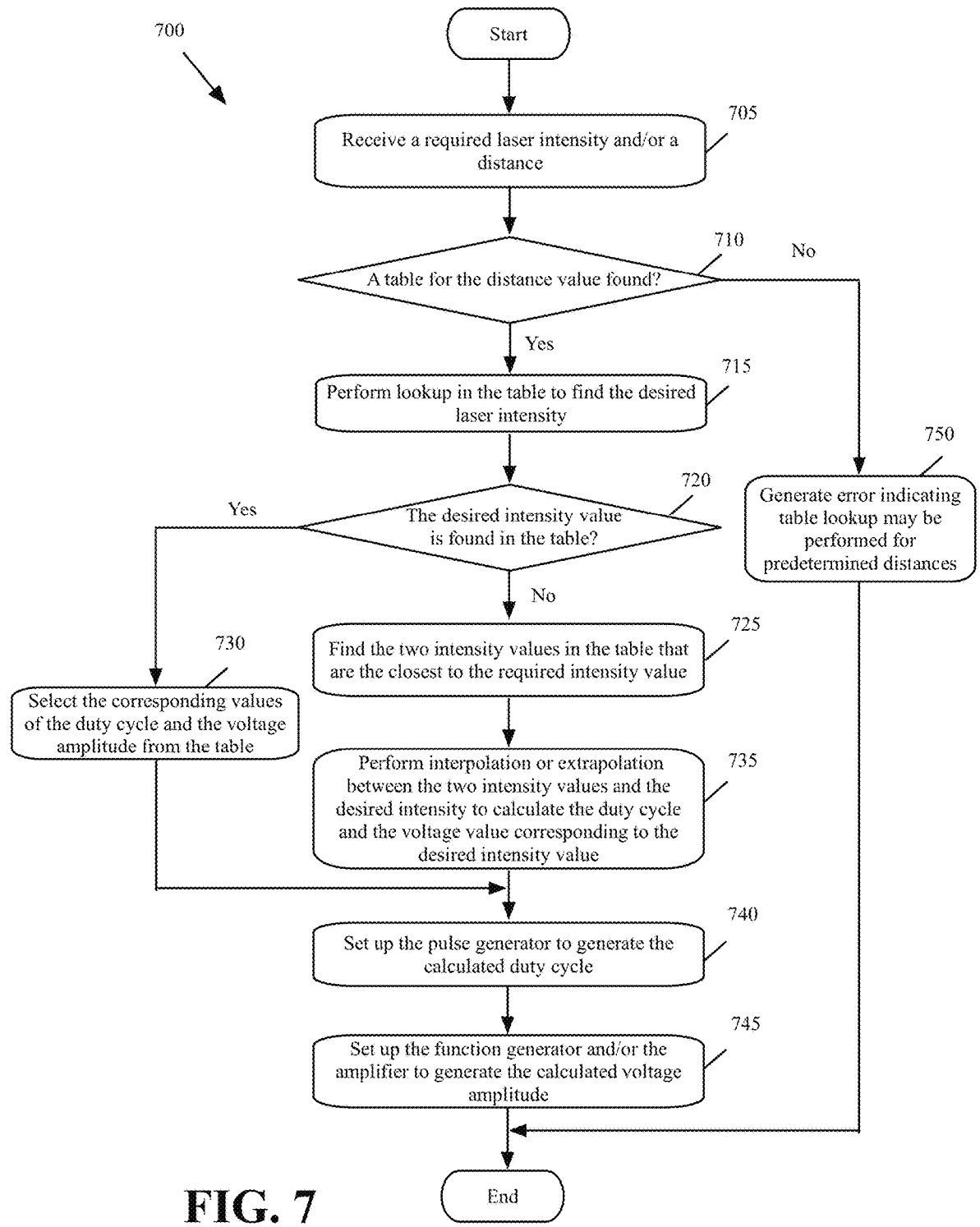
FIG. 7 is a flowchart illustrating an example process for determining the duty cycle and the voltage amplitude setting of the acousto-optic modulator's controller for a given laser intensity and distance, according to various aspects of the present disclosure.

FIG. 7 is a flowchart illustrating an example process 700 for determining the duty cycle and the voltage amplitude setting of the $C^2AM$ controller for a given laser intensity and distance, according to various aspects of the present disclosure. The process 700, in some of the present embodiments, may be performed by the processor 160 of FIGS. 1A and 1C.

With reference to FIG. 7, a required laser intensity and/or a distance may be received (at block 705). For example, the process may receive a laser intensity and a distance that is required for a particular application of the $C^2AM$ probe 120 of FIG. 1A-1D. A determination may be made (at block 710) whether a table for the distance value is found.

When a table for the distance value is not found, an error may be generated (at block 750) indicating that table lookup may be performed for the predetermined distances for which the table are generated. The process 700 may then end. In some embodiments, tables, such as Tables 1-5 of FIG. 5 are generated for many distances and the distance for each application of the $C^2AM$ probe is selected from one of these pre-determined values.

With continued reference to FIG. 7, when a table for the distance value is found, a table lookup may be performed (at block 715) in the identified table to find the desired laser intensity. A determination may be made (at block 720) whether the desired intensity value is found. When the desired intensity value is found, the corresponding values of the duty cycle and the voltage amplitude may be selected (at block 730) from the table. The process may then proceed to block 740, which is described below.

When the desired intensity value is not found, the two intensity values in the table that are closest to the required intensity may be found (at block 725). An interpolation or extrapolation may be performed (at block 735) between the two intensity values and the desired intensity to calculate the duty cycle and the voltage value corresponding to the desired intensity value.

At block 740, the pulse generator may be set up (at block 740) to generate the calculated duty cycle. For example, the processor 160 (FIGS. 1A and 1C) may set the pulse generator 165 to generate a pulse with the calculated duty cycle, as described above with reference to pulse 450 of FIG. 4. The function generator and/or the amplifier may be set up (at block 745) to generate the calculated voltage amplitude. For example, the processor 160 (FIGS. 1A and 1C) may set the function generator 170 to generate the signal 440 with the calculated voltage amplitude, as described above with reference to signal 440 of FIG. 4. The process 700 may then end.

The specific operations of the process 700 may not be performed in the exact order shown and described. Furthermore, the specific operations described with reference to FIG. 7 may not be performed in one continuous series of operations, in some aspects of the present disclosure, and different specific operations may be performed in different embodiments.

For instance, in some aspects of the present embodiments, when a table for the distance value is not found, instead of generating (at block 750) an error, a temporary table may be constructed by finding two tables for two distances that are the closest to the specified distance. Interpolation or extrapolation may be performed between the two distance values and the desired distance value to calculate intensity values for the temporary table. The temporary table may then be used in operations 715-745 to calculate the duty cycle and the voltage value corresponding to the desired intensity value.

The values of the duty cycle of the pulse generator and the voltage amplitude of the function generator, in some embodiments, may be calculated by an algorithm. For example, the processor 160 may receive a required laser intensity, a distance, the type of medium, the type of laser, and other parameters of the C²AM system and may calculate the duty cycle of the pulse generator and the voltage amplitude of the function generator from a set of mathematical formulas.

c. Reconfiguring a C²AM Probe from Co-Propagating to Counter Propagating and Vice Versa In some embodiments, the C²AM probe may be configurable to allow reconfiguring the C²AM probe from co-propagating to counter propagating or vice versa. The C²AM probe may be reconfigured in the field for each specific application. The C²AM probe may be configured prior to the deployment or prior to the shipment.

Figure 8:
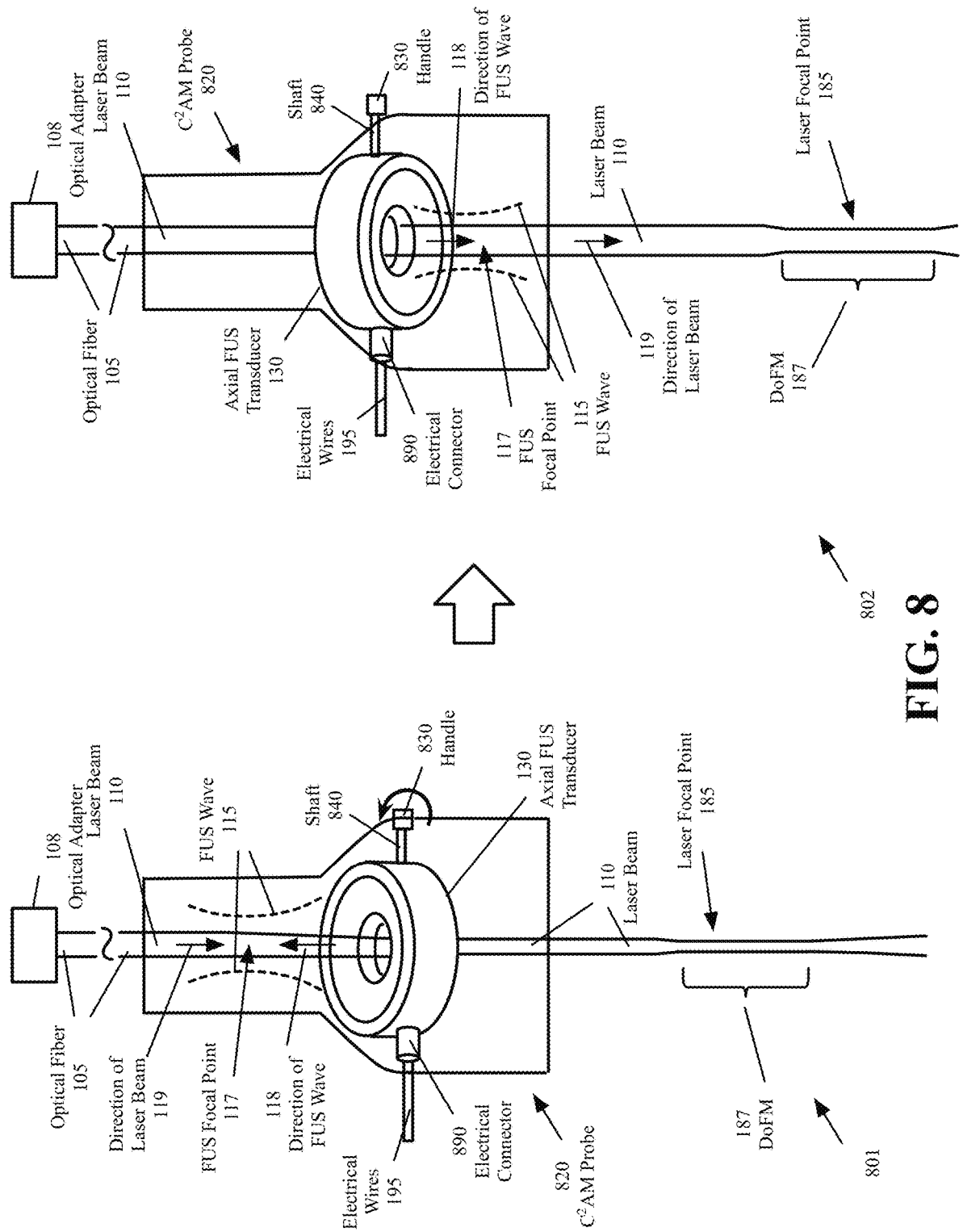
FIG. 8 is a functional diagram illustrating an embodiment of a reconfigurable coaxial acousto-optic modulator probe that includes a handle or knob to reconfigure the probe from a co-propagating configuration to a counter propagating configuration and vice versa, according to various aspects of the present disclosure.

FIG. 8 is a functional diagram illustrating an embodiment of a reconfigurable C²AM probe 820 that includes a handle or knob to reconfigure the probe from a co-propagating configuration to a counter propagating configuration and vice versa, according to various aspects of the present disclosure. With reference to FIG. 8, the C²AM probe 820 may include components similar to the C²AM probe 120 of FIGS. 1A-1D. In addition, the C²AM probe 820 may include a handle (or knob) 830. The handle 830 may be connected to the axial FUS transducer 130 by a shaft (or rod) 840.

The figure, as shown, includes two stages 801-802. In stage 801, the aperture of the axial FUS transducer 130 is positioned such that the direction 118 the US wave 115 is opposite to the direction 119 of the laser beam 110. In stage 802, the handle 830 is rotated such that the attached shaft 840 and the axial FUS transducer 130 are rotated by 180 degrees. As shown in stage 802, the aperture of the axial FUS transducer 130 is positioned such that the direction 118 the US wave 115 is same as the direction 119 of the laser beam 110.

In some embodiments, the electrical connector 890 may be a rotating connector ring, also referred to as a slip ring, that may maintain the electrical link between the FUS transducer 130 and the electrical wires 195 while the FUS transducer 130 rotates. In other embodiments, the electrical connector 890 may be removed from the FUS transducer 130 prior to rotating the FUS transducer 130 and may be reconnected to the FUS transducer 130 after the rotation.

The handle 830, may be rotated manually or by a precision device to ensure the 180 degree of rotation. The handle may be rotated again, whenever there is a need to reconfigure the C²AM probe 820 back to the counter propagating configuration. Since the distance between the US focal point 117 and the laser focal point 185 in both the co-propagating and the counter propagating configurations are substantially the same, the C²AM probe 820 may be switched between the co-propagation and the counter propagation configurations to achieve different depth of fields from the body of the C²AM probe 820.

Figure 9:
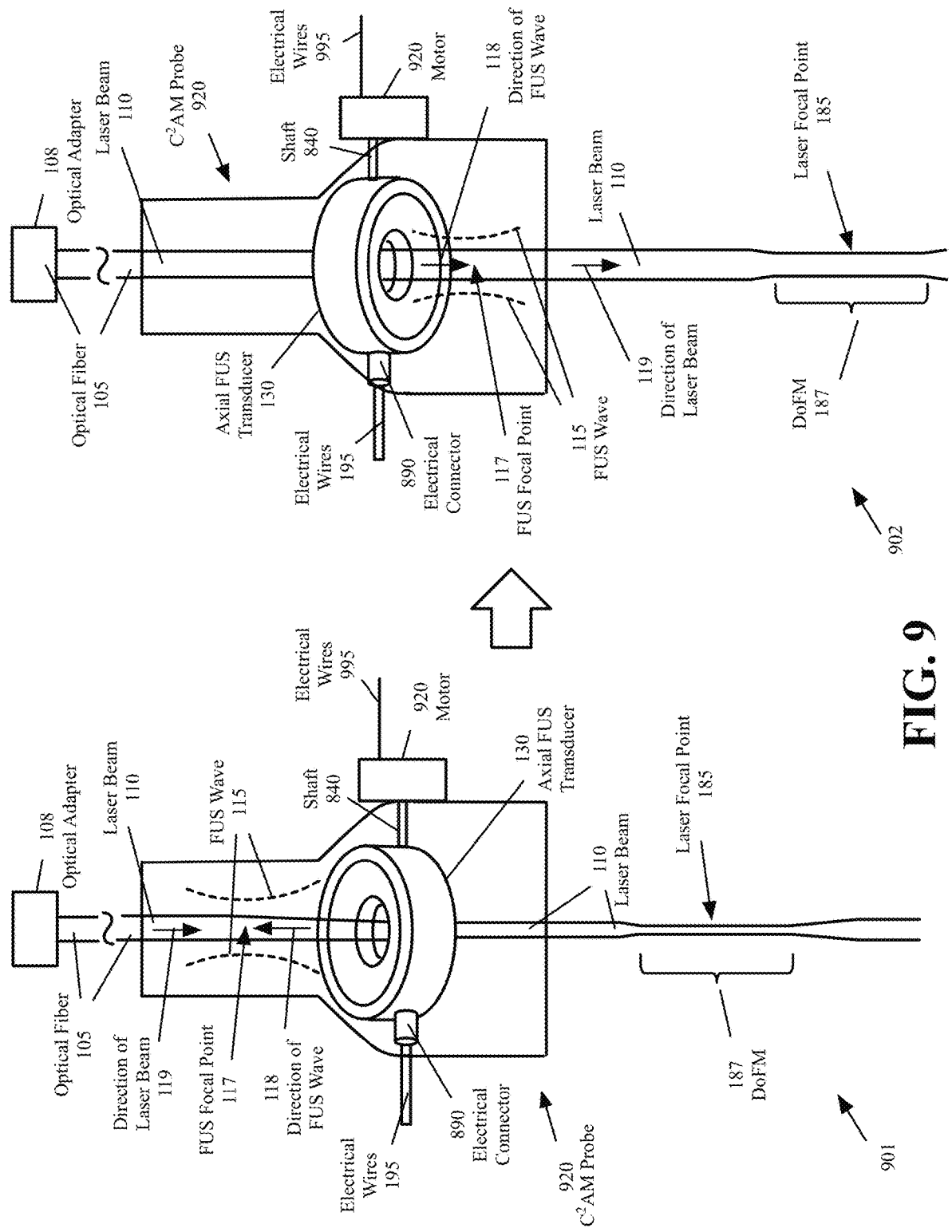
FIG. 9 is a functional diagram illustrating an embodiment of a reconfigurable coaxial acousto-optic modulator probe that includes a motor to reconfigure the probe from a co-propagating configuration to a counter propagating configuration and vice versa, according to various aspects of the present disclosure.

FIG. 9 is a functional diagram illustrating an embodiment of a reconfigurable C²AM probe 920 that includes a motor to reconfigure the probe from a co-propagating configuration to a counter propagating configuration and vice versa, according to various aspects of the present disclosure. With reference to FIG. 9, the C²AM probe 920 may include components similar to the C²AM probe 120 of FIGS. 1A-1D. In addition, the C²AM probe 920 may include a motor 922. The motor 922 may be connected to the axial FUS transducer 130 by a shaft (or rod) 840.

The figure, as shown, includes two stages 901-902. In stage 901, the aperture of the axial FUS transducer 130 may be positioned such that the direction 118 the US wave 115 is opposite to the direction 119 of the laser beam 110. In stage 902, the motor rotates (e.g., and without limitations after receiving one or more signals from the processor 160 of the C²AM controller 150 of FIGS. 1A and 1C) such that the attached shaft 840 and the axial FUS transducer 130 are rotated by 180 degrees. As shown in stage 902, the aperture of the axial FUS transducer 130 is positioned such that the direction 118 the US wave 115 is same as the direction 119 of the laser beam 110.

In some embodiments, the electrical connector 890 may be a rotating connector ring. In other embodiments, the electrical connector 890 may be removed from the FUS transducer 130 prior to rotating the FUS transducer 130 and may be reconnected to the FUS transducer 130 after the rotation. The motor 922, in some embodiments, may be, for example, and without limitations, a step motor. The step motor 922 may receive electrical power and/or electrical signals from the C²AM controller 150 through the electrical wires 995.

Although FIGS. 8 and 9 were described with reference to a single element axial FUS transducer, the same mechanisms of a handle or a motor connected to a shaft may be used, in some embodiments, to reconfigure an axial linear, annular or phased array FUS transducer (e.g., the linear phased array 250 of FIG. 2B, the annular phased array 280 of FIG. 2D, the two-dimensional phased array 260 of FIG. 2E, etc.) from a co-propagating configuration to a counter propagating configuration and vice versa. The same mechanisms of a handle or motor connected to a shaft may be used in some embodiments to reconfigure the C²AM probe 320 of FIGS. 3A-3C by for example, rotating the axial transducer 330 to reconfigure the transducer 330 from co-propagating to counter propagating and vice versa, switching from the configuration of FIG. 3A to the configuration of FIG. 3C and vice versa.

d. CAM Probe with an Internal Optical Cavity

Figure 10A:
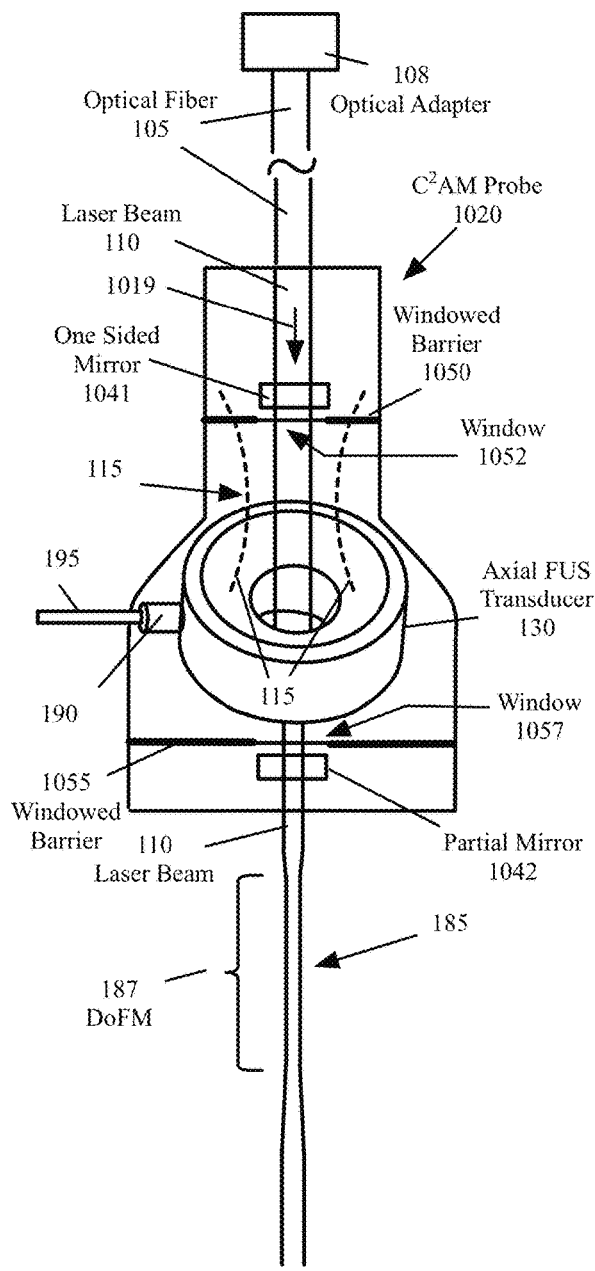
FIG. 10A is a functional diagram illustrating a counter propagating coaxial acousto-optic modulator probe that includes an optical cavity, according to various aspects of the present disclosure.

Some embodiments may include an optical cavity inside the C²AM probe in order to increase the laser intensity. FIG. 10A is a functional diagram illustrating a counter propagating C²AM probe that includes an optical cavity, according to various aspects of the present disclosure. An optical cavity (or optical resonator) may be formed by two mirrors. The optical cavity may have several resonance frequencies, which may depend on the distance between the mirrors.

With reference to FIG. 10A, the C²AM probe 1020 may include two mirrors 1041 and 1042, where an optical cavity may be formed between the two mirrors 1041-1042. The mirror 1041 may be configured to allow the laser beam that the C²AM probe 1020 may receive from outside (in the direction of the arrow 1019) to pass through. The mirror 1041 may be configured to reflect the laser beam that is received from the mirror 1042. The mirror 1042 may be a partial mirror that may only pass a fraction (e.g., and without limitations, 20%-40%) of the incident light and may reflect the rest of the incident light back towards the mirror 1041. The reflective side of the mirrors 1041 and 1042 may face each other.

The mirrors 1041 and 1042 may form an optical cavity between them. The mirrors 1041 and 1042 may have a curved body and the focal lengths of the mirrors and the distance between the mirrors may be selected such that the frequency of the light beam generated between the mirrors is close to one of the resonance frequencies of the optical cavity in order for the light beam to remain stable.

In the embodiment of FIG. 10A, the mirrors 1041 and 1042 may be outside the medium (e.g., and without limitations, water) that surrounds the axial FUS transducer 130. As shown, two windowed barriers 1050 and 1055 may separate the mirrors 1041 and 1042 from the medium that surrounds the axial FUS transducer 130. The transparent windows 1052 and 1057 may allow the laser beam 110 to pass through. Other components of the $C^2AM$ probe 1020 may be similar to the $C^2AM$ probe 120 of FIGS. 1A-1B.

The optical cavity formed between the two mirrors 1041 and 1042 may increase the intensity of the laser beam 110. The laser beam may be further intensified by the effects of the FUS wave 115, as discussed above with reference to FIGS. 1A-1B.

Figure 10B:
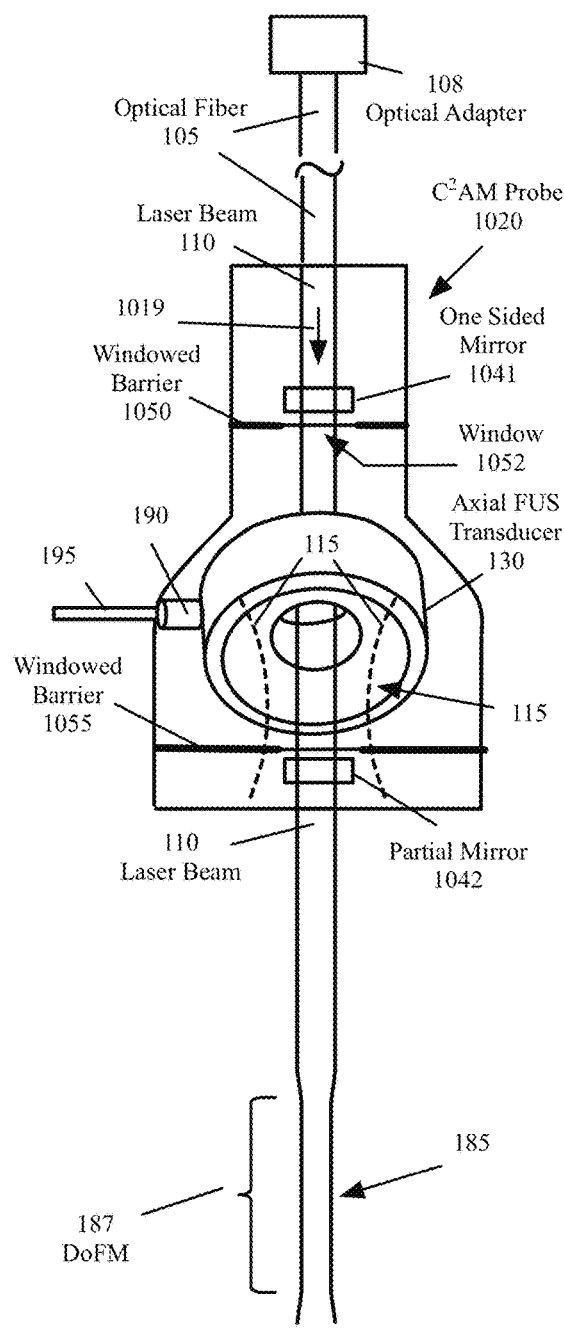
FIG. 10B is a functional diagram illustrating a co-propagating coaxial acousto-optic modulator probe that includes an optical cavity, according to various aspects of the present disclosure.

FIG. 10B is a functional diagram illustrating a co-propagating $C^2AM$ probe that includes an optical cavity, according to various aspects of the present disclosure. The $C^2AM$ probe 120 of FIG. 10B may be similar to the $C^2AM$ probe 120 of FIG. 10B, except that the axial FUS transducer 130 in FIG. 10B is configured to counter propagate with reference to the laser beam 110.

Figure 10C:
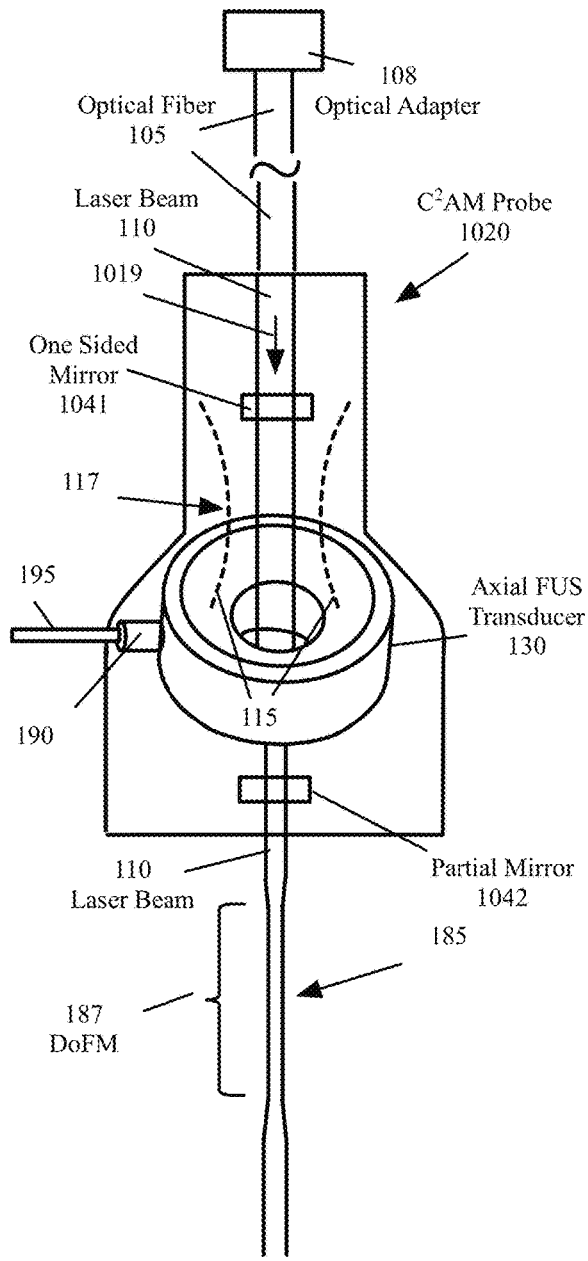
FIG. 10C is a functional diagram illustrating a counter propagating coaxial acousto-optic modulator probe that includes an optical cavity where the two mirrors that make the optical cavity are inside the probe's medium, according to various aspects of the present disclosure.
Figure 10D:
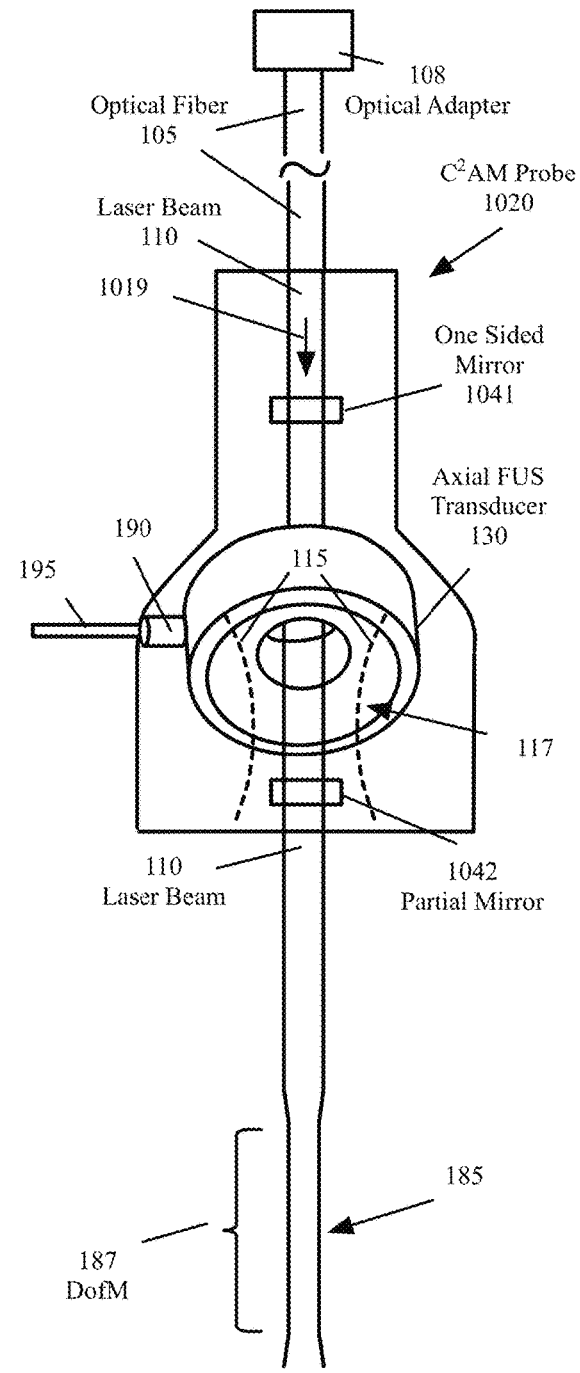
FIG. 10D is a functional diagram illustrating a co-propagating coaxial acousto-optic modulator probe that includes an optical cavity where the two mirrors that make the optical cavity are inside the probe's medium, according to various aspects of the present disclosure.

In some embodiments, the mirrors 1041 and 1042 may be inside the medium that surrounds the axial FUS transducer 130. FIG. 10C is a functional diagram illustrating a counter propagating $C^2AM$ probe that includes an optical cavity where the two mirrors that make the optical cavity are inside the $C^2AM$ probe's medium, according to various aspects of the present disclosure. FIG. 10D is a functional diagram illustrating a co-propagating $C^2AM$ probe that includes an optical cavity where the two mirrors that make the optical cavity are inside the $C^2AM$ probe's medium, according to various aspects of the present disclosure.

With reference to FIGS. 10C and 10D, the mirrors 1041 and 1042 may be inside the medium that surrounds the axial FUS transducer 130. These embodiments may not include the windowed barriers 1050 and 1055 and the windows 1052 and 1057 that were included in the embodiments of FIGS. 10A and 10B.

e. $C^2AM$ Probe with Steering Mirror

Figure 11A:
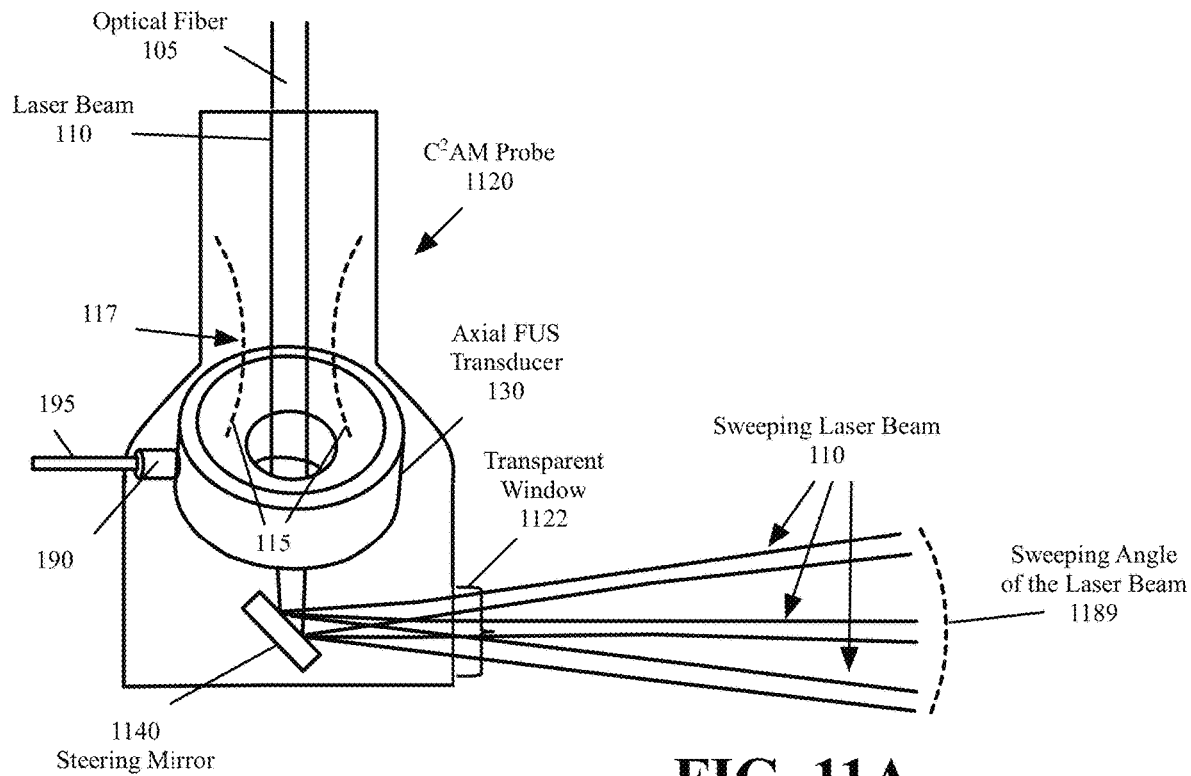
FIG. 11A is a functional diagram illustrating a counter-propagating coaxial acousto-optic modulator probe that includes a steering mirror, according to various aspects of the present disclosure.
Figure 11B:
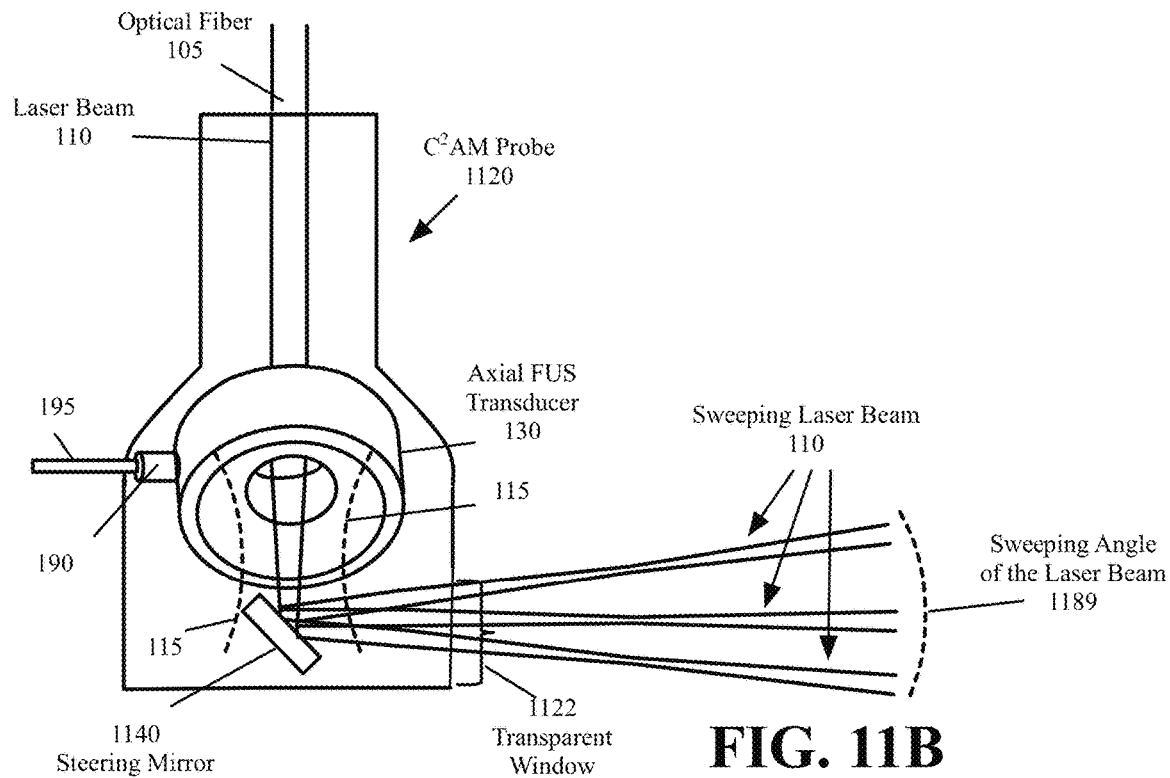
FIG. 11B is a functional diagram illustrating a counter propagating coaxial acousto-optic modulator probe that includes a steering mirror, according to various aspects of the present disclosure.

Some embodiments may include a steering mirror inside the $C^2AM$ probe in order to sweep the laser beam over a wider area. FIG. 11A is a functional diagram illustrating a counter propagating $C^2AM$ 1120 probe that includes a steering mirror, according to various aspects of the present disclosure. FIG. 11B is a functional diagram illustrating a counter propagating $C^2AM$ 1120 probe that includes a steering mirror, according to various aspects of the present disclosure.

With reference to FIGS. 11A and 11B, the $C^2AM$ probe 1120 may include a steering mirror 1140 (also referred to as a fast steering mirror), which may be configured to steer the laser beam 110 over an angle 1189. As described below with reference to FIG. 59C, the $C^2AM$ probe 1120 of FIGS. 11A and 11B may be used in a dynamic photoacoustic communication system to amplify acoustic waves. The $C^2AM$ probe 1120 may include a transparent window 1122 that is wide enough to allow the sweeping laser beam 110 to exit the $C^2AM$ probe 1120.

The $C^2AM$ controller 150 (FIGS. 1A and 1C), in some embodiments, may include a fast steering mirror controller (not shown) that generates a plurality of signals to steer the steering mirror 1140 at a steering rate. The steering rate may be, for example, and without limitations determined by the processor 160 (FIGS. 1A, 1C), may be manually entered (e.g., thorough the display 155 or a keyboard), or through a separate electronic device such as, for example, and without limitations, a mobile device, a computer, a server, etc. The plurality of signals may be delivered from the $C^2AM$ controller 150 to the mirror 1140 through a set of wires (not shown).

f. Generalized Configuration of the $C^2AM$ Probe

Figure 12A:
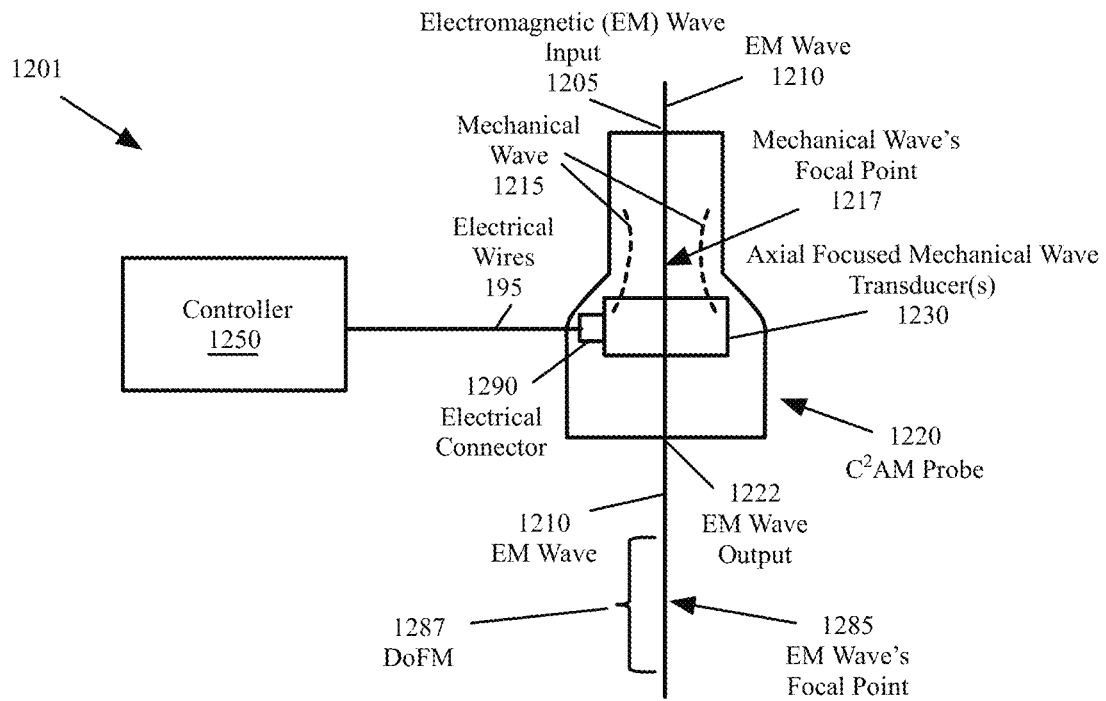
FIG. 12A is a functional diagram illustrating a generalized embodiment of a counter propagating mechanical-EM modulator system, according to various aspects of the present disclosure.

Several examples are described in the following sections that may use one or more $C^2AM$ probes. The $C^2AM$ probe(s) in these examples may include one or more features of the $C^2AM$ probes described above. FIG. 12A is a functional diagram illustrating a generalized embodiment of a counter propagating mechanical-EM modulator system 1201, according to various aspects of the present disclosure.

With reference to FIG. 12A, the $C^2AM$ probe 1220 may include one or more axial focused mechanical transducers 1230. The transducer(s) 1230 may use a mechanical forces, for example, and without limitations, sound waves, US waves, air movements, gravity waves, etc., to generate an oscillation in the medium surrounding the transducer to transfer a mechanical momentum coaxial to the propagation axis an electromagnetic (EM) wave. The examples of the EM wave may include, for example, and without limitations, radio waves, microwaves, infrared light waves, visible light waves (e.g., white light waves, laser, which is a monochrome, directional, and coherent type of light wave), ultraviolet light waves, X rays, gamma rays, etc. Such a coaxial propagation of the mechanical momentum (e.g., the US waves) and the EM waves (e.g., laser), in the present embodiments, causes increase in the EM wave's focus, causes increase in the EM waves' intensity, and keeps the EM wave's lensing power positive (with small positive fluctuations instead of fluctuating between positive and negative values) as long as the mechanical momentum is applied.

With reference to FIG. 12A, the mechanical-EM modulator system 1201 may include a $C^2AM$ probe 1220 and a $C^2AM$ controller 1250. The $C^2AM$ controller 1250 may include, for example, and without limitations, a pulse generator, a function generator, and an amplifier similar to the corresponding components as described above with reference to FIGS. 1A and 1C. The pulse generator, the function generator, and the amplifier, in some embodiments, may be separate hardware units. In other embodiments, the functionality of two or all three of them may be provided by one hardware unit.

The $C^2AM$ controller 1250, in some embodiments, may include an EM wave generator, such as, for example, and without limitations, a laser device, a visible light source, etc. For example, the laser device may be as described above with reference to FIGS. 1A and 1C. The laser may be a low power laser, for example, and without limitations, a laser with less than 1 milliwatt of power. In some embodiments, the C²AM controller 1250 may not include a laser. The C²AM controller 1250 may, in some embodiments, include a controller to generate signals to steer a fast steering mirror, as described above with reference to FIGS. 11A-11B.

The C²AM controller 1250, in some embodiments, may include a display similar to the display 155 of FIGS. 1A and 1C. In some embodiments, the display may be a separate device coupled to the C²AM controller 1250. The display, in other embodiments, may be a part of the C²AM controller 1250. For example, and without limitations, the display may be a display panel on the external perimeter of the C²AM controller 1250 enclosure. The display, in other embodiments, may be part of an electronic device, such as, for example, and without limitations, a mobile device, a server, a computing device that may be communicatively coupled to the C²AM controller 1250. The C²AM controller 1250, in some embodiments, may include a keyboard and/or a keypad.

The C²AM controller 1250, in some embodiments, may include a processor similar to the processor 160 of FIGS. 1A and 1C. The processor 160 may control the operations of the pulse delay generator, the function generator, the amplifier, the EM wave generator (e.g., the laser device), and/or the display of the system 1201, as described above.

With further reference to FIG. 12A, the C²AM probe 1220 may include one or more axial focused mechanical transducers 1230. The axial focused mechanical transducer(s) 1230, in some embodiments, may be US and/or an audible sound transducer(s). The focal point 1215 of the acoustic wave 1215 generated by the axial focused acoustic transducer(s) 1230, in some embodiment, may be within the C²AM probe's 1220 enclosure. In some embodiments, the acoustic wave 1215 may be attenuated such that no significant amount of acoustic wave may leave the C²AM probe 1220.

The axial focused acoustic transducer(s) 1230 may be, for example, and without limitations, an axial FUS transducer similar to the single element FUS transducer 130 (FIG. 2A), similar to the linear (phased) array FUS transducer 250 (FIG. 2B), similar to the annular (phased) array FUS transducer 280 (FIG. 2D), similar to the two-dimensional (phased) array FUS transducer 260 (FIG. 2E), similar to the two transducers 330 and 340 (FIGS. 3A-3C), or a phased array with a different arrangement of elements, as described above. The axial acoustic transducer(s) 1230, in some embodiments, may include two axial acoustic transducers 330 and 340, as described above with reference to FIGS. 3A and 3B. In these embodiments, the focal point of the acoustic wave generated by at least one of the two axial acoustic transducers may be outside the enclosure of the CAM probe 1220.

In some embodiments, one or more of the transducers 1210 may be covered by a piezoelectric material, such as, for example, and without limitations, zirconate titanate (PZT) and/or lithium niobite (LiNbO3). In some embodiments, one or more of the transducers 1210 may use transduction methods other than piezoelectric conducting. For example, one or more of the transducers 1210, in some embodiments, may be a CMUT.

The C²AM probe 1220, in some embodiments, may include a handle and a shaft (as described above with reference to FIG. 8) or a motor and a shaft (as described above with reference to FIG. 9) to reconfigure the C²AM probe 1220 from a counter propagating configuration to a co-propagating configuration and vice versa. The axial focused acoustic transducer(s) 1230 may be connected to the controller by the electrical wires 195 and the electrical connector 1290. In the reconfigurable embodiments, the electrical connector 1290 may be a rotating connector ring or a removable connector as described above with reference to FIGS. 8 and 9 to facilitate the rotation of the axial focused acoustic transducer(s) 1230 during reconfiguration.

With continued reference to FIG. 12A, the C²AM probe 1220 may include an input 1205 for the EM wave 1210 to enter the C²AM probe 1220 and an output 1222 for the EM wave 1210 to exit. The input for the EM wave 1210 may be, for example, and without limitations, an optical fiber or a transparent window as discussed above with reference to FIGS. 1B and 1D. The output for the EM wave 1210 may be, for example, and without limitations, an optical fiber or a transparent window as discussed above with reference to FIGS. 1B and 1D.

As shown, the focal point 1285 of the EM wave 1210 may be outside of the CAM probe 1220. The lensing power of the EM wave 1210 may remain constant (as shown by the modulated EM beam forming and dynamic focusing region 1287) with very small fluctuations over time as long as the acoustic wave 1215 is generated by the axial focused acoustic transducer(s) 1230. The C²AM probe 1220 may include two mirrors, as described above with reference to FIG. 10A. The C²AM probe 1220 may include a steering mirror, as described above with reference to FIG. 11A.

Figure 12B:
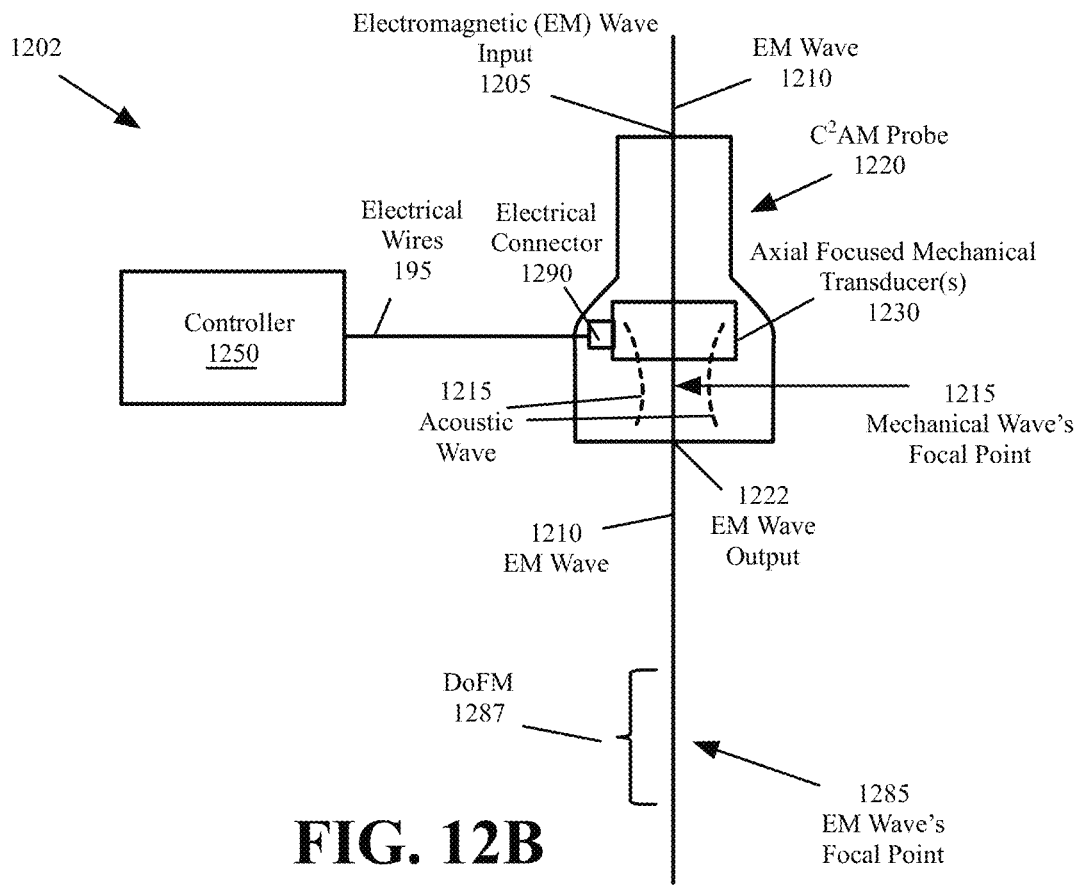
FIG. 12B is a functional diagram illustrating a generalized embodiment of a co-propagating mechanical-EM modulator system, according to various aspects of the present disclosure.

FIG. 12B is a functional diagram illustrating a generalized embodiment of a co-propagating mechanical-EM modulator system 1202, according to various aspects of the present disclosure. With reference to FIG. 12B, the system 1202 may have similar components as the system 1201 of FIG. 12, except that the axial focused mechanical transducer(s) 1230 is/are configured such that the mechanical wave 1215 and the EM wave 1210 propagate in the same direction. In the reconfigurable embodiments, the C²AM probe 1220 of FIG. 12B may include a handle and a shaft (as described above with reference to FIG. 8) or a motor and a shaft (as described above with reference to FIG. 9) to reconfigure the C²AM probe 1220 from a co-propagating configuration to a counter propagating configuration and vice versa. In these embodiments, the system 1202 of FIG. 12B may be reconfigured to be similar to the system 1201 of FIG. 12A and vice versa.

II. Lab Experimentation and Simulations

The followings describe the results of lab experimentations and simulations. Simulation was used to compute the pressure field that produced by a torus high intensity FUS transducer in the media. In these experimentations, the intrinsic (mediator-free) interaction between pure mechanical (US) and EM (laser) waves are studied at a fundamental level in a laboratory setting under simple but controlled conditions in a relatively boundless path of interplay as a result of the present embodiments' unexpected co- and counter propagating alignments and without the presence of any other intervening sources.

The system of present embodiments is referred to herein as mediator-free because other studies have introduced mediating objects such as air bubbles, oil droplets, or artificial light manipulation, which have resulted in complicated setups, instability, decay over time, high cost, and long run-times, thus reducing their scope of implementation. Moreover, pure interactions of the EM and mechanical waves are unfortunately infringed in these studies. Whereas, different investigators have reduced the interaction between the laser and US waves to a finite constrained space and time as found in perpendicular alignments between laser and US, the present embodiments unfold the unexpected strong and time-stable effect of the US on EM waves as the two waves coaxially propagate without any mediators.

Figures 13A, 13B, 13C, 13D, 13E:
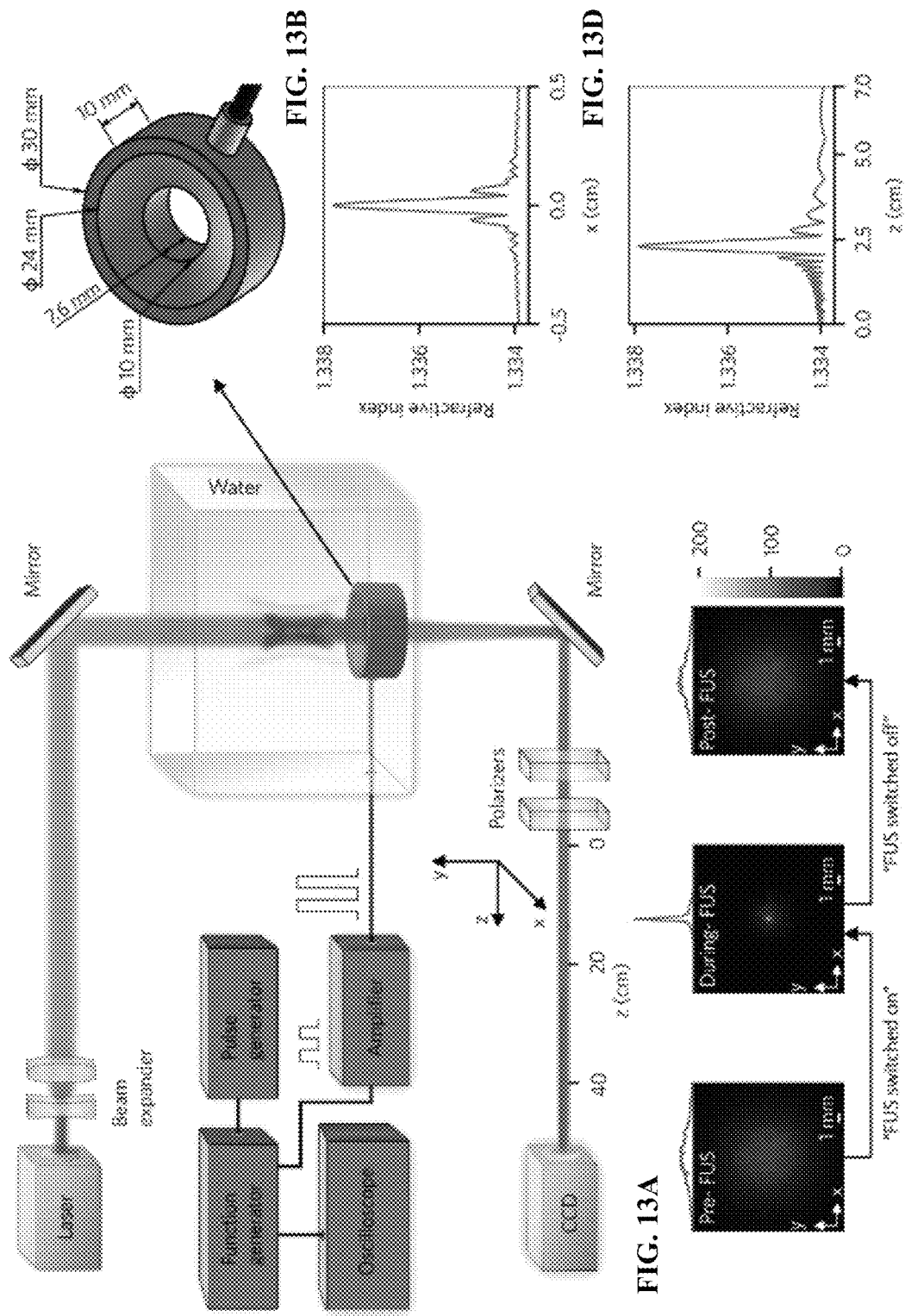
FIG. 13A illustrates the schematic of the $C^2AM$ experimental setup for counter-propagating alignment, according to various aspects of the present disclosure.
FIG. 13B illustrates a schematic of the geometrically focused, forward-looking, hollow, single-element ultrasound transducer, which has a center frequency of 3.3 MHz, focal point of 23 mm, and low acoustic intensity of 119 W/cm$^2$, according to various aspects of the present disclosure.
FIG. 13C illustrates a sample set of experimental results of the modulated laser beam captured with CCD in three sequential FUS modes (pre-, during-, and post-FUS), according to various aspects of the present disclosure.
FIGS. 13D and 13E illustrate the calculated refractive index profile in lateral (at the FUS probe focal point) and axial directions, respectively, according to various aspects of the present disclosure.

The experimentation described in the present embodiments use a simple setup that employs a low-power helium-neon (HiNe) laser (0.95 mW) and a low intensity (119 W/cm2) small, single-element, FUS transducer. The results provided herein show that without any mediating agents or beam-manipulating software or hardware, a series of phenomena occurs when the two waves travel coaxially in co-propagating and counter propagating directions in water. The US pressure field reshapes the optical beam profile and freezes the 3D laser beam and the laser beam's intensity in real time, amplifying the optical intensity and power density by reducing the beam diameter. The US pressure field also dynamically elongates the DoFM to more than 28 cm while achieving optical dynamic focusing with a broad dynamic range and temporally stabilizes the lensing power, intensity, and FWHM of the beam. These effects are quickly reversible in response to switching the acoustic wave on or off and may be selected by the US input voltage and duty cycle. The universal acousto-optic system of the present embodiments has potential applications in astronomy, oceanography, earth sciences, biology, imaging, and medicine.

a. Results i. Revealing Intrinsic Optical Focusing Using Co- and Counter-Propagating FUS The following discussions are made with reference to the following figures, according to various aspects of the present disclosure. FIG. 13A illustrates the schematic of the $C^2AM$ experimental setup for counter-propagating alignment (see FIG. 19 for co-propagating setup and details). The initially expanded continuous laser (no modulation) passes through the acoustic focal zone, then the inner hole of the focused ultrasound (FUS) transducer. The resulting modulated beam is imaged using a charge-coupled device (CCD) camera FIG. 13B illustrates a schematic of the geometrically focused, forward-looking, hollow, single-element ultrasound transducer, which has a center frequency of 3.3 MHz, focal point of 23 mm, and low acoustic intensity of 119 W/cm2. FIG. 13C illustrates a sample set of experimental results of the modulated laser beam captured with CCD in three sequential FUS modes (pre-, during-, and post-FUS). Distributions of measured intensities (solid blue lines) over the lateral direction of the beam are displayed at the top outer edge of the CCD images. FIGS. 13D and 13E illustrate the calculated refractive index profile in lateral (at the FUS probe focal point) and axial directions, respectively.

FIGS. 14A-14C illustrate the 2D images of the light showing intensity patterns recorded by CCD in pre-, during-, and post-FUS modes, respectively. Light intensity distributions (maroon lines) are shown on the top and left outer edges of the CCD images, identifying beam diameter measures along x and y directions, respectively. The images are obtained using the configuration shown in FIG. 13A. The FWHM and beam diameter of the modulated laser measure 0.16×0.18 mm and 0.39×0.54 mm, respectively, defining ~450- and 177-fold reductions, compared to pre- and post-FUS modes (FUS transducer received voltage of 84 V with duty cycle of 2%).

Figure 21:
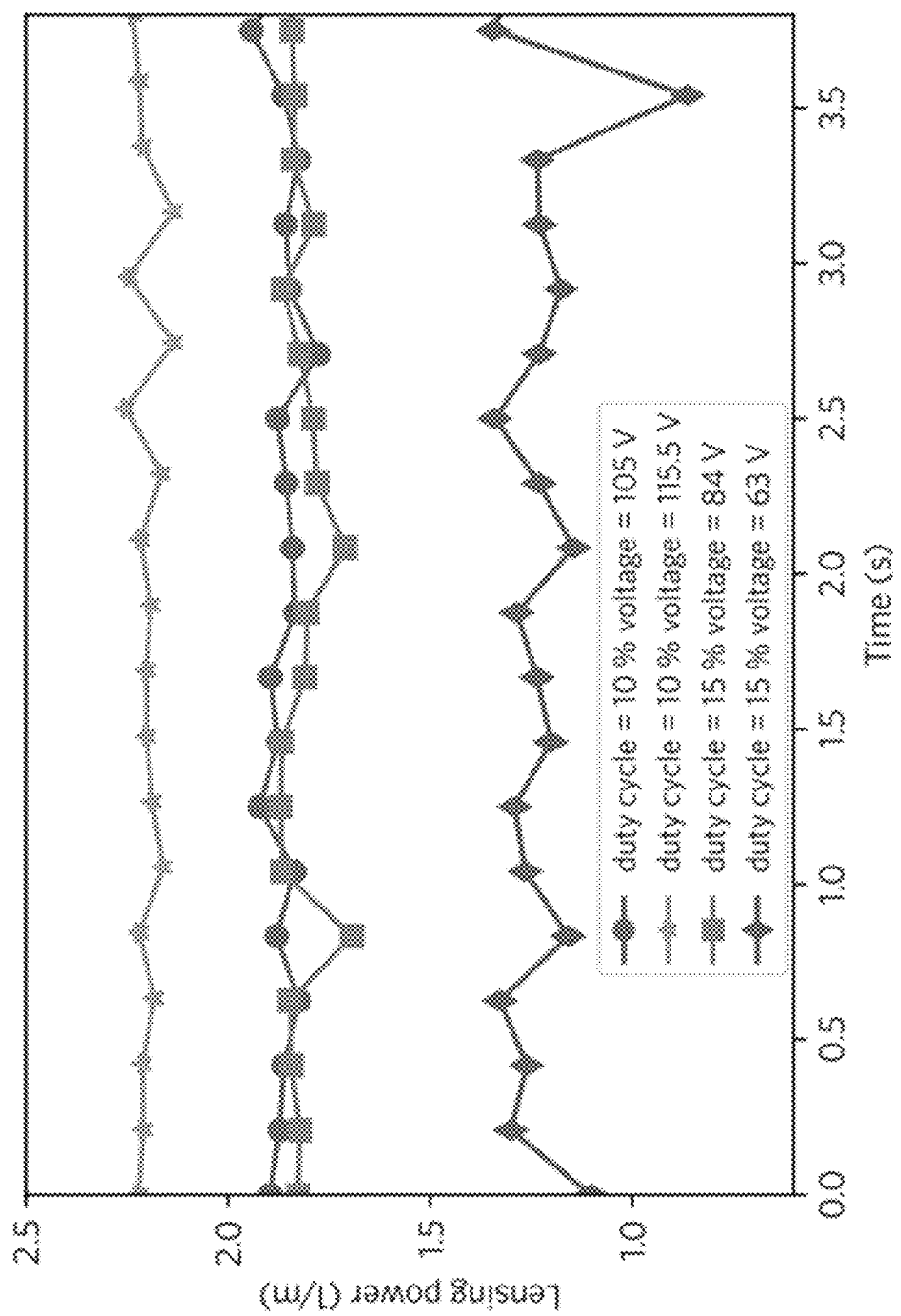
FIG. 21 illustrates the lensing power with varied input parameters for counter-propagating $C^2AM$, according to various aspects of the present disclosure.
Figure 22A:
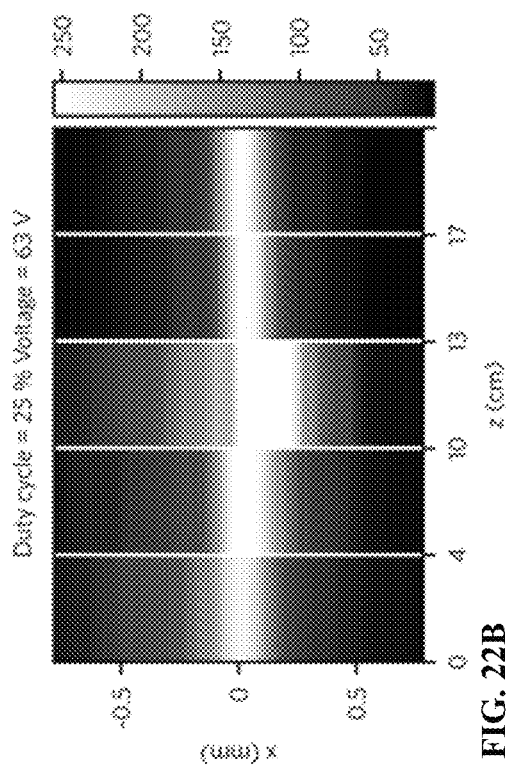
FIGS. 22A-22D illustrate the experimental results of two dimensional lasing intensities along the propagation axis (counter-propagating) with varied FUS-input duty cycles and voltages, according to various aspects of the present disclosure.
Figure 22C:
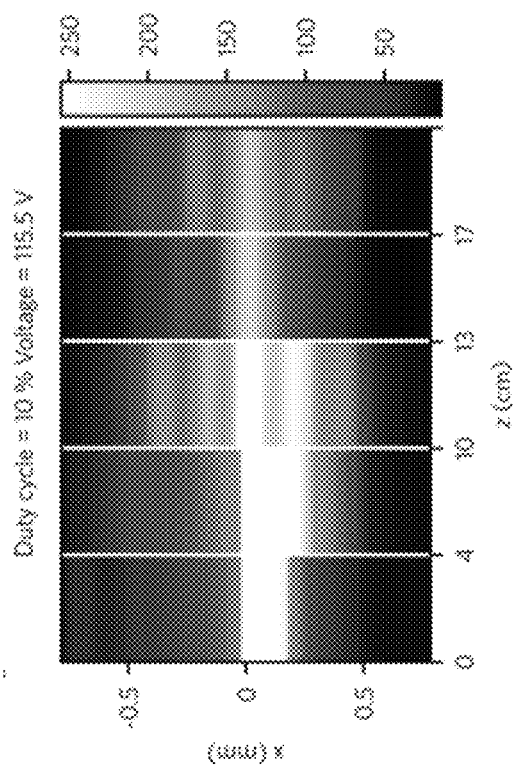
Figure 22B:
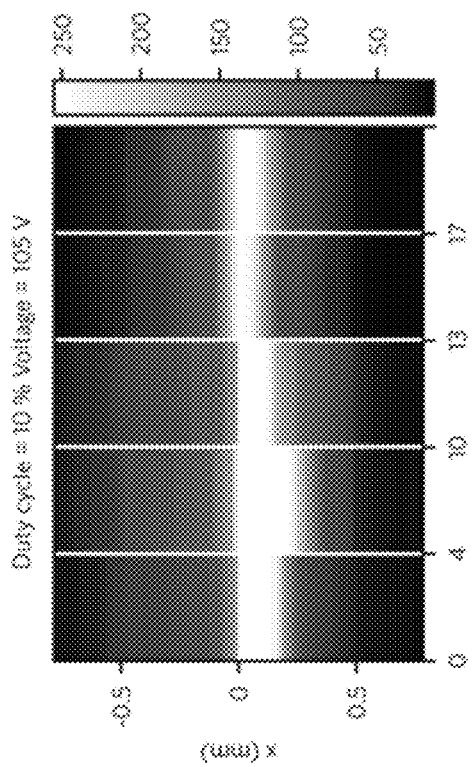
Figure 22D:
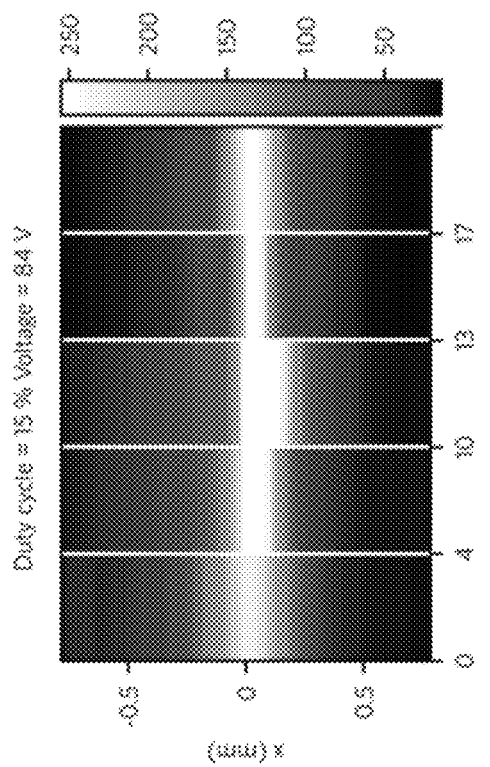

FIGS. 14D-14F illustrate 3D image intensity profiles of the US-modulated light for duty cycle of 20% at 84 V in pre-, during-, and post-FUS modes, respectively. The intensity profiles when FUS is off (FIGS. 14D and 14F) are normalized to the peak value in FIG. 14E; the latter exhibits ~7.5-fold intensity enhancement over the former (see FIG. 20 for intensity patterns captured by the co-propagating setup at five other US-input parameters). FIG. 14G illustrate distribution of the measured lensing power $$\left(\frac{1}{\text{focal length of the modulated laser}}\right)$$

over time for two distant duty cycles of 2% (squares) and 20% (circles), respectively, revealing time stability in lensing power with only miniscule variations over time (see FIG. 21 for the observed time-stable lensing power at additional input parameters).

FIG. 15A illustrates a schematic portrait of the basic principle of the intrinsic acousto-optic modulation method ($C^2AM$) in the counter-propagating configuration. Having entered from the bottom left corner, the input continuous light (no modulation) emanates coaxially through the incoming US waves. The modulated light then unfolds a time-stable (which is referred to as frozen-in-time lensing effect) focusing and controllable depth of field and departs the scene from the right. FIGS. 15B-15E illustrate experimental results of 2D and 3D optical intensities along the propagation axis with FUS-input duty cycle of 20% (FIGS. 15B-15C), and 2% (FIGS. 15D-15E), both at 84 V. The present embodiments image more than 40 cm of the laser-illuminated axis by CCD. Consequently, the DoFM is measured to be around 28 cm (FIGS. 15B-15C) and 11.5 cm (FIGS. 15D-15E). Furthermore, by reducing the US-duty cycle, the maximum focal intensity shifts from ~14 cm (FIGS. 15B-15C), to ~8.5 cm (FIGS. 15D-15E). All scales display intensity (FIGS. 22A-22D illustrate optical intensities with other duty cycles and voltages).

Figure 23:
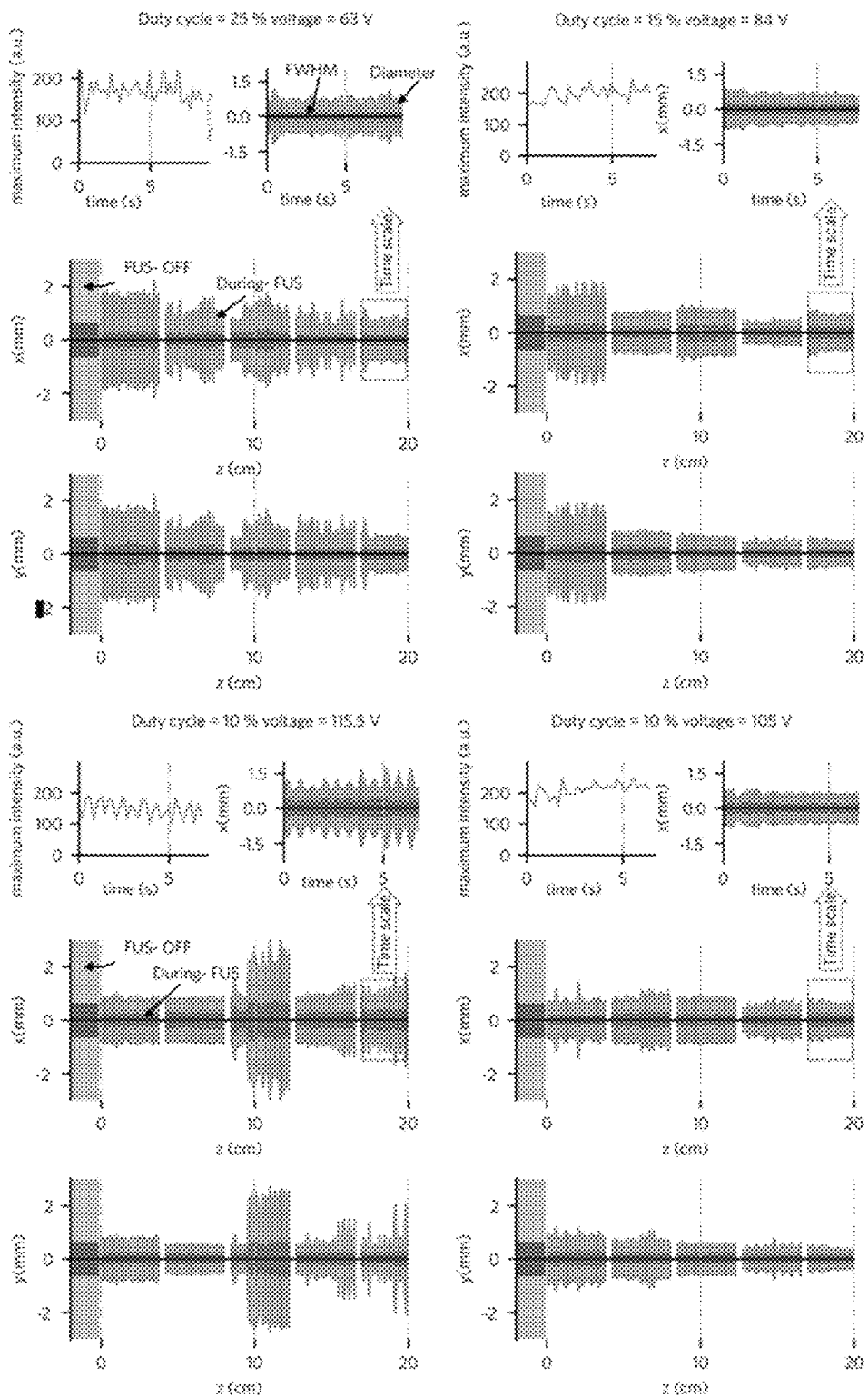
FIG. 23 illustrates the diameter and FWHM of the laser beam for different voltages and duty cycles (counter-propagating $C^2AM$), according to various aspects of the present disclosure.
Figure 24A:
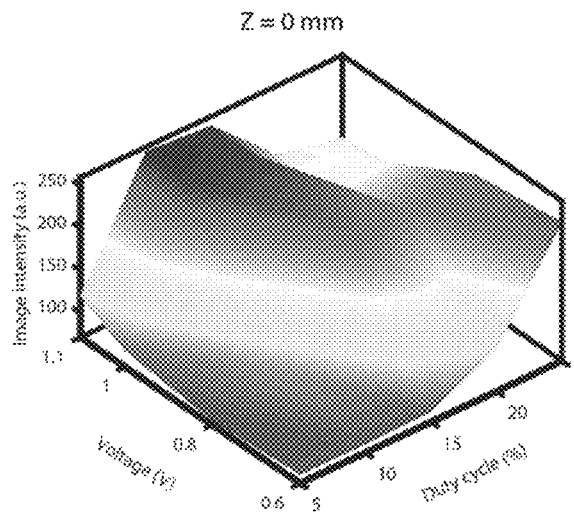
FIGS. 24A-24E illustrate guidance of lasing intensity via US input voltage and duty cycle, according to various aspects of the present disclosure.
Figure 24B:
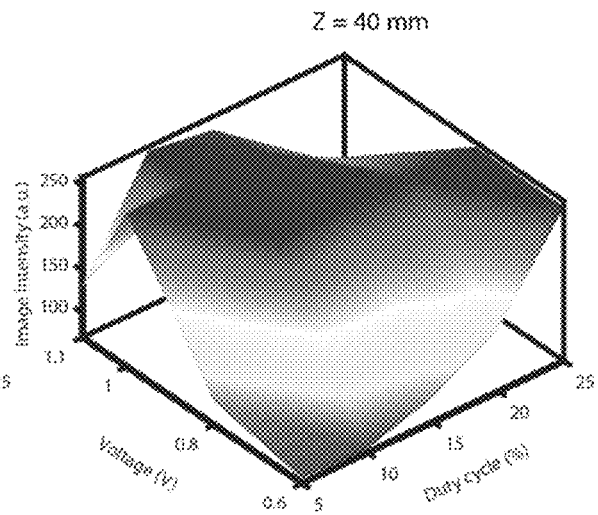
Figure 24C:
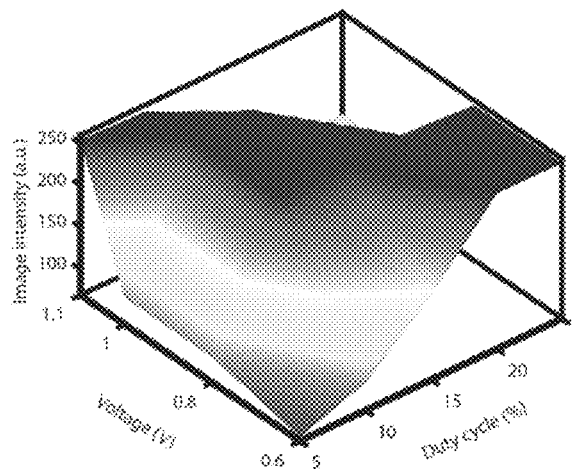
Figure 24D:
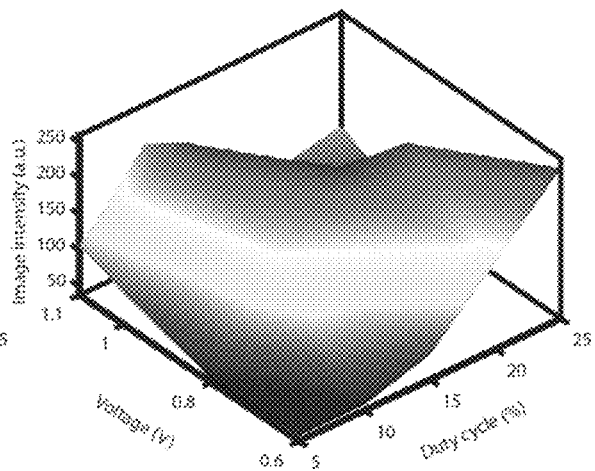
Figure 24E:
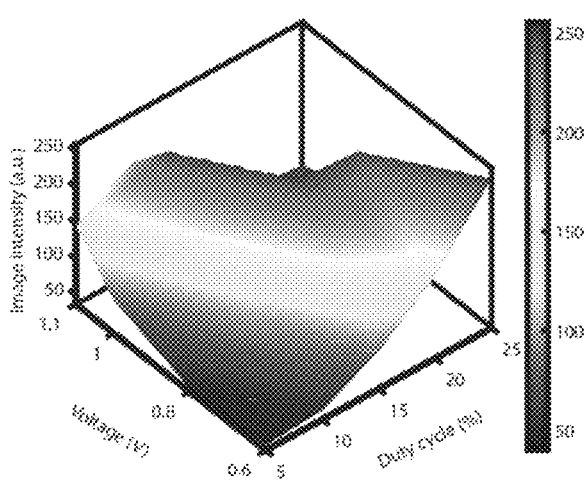

FIGS. 16A-16B reveal the frozen-in-time lensing effect in measured maximum intensity, FWHM, and beam diameter over US-input duty cycles of 2%. at 84 V. FIGS. 16C-16D reveal the frozen-in-time lensing effect in measured maximum intensity, FWHM, and beam diameter over US-input duty cycles of 20%. at 84 V (further measures of frozen-in-time lensing for more duty cycles and input voltages are illustrated in FIG. 23). FIGS. 16E-16H illustrate the 2D modulation of spatial resolution in propagating direction utilizing C2AM. Optical beam diameter and FWHM measurements in both x and y directions during the two duty cycles of 2% (FIGS. 16E and 16G) and 20% (FIGS. 16F and 16H), both at 84 V US-input voltage. Beam diameter and FWHM at pre- and post-FUS modes are represented by tall brown sections on the left side of each illustration (16E-16H), whereas during-FUS observations are displayed by short green segments. The diameter and FWHM of the laser beam narrow as soon as US is switched on.

FIGS. 17A-17D, in four rows of image sequences, illustrate intensity patterns recorded by CCD at selected US-input duty cycles and voltages. Each column represents six axial locations from z=0 cm to 17 cm. Note that the captured images with US-duty cycles of less than 5% (the first two rows) form closer focal lengths of about 4 cm and 8 cm, respectively. A higher duty cycle (20%), however, produces longer foci (about 10 cm and 13 cm, with 63 V and 84 V input-US voltages, respectively). At the lowest duty cycle (FIG. 17B), the best spatial resolution is acheived at z=8 cm with exceptionally round optical focusing (2D FWHM measured as 0.169 mm by 0.170 mm and beam diameter as 0.399 mm by 0.528 mm for x and y directions, respectively). The 2D FWHM and diameter of the focal point is measured at z=4 cm (FIG. 17A), measured as 0.251 mm by 0.320 mm and 1.37 mm by 1.55 mm; then at z=10 cm (c FIG. 17C), measured as 0.189 mm by 0.331 mm and 1.510 mm by 1.346 mm; and finally at z=13 cm (FIG. 17D), observed as 0.240 mm by 0.464 mm and 0.813 mm by 1.152 mm for x and y directions, respectively. All color scales display optical intensity. The scale bar is 1 mm.

FIGS. 18A-18E and 18K-18O illustrate comprehensive experimental results of light intensity variations as a function of, respectively, the US-input voltages and the duty cycles at different locations of propagation axis (z). FIGS. 18F-18J illustrate color scale 2D cross-sections of intensity variations for z=0 cm, 4 cm, 10 cm, 13 cm, and 17 cm as a reciprocal interplay of input voltages and duty cycles, collectively. An apex is noticed for intensity at each voltage (FIGS. 18A-18E) and duty cycle (FIGS. 18K-18O) in every five positions. In the second and third columns at z=4 cm and 10 cm locations, intensity is saturated in most conditions. Precluding saturation, i and j disclose a third-degree polynomial-like correlation of voltage and duty cycle, with two ramps and a nearly flat plateau in the middle. The voltage increases linearly as the duty cycle advances, plateaus between 10% and 15% duty cycles, then proceeds to rise. Due to the intensity saturation, the polynomial-like trend at f, g, h (z=0 cm, 4 cm, 10 cm) is not clear but is comprehensible. Other than CCD location, voltage, and duty cycles, all other parameters are kept constant (the intensity control with other duty cycles and voltages along the z-axis are shown in FIG. 24A-24E).

Figure 19:
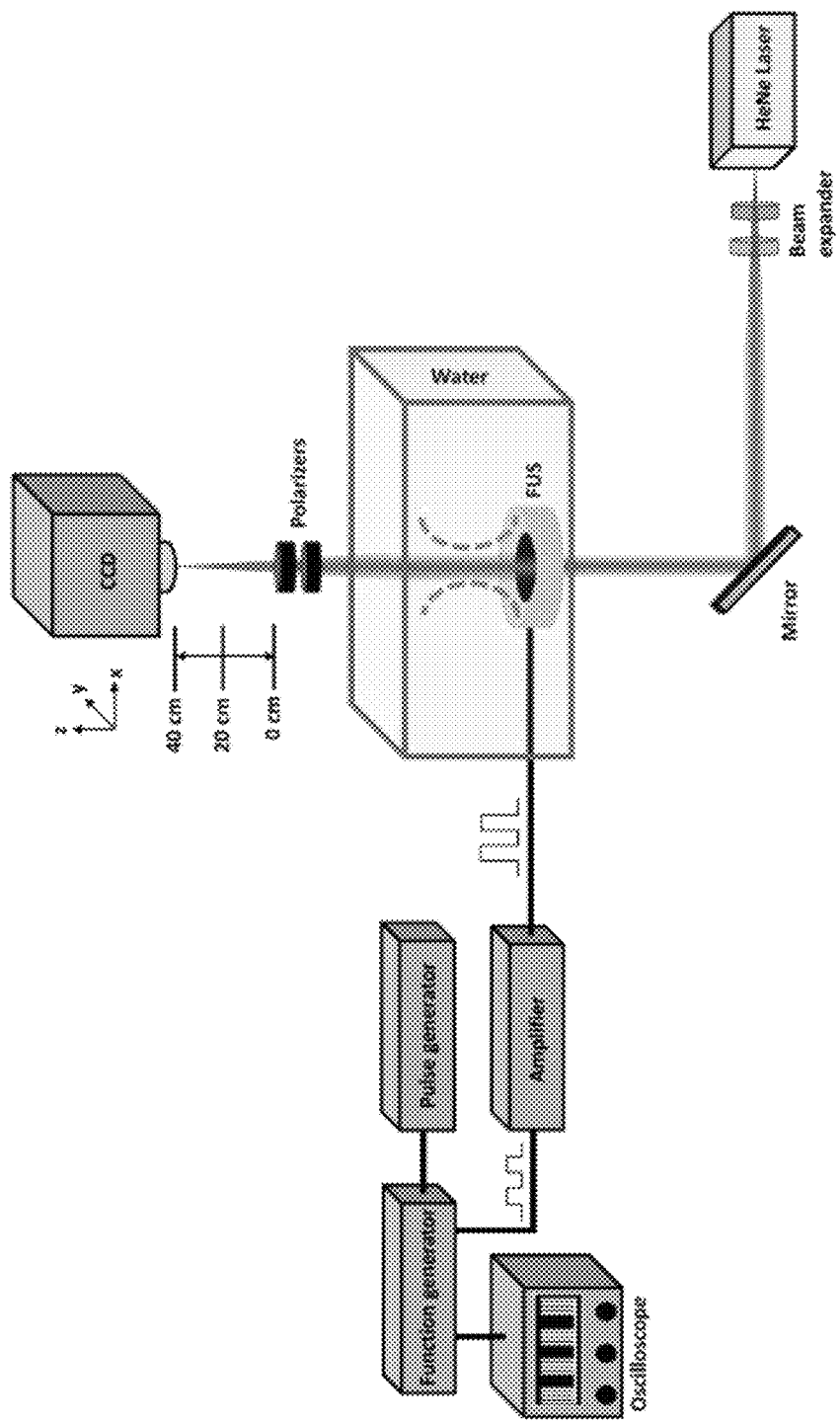
FIG. 19 illustrates the setup of the co-propagating $C^2AM$, according to various aspects of the present disclosure.
Figure 20:
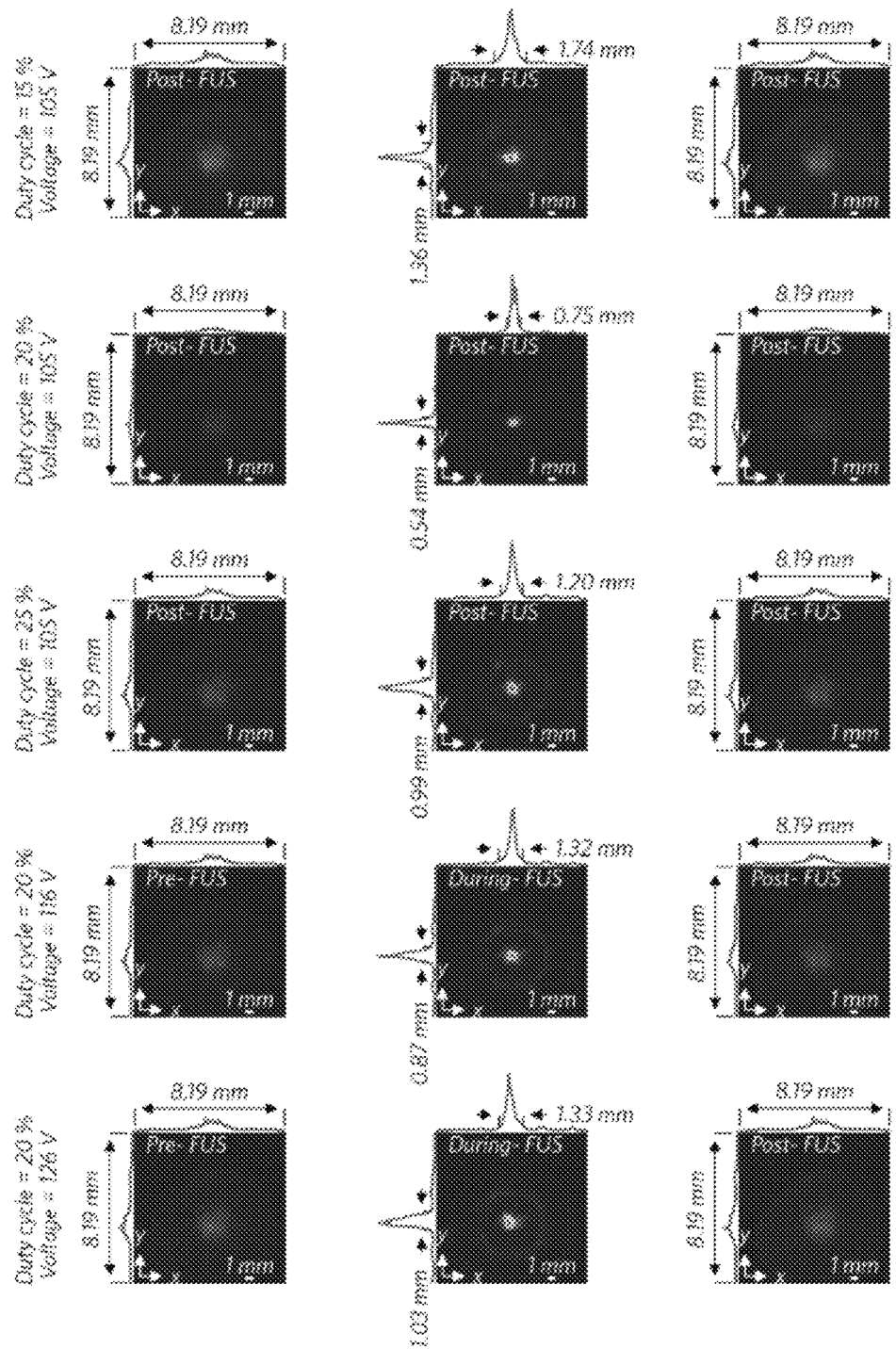
FIG. 20 illustrates the experimental results of natural laser focusing by co-propagating $C^2AM$, according to various aspects of the present disclosure.

FIG. 19 illustrates the setup of the co-propagating CAM. FIG. 20 illustrates the experimental results of natural laser focusing by co-propagating CAM. FIG. 21 illustrates the lensing power with varied input parameters for counter-propagating $C^2AM$. FIGS. 22A-22D illustrate the experimental results of two dimensional lasing intensities along the propagation axis (counter-propagating) with varied FUS-input duty cycles and voltages.

Figure 25B:
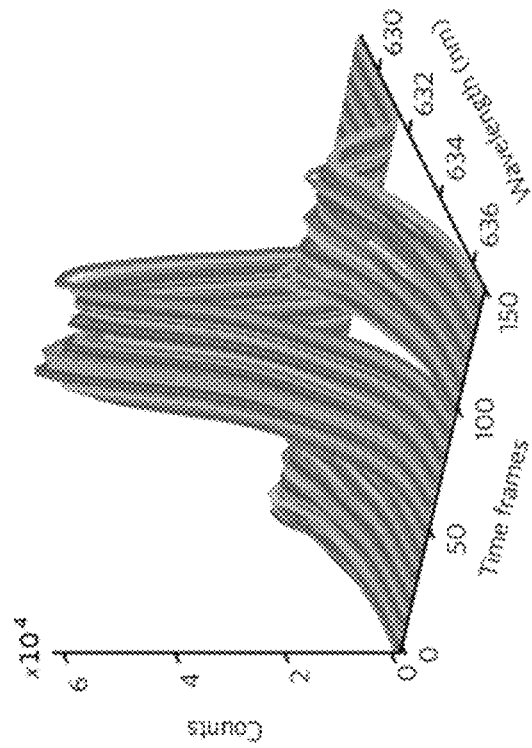
FIG. 25B illustrates the measurement was taken at three conditions for pre-, during-, and post-FUS, according to various aspects of the present disclosure.
Figure 25A:
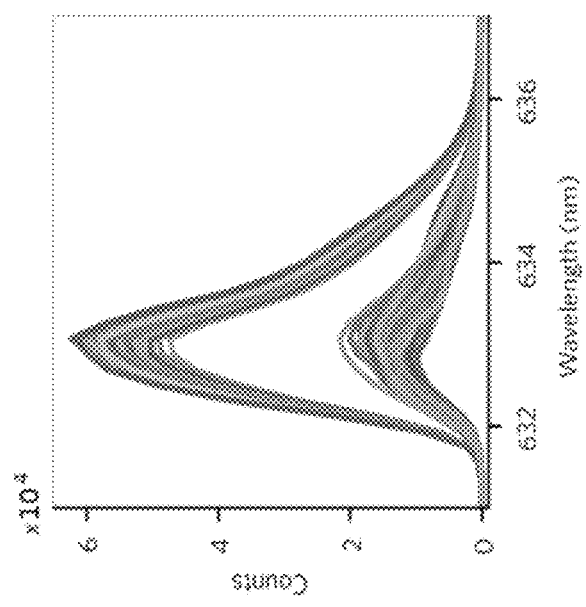
FIG. 25A illustrates the spectrum of the amplified pulse (nonlinear broadening) is asymmetric, according to various aspects of the present disclosure.
Figures 26A, 26B:
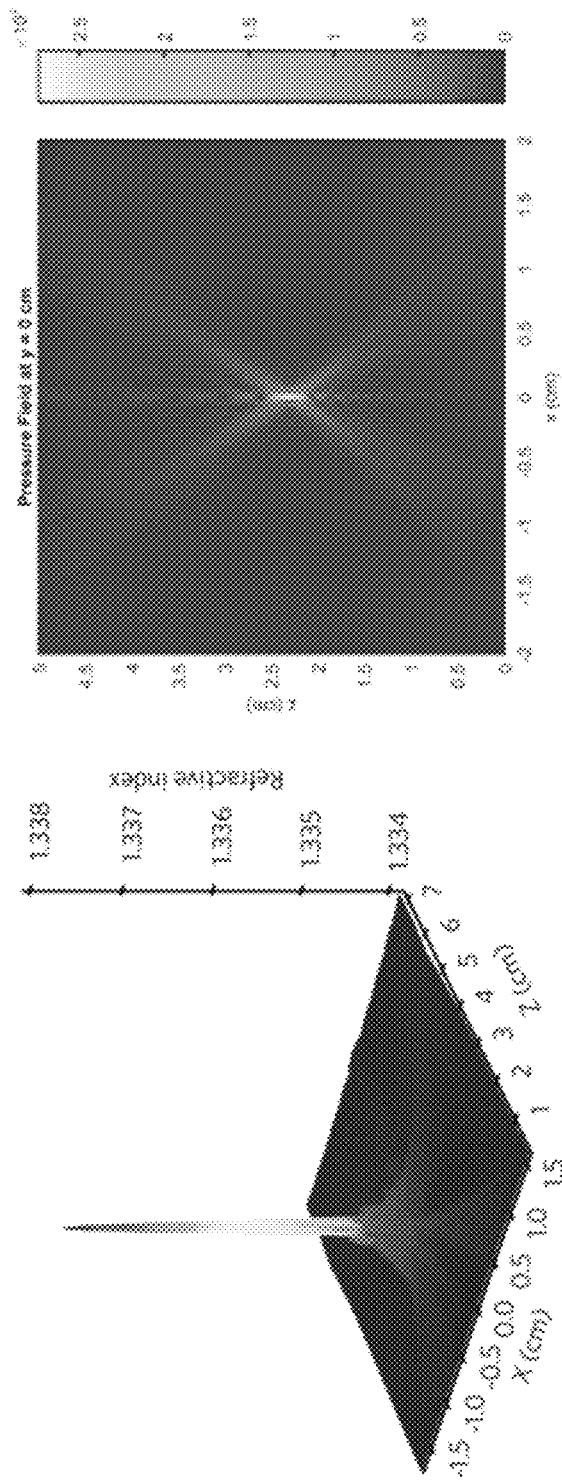
FIGS. 26A-26B illustrate the significant increase in total counts of photons at FUS-on compared to the FUS-off situation according to various aspects of the present disclosure.

FIG. 23 illustrates the diameter and FWHM of the laser beam for different voltages and duty cycles (counter-propagating $C^2AM$). FIGS. 24A-24E illustrate guidance of lasing intensity via US input voltage and duty cycle. The 3D intensity variations for z=0, 40, 100, 130, 170 mm as a function of input voltages and duty cycles. FIG. 25A illustrates the spectrum of the amplified pulse (nonlinear broadening) is asymmetric. The spectrum is broadened on both the red and blue sides. FIG. 25B illustrates the measurement was taken at three conditions for pre-, during-, and post-FUS. FIGS. 26A-26B illustrate the significant increase in total counts of photons at FUS-on compared to the FUS-off situation. This observation may possibly result in that FUS waves cause the change in the main frequency (Doppler shift) and the frequency bandwidth (spectral broadening) of the photons in light beam.

The relationship between pressure change and index of refraction variation in water, described by Eq. (1):

$$n(\bar{p}) = \sqrt{\frac{a_{14} + 2(a_{11}\bar{p} + a_{12}\bar{p}^2 + a_7\bar{p}^3)}{a_{15} - (a_{11}\bar{p} + a_{12}\bar{p}^2 + a_7\bar{p}^3)}} \quad \text{Eq. (1)}$$

FIG. 27 illustrates the coefficients for Eq. (1). The bulk modulus of water is considered to be 2.2 GPa:

$$\bar{P} = \frac{P}{\text{Bulk modulus}} \quad \text{Eq. (2)}$$

The pressure field of the FUS is simulated with the focus software, the simulated pressure field represents a continues acoustic wave with the frequency of 3.3 MHz. The dimensions of the FUS probe is also provided in the FIG. 13B. The relationship between refractive index and pressure is nonlinear, despise this nonlinearity the coefficients in Eq. (1) are small so that the calculated refractive index in respect to supplementary note 1 suggests an approximately linear relationship with pressure.

Optical properties of the water would change, as FUS waves propagate through it, according to the previous notes (acoustic waves build pressure and the pressure changes the refractive index so It has been suggested that the gradients of refractive index may guide the light through media). As it has been suggested in prior researches that the acoustic wavelength and light's beam width also plays a role in the opto-acoustic interactions, although in those researches the light and sound were propagating perpendicularly. The true and fully correct nature of this phenomena may be that the other parameters such as acoustic waves beam width and propagation of different acoustic waves (shear and longitudinal) emitted by the FUS is suspected to be play a role in the explanation of this study.

The present embodiments realize intrinsic optical focusing using both counter-propagating and co-propagating acousto-optic modulators ($C^2AM$); their setups are illustrated in FIG. 13A and FIG. 19, respectively. Laser light emitted from a continuous wave helium-neon laser is expanded and directed into a water tank to pass through an ultrasonic pressure field in a counter-propagating direction (FIG. 13A). US waves are generated by a single-element, forward-looking, hollow FUS transducer (FIG. 13B) inside the tank aligned in the direction of the laser beam. The energy density emitted from the laser at pre-post-FUS (when FUS is off) was ~3.39 mWcm-2, for an illuminated beam diameter of ~6.12 mm. The maximum refractive index contrast by virtue of acoustic pressure field in the FUS focal zone was calculated as ~0.0048 in lateral and axial directions, respectively (FIGS. 13D and 13E). The intensity profile of the modulated laser was captured by an electron-multiplying charge-coupled device (CCD) camera. The results for both co- and counter-propagating C2AM reveal that when FUS is on, the laser beam becomes focused and its intensity sharply increases with ~7.5-fold enhancement (FIGS. 13C, 14A-14F, and 20), due to an acoustic pressure-enhanced refractive index. Furthermore, the measured FWHM and beam diameter of the modulated laser exhibited ~450- and 177-fold reductions compared to pre- and post-FUS laser (see top and left outer sides of CCD images in FIGS. 14A-14C). By switching the FUS on, the Gaussian beam profile becomes pronounced (FIGS. 13C and 14A-14C, outer edges). These results provide an important step toward free-form optical modulation using mass oscillation.

ii. Time Stability of Intrinsic Optical Modulation Using CAM

The principle of time stability of the US-light modulation setup ($C^2AM$) in the counter-propagating configuration is portrayed in FIG. 15A. Upon US-laser interaction, time-stable optical focusing occurs after the FUS transducer. The unprecedented time stability (which is referred herein as frozen-in-time lensing effect, FIG. 15A) is realized as a seemingly instant-locking impact on the measured lensing power $$\left(\frac{1}{\text{focal length of the modulated laser}}\right),$$

intensity, diameter, and FWHM of the modulated laser under various US inputs (FIGS. 14G, 16A-16D, 21, and 22A-22D). The resulting means±standard deviations for lensing power of 2% and 20% US-duty cycles are $$2.55 \pm 0.02 \frac{1}{m} \text{ and } 1.88 \pm 0.04 \frac{1}{m},$$

respectively (FIG. 14G).

iii. Selective 3D Focal Intensity and Spatial Resolution of Light Across Depth of Field The control over measured DoFM, defined as a domain over the propagation axis (z) where the intensity of US-modulated laser remains above −3 dB intensity (half maximum) relative to the maximum intensity (I>Imax/2), and focal intensities along the propagation axis during various US-inputs are shown in FIGS. 15B-15E and 22A-22D. More than 40 cm of the laser-illuminated space is imaged with the CCD. Switching the US-duty cycle from 20% to 2% changes the DoFM and focal length from ~28 to 11.5 cm and ~14 to 8.5 cm, respectively (FIGS. 15F and 15D). Furthermore, the lateral (x) and elevational (y) optical resolutions over axial direction (z) utilizing C²AM are measured at different FUS-input duty cycles and voltages (FIGS. 16E-16H and 23). With the FUS on, the narrowed diameter and FWHM of the laser beam hold their confinement over time (frozen-in-time lensing, FIGS. 16A-16D). The measured confinement zone, during which the beam diameter and FWHM is sharply focused, increases from less than 20 cm to ~40 cm when duty cycle switches from 20% to 2% (FIGS. 16F, 16H, 16E, 16G, respectively).

iv. Controlled Optical Focusing Across DoFM by Tuning FUS

Figure 17A:
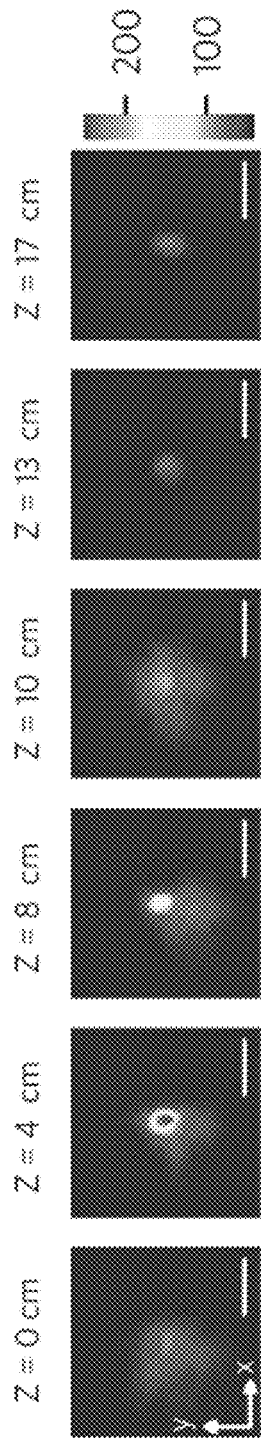
FIGS. 17A-17D, in four rows of image sequences, illustrate intensity patterns recorded by CCD at selected US-input duty cycles and voltages. Each column represents six axial locations from z=0 cm to 17 cm, according to various aspects of the present disclosure.
Figure 17B:
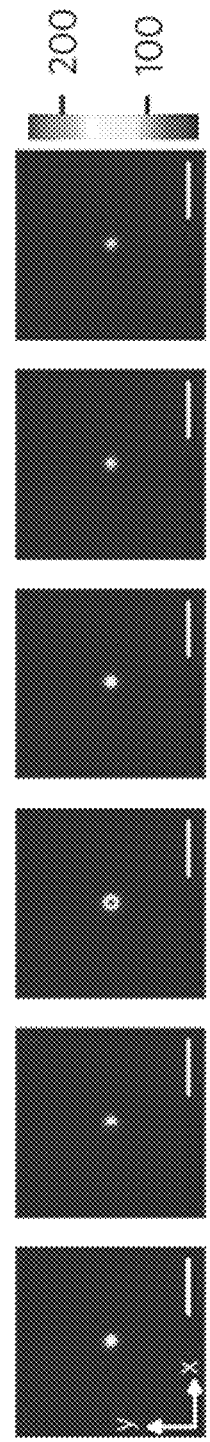
Figure 17C:
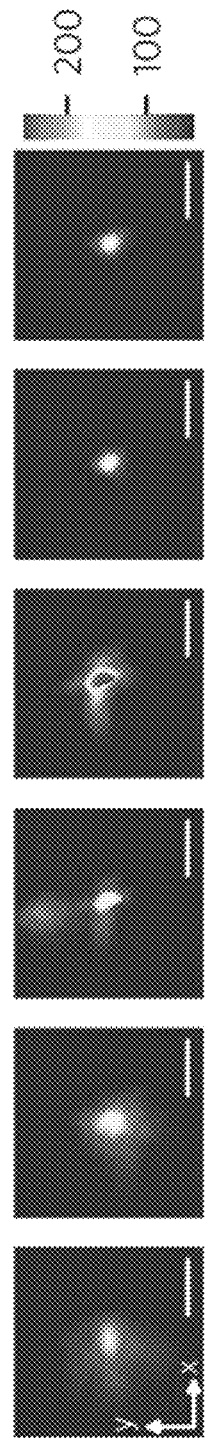
Figure 17D:
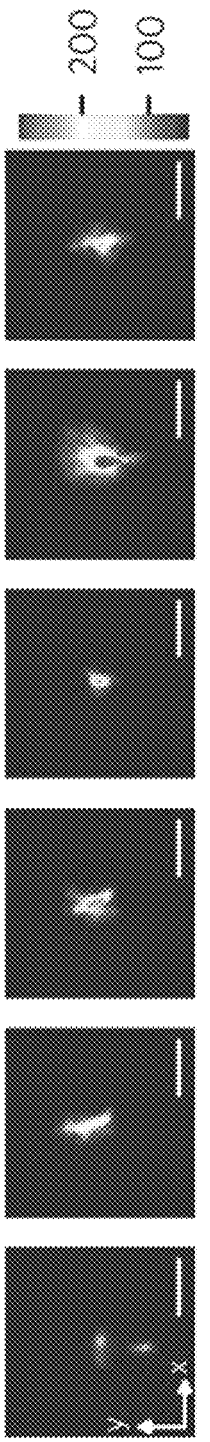

The present embodiments demonstrate dynamic control over optical focusing with C2AM. An alteration of the US pressure by selecting input parameters yields respective change of the refractive index. Thus, the position of the focal plane is tunable via US-input parameters at C2AM (FIGS. 17A-17D). Intensity patterns are imaged by CCD at various propagation positions from z=0 mm to 170 mm. Focusing with shorter US-duty cycles (5% and 2%) forms shorter focal lengths of ~40 mm and 80 mm, respectively (FIGS. 17A and 17B). A higher duty cycle (20%) pushes the focus to about 100 mm and 130 mm for 63 V and 84 V, respectively. It also substantially increases the intensity, enough to saturate the CCD (FIGS. 17C and 17D. Thus, tuning duty cycle from 2% to 20% allows for controlling the measured focal length from 4 cm to 13 cm and the focal diameter (defining the resolution) from 0.39 mm to 1.55 mm (FIGS. 17B and 17A), corresponding to dynamic ranges of 225% and 297%, respectively.

Furthermore, to investigate the light intensity behavior along the propagation axis, test conditions are measured using CCD at multiple US pressures by varying duty cycles and voltages (FIGS. 18A-18O and 24A-24E). The modulated light intensity is measured at four FUS input voltages and five duty cycles while changing the CCD positions from z=0 mm to 170 mm. FIGS. 18A-18E and 18K-18O represent the relationship between the lensing intensity versus the US-driving duty cycles and voltages, respectively. FIGS. 18F-18J illustrate 2D cross-sections of intensity variations at five CCD positions. In each location, the effect of reciprocal interaction between selected input voltages and duty cycles on lensing intensity is displayed. Avoiding intensity saturation revealed a third-degree polynomial-like relationship between voltage and duty cycle (FIGS. 18I and 18J). In certain conditions (FIGS. 18B, 18C, 18G, 18H, 18L, and 18M), intensity reaches its maximum and saturates the CCD, leading to elongation of DoFM.

v. Discussion

The described experimentation present how the intrinsic coaxial interaction between mechanical waves (generated by FUS) and EM (laser) waves without any auxiliary sources unexpectedly offers remarkable lensing enhancements. To date, most optical focusing investigations using US waves have used restrictive setups and techniques resorting to special software, hardware, and mediators. To overcome these impediments to optical modulation, the present embodiments illustrate how the C²AM, an unconventional simple architecture, exercises innate mediator-free coaxial interplay between laser and US. The promise of the C²AM is emphasized experimentally by several findings. First, unaided universal lensing enhancement across an ultra-deep controllable DoFM are successfully obtained (FIGS. 15B-15E and 16E-16H) with a notable frozen-in-time lensing effect (FIGS. 14G and 16A-16D). The FWHM of the beam profile is more than 450-fold narrower than those of the pre- or post-FUS laser (FIGS. 14A-14C). Moreover, the measured optical intensity offers a ~7.7-fold increase (FIGS. 14D-14F), enhancing power density by more than two orders of magnitude (~246-fold) with respect to pre- and post-FUS conditions. It was also observed that not only is the DoFM deeper than 28 cm, but the maximum focal intensity shifts more than 9 cm along the z-axis by tuning US-input parameters (FIG. 17).

In contrast to the existing US-induced optical modulating approaches, the CAM is the only one to experimentally achieve time stability for lensing power, intensity, and FWHM (FIGS. 14G, 16A-16D, 21, and 23). The frozen-in-time lensing effect is obtained using the coaxial and intrinsic motif of US-laser interplay, thus avoiding the unwanted fully reversed sinusoidal fluctuations around zero over time in other studies. Here, time-stable lensing is achieved with standard deviations of lensing power as low as $$0.02 \frac{1}{m}$$

(FIG. 14G). The combination of these factors enables laser light to penetrate deeply, holding its sharply increased intensity, power density, and fine spatial resolution temporally stable for the first time.

Furthermore, the C²AM intrinsic characteristics preclude the need for mediators and stymieing hardware or software associated with acousto-optic modulation techniques used in existing studies. One specific observed downside of mediators (e.g., oil droplet) is the continuous decay of lensing intensity as acousto-optic modulation repeats, which hinders optical enhancement. The FUS driving conditions in the present embodiments do not generate cavitation air bubbles, thus, Mie scattering does not play a role in the occurred lensing effect of the present embodiments. In addition, no temperature change are observed at the FUS focal zone, accurate to 0.01° F. This is particularly advantageous regarding the effectiveness and feasibility of light-based devices.

Time stability and intrinsic optical focusing using $C^2AM$ are not the sole requirements for universal light modulation, however. Maneuvering the focal zone of the modulated laser across the DoFM (to control the highest optical intensity in real time) is essential for many practical applications such as optical communications, medicine, microscopy, material processing, and confocal profilometry. The present embodiments reconfigure the pattern of the US pressure field in the media simply by varying the FUS input parameters. Accordingly, changing the applied US pressure affects the refractive index, which shifts the $C^2AM$ focal planes. Throughout the DoFM, optical dynamic focusing occurs in sub-millisecond response times (FIGS. 17A-17D). The quick run-time in this study is a natural product of intrinsic (mediator-free) $C^2AM$, which does not require iterations or auxiliary complex software or hardware to obtain optical focusing, unlike previous systems that featured long optimization times. The inexpensive, near-instantaneous $C^2AM$ laser modulation and its universal mechanism make it a proper choice for fast dynamic control of optical focusing.

The coaxial free-form arrangement in this study allows for acoustic and EM waves to interact over a presumably limitless space and time. This is particularly advantageous because it not only permits readily achievable and broad optical applications, but also may disseminate effects of the US-EM interactions over boundless space and time. Thus, US may imprint information onto the EM wave. When the configuration is perpendicular, the EM and US waves interact in a small restricted space over an insignificant time and thus, are unlikely to embed a lasting signature on the passing modulated laser. Optomechanical data communication and memory may also be done with $C^2AM$.

The 2D and 3D illustrations in FIGS. 18A-18O and 24A-24E present experimental evidence for a likely nonlinear relationship between US input parameters and optical intensity along the z-axis. There are optimum FUS-driving conditions for these acousto-optic effects to occur at each distance. The lower the voltage (duty cycle), the higher the duty cycle (voltage); conversely, the higher the voltage (duty cycle), the lower the duty cycles (voltage) to obtain optimum focal intensity. When both voltage and duty cycle are low, the lensing enhancement is not as prevalent.

Currently, $C^2AM$ faces some technical limitations. First, although the received light at the CCD for FUS-off conditions is set to the lowest detectable luminosity, the CCD is saturated in a few observed conditions with FUS on (e.g., FIGS. 18A-18O and FIG. 24A-24E at z=40 mm and 100 mm). The CCD camera has a readout rate of 32 frames per second and a dynamic range of ~15,000, which may not be easily compensated by calibration. A camera with broader dynamic range and lower noise would allow better measurement of the $C^2AM$ output. Second, the US-duty cycle is restricted by the permissible FUS transducer specifications, currently up to 25%. To advance lensing enhancement at higher duty cycles, a larger capacity US transducer may be employed. Third, comprehensive optimization of $C^2AM$ input parameters may result in an automated $C^2AM$. Fourth, whereas the present study uses water as the media for the FUS transducer, the effect of the US pressure field on the refractive index exists in compressible materials. Hence, although represented here with a single element FUS transducer, $C^2AM$ is possible in various media by optimizing the choice of US transducer (annular, linear, phased array), acousto-optic excitation, and detector sensitivity.

the present embodiments have demonstrated intrinsic dynamic control of an optical focusing scheme ($C^2AM$) to break the penetration depth limit, system complexities, and utilization impediments. The advantage of $C^2AM$ is its simplicity; it only requires a coaxially aligned low-power laser and simple single-element FUS probe. $C^2AM$ represents time-stable free-form optical modulation and dynamic focusing across the ultra-deep DoFM and more than two orders of magnitude enhancement of power density by increasing the spatial resolution and intensity of the modulated light. Furthermore, the present embodiments control DoFM, focal length, and diameter with a dynamic range of more than 144%, 225%, and 297%, respectively. The $C^2AM$ may significantly transform optical modulation, low-loss light delivery, and propagation limits compared to current approaches.

III. ALTERNATIVE THEORY AND EXPERIMENTATION a. Principle i. Refractive Index as a Function of Pressure

In order to derive the relationships between pressure change and refractive index the Lorentz-Lorenz equation may be applied, which describes the refractive index of a substance to its mean polarizability as shown in Eq. (3):

$$\alpha = \frac{3}{4\pi N} \frac{n^2 - 1}{n^2 + 2} \tag{3}$$

where n is the refractive index, a is the mean polarizability and N is the number of molecules per unit volume, respectively. Instead of mean polarizability it is common to use another quantity which is molar refractivity. Molar refractivity is defined as shown in Eq. (4):

$$A = \frac{4\pi}{3} N_{av} \alpha \tag{4}$$

where A is molar refractivity, $N_{av}$ is the Avogadro constant, which is approximately $6.022 \times 10^{23}$, and a is the mean polarizability. Hence, Eq. (1) may be reiterated as Eq. (5):

$$n = \sqrt{\frac{w + 2A\rho}{w - A\rho}} \tag{5}$$

where ρ is the density of the media and w is molecular weight. The relationship between strain and the change in volume of media are determined. A formulation that relates the strain in a media to change in volume is given by Eq. (6):

$$\frac{\Delta V}{V} \cong 3\epsilon + \frac{15}{2}\epsilon^2 \tag{6}$$

where $\in$ is strain and V is volume. According to Hooke's law, additional pressure, P, is approximately proportional to strain as shown in Eq. (7):

$$P = B_w \in \quad (7)$$

where $B_w$ is the bulk modulus of elasticity and E is strain. From Eq. (6) and Eq. (7), Eq. (68) may be driven:

$$\frac{\Delta V}{V} \cong 3\left(\frac{P}{B_w}\right) + \frac{15}{2}\left(\frac{P}{B_w}\right)^2 \quad (8)$$

To acquire the changes in the refractive index, the derivative of Eq. (5) may be defined as shown in Eq. (9):

$$2n\Delta n = \frac{3Aw + 4A^2\rho}{(w - A\rho)^2}\Delta\rho \quad (9)$$

The changes in density may be realized by another derivative, as shown in Eq. (10):

$$\Delta \rho = \rho \cdot \frac{\Delta V}{V} \quad (10)$$

By combining Eq. (6) and Eq. (10), Eq. (11) may be driven:

$$\Delta \rho = \rho \cdot \left(3\left(\frac{P}{B_w}\right) + \frac{15}{2}\left(\frac{P}{B_w}\right)^2\right) \quad (11)$$

By substituting Eq. (9) in Eq. (7), the changes of refractive index may be stated as Eq (12):

$$\Delta n = \frac{\rho(3Aw + 4A^2\rho)}{2\sqrt{\frac{w + 2A\rho}{w - A\rho}}(w - A\rho)^2}\left[3\left(\frac{P}{B_w}\right) + \frac{15}{2}\left(\frac{P}{B_w}\right)^2\right] \quad (12)$$

which finally reveals the refractive index as function of pressure shown in Eq. (13):

$$n_f = n_i + \frac{\rho(3Aw + 4A^2\rho)}{2\sqrt{\frac{w + 2A\rho}{w - A\rho}}(w - A\rho)^2}\left[3\left(\frac{P}{B_w}\right) + \frac{15}{2}\left(\frac{P}{B_w}\right)^2\right] \quad (13)$$

The above calculations assume that the increase in temperature or the presence of bubbles are negligible. Hence, the change in the refractive index is developed mainly by the virtue of density variations. This assumption was consistent with the experimental results described below.

ii. Pressure Field of Ultrasound

Knowing the physics that governs this effect, the emitted field may be found by solving the wave equation for velocity potential $\varphi$ as shown in Eq. (14):

$$\nabla^2 \varphi - \frac{1}{c_0^2}\frac{\partial^2 \varphi}{\partial^2 t} = 0 \quad (14)$$

From which the medium pressure is calculated as shown in Eq. (15):

$$p(\vec{r}, t) = \rho \frac{\partial \varphi}{\partial t} \quad (15)$$

where $\rho$ is the mean density.

b. LAB Experimentation and Simulations

Figure 28:
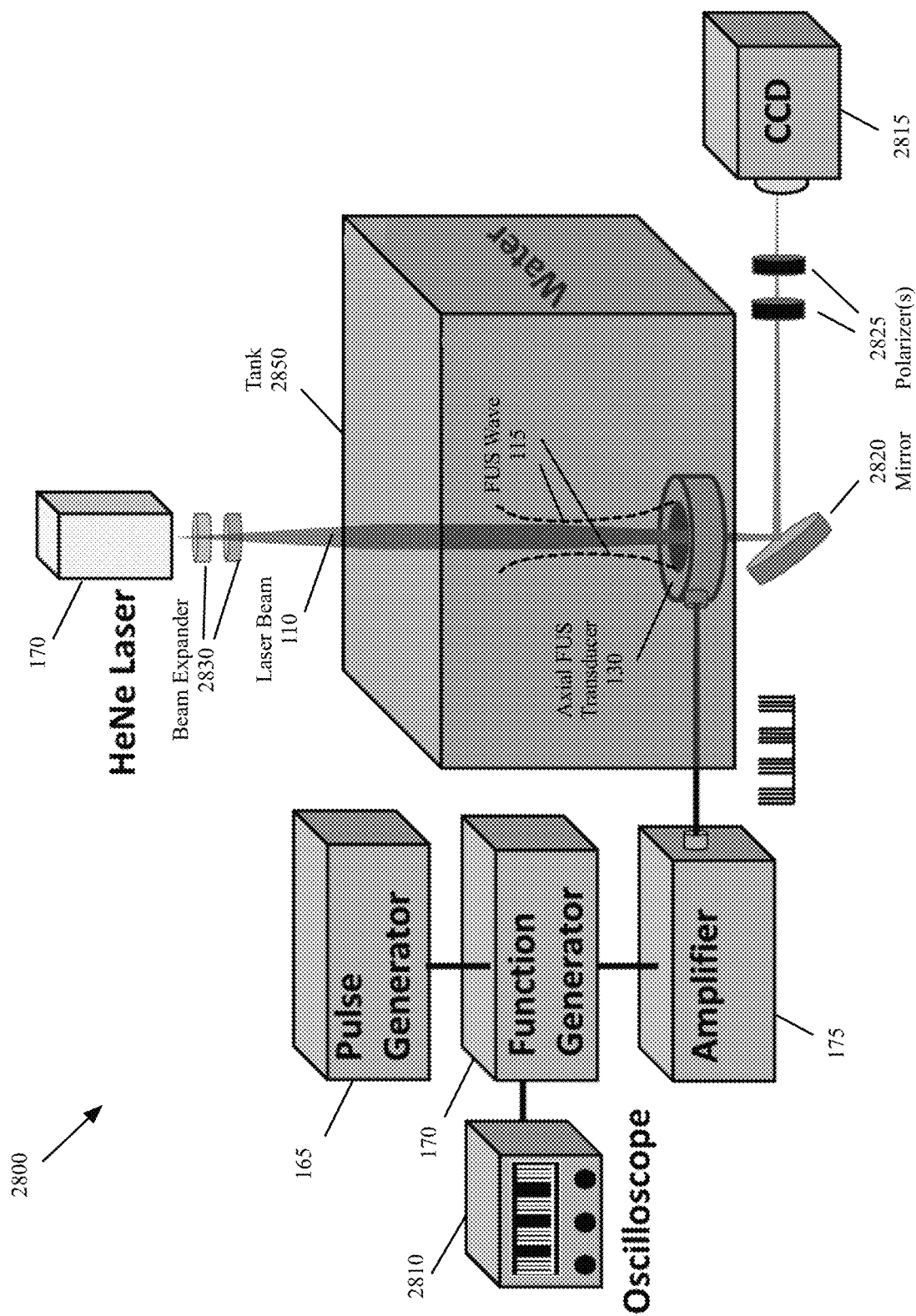
FIG. 28 is a functional diagram illustrating an example experimental set up for a counter propagating alignment of a low-intensity FUS wave and a laser beam, according to various aspects of the present disclosure.

FIG. 28 is a functional diagram illustrating an example experimental set up for a counter propagating alignment of a low-intensity FUS wave and a laser beam, according to various aspects of the present disclosure. With reference to FIG. 28, the system 2800 of FIG. 28 may include a laser device 170, an axial FUS transducer 130, a pulse generator 165, a function generator 170, and an amplifier 175, which may be similar to the corresponding components of FIGS. 1A-1D. The lab system 2800 may include an oscilloscope 2810, a CCD camera 2815, a mirror 2820, one or more polarizers 2825, and a beam expander 2830. In the example of FIG. 28, the laser 170 may be a helium-neon (HeNe) laser.

For a co-propagating alignment of the FUS wave 115 and the laser beam 110, the position of the He—Ne laser 170 and the beam expander 2830 set may be switched with the CCD 2815 and the polarizers set 2825. The FUS transducer 130 may be kept in the same orientation in both co-propagating and counter propagating configurations. The FUS transducer, in the example of FIG. 28, have a center frequency of 3.3 MHz and focal point of 23 mm, with similar dimensions as the FUS transducer 130 of FIG. 2A.

The aperture of the FUS transducer 130 may be filled, or partially filled, with a fluid to form a $C^2AM$ that may be used and implemented in a number of different laser-bases applications as illustrated and described in this disclosure. The fluid deposited in the aperture may be a gas, such as air, a liquid, such as water or oil, or a gel. In the example of FIG. 28, the medium is water (e.g., deionized nanopure water) and the FUS transducer 130 is kept in a tank 2850, which is filled with water.

c. Theoretical Findings of Refractive Index Versus Acoustic

Figure 29:
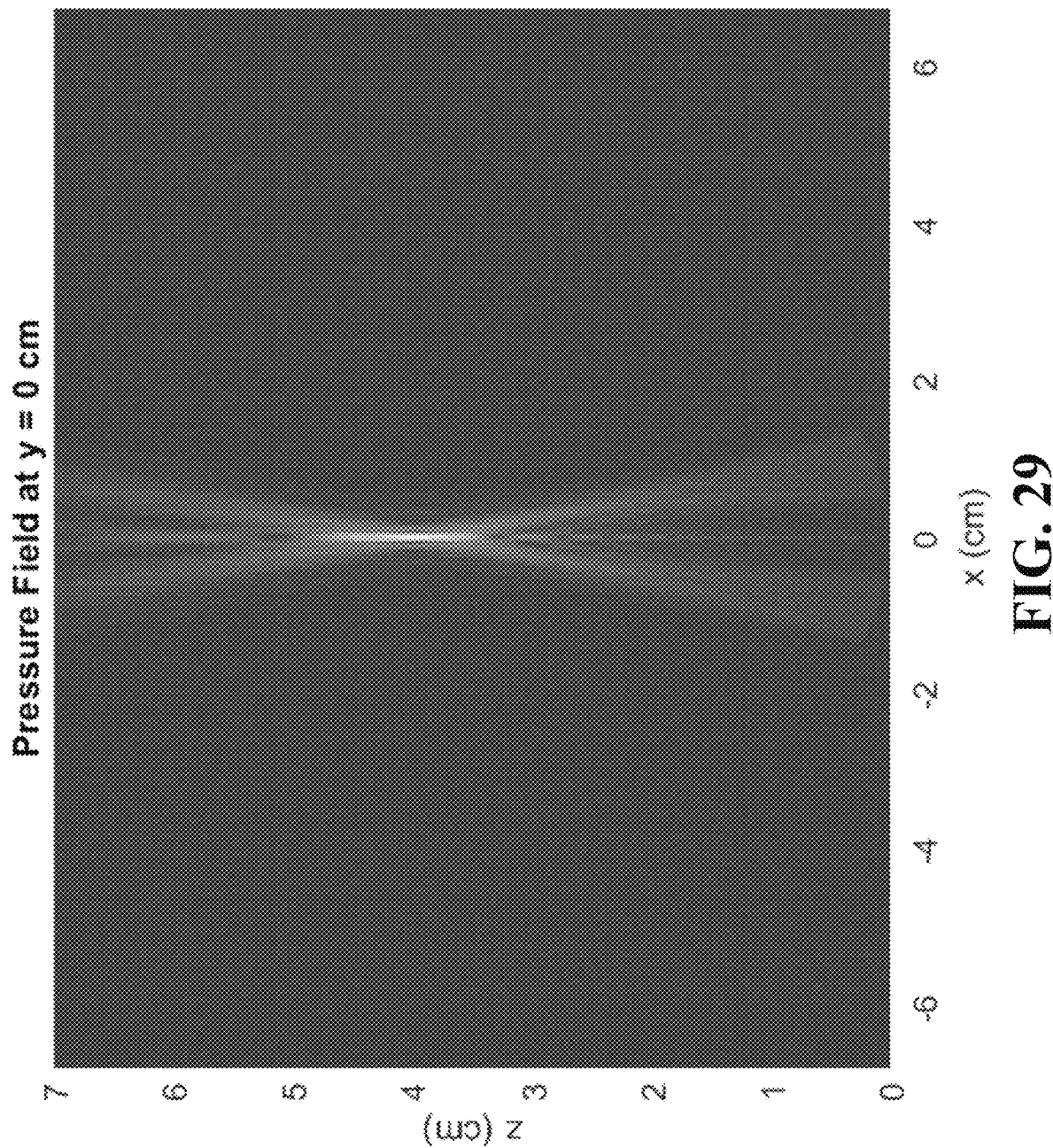
FIG. 29 illustrates the calculated pressure field induced by the acoustic wave in water using numerical methods, according to various aspects of the present disclosure.

An analytical result to obtain the laser behavior in the media affected by acoustic wave using Eq. (13) is quite challenging due to absence of a viable analytical equation for the US pressure field of this type of ring FUS transducer 130. Thus, a numerical analysis (finite element modeling) was implemented to simulate the laser behavior in the acoustic wave induced media. FIG. 29 illustrates the calculated pressure field induced by the acoustic wave in water using numerical methods, according to various aspects of the present disclosure.

i. Simulations and Modeling

The changes in the refractive index as a result of an acoustic wave created by a tours shape FUS transducer in water may be driven. The acoustic wave that is generated by a torus radiator may be numerically modeled using specialized software, such as, for example, and without limitations, FOCUS software or Field II simulation software.

Figure 30:
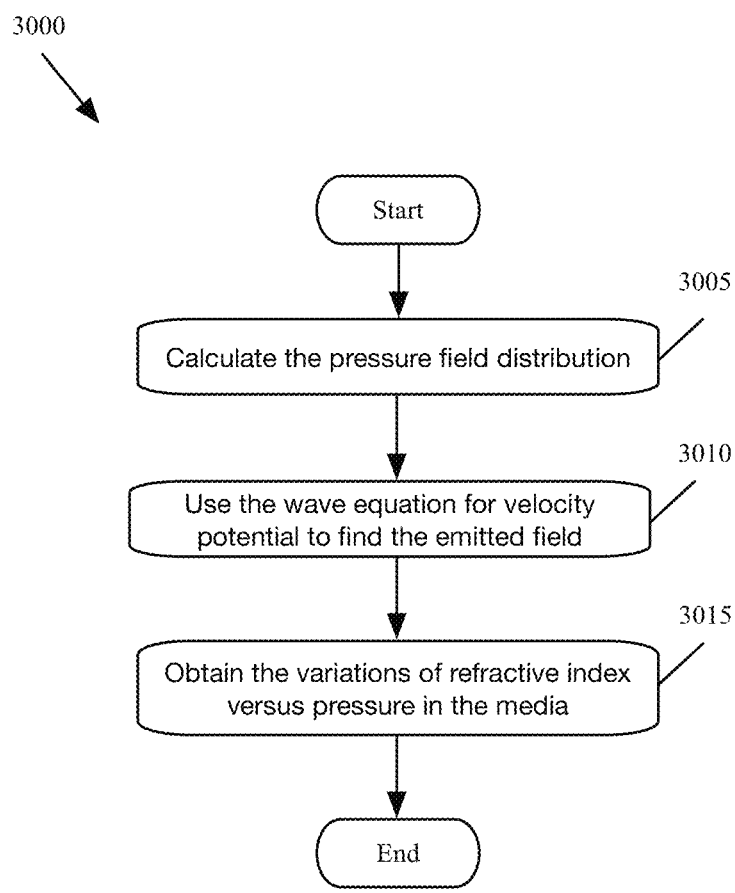
FIG. 30 is a flowchart illustrating an example process for calculation of laser interaction with an acoustic wave, according to various aspects of the present disclosure.

FIG. 30 is a flowchart illustrating an example process 3000 for calculation of laser interaction with an acoustic wave, according to various aspects of the present disclosure. The figure shows the procedure of developing a numerical model in order to analyze the laser entanglement with a US wave.

With reference to FIG. 30, the pressure field distribution may be calculated (at block 3005). For example, Eq. (15) may be used to calculate the pressure field distribution. Next, the emitted field may be found by using the wave equation for velocity potential. For example, Eq. (14) may be used to derive (at block 3010) the values for the emitted field. The variations of refractive index versus pressure in the media may then be obtained (at block 3015). For example, Eq. (13) that expresses the refractive index as function of pressure may be used. The process 3000 may then end.

Figure 31A:
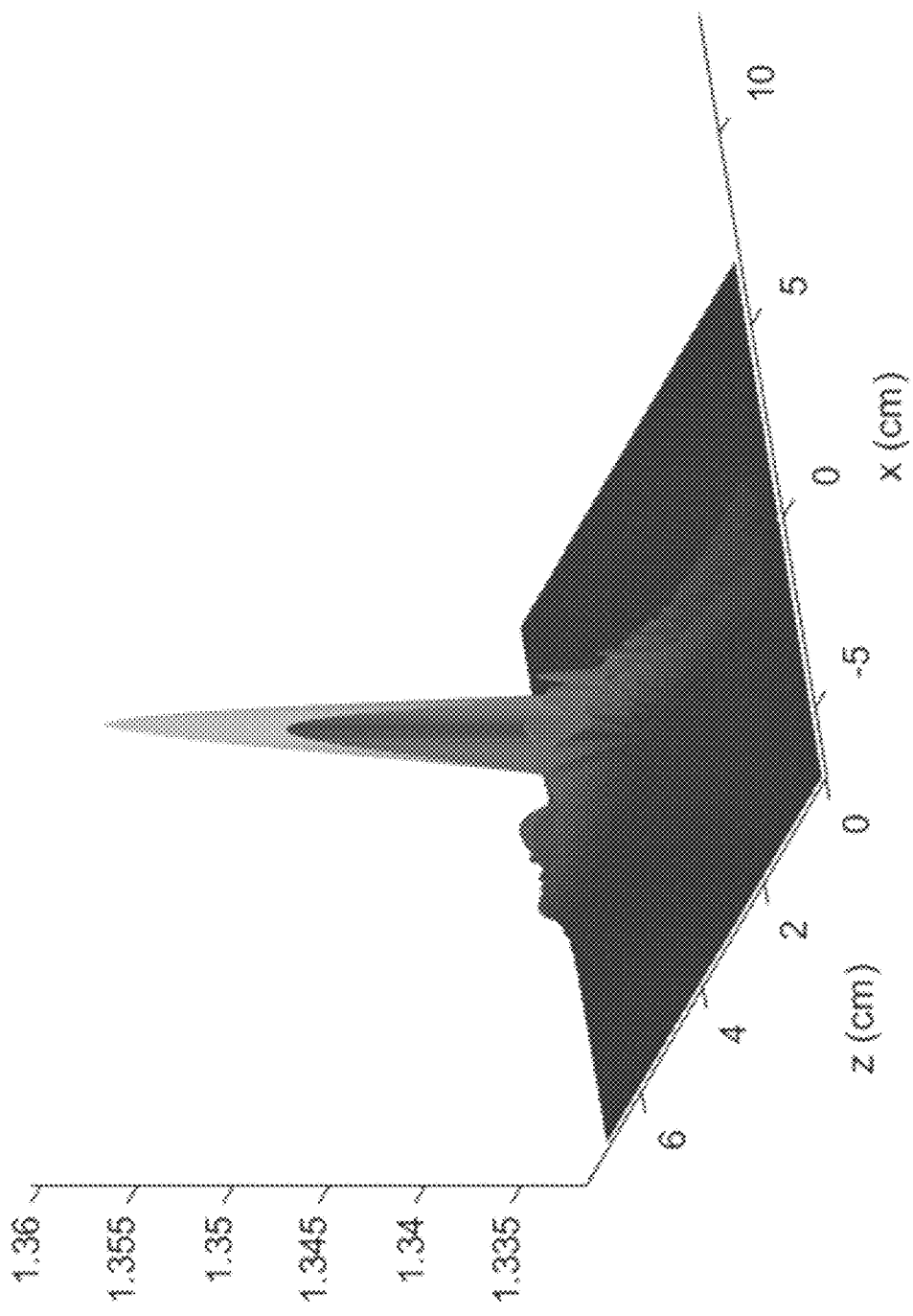
FIG. 31A is a three-dimensional (3D) graph and FIG. 31B is a two-dimensional (2D) graph illustrating the calculated refractive index for water undergoing acoustic modulation, according to various aspects of the present disclosure.
Figure 31B:
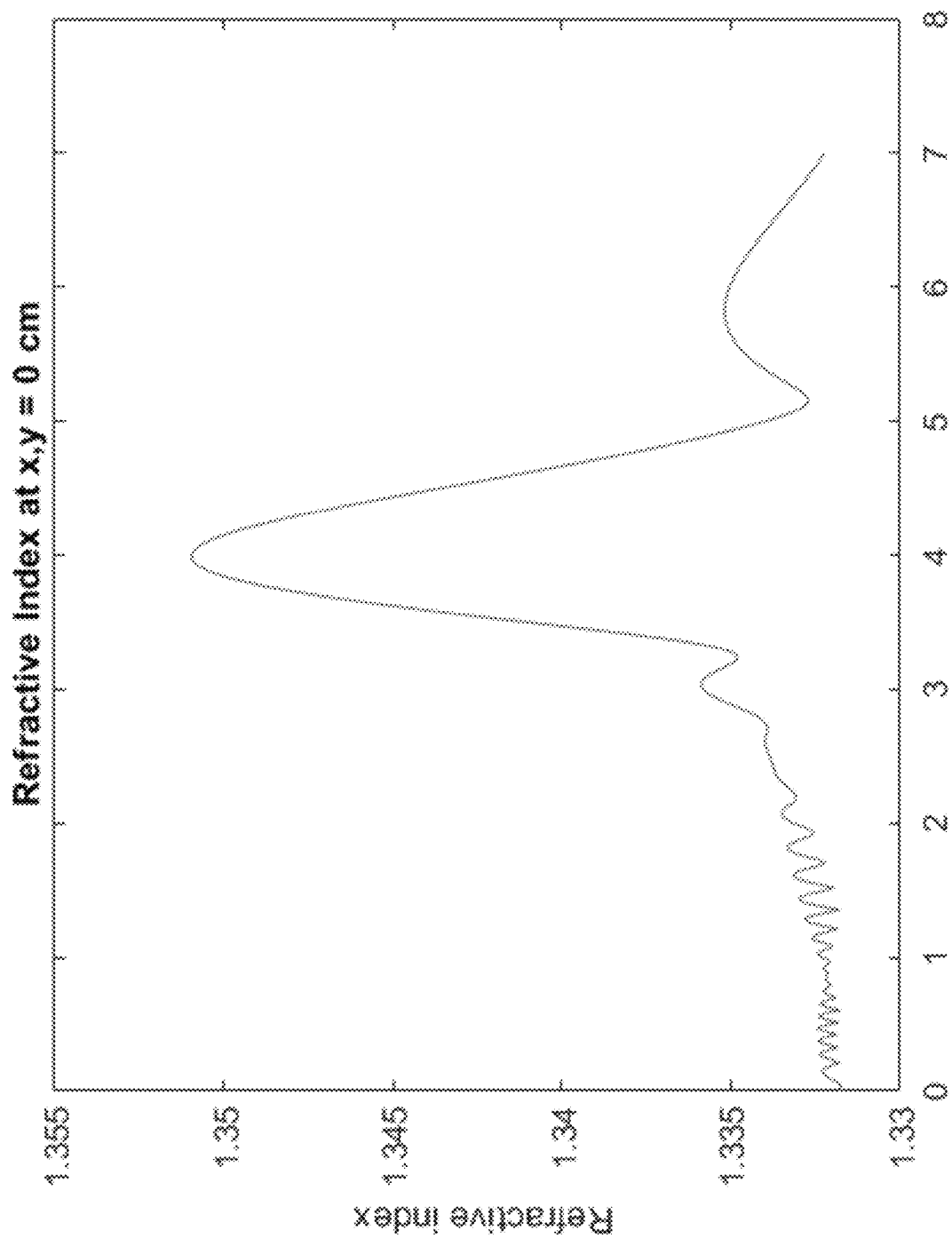
Figure 32A:
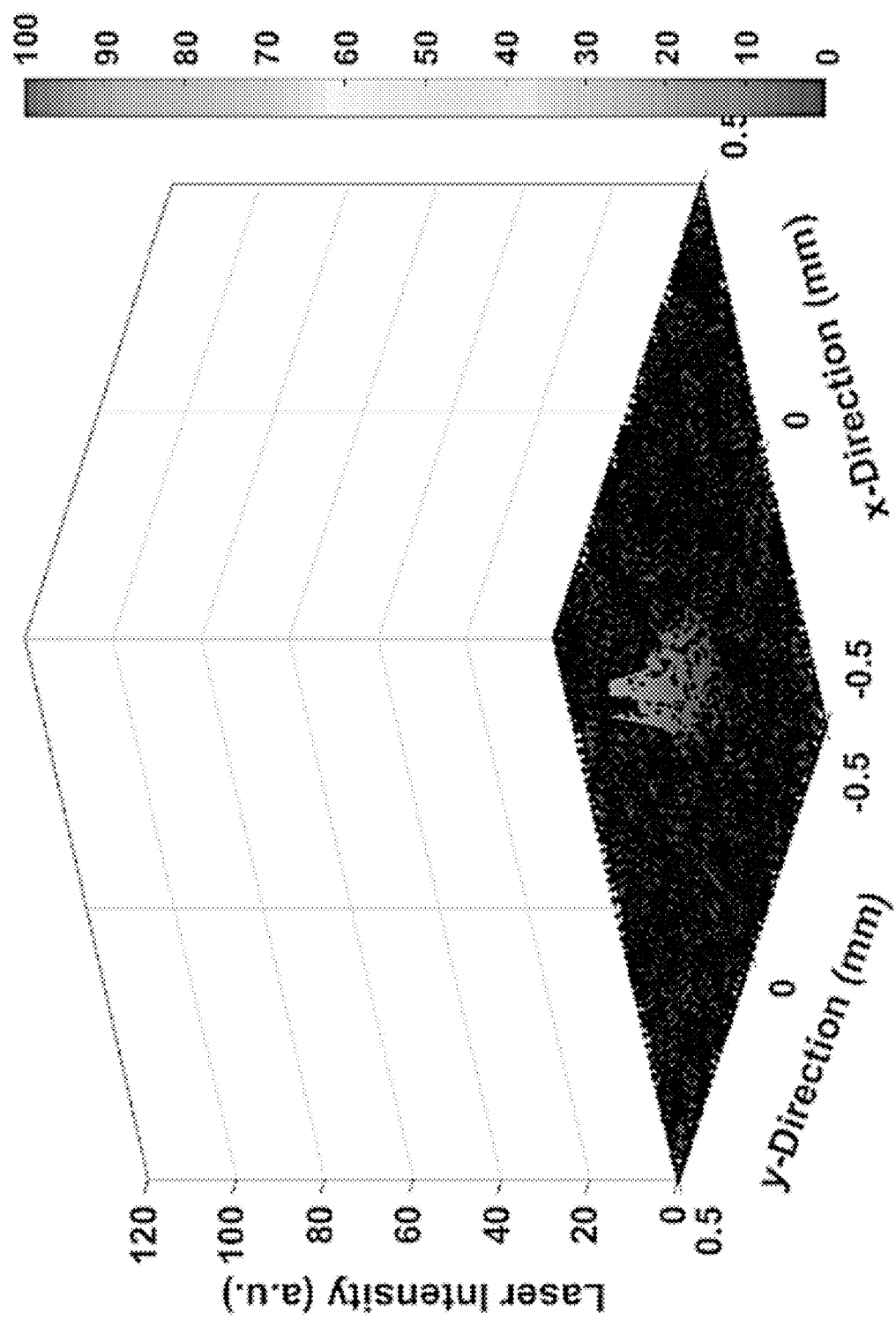
FIGS. 32A-32D show the simulation results of laser intensity using the finite element method, according to various aspects of the present disclosure.
Figure 32B:
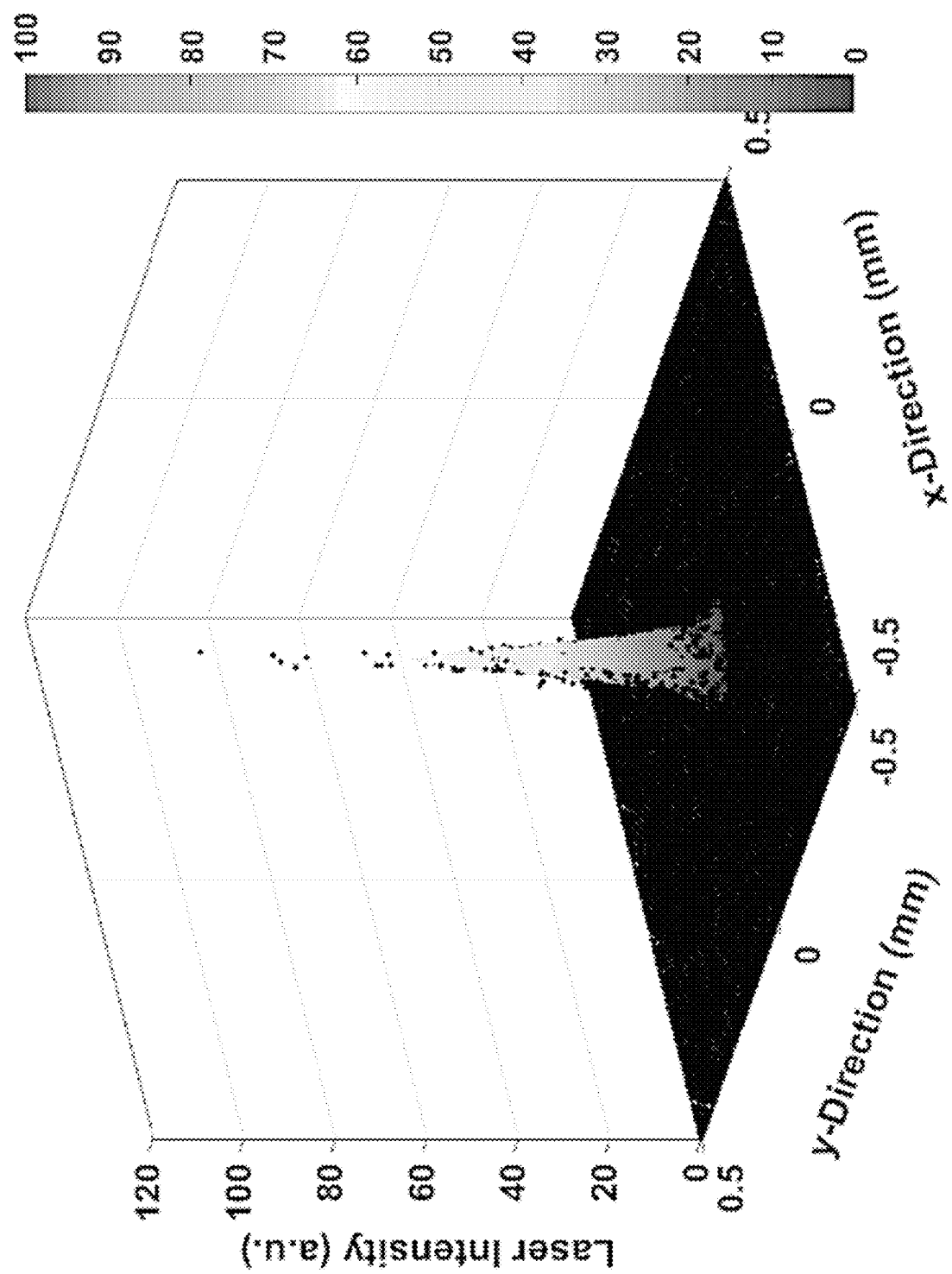
Figure 32C:
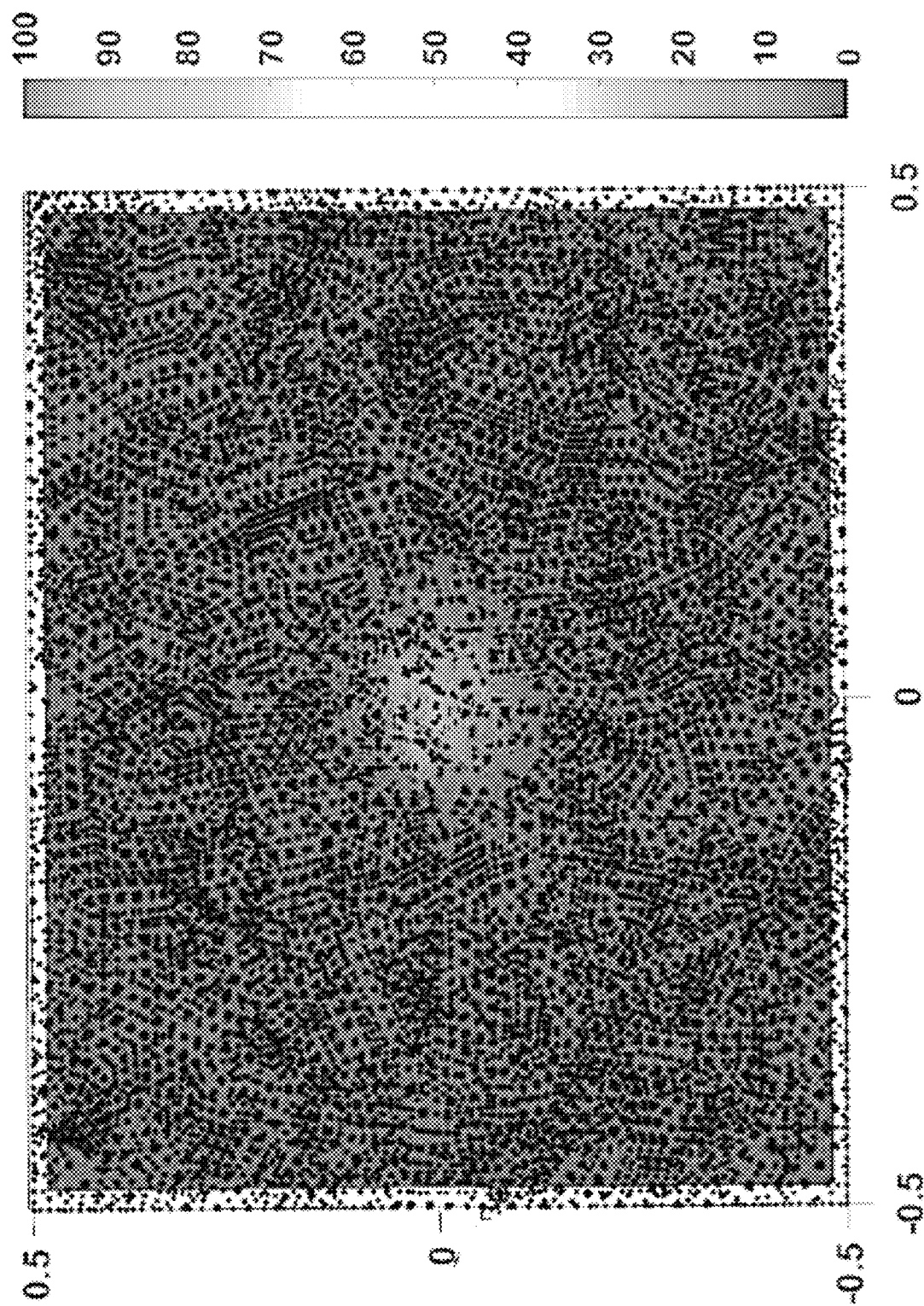
Figure 32D:
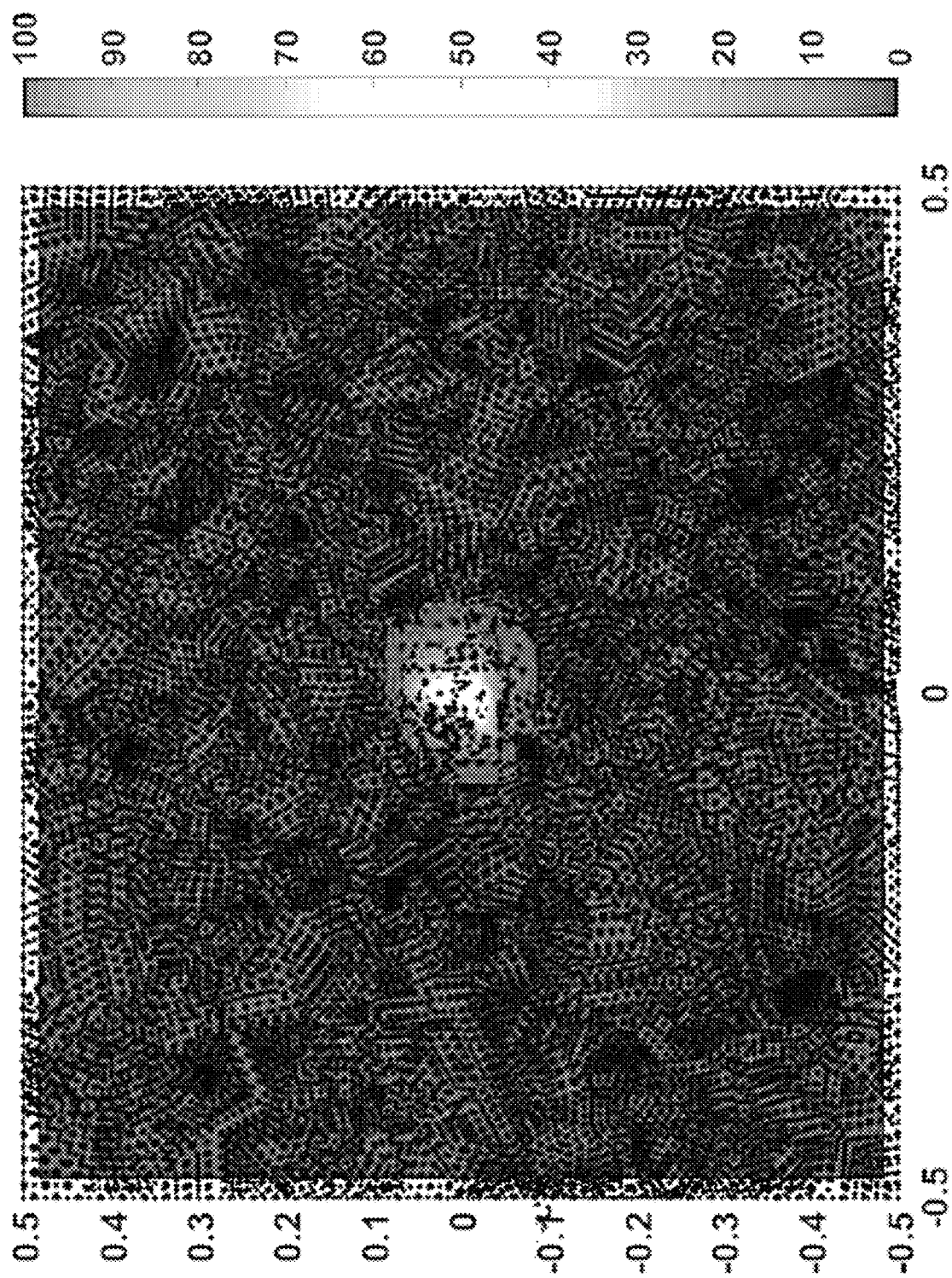

FIG. 31A is a three-dimensional (3D) graph and FIG. 31B is a two-dimensional (2D) graph illustrating the calculated refractive index for water undergoing acoustic modulation, according to various aspects of the present disclosure. With reference to FIGS. 31A-31B, the output of the process 3000 of FIG. 30 is used as solution to the derived equations, Eq. (13), Eq. (14), and Eq. (15). With the refractive index maps 3101 and 3102 obtained via numerical methods, the laser behavior in effected water tank may be studied. Both co-propagating and counter propagating laser and acoustic wave were studied.

ii. Amplification of Light Intensity

The ability of the acoustic wave to increase the intensity of laser in same propagating axis depends primarily on the density change. Obtaining a finite element model (FEM) for calculating the effects of the acoustic wave in laser intensity is required. Using data of FIG. 31 in the finite element model, the light intensity of the laser before and after the acoustic wave may be calculated.

The incident Gaussian beam is affected by the change of refractive index caused by acoustic wave. Table 1 shows the values of input parameters for the finite element model. The table

TABLE 1

| Frequency of ultrasound = 3.3 MHz | Outer Diameter of ultrasound = 30 mm |
|---|---|
| PRF = 100 Hz | Height of ultrasound = 10 mm |
| Voltage of ultrasound = 105 v | Material of transducer: PZT - 5H |

FIGS. 32A-32D show the simulation results of laser intensity using the finite element method, according to various aspects of the present disclosure. The increase in intensity is brought about by the US wave modulation (in this example, in the co-propagating direction). The US wave is off in FIGS. 32A and 32C, and is on in FIGS. 32B and 32D. The black dots are simulated data points.

Figure 33B:
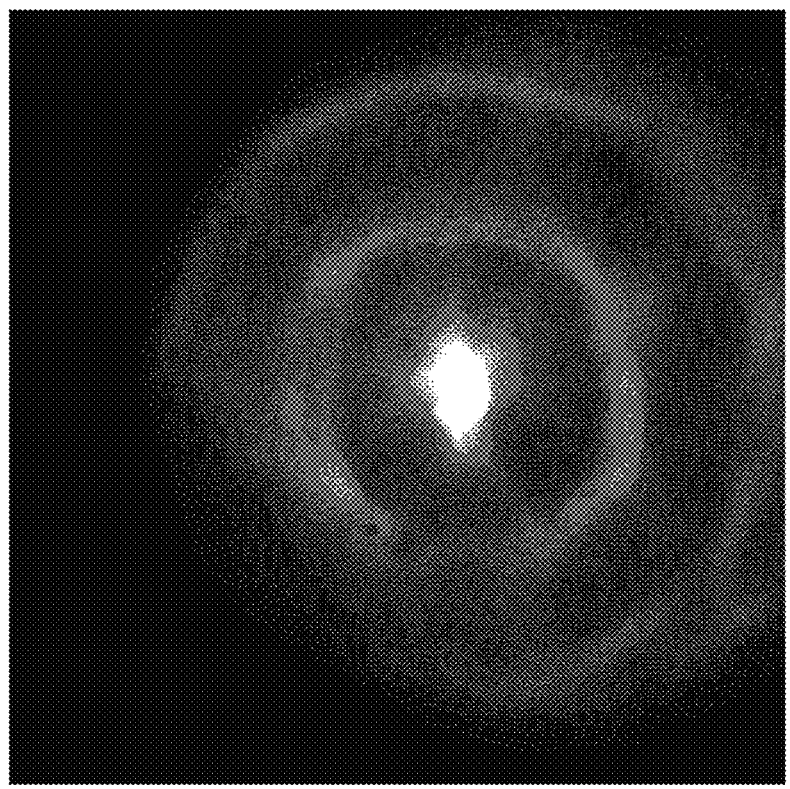
FIGS. 33A-33F illustrate the experimental data that were recorded by the CCD for the co-propagating and counter propagating of laser/US configurations, according to various aspects of the present disclosure.
Figure 33A:
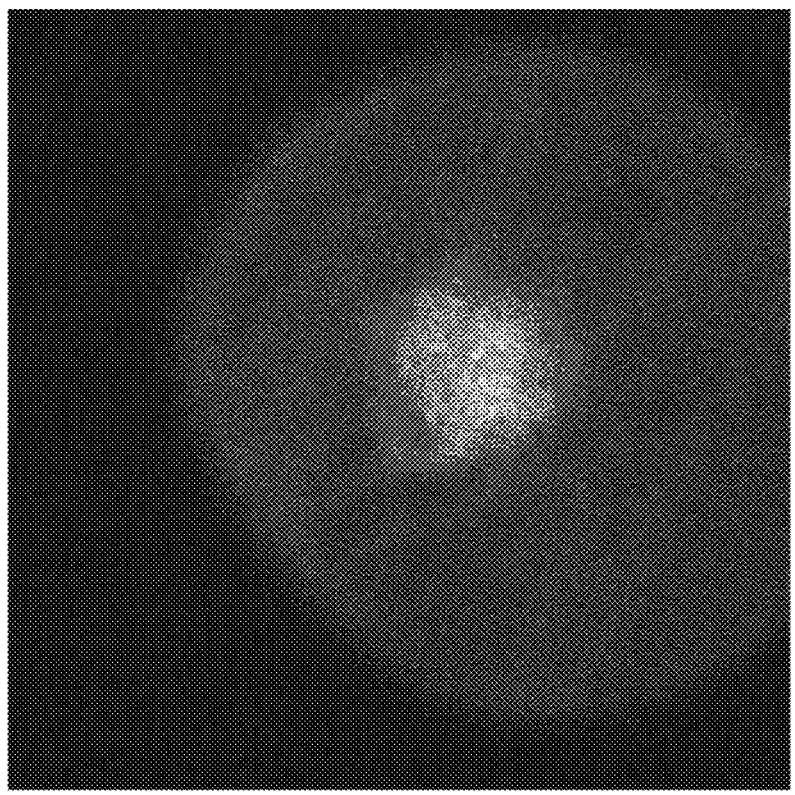
Figure 33D:
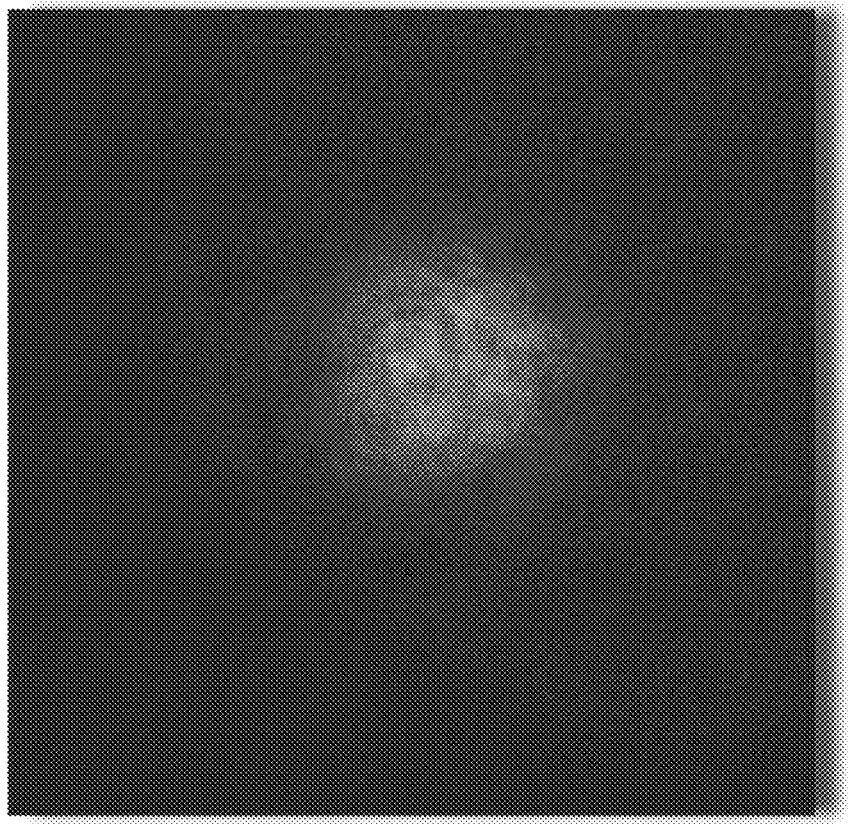
Figure 33C:
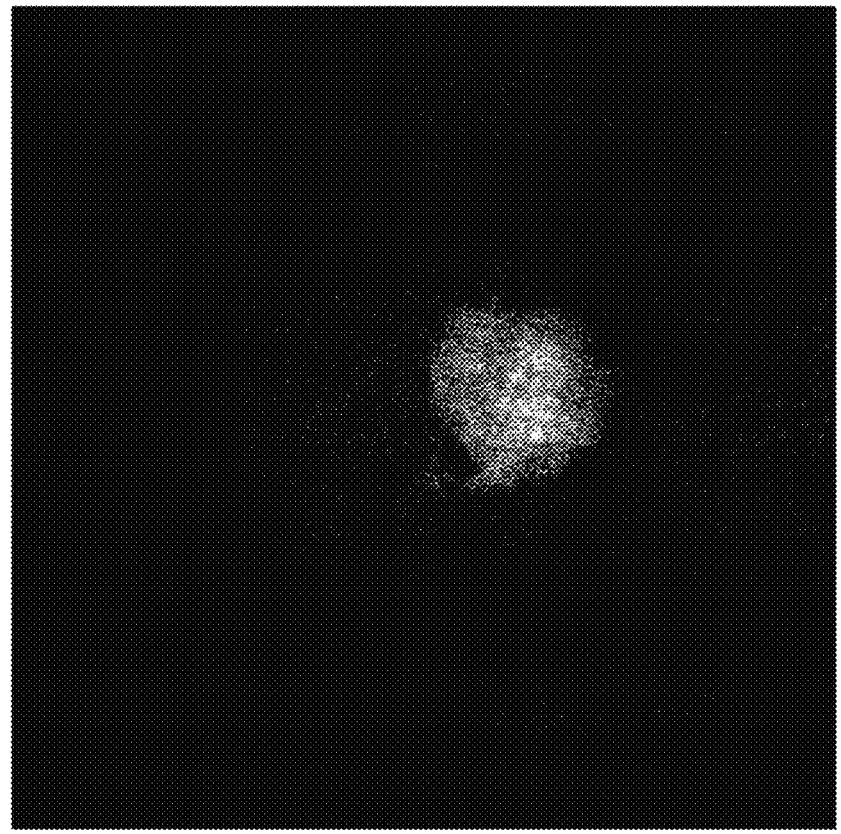
Figure 33E:
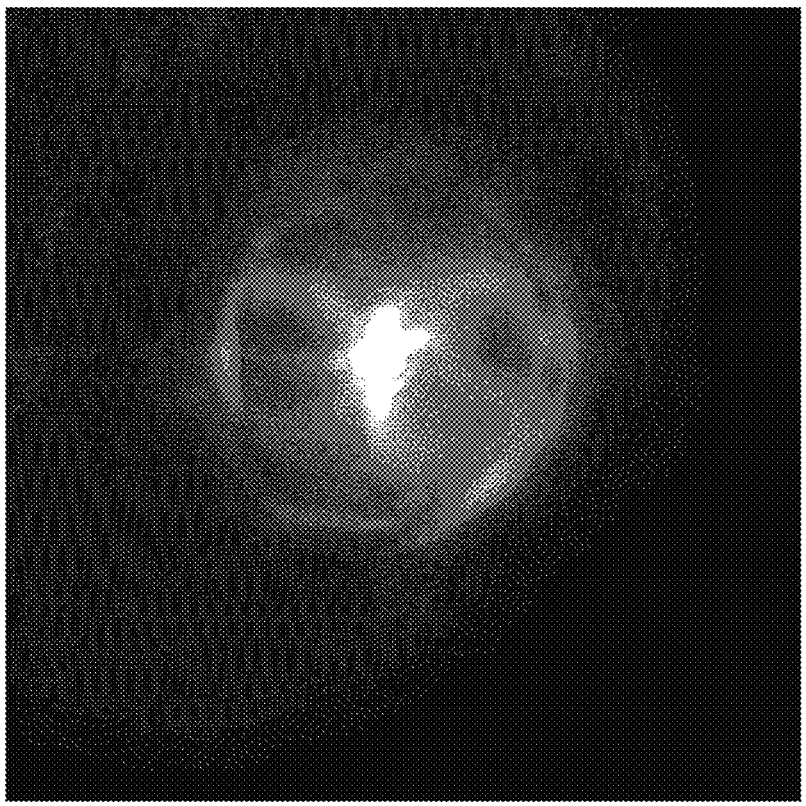
Figure 33F:
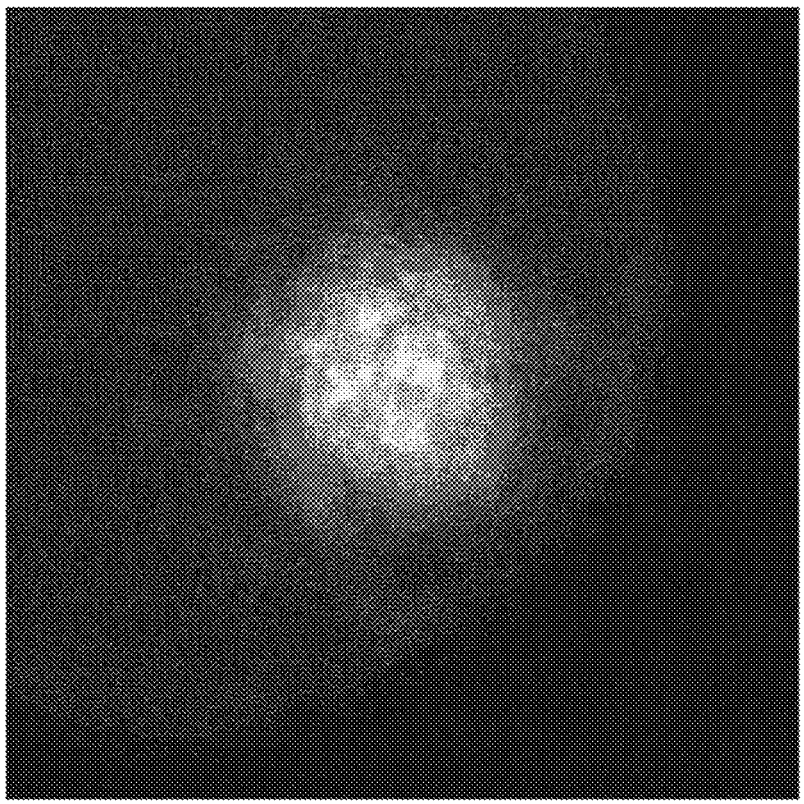

2. Experiment a. Light Intensity Enhanced Unconditionally by Focused US without any Mediator The low power (0.95 mW) laser intensity enhancement was investigated in an unrestrained experimental set up of co and counter propagating of the laser and the US acoustic waves with no mediator substance in deionized nanopure water. FIGS. 33A-33F illustrate the experimental data that were recorded by the CCD for the co-propagating and counter propagating of laser/US configurations, according to various aspects of the present disclosure. FIGS. 33A-33C show results for the co-propagating setup and FIGS. 33D-33F show the results for counter propagating setup.

FIGS. 33A, 33B, and 33C show, respectively, the laser beam recorded by the CCD before the FUS is turned on, during the time the FUS was on, and after the FUS is turned back to off. FIGS. 33D, 33E, and 33F show, respectively, the laser beam recorded by the CCD before the FUS is turned on, during the time the FUS was on, and after the FUS is turned back to off. As shown, the effects of the FUS on the laser is reversible. As soon as the FUS is turned off, the laser beam turns back to its original shape and form with no delay.

Figure 34A:
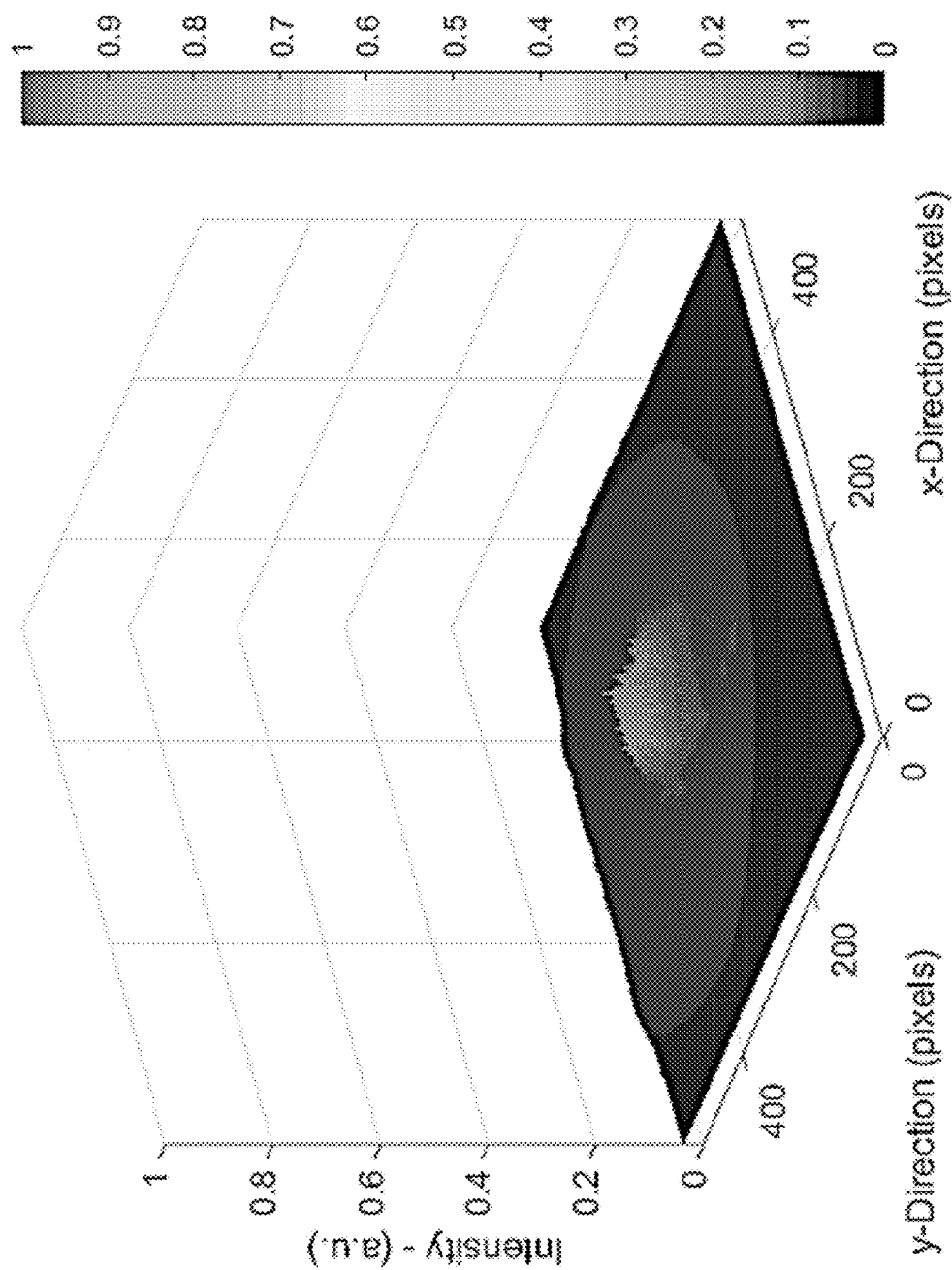
FIGS. 34A-34F illustrate the experimental results for normalized light intensity in the co-propagating setup.
Figure 34B:
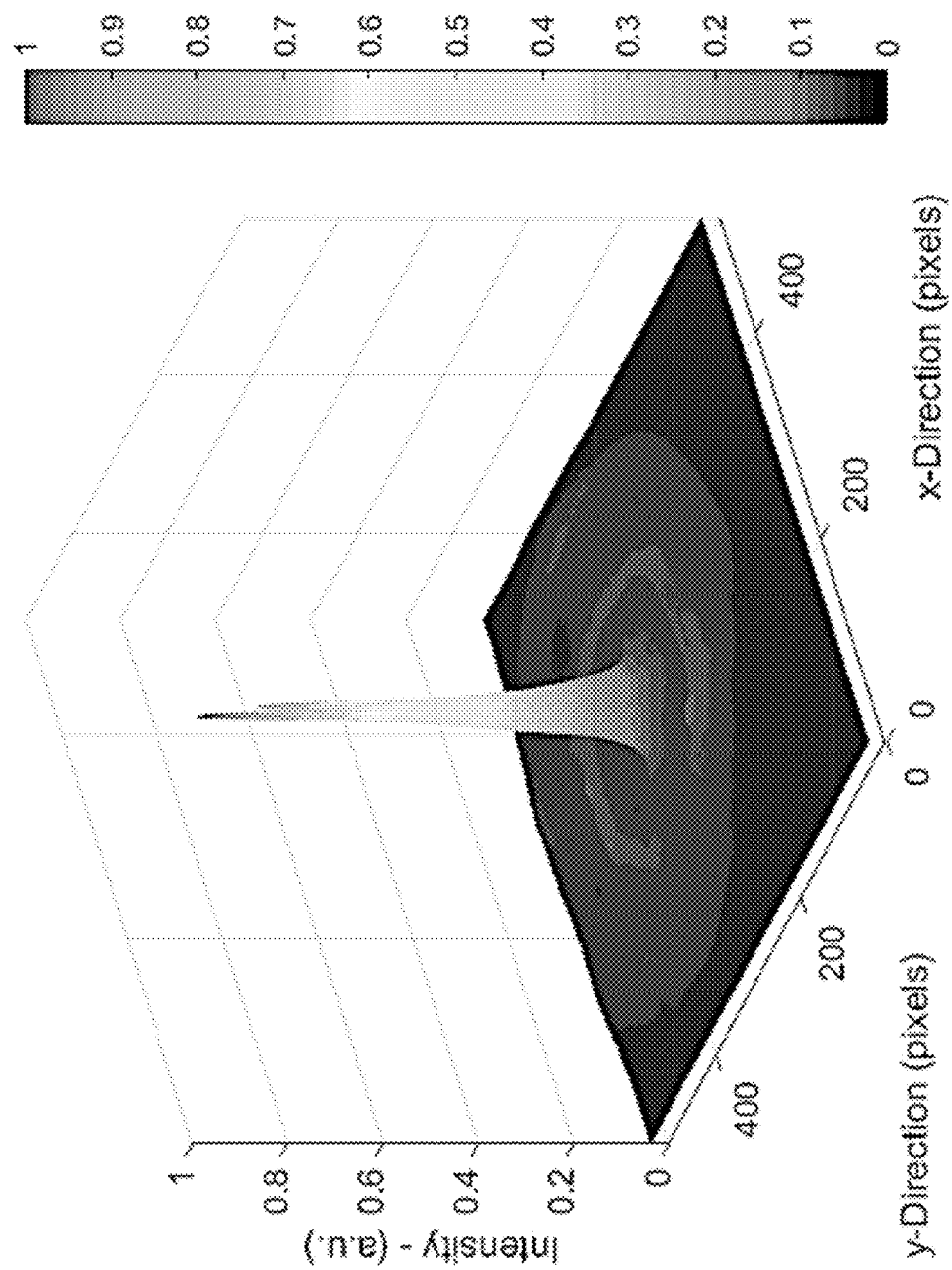
Figure 34C:
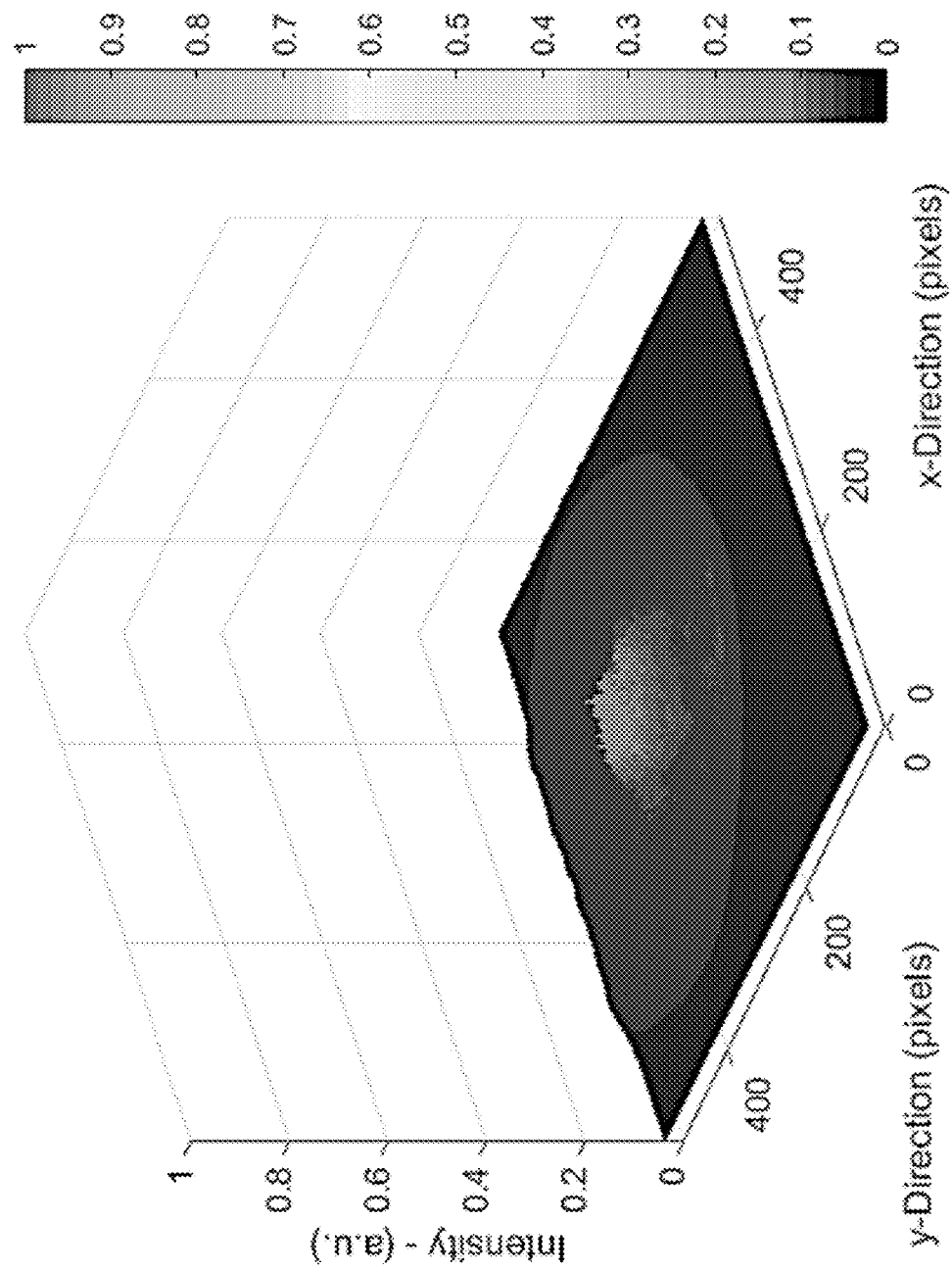
Figure 34D:
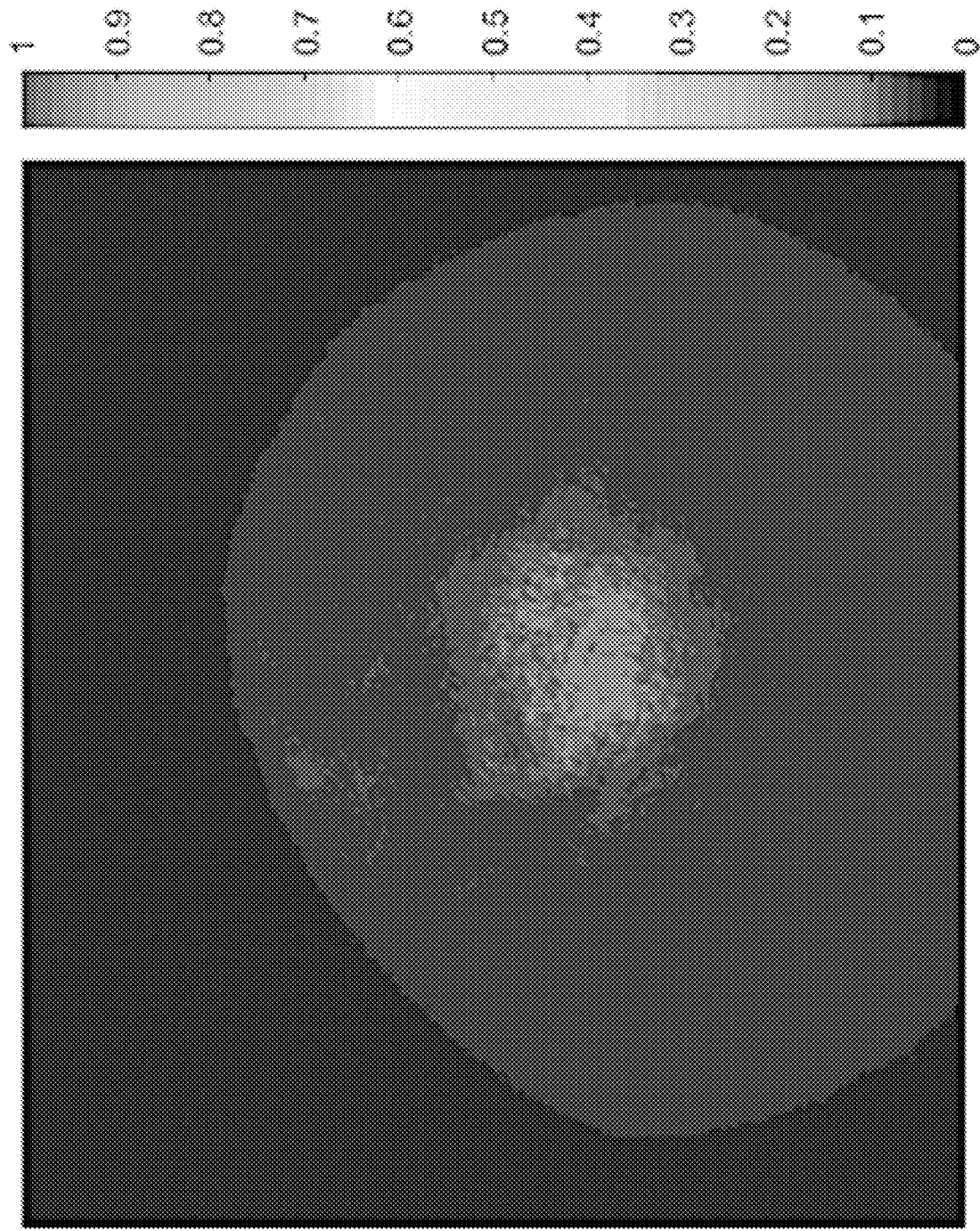
Figure 34E:
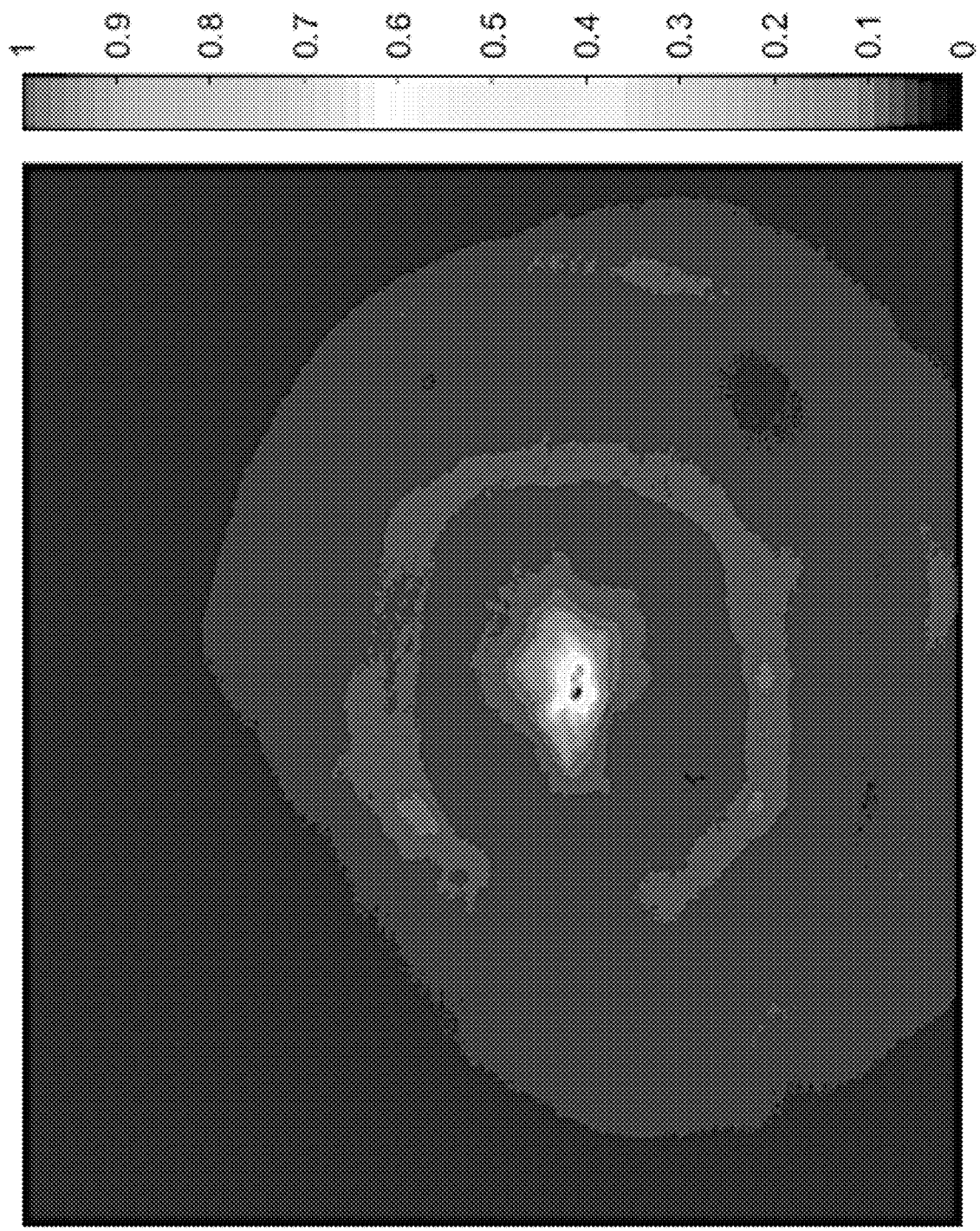
Figure 34F:
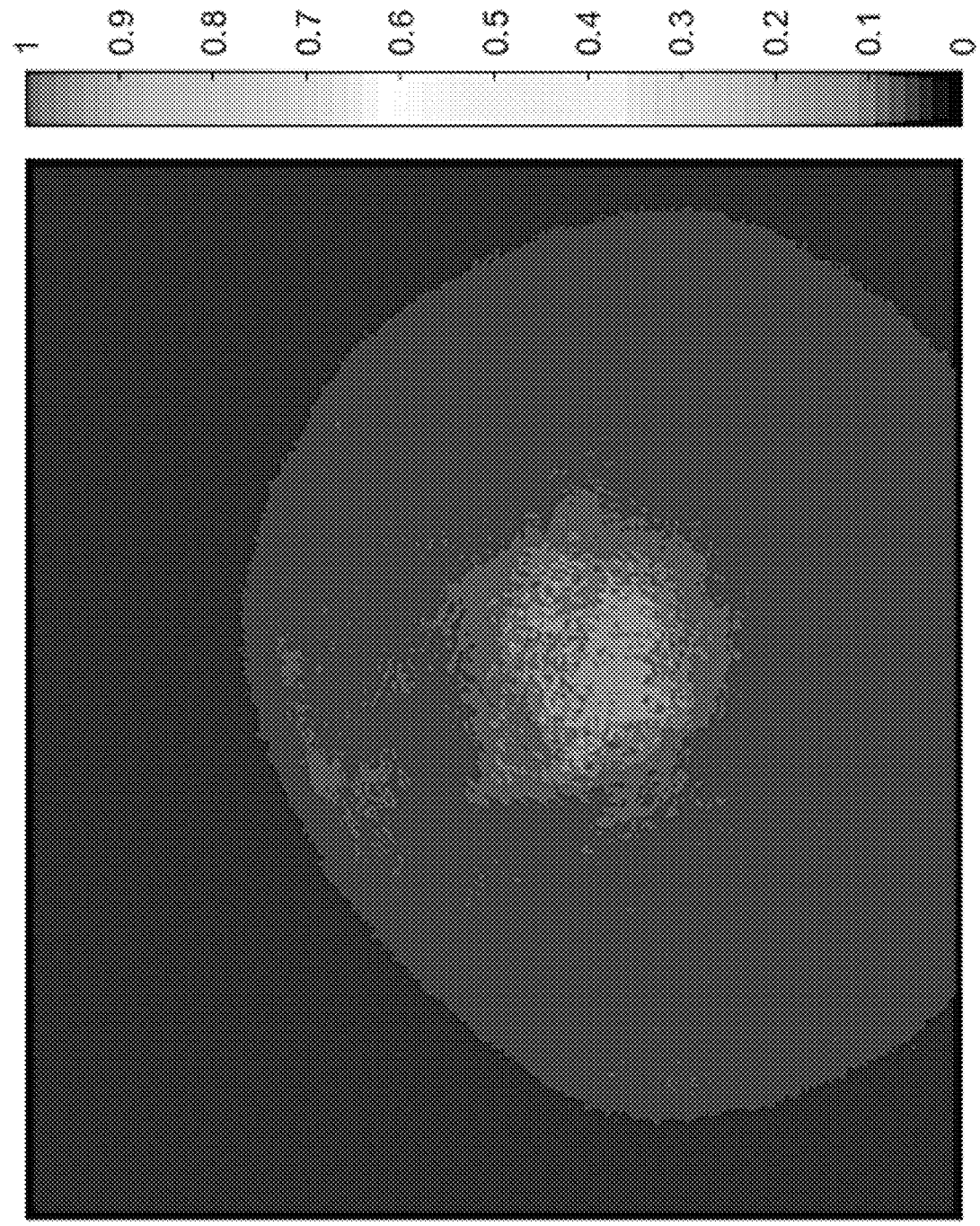

FIGS. 34A-34F illustrate the experimental results for normalized light intensity in the co-propagating setup. FIGS. 34A-34C show the 3D light intensity distributions. FIGS. 34D-34F show the 2D light intensity distribution in order to show the lensing effect of the US modulation.

FIGS. 34A, 34B, and 34C show, respectively, the light intensity before the FUS is turned on, during the time the FUS was on, and after the FUS is turned back to off. FIGS. 34D, 34E, and 34F show, respectively, the light intensity before the FUS is turned on, during the time the FUS was on, and after the FUS is turned back to off. As shown, the effects of the FUS on the laser is reversible. As soon as the FUS is turned off, the laser beam turns back to its original shape and form with no delay.

With reference to FIGS. 33A-33F and 34A-337F, the analysis of the experimental results for above two setups on the intensity distribution of the laser beam profile, demonstrates that the presence of focused US waves brought about a sharp high intensity pick in the center, while when US is off, the laser beam intensity is quite insignificant.

Upon US modulation, the peak intensity of the beam profile increases by about five times, as illustrated in FIGS. 34A and 34B. FIG. 34C, shows that the beam profile returns to the original shape after switching off the US modulation. This reversibility of the beam profile and intensity in the absence of the US modulation shows that the change in the beam profile is due to the modulation of water by US. This reversibility of the light intensity distribution in the absence of the US modulation is an important result of the observations to deduce that the changing in the light intensity distribution is merely the consequence of the US modulation effect, when they are in interaction with the laser as it propagates through the focal area of the focused US. The change in the light intensity distribution is neither the effect of the change in the chemical nor the physical characteristics of the deionized nanopure water.

Figure 35A:
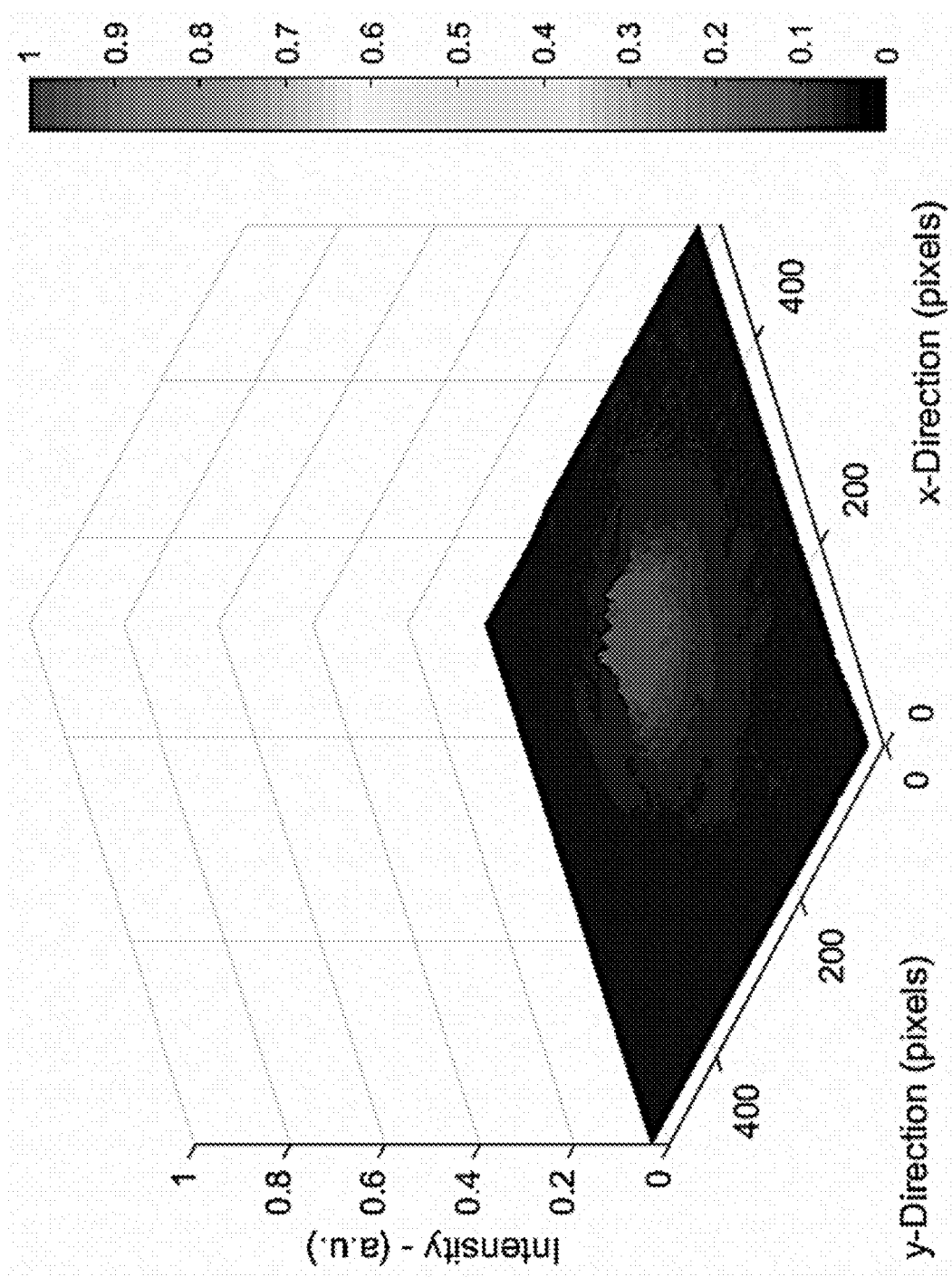
FIGS. 35A-35F illustrate the experimentally observed light intensity in a counter propagating setup, according to various aspects of the present disclosure.
Figure 35B:
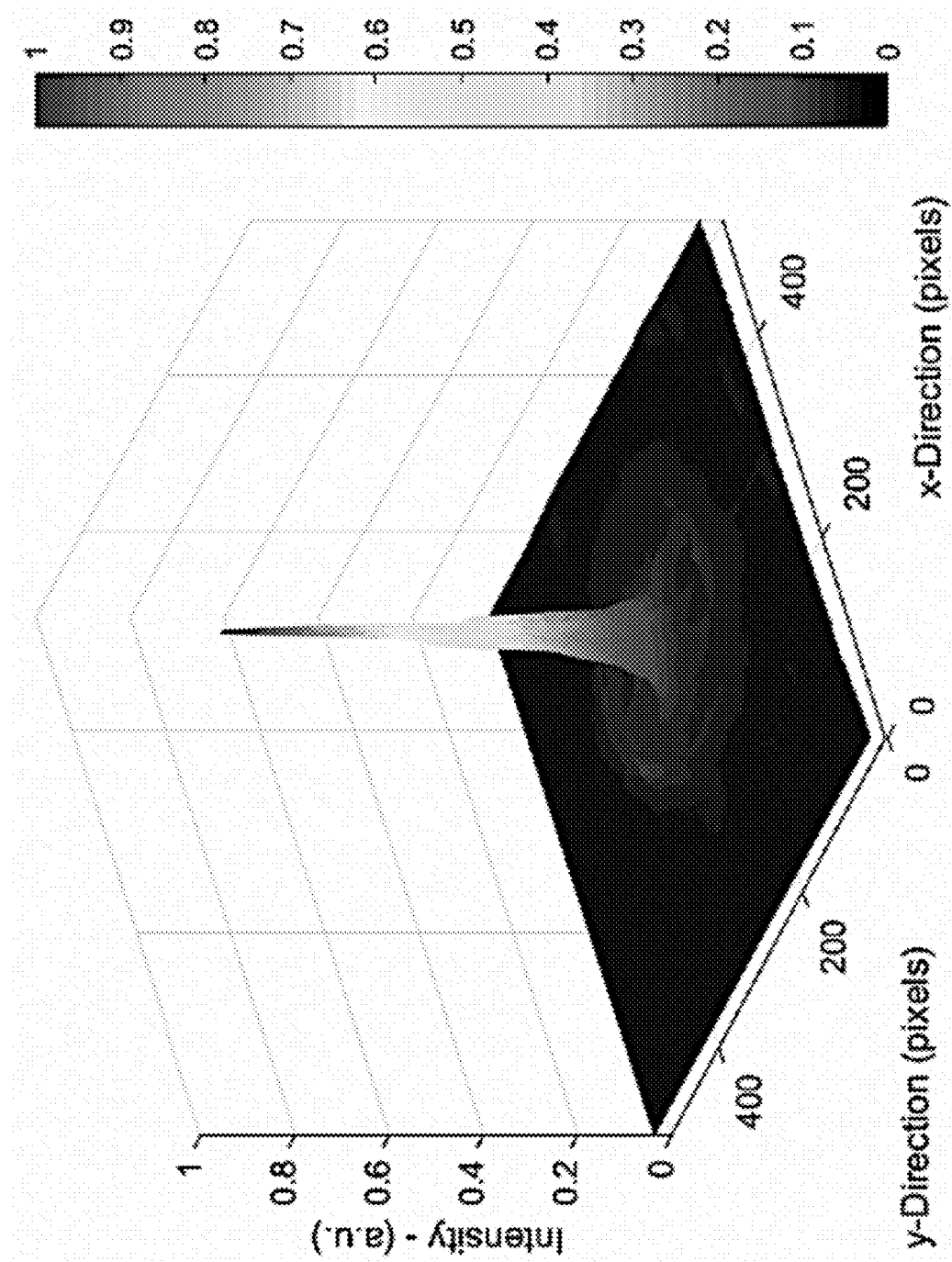
Figure 35C:
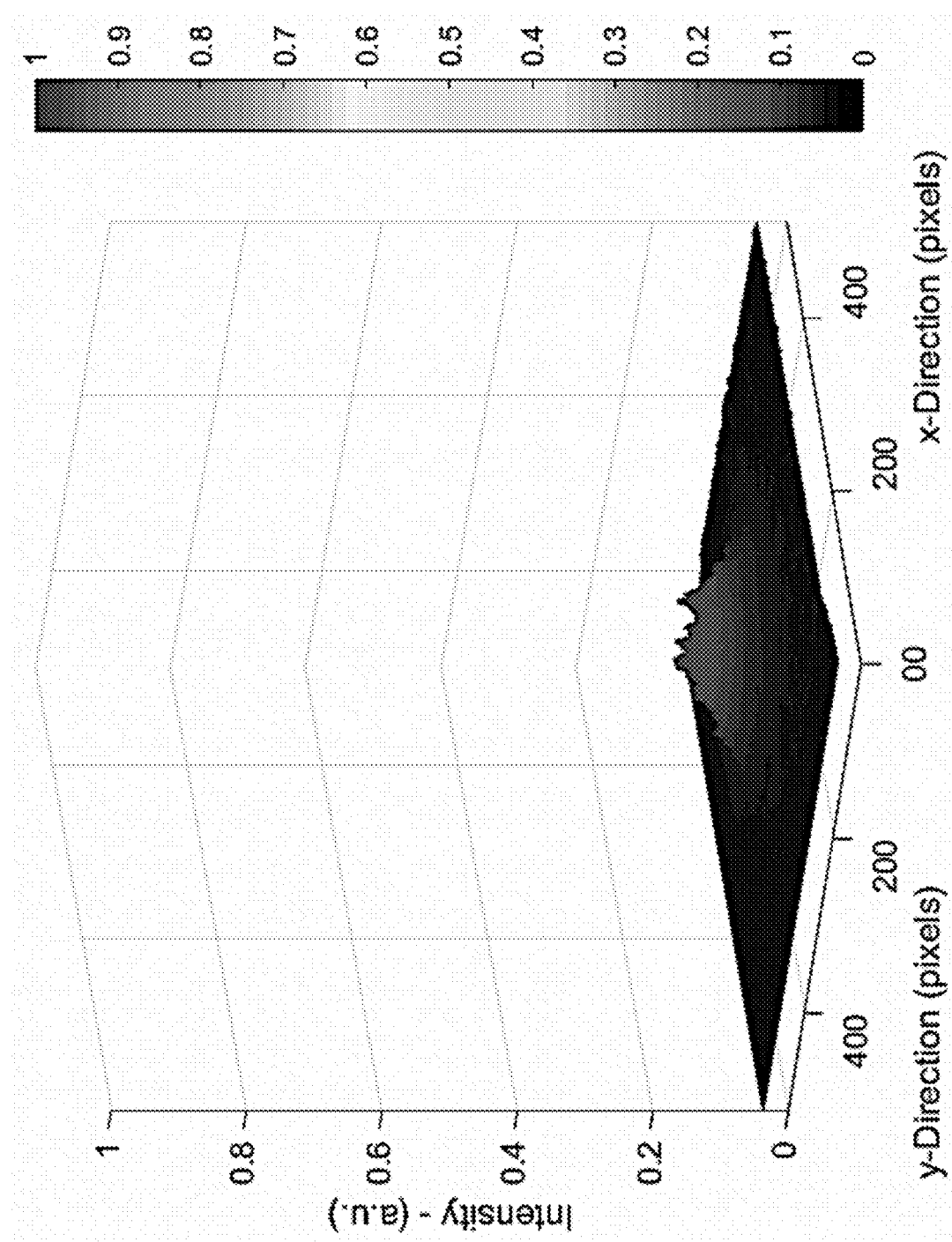
Figure 35D:
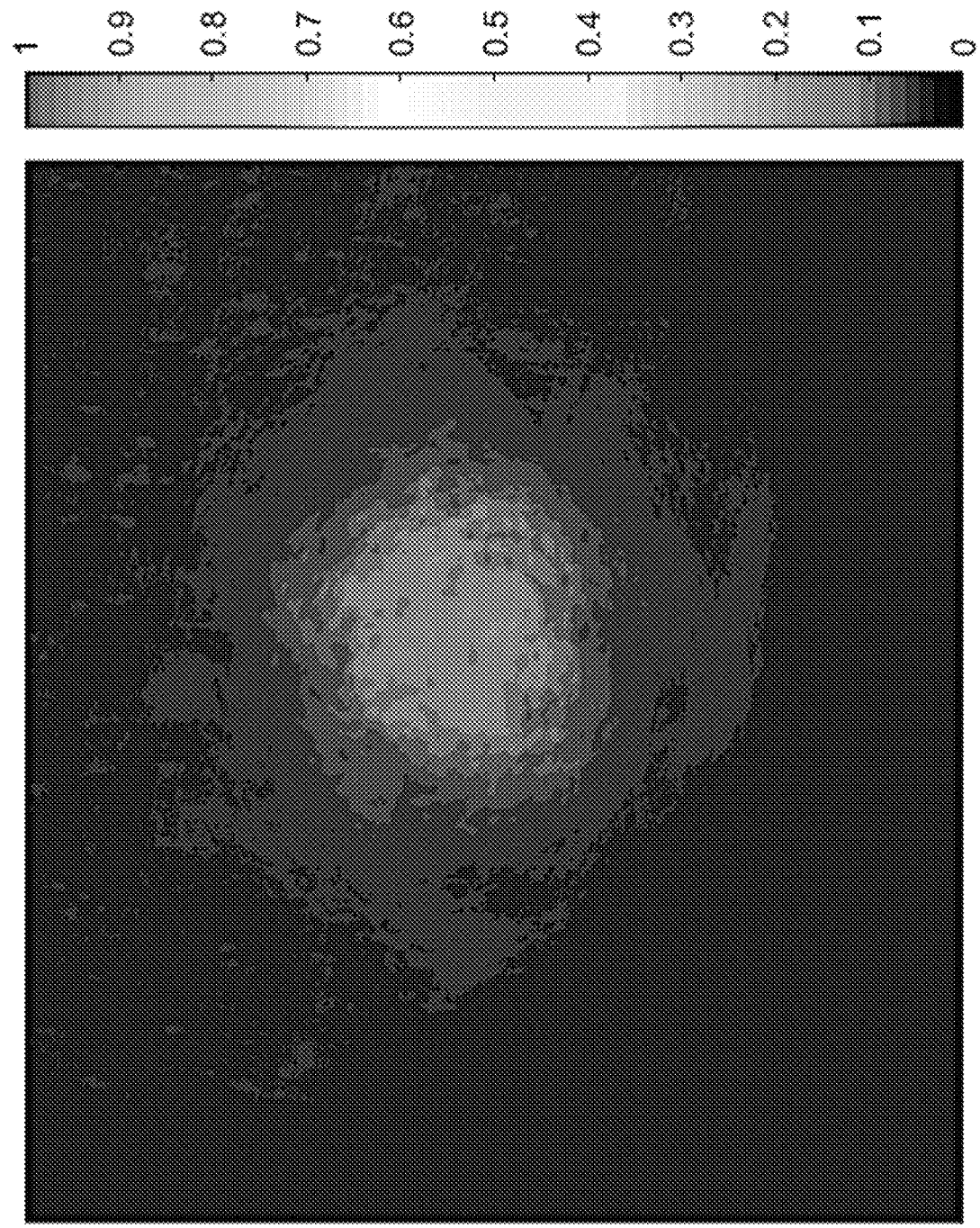
Figure 35E:
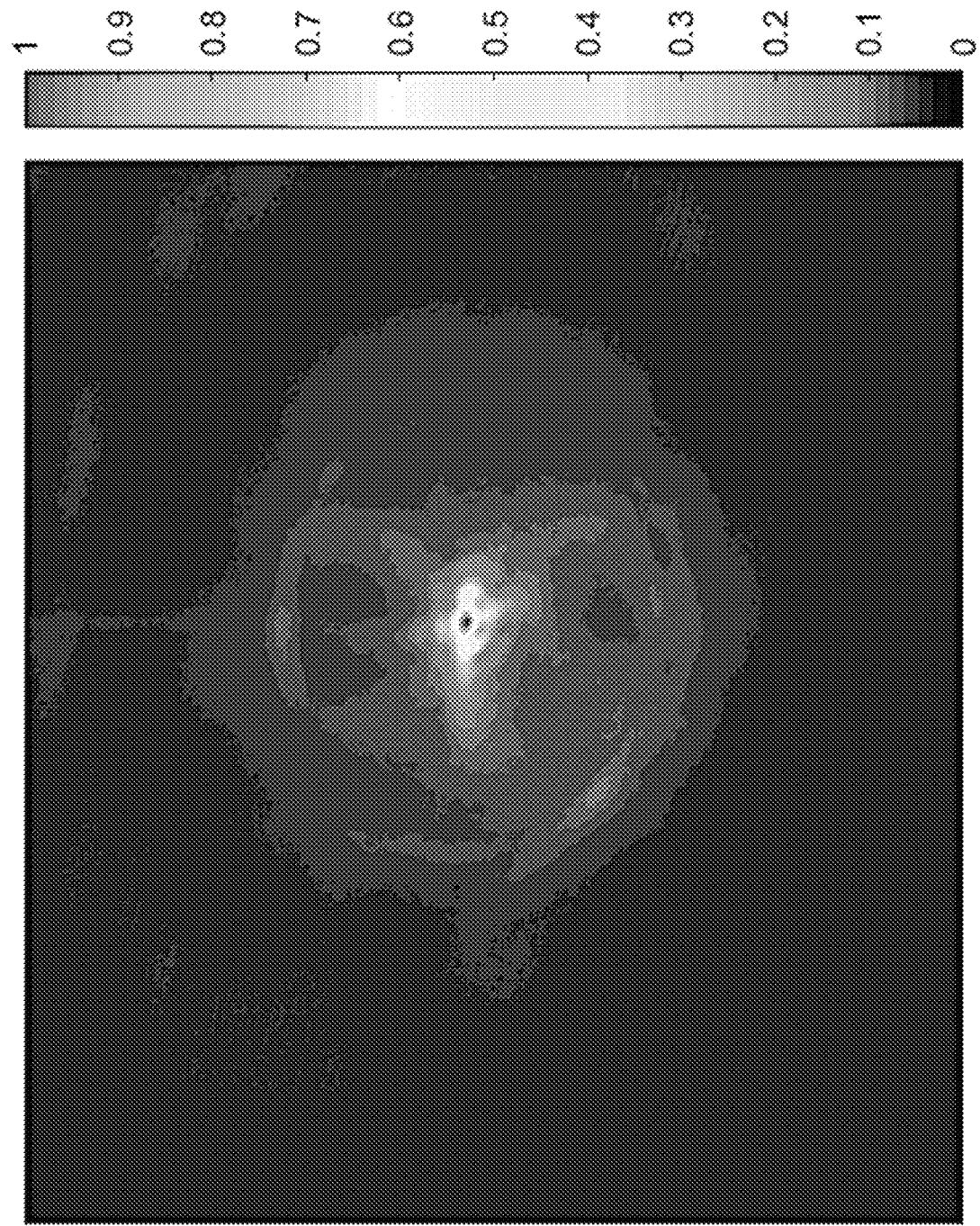
Figure 35F:
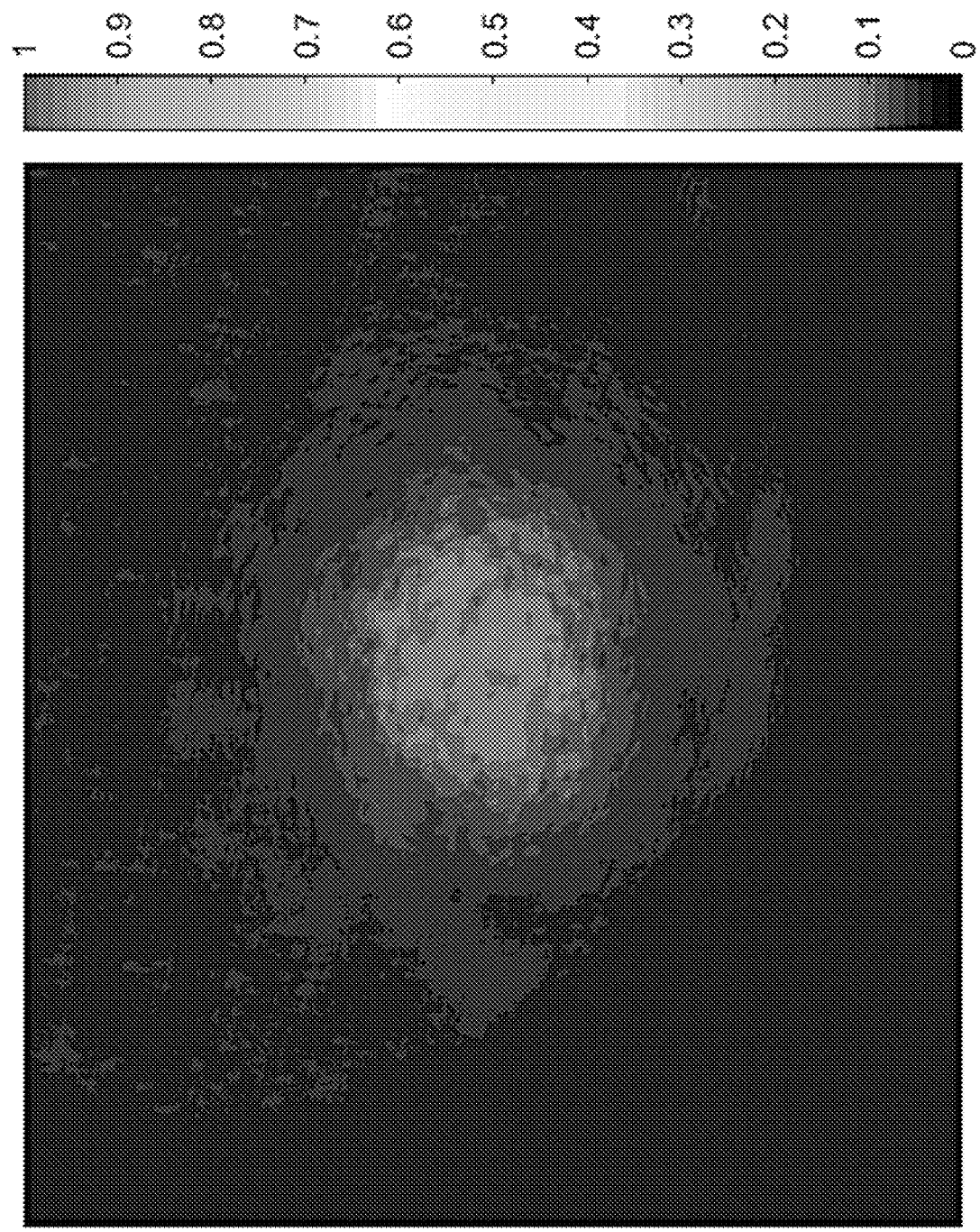

The images shown in FIGS. 33D-33F are recorded with CCD for the counter propagating alignment between laser wave and US wave. With the same analysis on the images of 36D-33F, similar results as the co-propagating experimental setup are obtained, which are shown in FIGS. 35A-35F. FIGS. 35A-35F illustrate the experimentally observed light intensity in a counter propagating setup, according to various aspects of the present disclosure. FIGS. 35A-35C show the 3D light intensity distributions and FIGS. 35A-35C show the 2D light intensity distribution, showing the lensing effect of the US modulation.

FIGS. 35A, 35B, and 35C show, respectively, the 3D light intensity before the FUS is turned on, during the time the FUS was on, and after the FUS is turned back to off. FIGS.

35D, 35E, and 35F show, respectively, the 2D light intensity before the FUS is turned on, during the time the FUS was on, and after the FUS is turned back to off. As shown, the effects of the FUS on the laser is reversible. As soon as the FUS is turned off, the laser beam turns back to its original shape and form with no delay. The results shows in FIGS. 33A-33F, 34A-34F, and 35A-35F were obtained with analysis on the experimental results, which are approximately the same and are consistent with the simulation results that were obtained with numerical methods and illustrated in FIGS. 32A-32D.

b. Beam Profiles of US Modulated Laser Beams

To quantify the changes in the beam diameter, the FWHM is measured for the two co-propagating and counter propagating set ups of the laser and the FUS. FIGS. 36A-36F illustrate the FWHM measurement, according to various embodiments of the present disclosure.

Figure 36A:
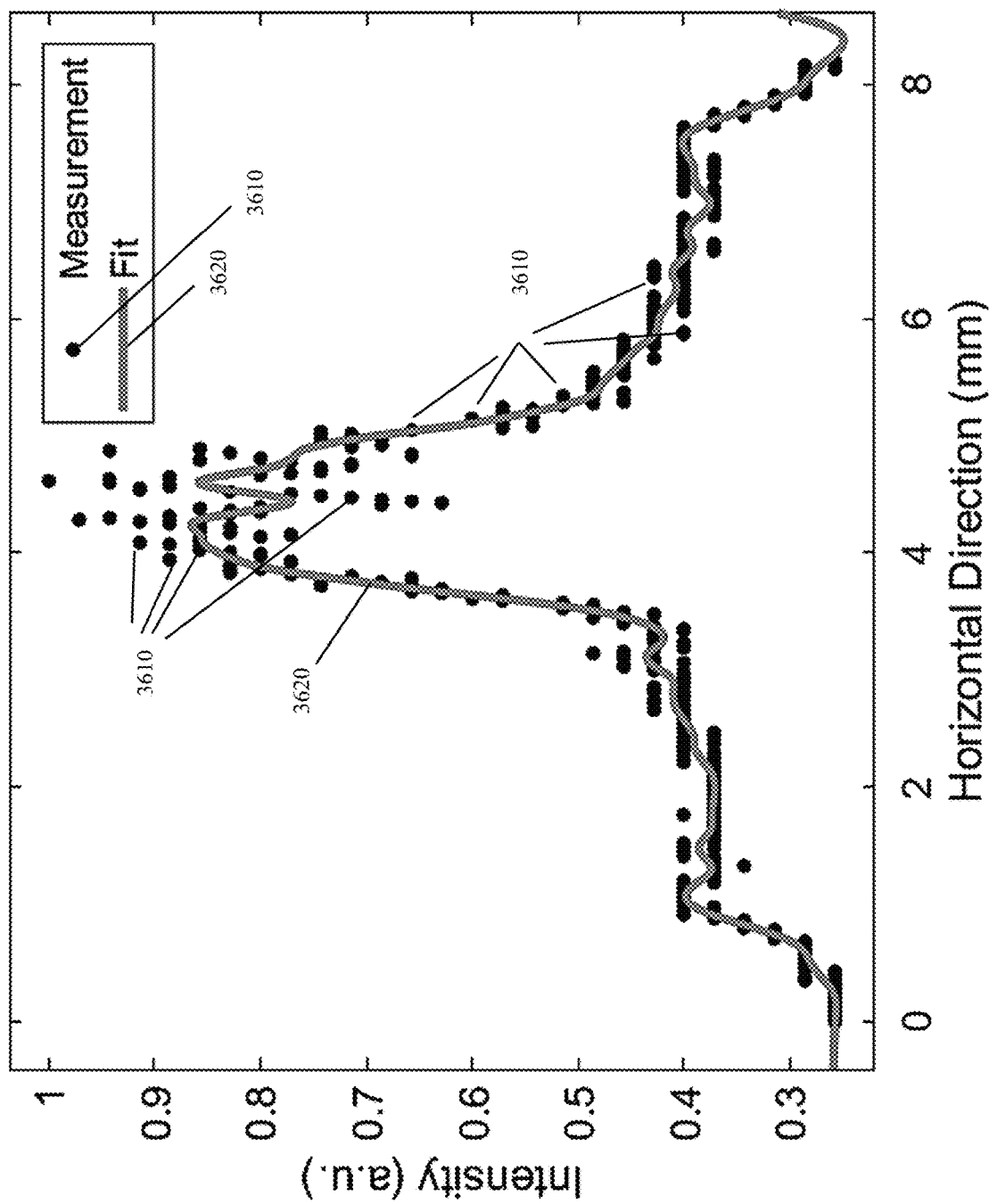
FIGS. 36A-36F illustrate the FWHM measurement, according to various embodiments of the present disclosure.
Figure 36B:
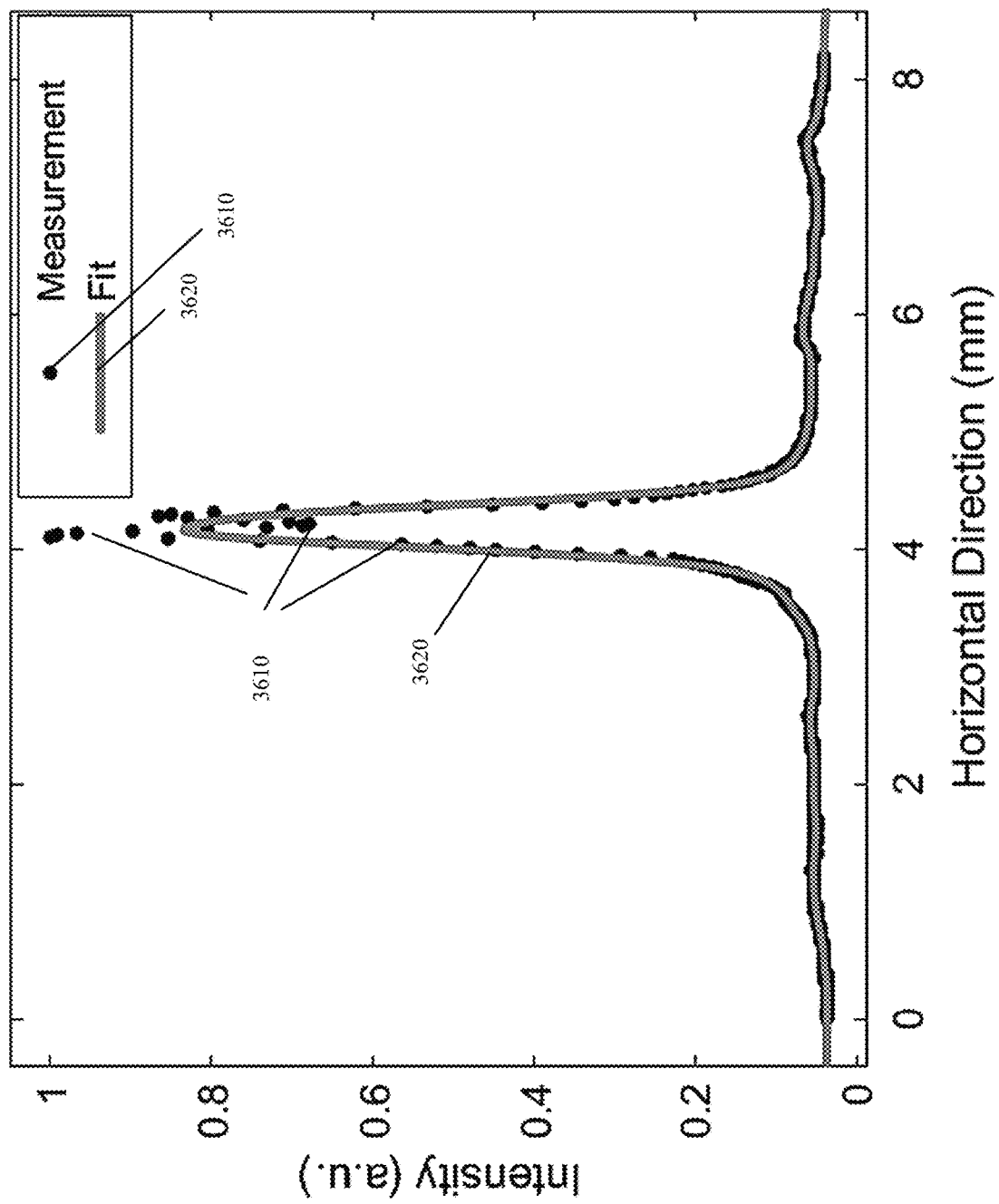
Figure 36C:
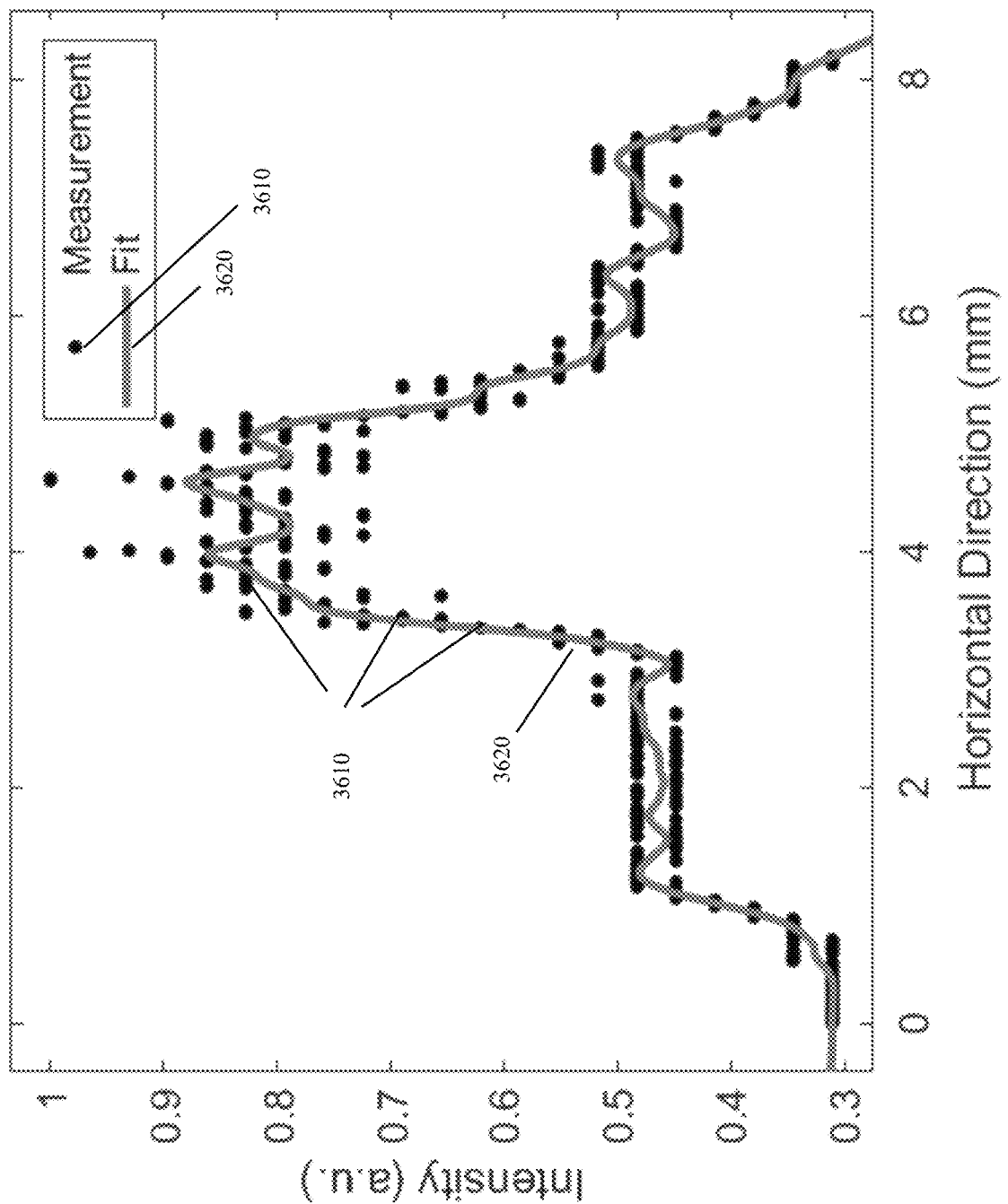
Figure 36D:
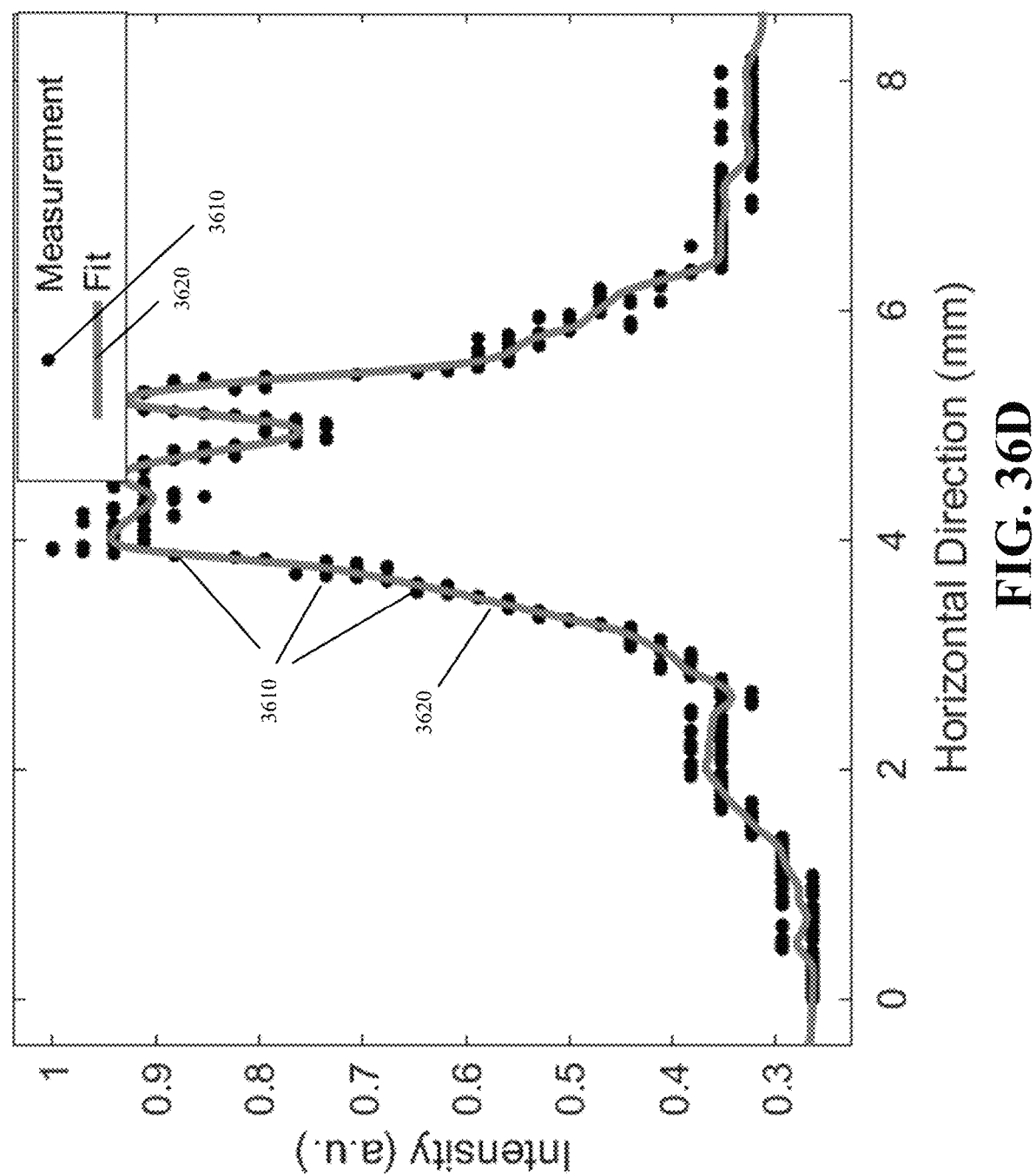
Figure 36E:
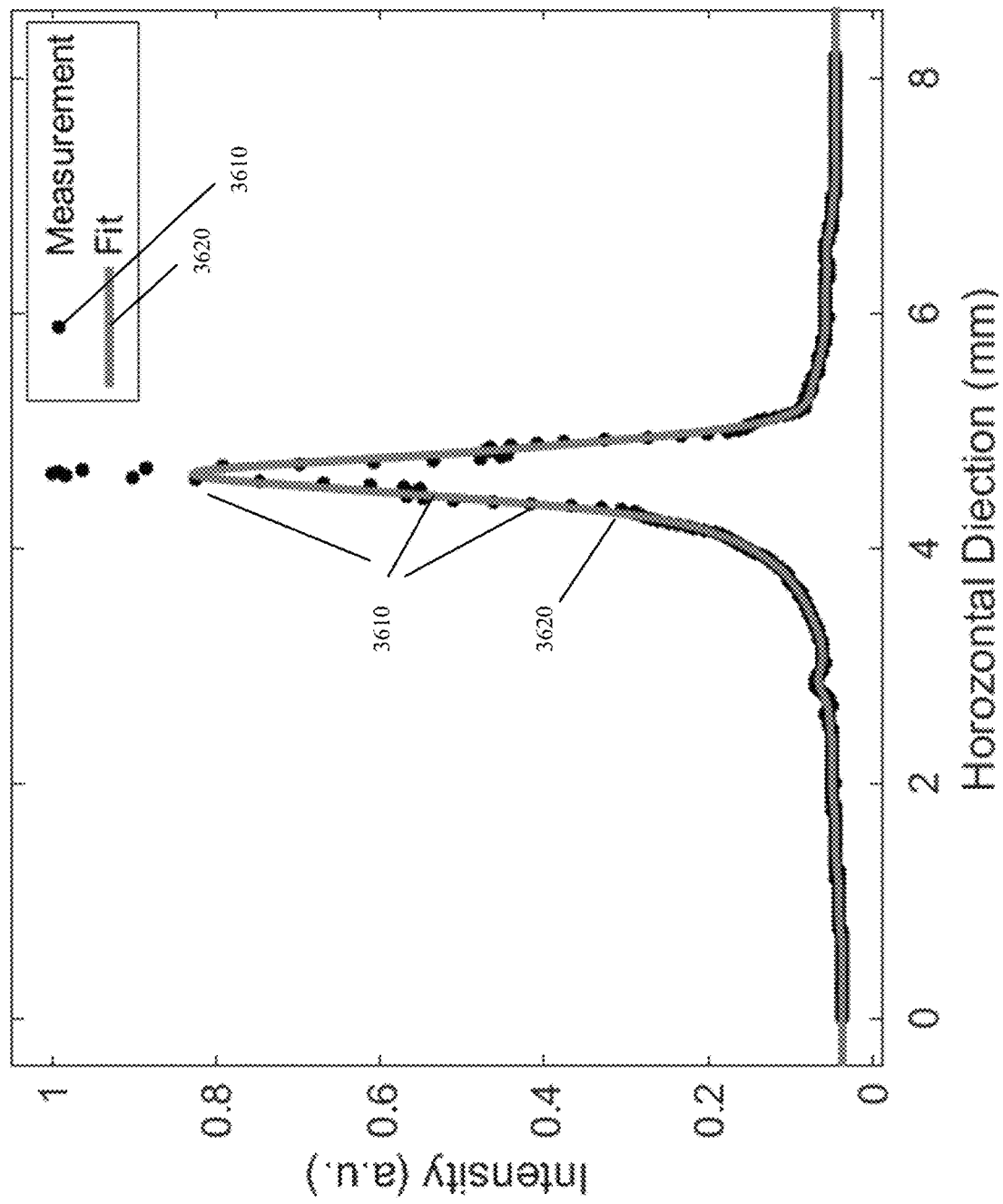
Figure 36F:
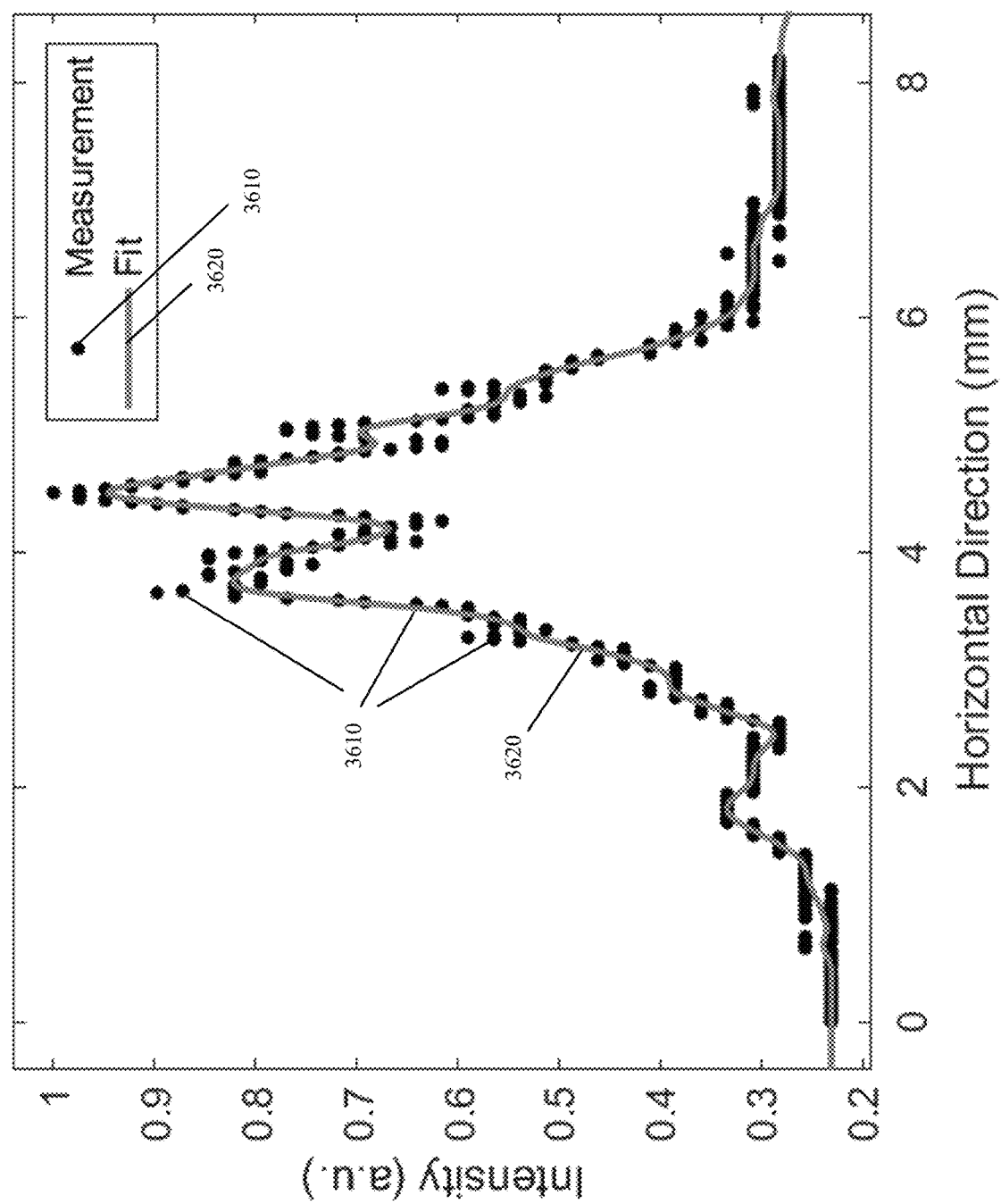

The measurements for the co-propagating setup are shown in FIGS. 36A-36C and the measurements for the counter propagating setup are shown in FIGS. 36D-36F. The FWHM is measured before the FUS is turned on (FIGS. 36A and 36D), while the FUS is on (FIGS. 36B and 36E), and after the FUS is turned off (FIGS. 36C and 36F).

FIGS. 36A-36F demonstrate one of the important technological advantages of the present embodiments. As shown in FIGS. 36A, 36C, 36D, and 36F), having passed through the scattered media, the shape of laser beam deviates compared to its original shape as a Gaussian beam. Therefore, the Gaussian curve does not match the scattered data of the laser beam when FUS is off. However, as shown in FIGS. 36B and 36C), as soon as the FUS turns on, the laser beam is substantially focused and the laser beam's FWHM decreases considerably in such a way that the obtained experimental data could be fit with a Gaussian curve.

With reference to FIGS. 36A-36F, the measured profiles are represented with the dots 3610. The traced curve 3620 that makes a best fit through the dots 3610, in FIGS. 36A, 36C, 36D, and 36F (where the FUS is off), corresponds to a smoothing spline that deviates from a Gaussian curve, while the traced curve 3620, in FIGS. 36B and 36E, corresponds to a first-order Gaussian fit of under 5% uncertainty.

Figure 37A:
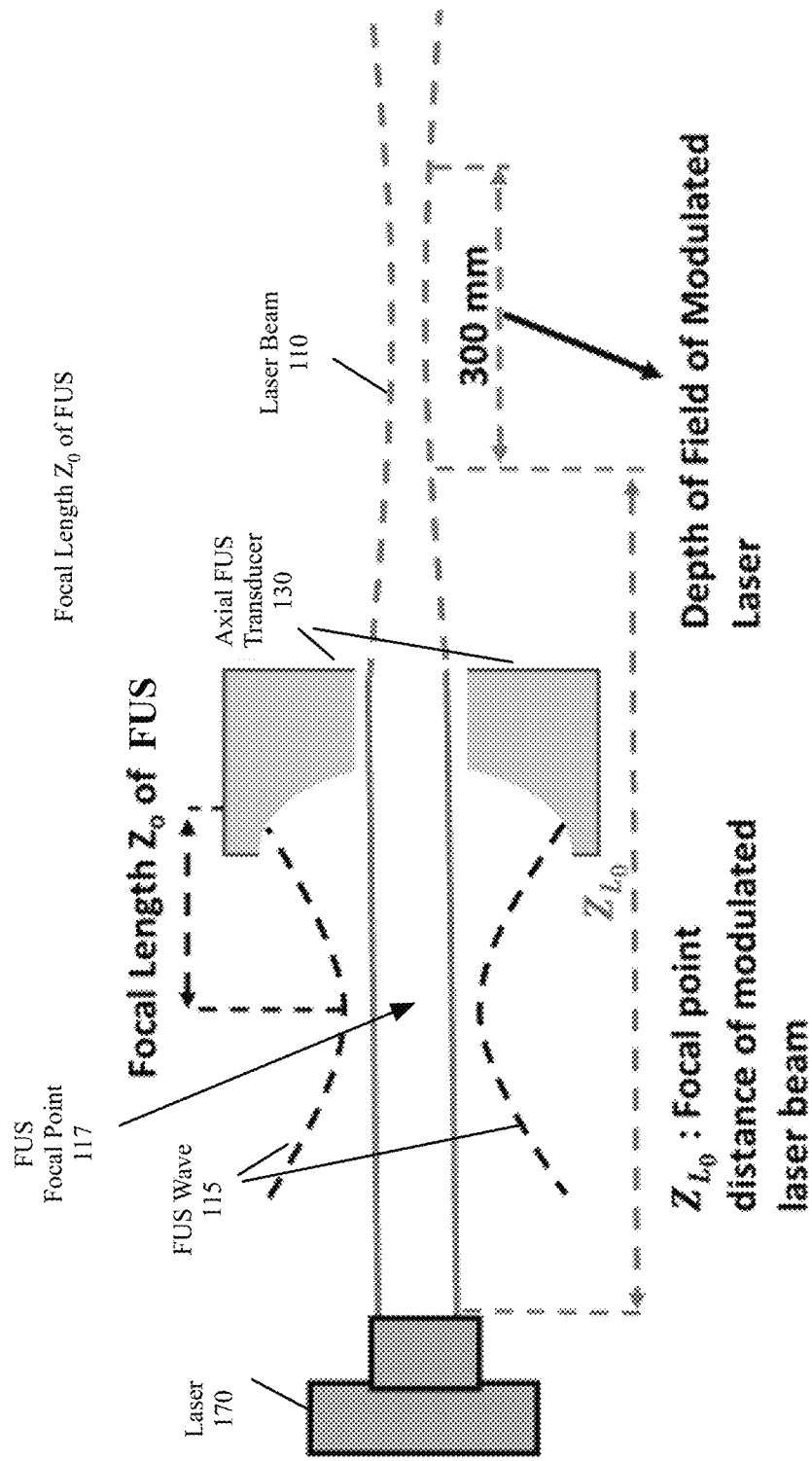
FIG. 37A illustrates a schematic diagram of an experimental modulated laser beam travelling through the FUS field, according to various embodiments of the present disclosure.

The FWHM of the laser beam before entering the water and after exiting the water measured as 1.29 mm and 3.83 mm respectively. Upon US modulation (when the FUS is on) the FWHM drastically shrinks to 0.38 mm for co-propagating setup (FIG. 36B), and to 0.48 mm for the counter propagating setup (FIG. 36E). The beam profile returns to the initial state right after switching the FUS off.

c. Length of the Laser Focal Area May be Tuned by Adjusting the FUS Parameters FIG. 37A illustrates a schematic diagram of an experimental modulated laser beam travelling through the FUS field, according to various embodiments of the present disclosure. With reference to FIG. 37A, the depth of field of the laser wave is greater than 300 mm.

Figure 37B:
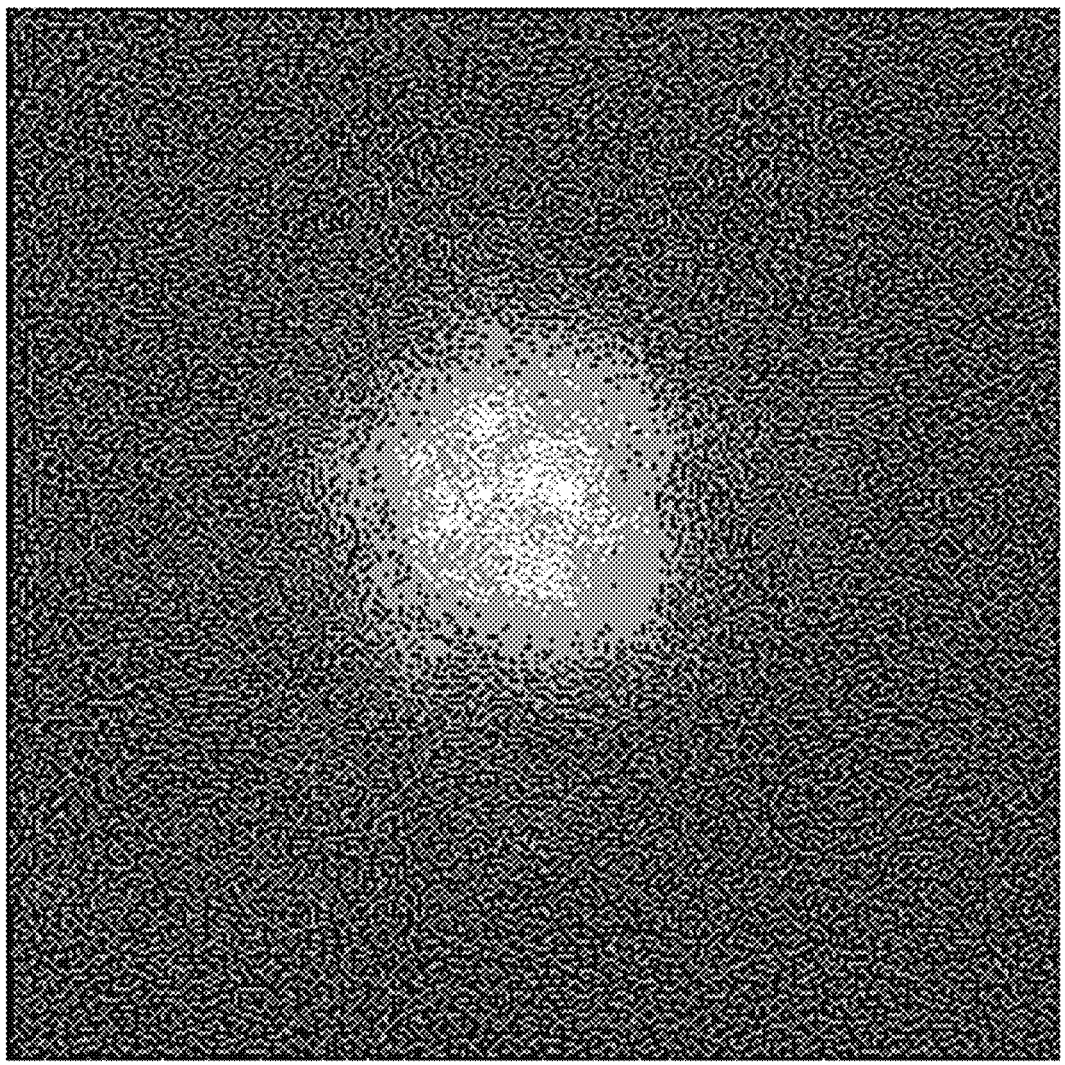
FIG. 37B illustrates the expanded laser beam recorded by the CCD showing very low light intensity in a random speckle pattern, according to various embodiments of the present disclosure.
Figure 37C:
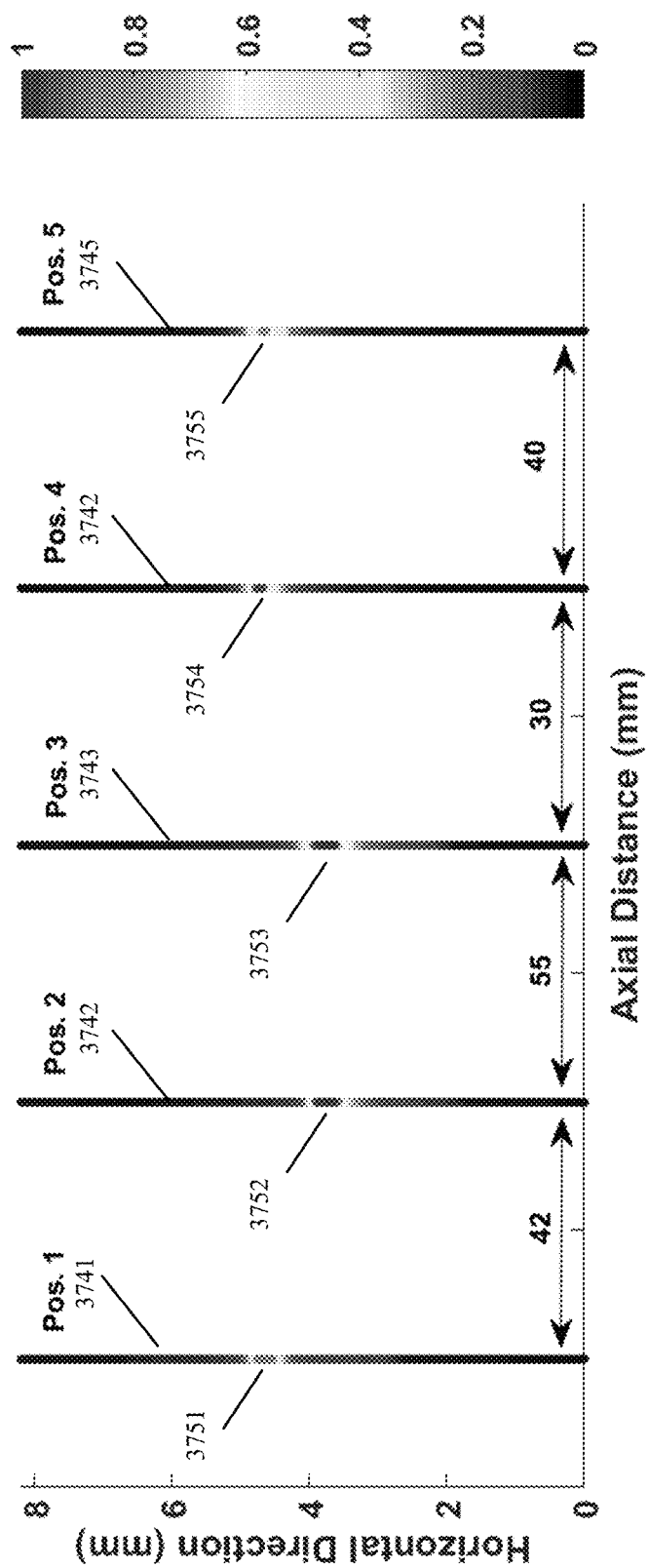
FIG. 37C illustrates the FUS modulated light intensity distribution at five positions of the CCD camera along the laser/FUS axial direction, according to various embodiments of the present disclosure.

FIG. 37B illustrates the expanded laser beam recorded by the CCD showing very low light intensity in a random speckle pattern, according to various embodiments of the present disclosure. FIG. 37C illustrates the FUS modulated light intensity distribution at five positions 3741-3745 of the CCD camera along the laser/FUS axial direction, according to various embodiments of the present disclosure. With reference to the setting of FIG. 37C, the FUS input voltage is 84 V and the duty cycle is 20%. The location of the CCD along laser beam axis is then changed several times to record the laser beam change. According to the five steps CCD capturing, the depth of focus was measured as over 30 cm. The intensities of the modulated laser beam in FIG. 37C is maximum at "position 2" 3742, and "position 3" 3743. As shown, despite the fluctuations, the laser focusing 3751-3755 is maintained throughout the five positions 3741-3745 and beyond.

FIGS. 37B, 33A, 33C, 33D, 33F, 34A, 34C, 34D, 34F, 35A, 35C, 35D, 35F, 36A, 36C, 36D, and 36F illustrate that, in the absence of FUS waves, the laser light exhibits a random scattered speckle pattern in the CCD image. However, during the coaxial FUS modulation (as shown in FIGS. 33B, 33E, 34B, 34E, 35B, 35E, 36B, and 36E) an instant increase in the focusing of the laser light is observed, where there is a high-intensity needle-size spot in the center position of the beam and the peak of the light intensity distribution drastically increased.

The above experiments demonstrate another technical advantage of the present embodiments, in which not only straight laser focusing is produced without any mediator (e.g., without any bubbles, shear waves, heat, oil droplets, etc.) but more importantly, the laser maintains the focused amplified laser spot and energy density for the length of over 300 mm.

d. The Depth of Focusing is Driven by the FUS Parameters

FIGS. 38A-38E illustrate the 3D experimental results for 100 data sets of FUS modulated laser light intensity for five different duty-cycles and four different voltages at five different positions in the Z-axis (along the laser and FUS propagation), according to various embodiments of the present disclosure. FIGS. 38F-38J illustrate the 2D experimental results corresponding to FIGS. 38A-38E, respectively.

With respect to FIGS. 38A-38J, the CCD camera is positioned at 5 locations in 30-55 cm increments each, as described above with reference to FIG. 37C. FIGS. 38A-38E, and the corresponding FIGS. 38F-38J, show the results for the CCD at positions 1 to 5, respectively. FIGS. 38A-38E illustrate the 3D plots, and FIGS. 38F-38J illustrate the corresponding 2D views of the duty cycles and input FUS voltages (FUS intensities) versus light intensity.

FIGS. 38A-38J exhibit modulated light intensity versus four different US input voltages in five different duty cycles for 5% to 25%, which were captured in five positions of CCD in the US/laser axial direction with varying 30-55 cm increments each (FIG. 37C). FIGS. 38A-38J illustrate that in higher driving voltages of 1.0 and 1.1 V, the laser intensity is maximum at lower duty cycles (~10%), and as duty cycle increases it leads to a reduction at these higher voltages. On the other hand, for driving the US transducer with lower input voltages (0.6 and 0.8 V), the light intensity is at the bottom at shorter duty cycles and then begins to intensify and show the maximum at higher duty cycles (20%, and 25%).

Figure 39A:
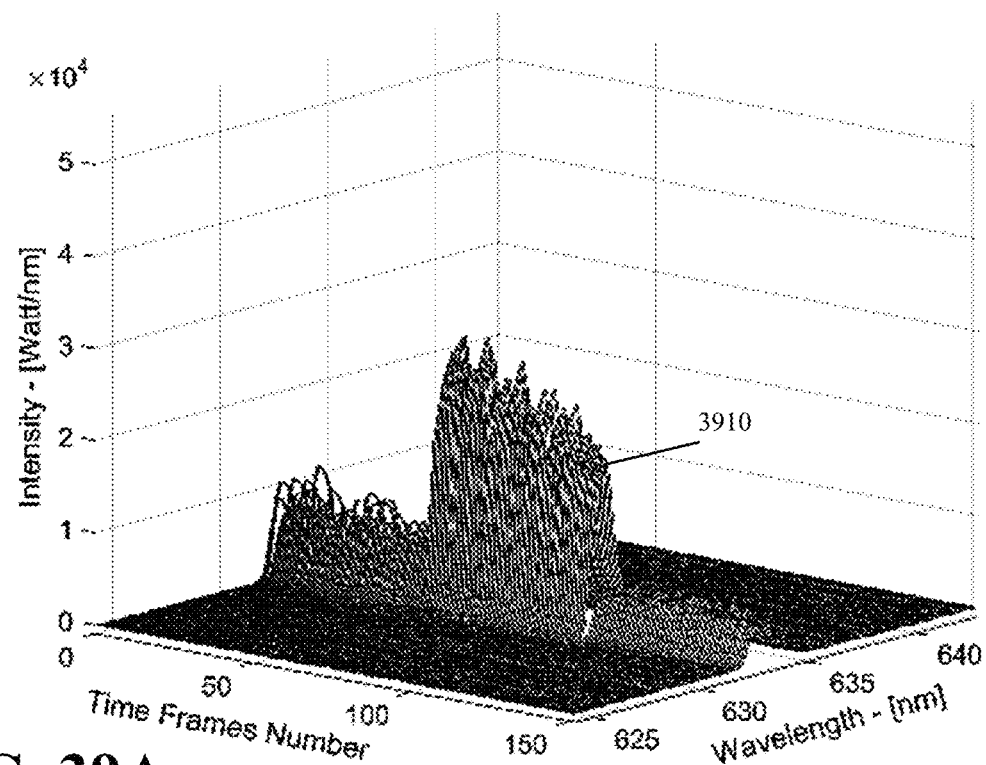
FIGS. 39A-39B illustrate the experimental results for traces from the optical spectrum analyzer for co-propagating setup of the laser/US, according to various embodiments of the present disclosure.
Figure 39B:
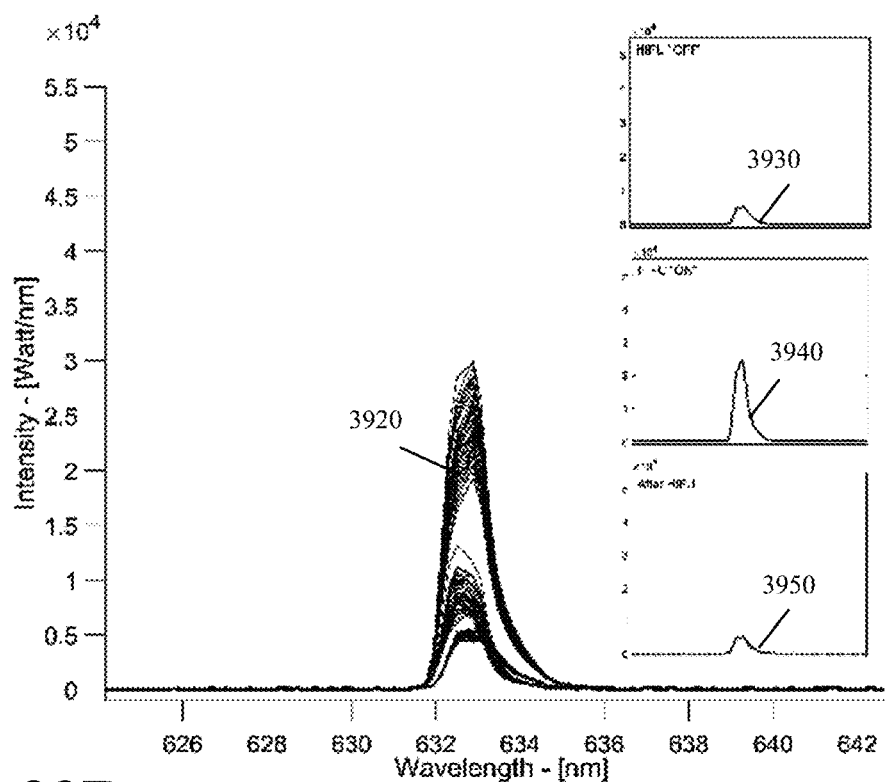

FIGS. 39A-39B illustrate the experimental results for traces from the optical spectrum analyzer for co-propagating setup of the laser/US, according to various embodiments of the present disclosure. FIG. 39A illustrates the plot 3910 of the intensity for 150 frames. FIG. 39B illustrate the side view 3910 of the FIG. 39A. The plots 3930-3950 are the calculated mean intensities for each case of before turning on, during, and after turning off of the FUS.

Figure 40A:
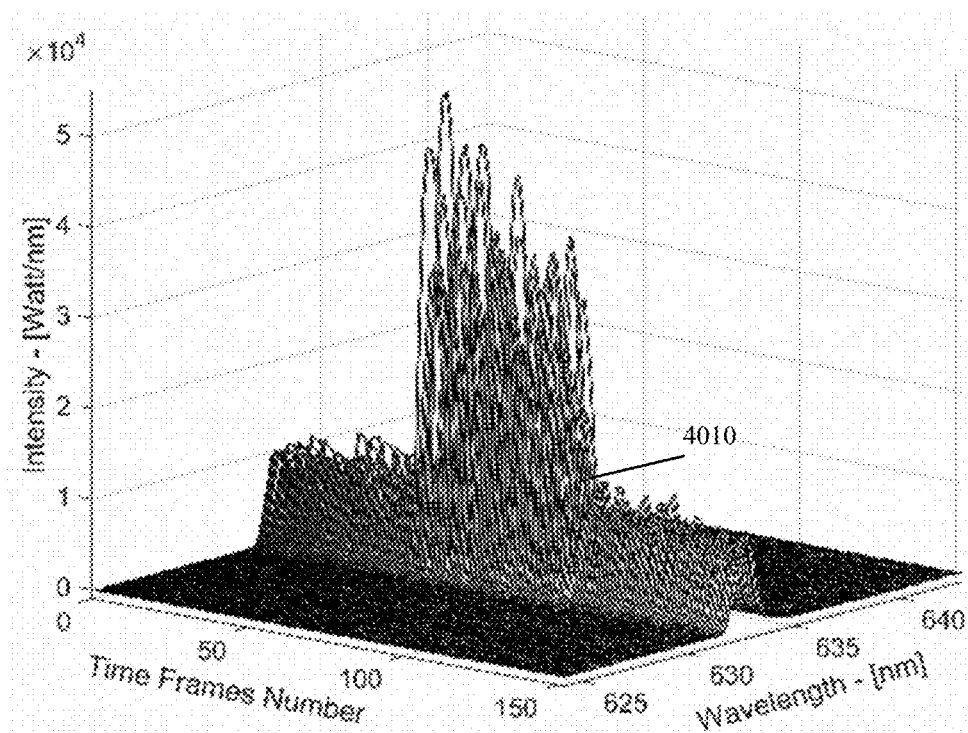
FIGS. 40A-40B illustrate the experimental results for traces from the optical spectrum analyzer for counter propagating setup of the laser/US, according to various embodiments of the present disclosure.
Figure 40B:
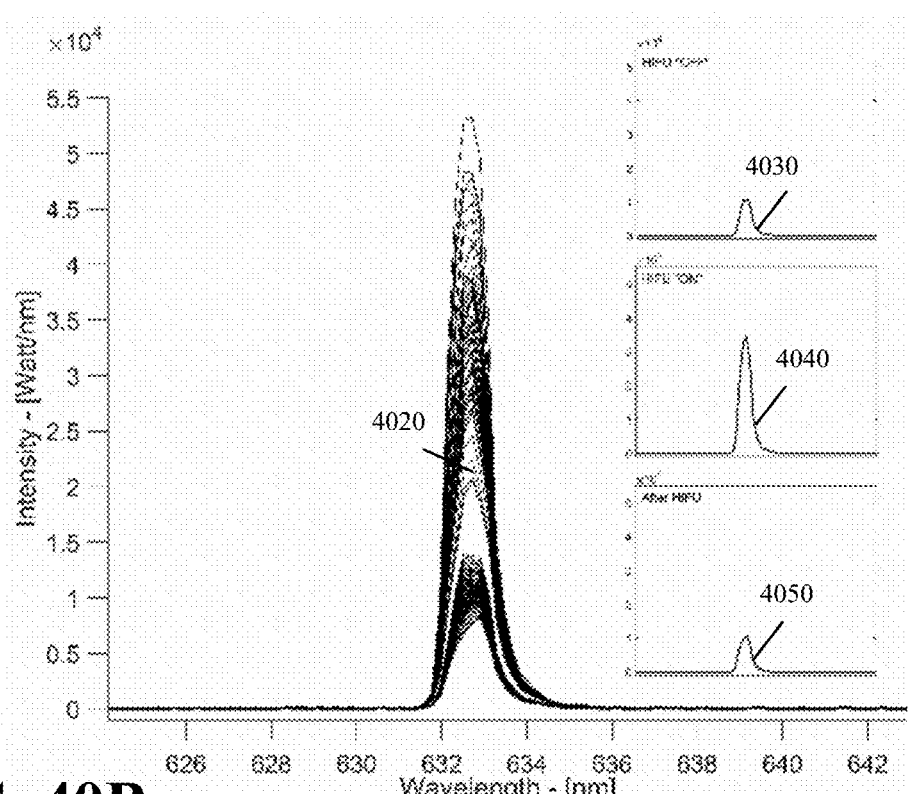

FIGS. 40A-40B illustrate the experimental results for traces from the optical spectrum analyzer for counter propagating setup of the laser/US, according to various embodiments of the present disclosure. FIG. 40A illustrates the plot 4010 of the intensity for 150 frames. FIG. 40B illustrate the side view 4010 of the FIG. 40A. The plots 4030-4050 are the calculated mean intensities for each case of before turning on, during, and after turning off of the FUS.

FIGS. 39A-39B and 40A-40B illustrate the spectral broadening measured by an optical spectrum analyzer in both co-propagating and counter propagating alignments of the laser and the FUS waves. The measurements were taken with 5 seconds the FUS off, 10 seconds the FUS on, and 5 seconds after the FUS is switched off. The respective phases were averaged to address possible movements of water. The plots 3920, 3940, 4020, and 4040 show that there is a broadening of the laser wavelength spectrum through the FUS modulation, shifting from a spectra width of 0.2 nm to 1 nm. The spectral broadening disappears as soon as the FUS is switched off, indicating that this effect is reversible and driven by the FUS modulation. Furthermore, the increase in the laser intensity is consistent with is observed in the beam profiles.

2. Discussion

The results of the experiments and simulations discussed above demonstrated that unconditional US modulation of water may be utilized to focus laser beam in co-propagating or counter propagating alignments with respect to the focal axis of a toroid shaped FUS transducer. The theory and simulation showed that the refractive index of water increases from 1.3317 to 1.3530 at areas of maximum pressure which is significant enough to induce lensing effect on laser beam (FIGS. 29, 31A-31B, and 32A-32D). The experiments illustrated that the focused spot of the laser is noticeable in the center of the halo around the spot (FIGS. 33B and 33E).

The FWHM of the modulated laser was shown to be improved by over 10 folds and 8 folds for co-propagating and counter propagating laser and FUS alignments, respectively.

The DoFM was defined as the region where the FWHM of the modulated beam is increased more than five times compared to unmodulated beam. The DoFM was measured to be over 300 mm (FIG. 37A). It has been shown that the lower the frequency of the FUS, the deeper the penetration of optical microscopy. In principle, if the FUS frequency is reduced (less than 3.3 MHz) the DoFM of the amplified laser is projected to be augmented even more.

Figure 38A:
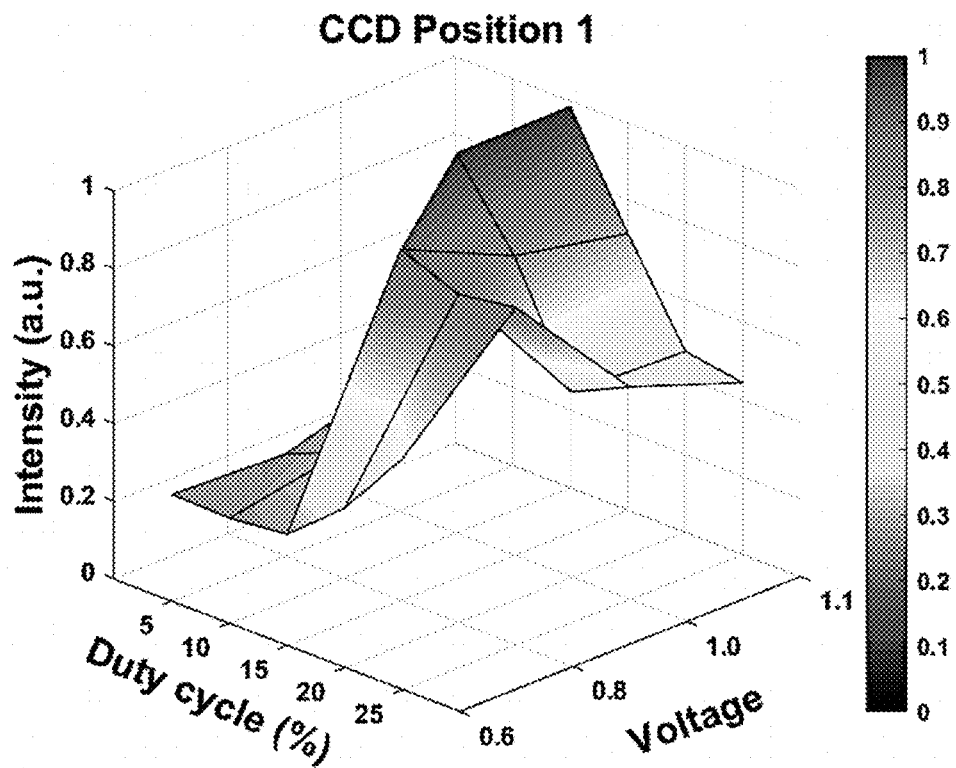
FIGS. 38A-38E illustrate the 3D experimental results for 100 data sets of FUS modulated laser light intensity for five different duty-cycles and four different voltages at five different positions in the Z-axis (along the laser and FUS propagation), according to various embodiments of the present disclosure
Figure 38B:
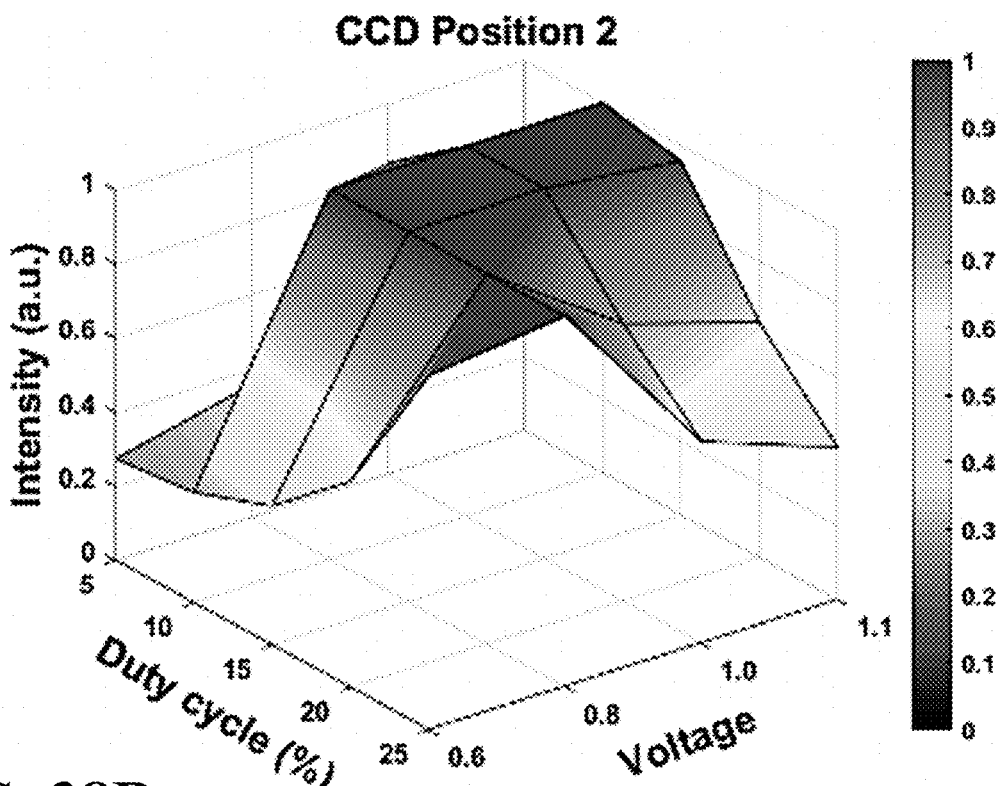
Figure 38C:
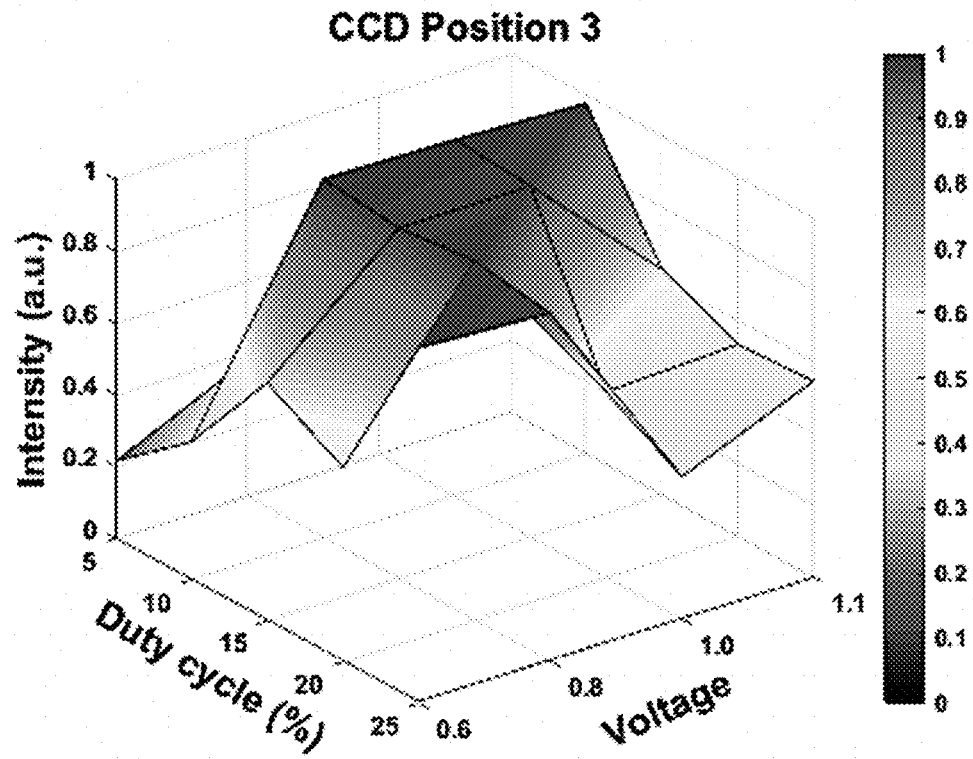
Figure 38D:
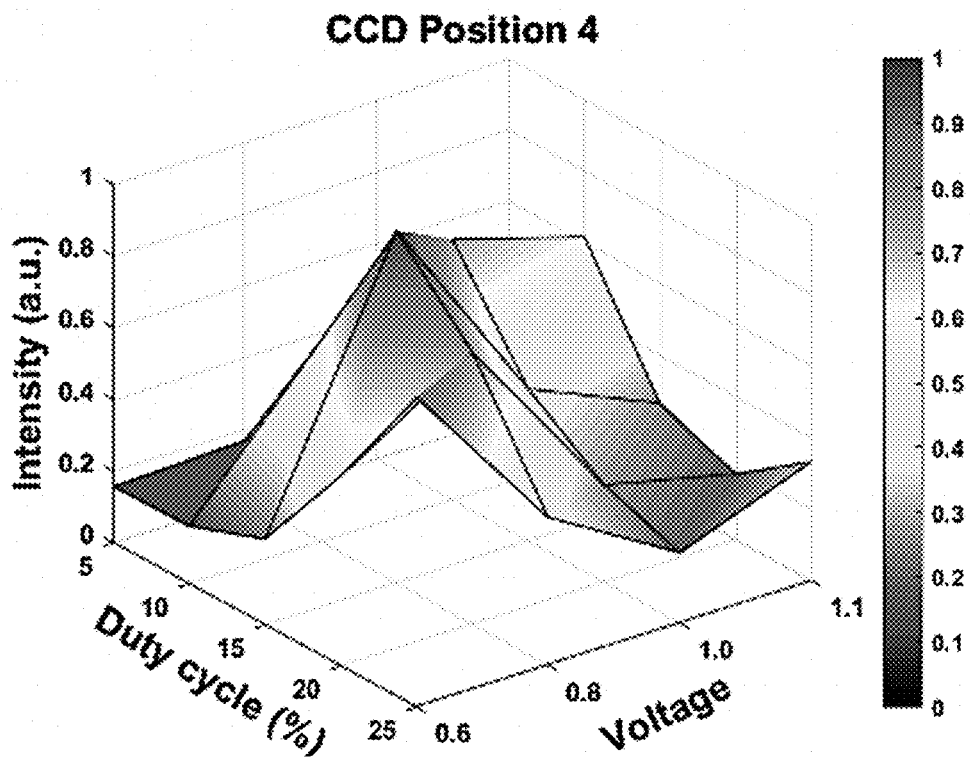
Figure 38E:
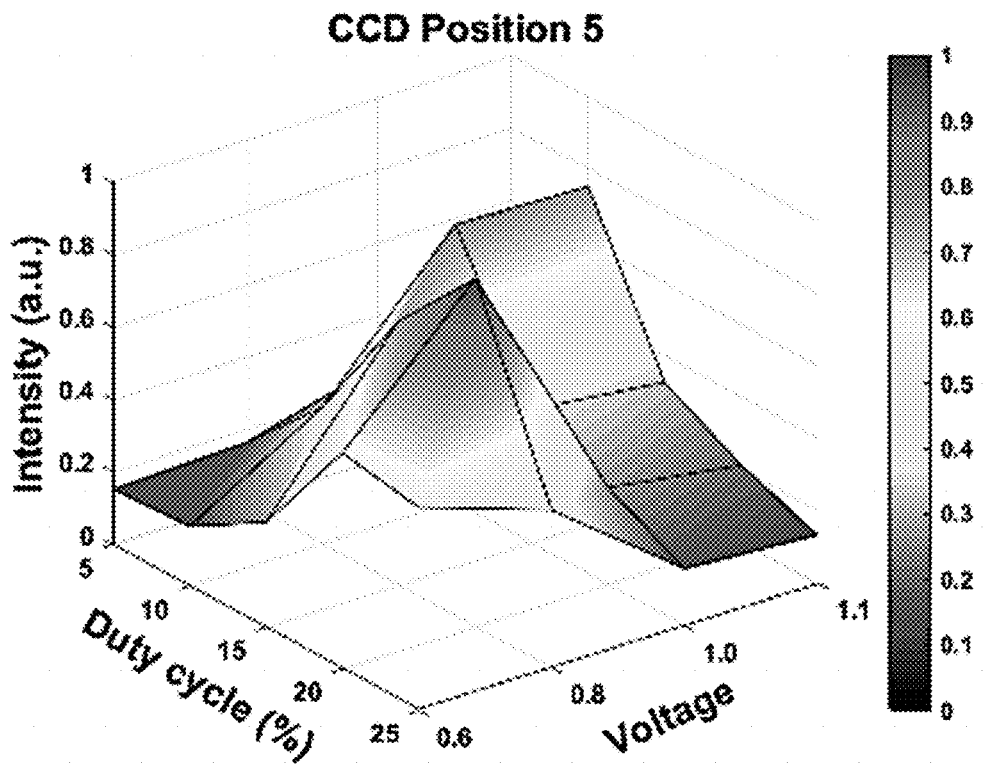
Figure 38F:
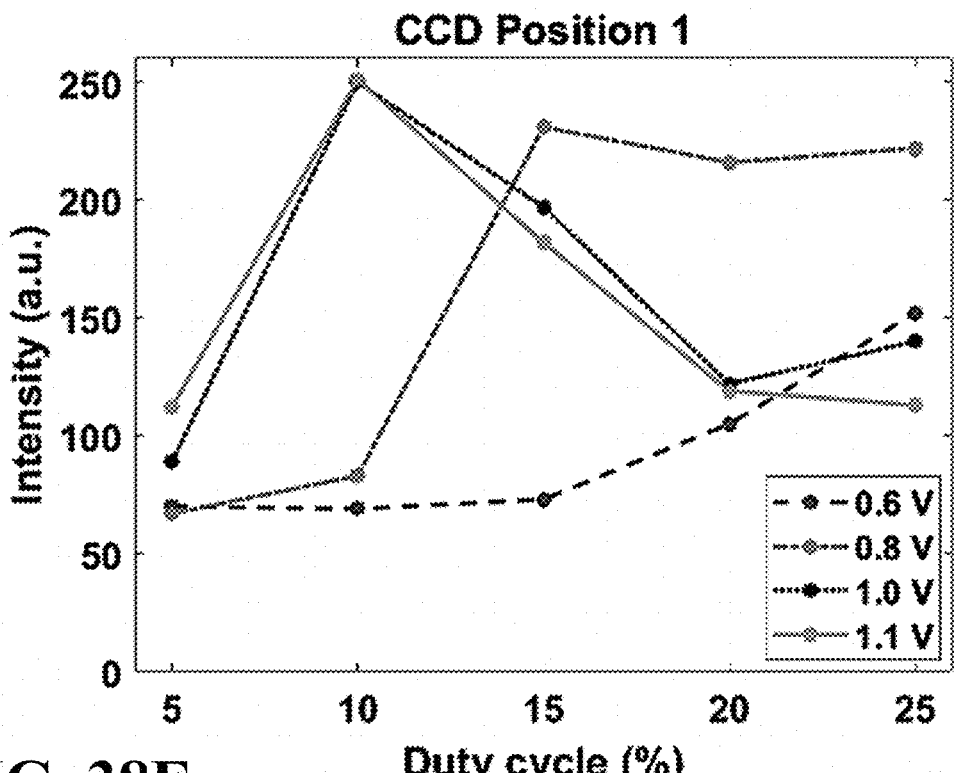
FIGS. 38F-38J illustrate the 2D experimental results corresponding to FIGS. 38A-38E, respectively.
Figure 38G:
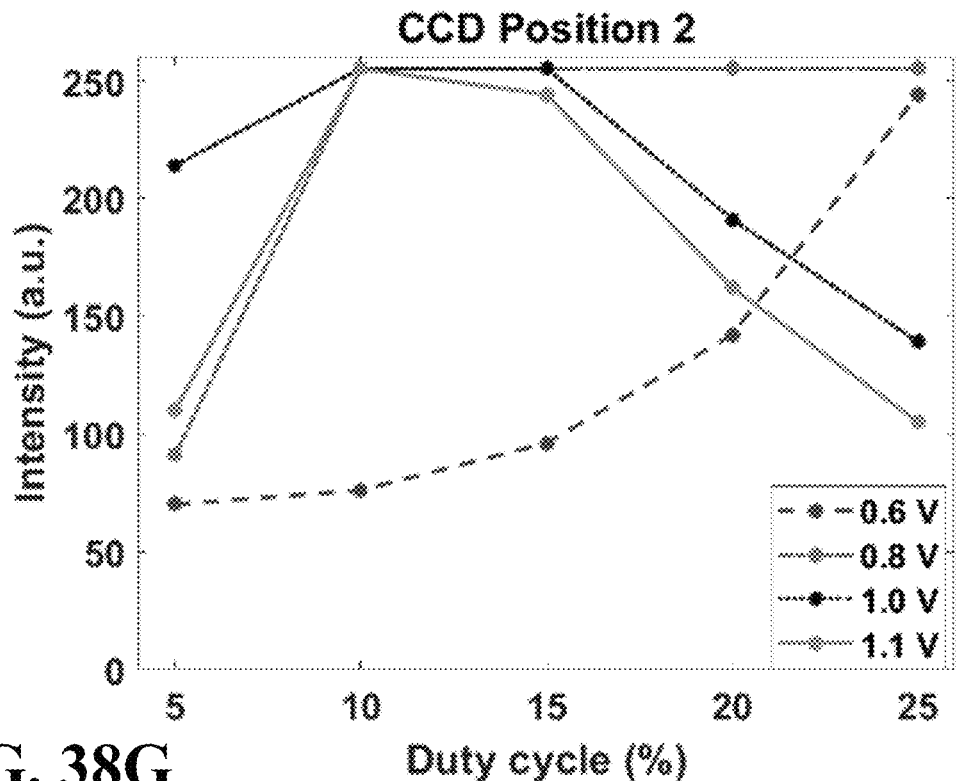
Figure 38H:
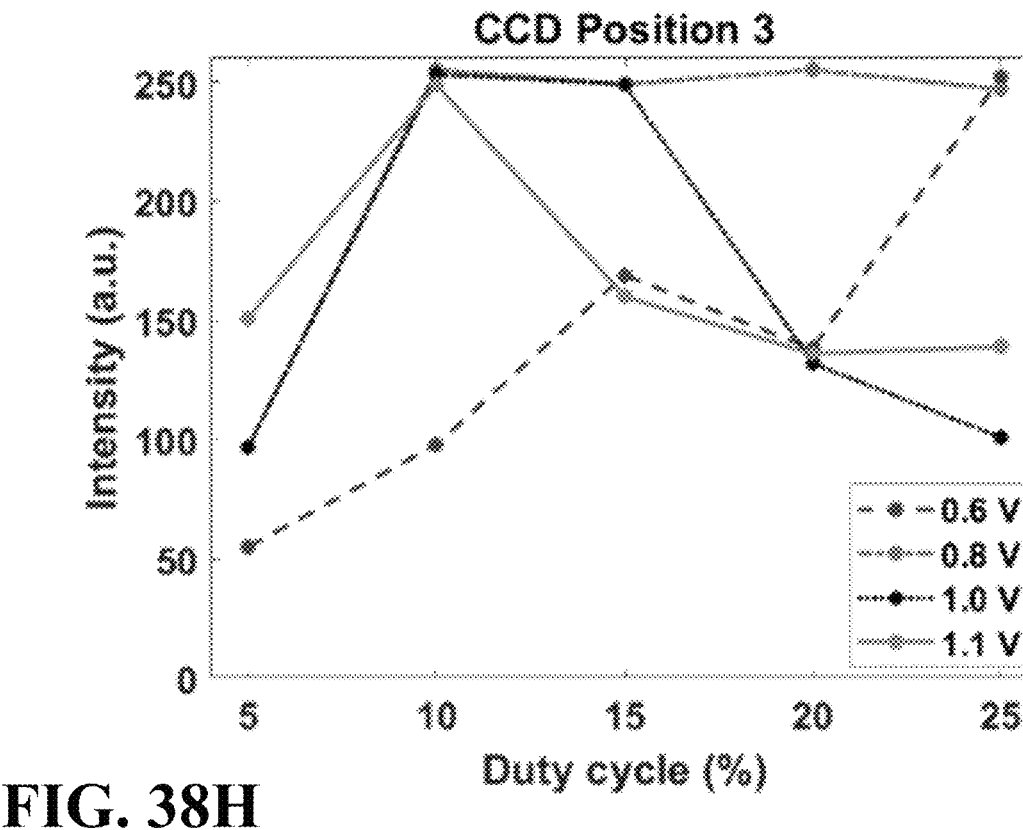
Figure 38I:
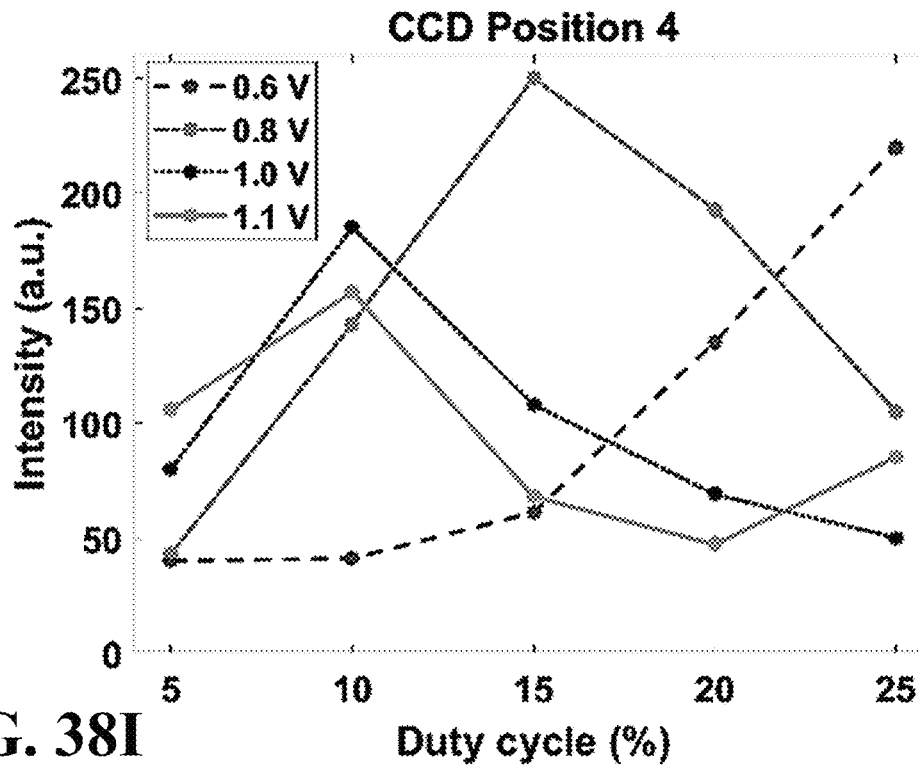
Figure 38J:
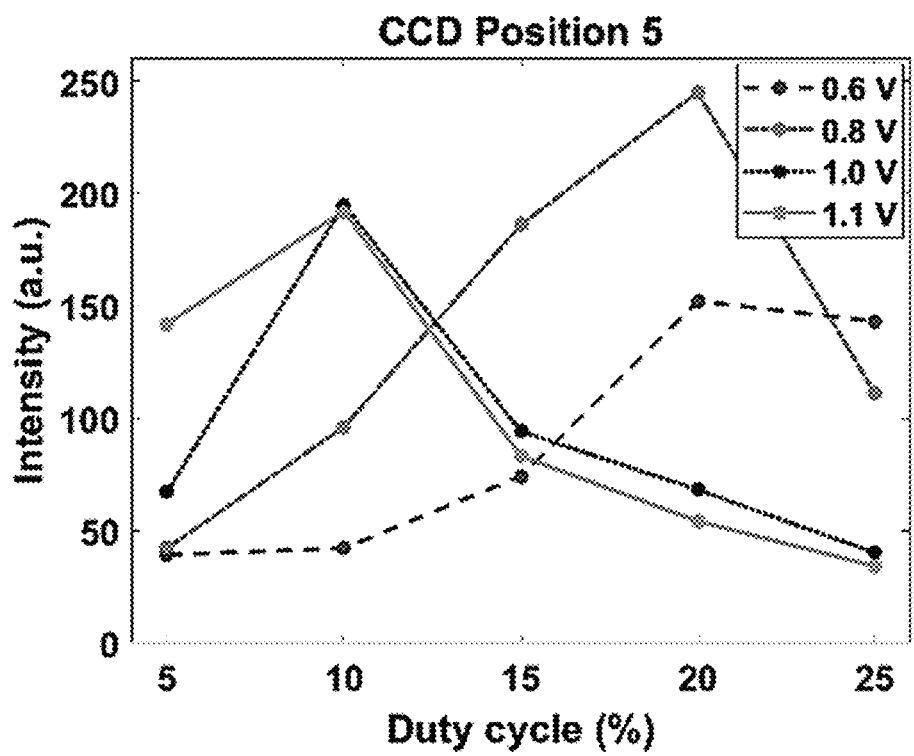

It was illustrated that there are optimum FUS driving conditions for the lensing effect to occur at a different focusing lengths (FIGS. 38-38J). Changing the pressure wave would affect the distribution of water molecules, which would effectively change the density and refractive index. Under lower voltages and duty cycles the effect of lensing is not as prevalent. However, it was shown that higher input voltage and larger duty cycle did not necessarily mean a greater intensity of laser beam. In other word, the intensity for higher input voltages decreases in duty cycles larger than 15% after reaching to an extremum. For lower voltages, the laser intensity keeps rising by increasing the duty cycles value. At the CCD positions 4, and 5 (FIG. 37C) lower voltages reach maximum at 15% and higher duty cycles.

The configuration of the present embodiments contrasts with other reported configurations that have investigated a similar phenomenon using perpendicular laser to the US transducer alignment or coaxial setting using air bubbles or oil. There has been no reports in prior art of the lensing effect in single media induced by the FUS as well as developing theory and formulations relating the entanglement of electro-magnetic wave and the FUS as two independent physical phenomena. The present embodiments presented that the laser propagation may be unpretentiously modulated as long as it is aligned with axis of US pressure field. Since the lensing effect occurs in a single medium with no specific requirements or restraints to media, the configuration of the present embodiments may generate a flexible lens in various fluidic media.

Figure 41A:
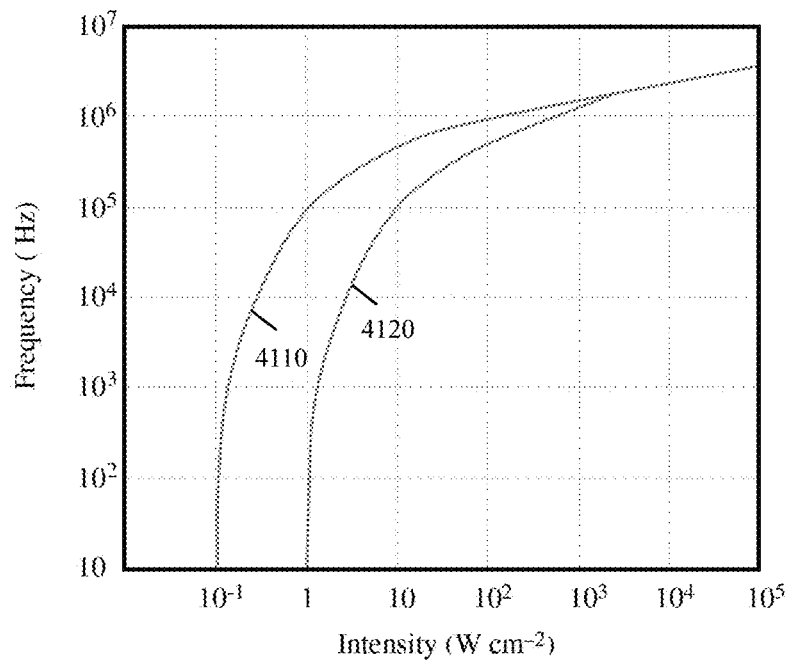
FIG. 41A illustrates the variation in threshold frequency versus intensity for aerated water and air-free water for producing cavitation, according to prior art.

According to various investigators, the FUS frequency (3.3 MHz) that is used in the lab experiments described above and the measured US intensity do not generate cavitation bubbles. FIG. 41A illustrate the variation in threshold frequency versus intensity for aerated water and air-free water for producing cavitation, according to prior art. With reference to FIG. 41A, the description of the graphs 4110 and 4120 are provided in the reference and handbook by Jose-Luis Capelo-Martinez, "Ultrasound in Chemistry: Analytical Applications," 2009, Page 3-4. The graphs 4110 and 4120 show the threshold frequency versus intensity for aerated water and air-free water. At high sonic frequencies, the production of cavitation bubbles becomes more difficult than at low sonic frequencies. As the sonic frequency increases, so the intensity of the applied sound must be increased to provide cavitation.

Figure 41B:
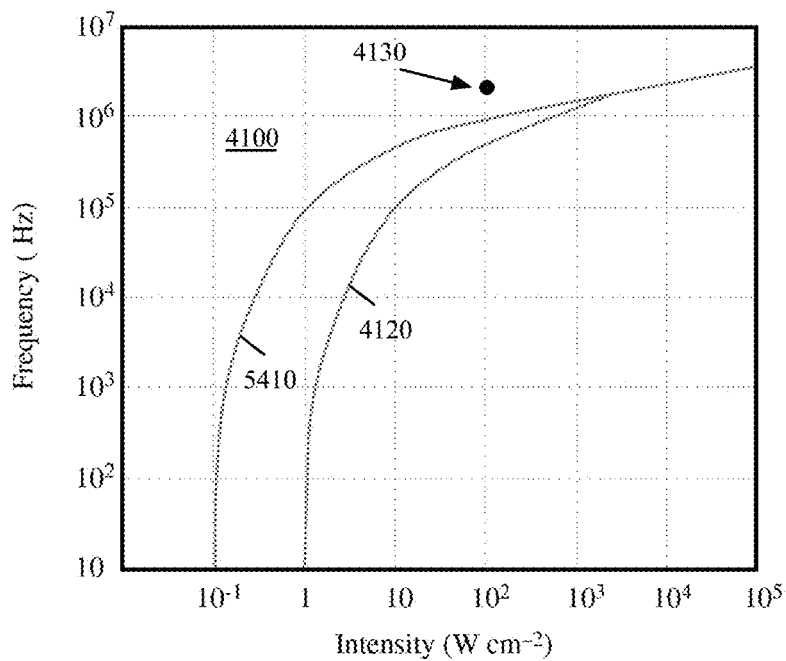
FIG. 41B illustrates the selection of a frequency and an intensity for ultrasound in a medium to avoid cavitation in the medium, according to various aspects of the present embodiments.

Since the present embodiments avoid cavitation generation, the frequency and the intensity of the ultrasound are selected such that cavitation is not generated in the medium. FIG. 41B illustrates the selection of a frequency and an intensity for ultrasound in a medium to avoid cavitation in the medium, according to various aspects of the present embodiments. As an example, some of the experiments described herein are performed in a water medium using a low intensity FUS of less than 119 W/cm$^2$, with a frequency of 3.3 MHz. As shown by the point 4130 in FIG. 41B, the values of 119 W/cm$^2$ and 3.3 MHz maps to a point on the upper region 4100 of both graphs 4110 and 4120, and therefore, does not cause cavitation in either type of water.

Some embodiments generate similar curves for different types of medium that may be used to surround the FUS transducers. As described above with reference to FIGS. 1A-1D and 12A-12B, the specific values of the duty cycle and the voltage amplitude generated by the controllers 150 and 1250 are selected such that no bubble or cavitation is formed in the medium surrounding the axial FUS transducers 130 and 1230 (the duty cycle and the voltage amplitude is also used to control the US focal point and the intensity of the US wave). The duty cycle and the voltage amplitude may be used by table lookups (which may be generated from graphs similar to the graphs 4110 and/or 4120) or by using an algorithm that uses a function generated based on graphs similar to the graphs 4110 and/or 4120 for each specific medium such as water, gas, gel, etc., such that no cavitation is generated in the medium.

As described above, the duty cycle and the voltage amplitude generated by the controllers 150 and 1250 may be set by the processor 160 of the controllers 150 and 1250, may be set manually (e.g., through a set of controls on the C$^2$AM controller 150), may be set by a separate electronic device (such as, for example, and without limitations, by a remote server, a client device, etc.).

Accordingly, in the experimented driving conditions, Mie scattering does not play a role for the occurred lensing effect as opposed to results obtain by other investigators. The temperature at the focal area of the applied FUS transducer has been measured in the above described experimentations and no increase in the temperature was observed with a precision of 0.1 degree F.

The average power density of the laser was observed to have a notable increase of 169-folds when modulated by the FUS. The intensity of input laser was calculated using area of beam in the FUS-off status from the measured beam profile (through calibrated captured CCD data of FIGS. 33A-35F). Amplification of the laser in both co- and counter propagation exhibits just over seven times increase in intensity (FIGS. 34A-35F). Having measured the diameter of the modulated beam (FIGS. 36B and 36E), the area of the needle sized (around $1.96e^{-3}$ cm$^2$) attuned laser beam was determined. The delivered average power density for this area became around 482.6 mW/cm$^2$, which is just over 169 times larger than the power density of the unmodulated laser.

This substantial power density amplification of over 169-fold has applications in chemistry, biochemistry, biology, material science, clinical, and industrial applications where low laser dosage is of paramount importance. A low power laser may be used and its power density may be amplified to over 169 times in the simplest configuration. The uncomplicated coaxial alignment of laser/FUS in this system allows for flexibility in biomedical applications. The effect of the FUS frequency and the probe design parameters (e.g., employing annular array FUS transducers, in which the focal point of FUS may be adjusted electronically, etc.) on the DoFM, and the spatial resolution of the modulated beam are among the technical advantages of the co/counter propagating configuration of the laser and the FUS waves of the present embodiments.

As described with reference to several examples below, an application of the C$^2$AM probes of the present embodiments is to increase the penetration depth of low energy light. Due to absorbers and scatterers in biological matter, visible light has a very short penetration depth in tissue. The acoustic modulation of media may be used to increase the penetration depth of visible light, opening the possibilities for use of dyes that may have better quantum yield than near-infrared dyes. The pulsed configuration delivers healthier and less invasive energy allowing for in vivo use.

2. Methods b. Driving Parameters of the FUS Transducer

The schematic of the FUS Transducer was shown in FIG. 2A. The FUS transducer may have a torus shaped design that may allow for laser propagation through the center of the transducer. The FUS transducer has an acoustic focal length of 23 mm and a center frequency of 3.3 MHz. The FUS transducer was driven with a high voltage amplifier (Amplified Research, Model 50W1000B) set at a gain of 105. The driving signal to the amplifier was a pulsed square wave generated through a combination of a pulse delay generator (e.g., Stanford Research Systems, DG353) and a function generator (e.g., Stanford Research Systems, DS345), which the driving signal was monitored on an oscilloscope (e.g., LeCroy, 9361). The duty cycle was tuned by adjusting the pulse generator, while the acoustic intensity was adjusted by changing the voltage amplitude in the function generator. The FUS transducer was operated at duty cycles of 5%, 10%, 15%, 20%, and 25% and with voltage amplitudes of 0.6, 0.8, 1.0, and 1.1 volts.

b. Experimental Setup

A helium-neon class-II laser (such as the laser of the Oriel Corporation) with an output power of 0.95 mW centered at 633.2 nm with a Gaussian beam profile was expanded and collimated with a beam expander formed by 35 mm and 200 mm biconvex lenses. The laser was sent to a raised ten-gallon glass fish tank with dimensions of 55 cm×30.48 cm×34.29 cm, filled half-way with deionized nanopure water. It was ensured that there were no bubbles throughout the experiment. The FUS transducer was submerged 10 cm below the surface of the index with the focal face pointing away from the bottom of the tank to avoid acoustic reflections from the glass. The laser was sent through the hole of the FUS transducer in a co-propagating or counter propagating alignment with respect to the direction of the FUS transducer focus and propagates through the bottom of the fish tank. A right-angle mirror at the bottom of the fish tank sends the laser to the detector.

The modulated laser was attenuated with two linear polarizers and the acoustically modulated beam profile was detected on an EM-CCD (e.g., Hamamatsu, C9100-13). The laser spot was recorded with CCD during the experiment, before, during and after the presence of US waves, then the CCD images were analyzed in order to obtain the real light intensity distributions for the laser which has a Gaussian bell shape.

To characterize the modulated beam profile at different depths, the EM-CCD was translated away from a right-angle mirror. Position 1 was denoted as the closest position to the right-angle mirror. Beam profiles were obtained from analyzing collected images in MATLAB. The spectral properties were also examined by coupling the modulated laser into a fiber optic attached an optical spectrum analyzer (Ocean Optics, USB4000).

IV. ALTERNATIVE THEORY AND EXPERIMENTATION

Maxwell equations are a set of partial differential equations that provide a mathematical model for propagation of electromagnetic waves in different media. In Maxwell equations, electric permittivity, ε, and magnetic permeability, μ, are the terms that relate the properties of medium with those of electromagnetic waves. These two terms come together and form refractive index n as shown in Eq. (16):

$$n=\sqrt{\varepsilon\mu} \qquad \text{Eq. (16)}$$

On the other hand, introduction of acoustic waves into the medium causes inhomogeneity of density which will directly change the refractive index. For air and other gases, there is a simple relationship between the refractive index and the gas density as shown in Eq. (17):

$$n-1=k\rho \qquad \text{Eq. (17)}$$

where k is Gladstone-Dale coefficient, n is the refractive index, and p is the gas density. However, for liquids, this simple relationship is not valid anymore and the more general form of this relationship, which is Clausius-Mosotti relation, applies. If one assumes that several distorted electrons per molecule with different resonant frequencies $v_i$ and oscillator strengths $f_i$ contribute to the induced electric dipole moment, then the refractive index n is given by the following relation shown in Eq. (18):

$$\frac{n^2-1}{n^2+2} = \frac{\rho l e^2}{3\pi m_e M} \sum_i \frac{f_i}{v_i^2 - v^2} \qquad \text{Eq.(18)}$$

where l is Loschmidt's number, M is the molar weight of the molecules of fluid, e is the charge of electron, and $m_e$ is the mass of electron.

Several researches have been carried out in the past to find out the dependency of density or pressure and refractive index in different media. In 1962, Waxler and Weir studied this relationship for water experimentally. The results of their measurements show that increase of pressure leads to increase of refractive index. At room temperature, 24.8° C., the best equation that is consistent with the results of their measurements is shown in Eq. (19):

$$n = -10^{-7} P_{(MPa)}^2 + 10^{-4} P_{(MPa)} + 1.3329 \qquad \text{Eq. (19)}$$

This relation of the refractive index to pressure is used, herein, to calculate and plot the changes of the refractive index around the acoustic source and simulate the acousto-optic effect of ultrasonic focal area. The experiments carried out to validate the results of simulations clearly verify that change of refractive index may be proposed as the main acousto-optic mechanism for the interaction of low intensity focused ultrasound and laser.

a. Finite Element Model

Figure 42:
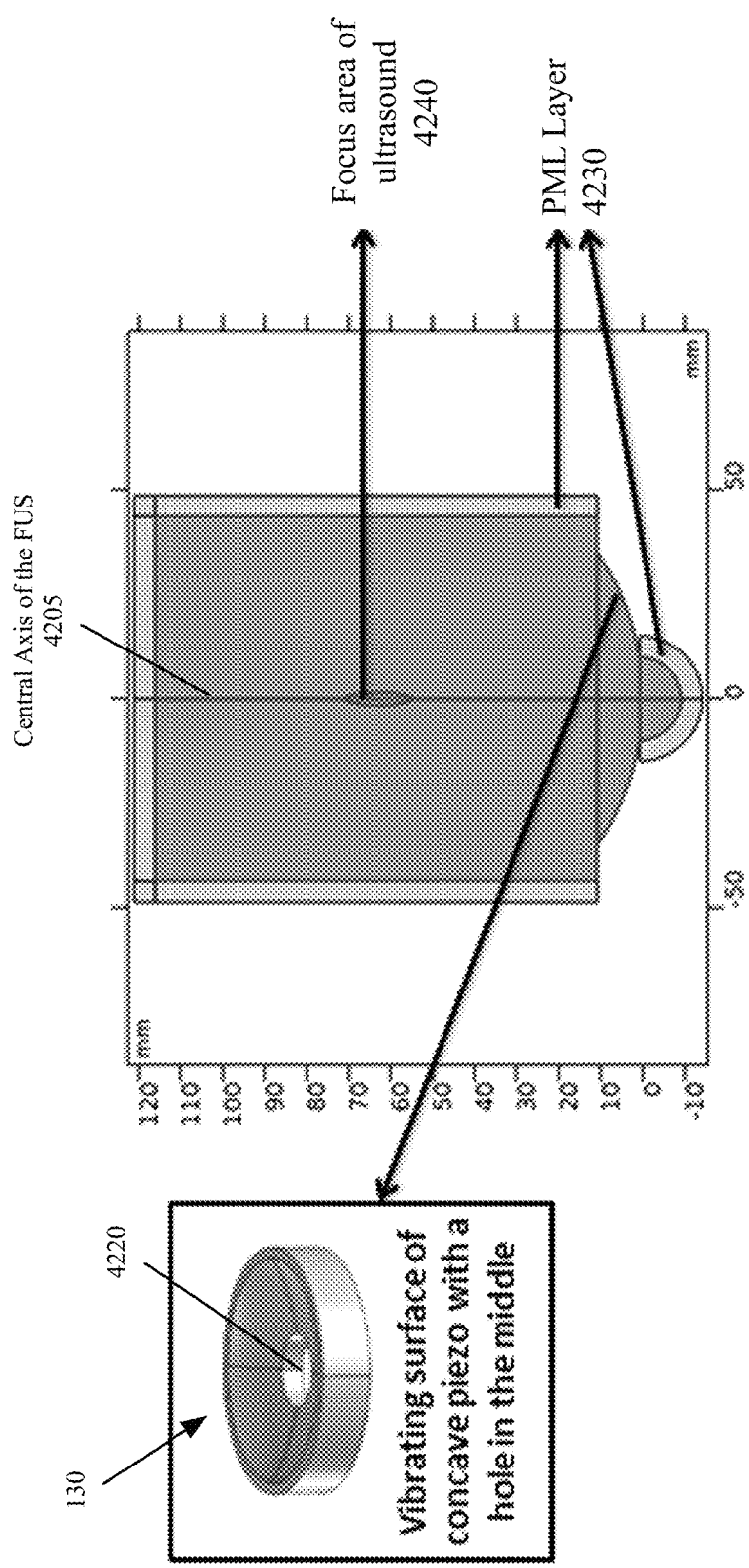
FIG. 42 is a functional diagram illustrating a cross section view of the geometry used for finite element modeling the medium in front of the FUS transducer, according to various aspects of the present embodiments.

In the finite element model simulations in this section, the source of the ultrasound wave is a concave ring FUS transducer with a hole in the middle, similar to the axial FUS transducer 130 described above with reference to FIG. 2A. FIG. 42 is a functional diagram illustrating a cross section view of the geometry used for finite element modeling the medium in front of the FUS transducer, according to various aspects of the present embodiments.

With reference to FIG. 42, the surface of the FUS transducer 130 facing the medium of interest is modeled as a vibrating surface with displacement amplitude of 1 μm and the frequency of 1.1 MHz. The whole area of the model, including the middle hole 4220 of the FUS transducer 130, is filled with water. The PML (Perfectly Matched Layer) 4230 is used in the outer boundaries of the model to make sure that boundaries are considered as infinity and the reflections of the acoustic waves off these walls do not affect the final pressure field results. the focal area 4240 of the FUS is shown as an oval in the middle. Finer meshes are applied in the oval-shaped focal region 4240 to resolve the sharp gradients in the pressure field.

In the first step, pressure field in front of the FUS transducer 130 is calculated. The result of this step is used as the initial value for calculation of the refractive index and ray trajectories in the second step. The relation between the refractive index and pressure is given by Eq. (18). Inhomogeneity of the pressure field leads to inhomogeneity of the refractive index. The medium may, therefore, be regarded as a graded index medium, with given refractive indices at each point. Laser light enters the medium from the central hole 4220 of the FUS transducer 130. Ray trajectories and the intensity of each ray are calculated by geometrical optics.

b. Setup

Figure 43:
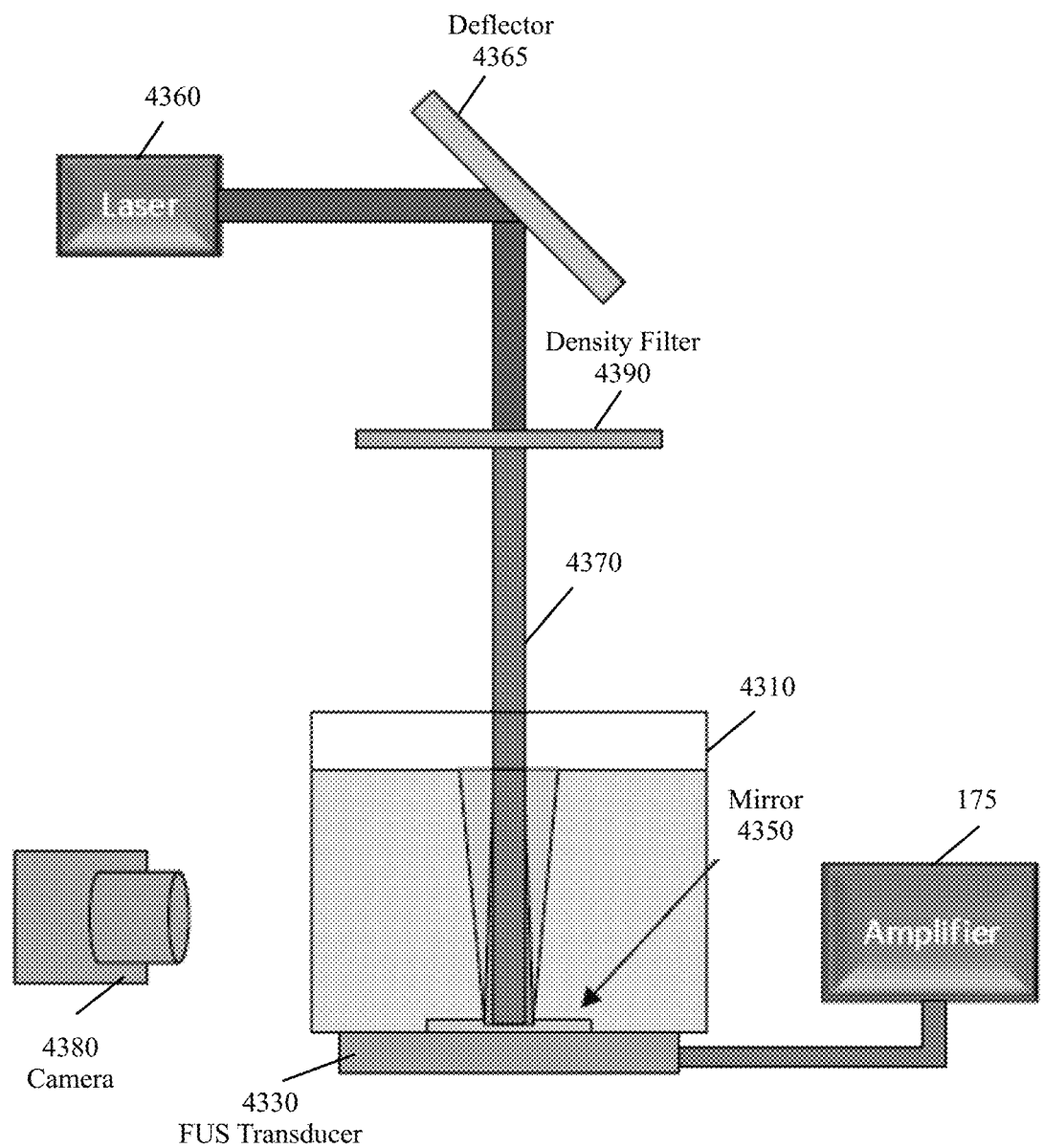
FIG. 43 is a functional diagram illustrating an example lab setup, according to various aspects of the present disclosure.

FIG. 43 is a functional diagram illustrating an example lab setup, according to various aspects of the present disclosure. With reference to FIG. 43, the FUS transducer 4330 may be placed at the bottom of the container 4310 and the laser light may be deflected by the deflector 4360 to enter water from the top of the container 4310. The FUS transducer 4330 used in the experiment of FIG. 43 is slightly concave but does not have a hole. A mirror 4350 (e.g., a round gold coated mirror) with the radius of about 2 mm is fixed at the center of FUS transducer 4330 to reflect the laser beam, in order to dispel the unwanted reflections of light from the surface of FUS transducer 4330 into the medium. The laser device 4360, the mirror 4350, and the FUS transducer 4330 are positioned in such a way that their axes are aligned. The focal distance of FUS transducer 4330 is about 2-3 cm in water and is located on the pathway of laser beam 4370. The frequency of the FUS transducer 4330 is 1.1 MHz and its initial intensity is about 0.8 W/cm$^2$. The FUS transducer 4330 may receive signals from a controller, such as, for example, and without limitations, the controller 150 of FIGS. 1A and 1C that may include the amplifier 175. Some of the components of the controller are not shown for simplicity.

The laser used in this experiment is a continuous wave (CW) laser with the wavelength of 635 nm and average intensity of about 10 milli watts per square centimeter (mW/cm$^2$. The density of the laser beam 4370 entering the container 4310 may be adjusted by the density filter 4390. The CCD camera 4380 is placed beside the container 4310 and records the changes of the laser beam's spatial width with changes of the ultrasound field. The frames of captured films may be analyzed with a software, such as, for example, and without limitations, MATLAB.

The experiments in this section are performed by a co-counter-propagating C$^2$AM transducer that creates a low-intensity FUS on the laser beam in the water medium without any mediator, software, or hardware, and in coaxial direction The experiments and simulations performed herein describe the local effect of low-FUS on the laser beam in water medium and are different from the previous researches in that, here, the intensity range of interest is less than 1 W/cm$^2$, which may not cause cavitation in the medium. Thus, the only optical effect of ultrasound is modification of the refractive index of the medium. The small contrast of the refractive index on the laser beam axis constrains the laser beam from scattering into the medium. It is demonstrated both numerically and experimentally that at low intensity FUS waves may focus the laser beam only by modifying the refractive index of the medium.

A. Results and Discussion

Figure 44A:
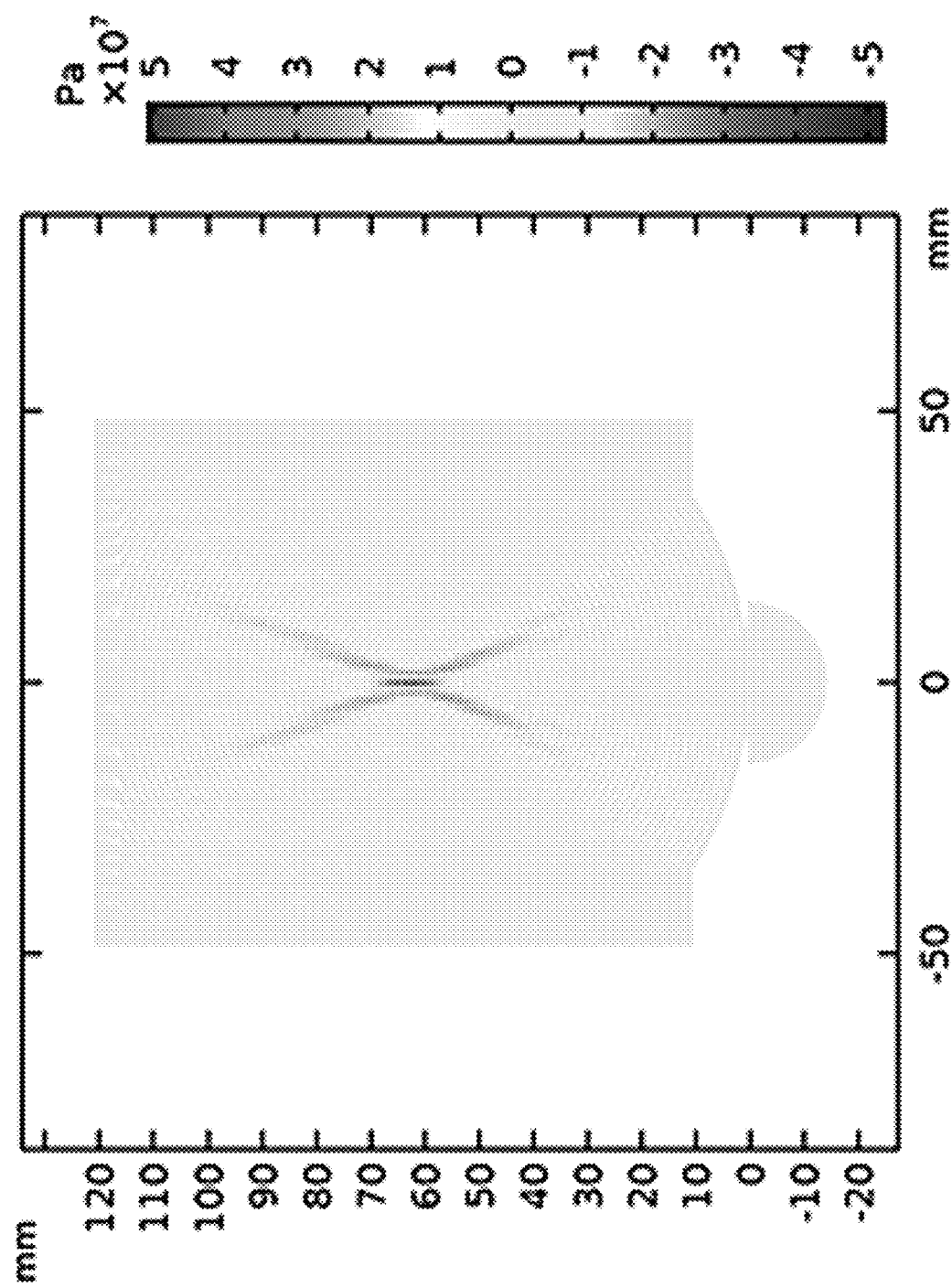
FIG. 44A illustrates the acoustic pressure level in Pascal (Pa)
Figure 44B:
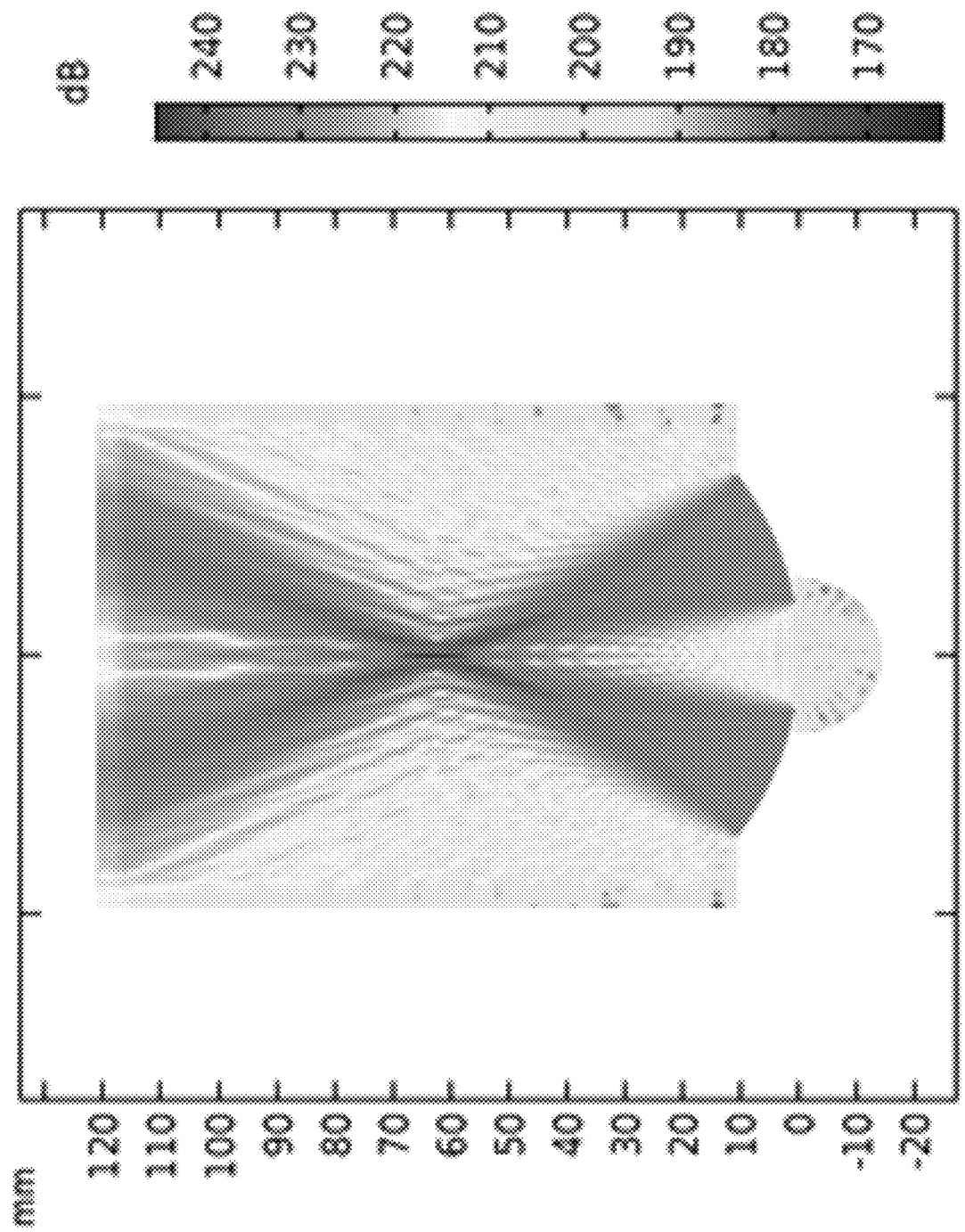
FIG. 44B illustrates the acoustic pressure level in decibels (dB), in front of the FUS transducer, according to various aspects of the present disclosure.

FIG. 44A illustrates the acoustic pressure level in Pascal (Pa), and FIG. 44B illustrates the acoustic pressure level in decibels (dB), in front of the FUS transducer, according to various aspects of the present disclosure. The figures shows that the acoustic waves are well focused in the expected oval-shaped focal zone.

Figure 45:
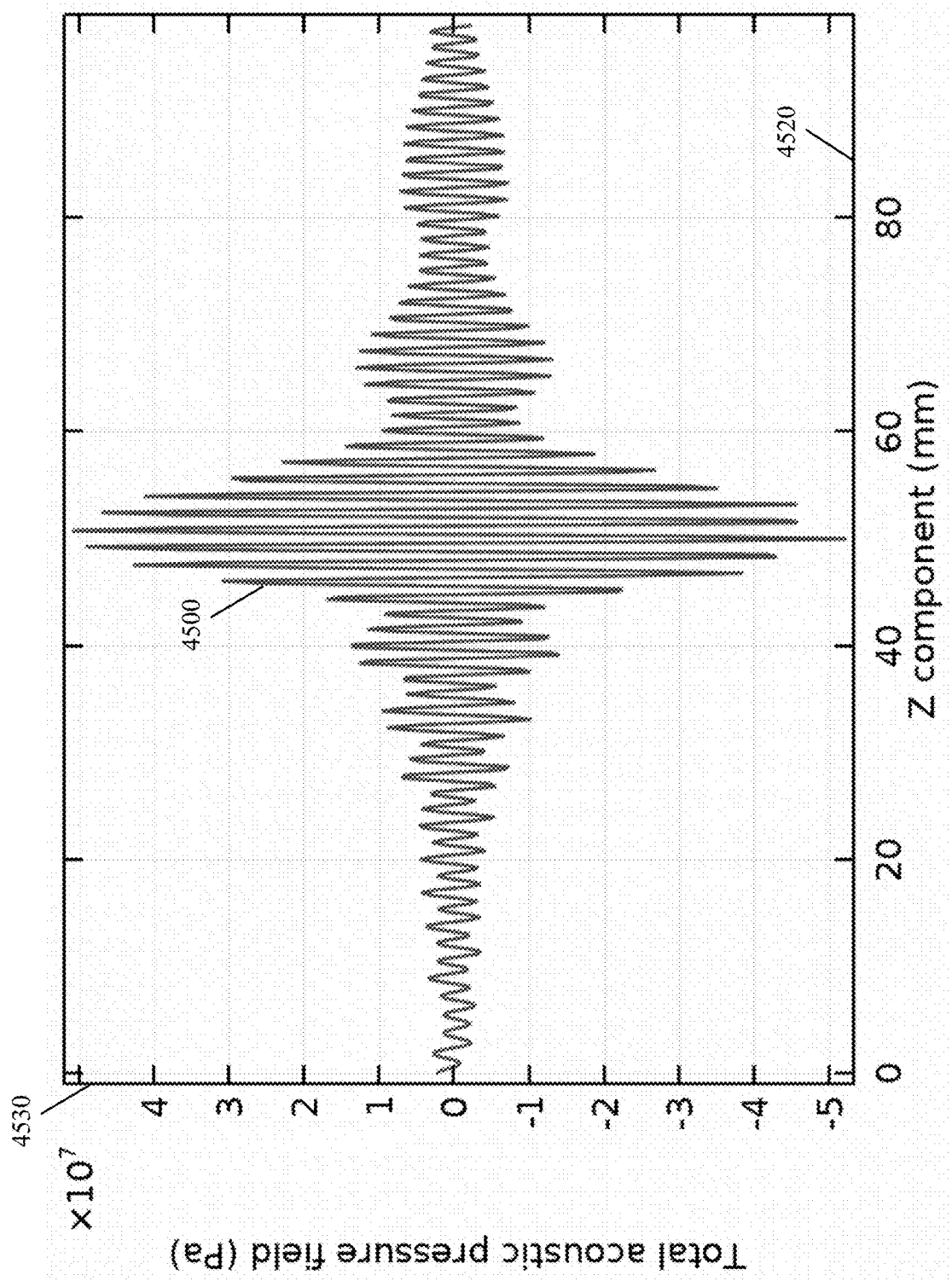
FIG. 45 is a graph illustrating the acoustic pressure along the central axis of the FUS transducer, according to various aspects of the present disclosure.

FIG. 45 is a graph 4500 illustrating the acoustic pressure along the central axis of the FUS transducer, according to various aspects of the present disclosure. With reference to FIG. 45, the acoustic pressure is plotted as a function of distance along the central axis 4205 of FIG. 42 (x=0). The distance 4520 from the FUS transducer is shown in mm and the acoustic pressure 4530 is shown in 10$^7$ Pascals. As shown in FIG. 45, at focus, the maximum pressure amplitude reaches 50 MPa. This amount of pressure may change the refractive index by 1% which in practice may only be sensed by very exact methods.

Figure 46:
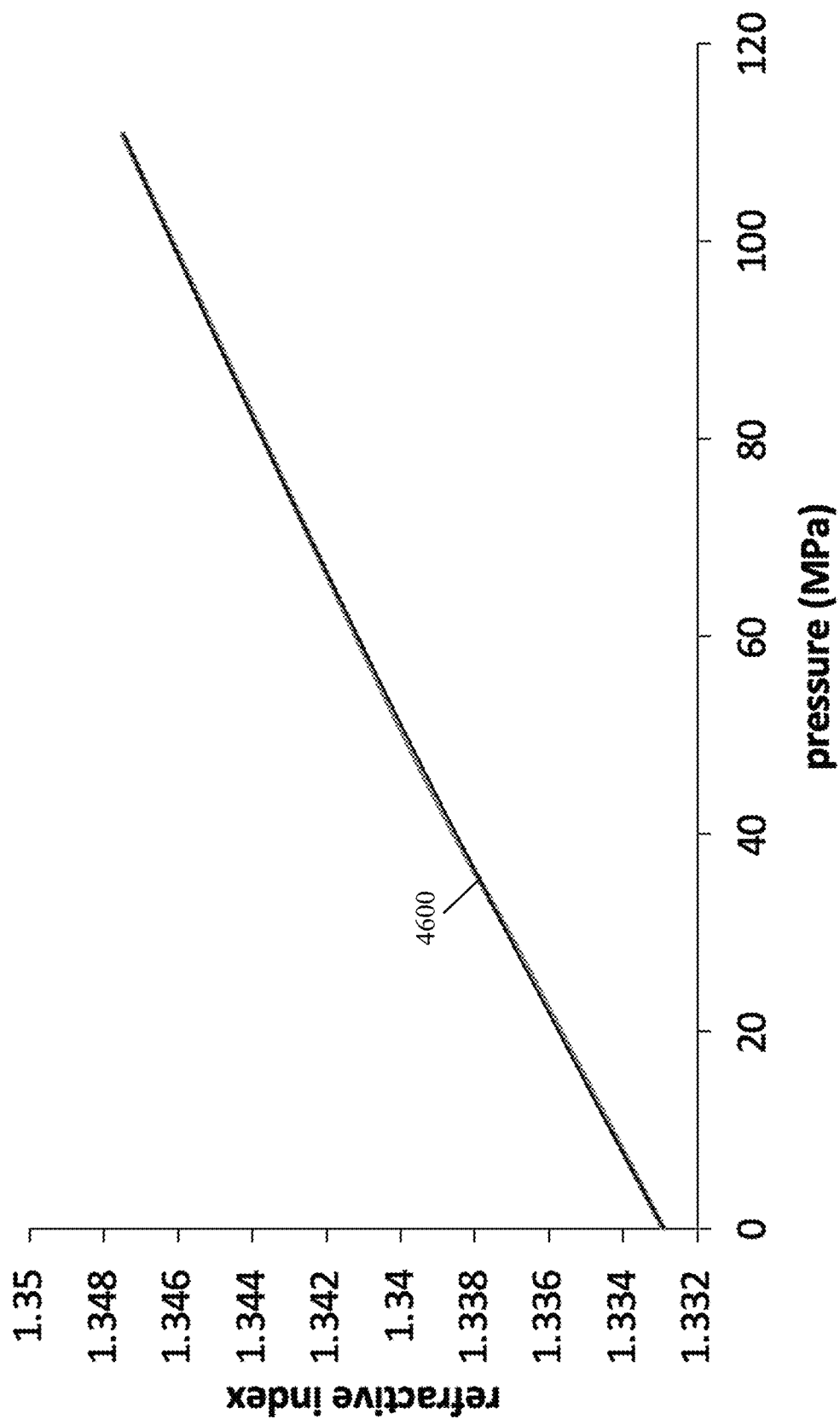
FIG. 46 is a graph illustrating the relation between the refractive index of water and the acoustic pressure in the media, according to various aspects of the present disclosure.
Figure 47:
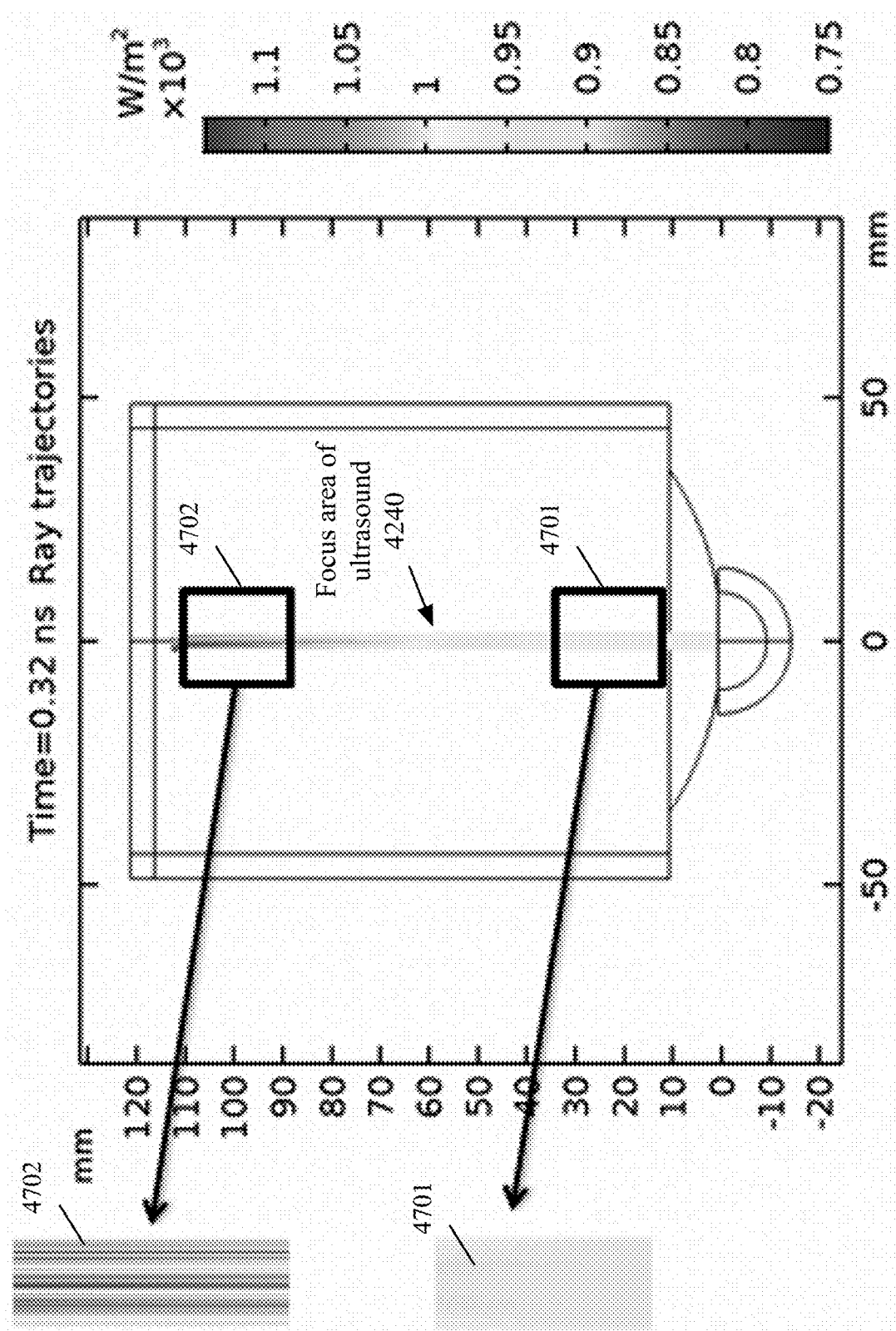
FIG. 47 illustrates the intensity of laser beam crossing the focal area of ultrasound wave, according to various aspects of the present disclosure.

FIG. 46 is a graph 4600 illustrating the relation between the refractive index of water and the acoustic pressure in the media, according to various aspects of the present disclosure. With reference to FIG. 46, the refractive index of water is plotted as a function of the acoustic pressure in MPa. FIG. 47 illustrates the intensity of laser beam crossing the focal area of ultrasound wave, according to various aspects of the present disclosure. With reference to FIG. 47, the laser wave and the FUS wave are arrange in co-propagating alignment (both waves move from bottom to top in the depicted orientation) The intensity of the laser beam 4710 is shown before 4701 and after 4702 the focal area of the ultrasound. As shown, when the light enters the medium with a homogeneous pressure field, the beam undergoes no change of intensity. However, when the light crosses the focal area 4240 of the FUS, which has inhomogeneous pressure field, the light gets more focused on the axis. Simulations predict an increase of the maximum intensity of the laser light on the beam axis from 1 to 1.12 watts per square meter (W/m$^2$) or approximately 12%.

Figure 48A:
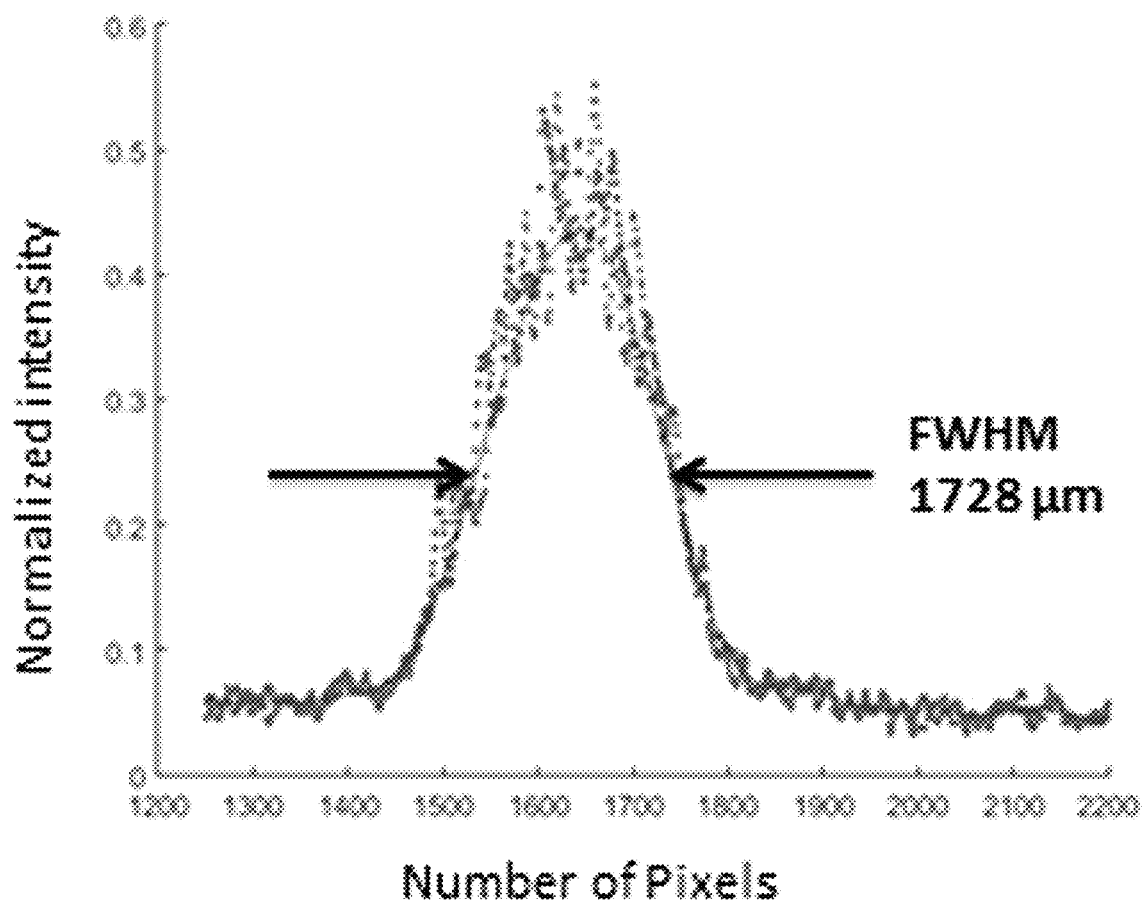
FIGS. 48A and 48B, respectively, illustrate the experimental results for the normalized average intensity of pixels on the horizontal axis, when the ultrasound is off, and on, according to various aspects of the present disclosure.
Figure 48B:
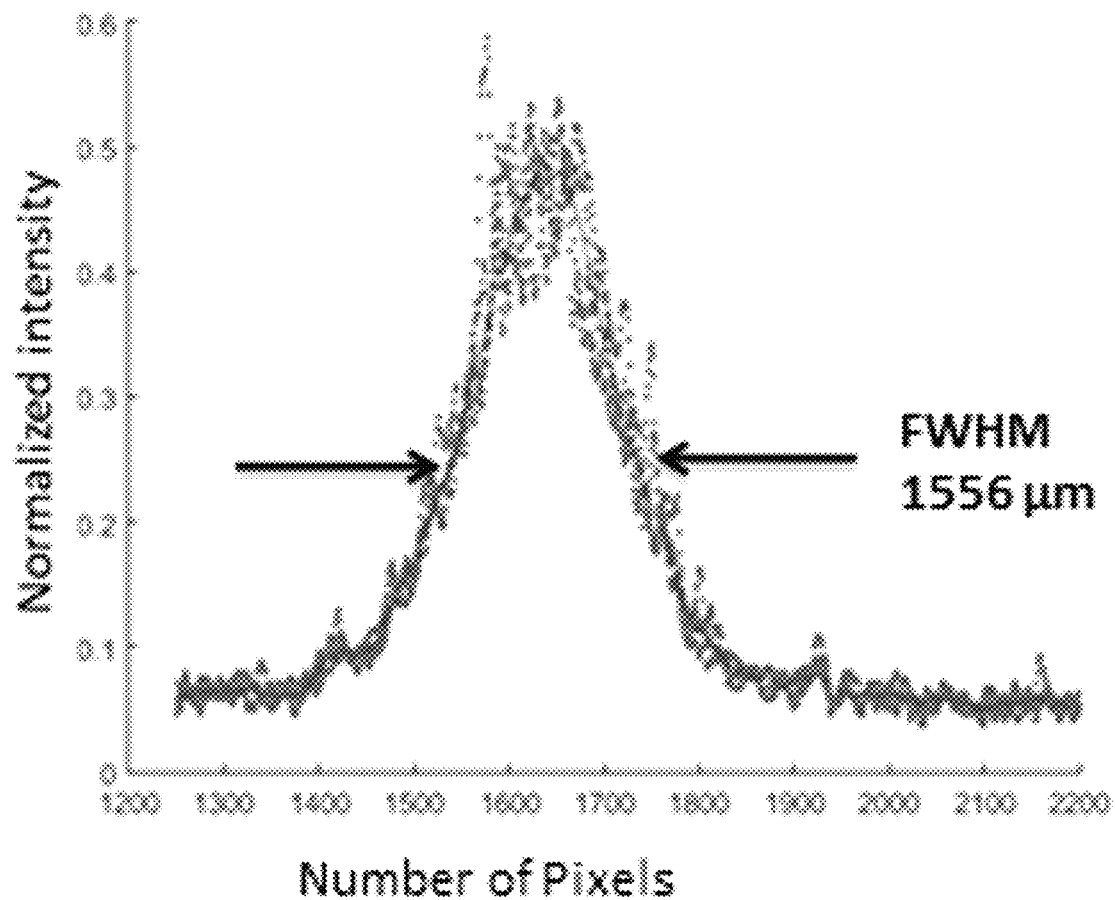

For experimental validation of the model, the effect of the ultrasound wave on the laser is examined by recording several images (e.g., pictures taken by a CCD camera) from the side view of the setup. The images were then analyzed by MATLAB. FIGS. 48A and 48B, respectively, illustrate the experimental results for the normalized average intensity of pixels on the horizontal axis, when the ultrasound is off, and on, according to various aspects of the present disclosure. The FWHM of the light focus was obtained by fitting a Gaussian function to the laser profile. The results show a reduction of the FWHM from 1728 μm (when the ultrasound is off in FIG. 48A) to 1556 μm (when the ultrasound is on in FIG. 48B) and increase of normalized peak intensity from 0.437 (when the ultrasound off in FIG. 48A) to 0.484 (when the ultrasound is on in FIG. 48B). The experiments, therefore, show a 10.75% increase of the peak intensity, which is slightly different with the result of simulations (12%). Hence despite the small differences between the results of the experiments and the simulations, there is a reasonable agreement between the two results.

This disclosure reports the focusing effect and increase in intensity of a laser beam by focused ultrasound waves using a CAM. The experimental set up to test the phenomenon was practically designed and prepared using low-intensity ultrasound transducers and different optical apparatus. The finite element model of the phenomenon was also developed, the result of which was in reasonable agreement with experimental findings. Both experiments and numerical studies show that when the ultrasound and the laser beam are aligned, presence of an ultrasonic high pressure zone in the path of a laser beam reduces scattering of light into the surrounding media. The acoustic high pressure zone has a higher refractive index in comparison with the neighboring area. When the laser beam travels through this zone, the laser beam converges and the spatial width of the beam is decreased. Consequently, the intensity of laser beam on the optical axis is increased. The experimental data shows that with the increase of ultrasound intensity from zero to 0.8 W/cm$^2$, the FWHM of the light focus is decreased.

The advantages provided by the CAM include 1) Focusing of laser beam without any mediating agents or special software or hardware, 2) the Laser wave and Ultrasound beam are coaxially mixed and propagating through each other, 3) The US pressure field amplifies the laser intensity and reduces FWHM, 4) The present embodiments require a low-intensity ring focused ultrasound transducer and low power laser, 5) No air bubble or cavitation is generated at the focal point of Ultrasound, and 6) The effects of the FUS on laser beam is reversible. As soon as the FUS is turned off, the laser beam turns back to its original shape and form with no delay.

The achievable penetration depth of the optical imaging in therapeutic window (photoacoustic tomography (PAT), photodynamic therapy (PDT) for cancer treatment, Forster resonance energy transfer (FRET) microscopy, etc.) in biological tissue is usually less than 1-2 mm. This challenge, which is primarily due to optical scattering in biological media, limits its application for in vivo studies. The present embodiments provides the effect of focused ultrasound on laser beam in water medium. As demonstrated by the experiments and simulations, the FUS may narrow the laser beam light, when aligned with laser. Therefore, the combination of the low intensity FUS and the laser beam is proved to be promising in focusing the laser beam. The combination may be used in a turbid medium, such as, for example, and without limitations, tissue, to lead to increasing depth of penetration. Findings of the experimental tests, hereon, has agreed with the modeled performance. Such agreement shows that for low intensity FUS, the variation of the refractive index due to the acoustic waves may be considered as the main mechanism for focusing the laser beam. Due to the fact that this technique is based on creating a graded index medium and not creating bubble, the technique may be used safely in water and biological tissues. Several technique on medical laser-based devices are described below to enhance the devices' diagnostic and therapeutic capabilities.

V. Using the C$^2$Am Probe in Optical Coherence Tomography

Several examples are described below that may use the CAM probe 1220 of FIG. 12A or 12B. Unless otherwise indicated, the co-propagating and the counter propagating CAM probe are interchangeable in any of the examples discussed below.

Optical coherence tomography (OCT) is an imaging technique that uses low-coherence light to capture images from within optical scattering media such as, for example, and without limitations, biological tissues. OCT may be used in non-invasive medical imaging. The applications of OCT includes, for example, and without limitations, ophthalmology, dermatology, gastroenterology, dentistry, endoscopic intra-arterial imaging, etc.

In addition to being non-invasive, OCT provides the advantages of being a high resolution imaging technique. However, OCT, as used in the prior art, has limited penetration depth in scattering media such as tissue and may require high power lasers.

a. Using the C$^2$AM in a Michelson Type OCT Interferometer

Figure 49A:
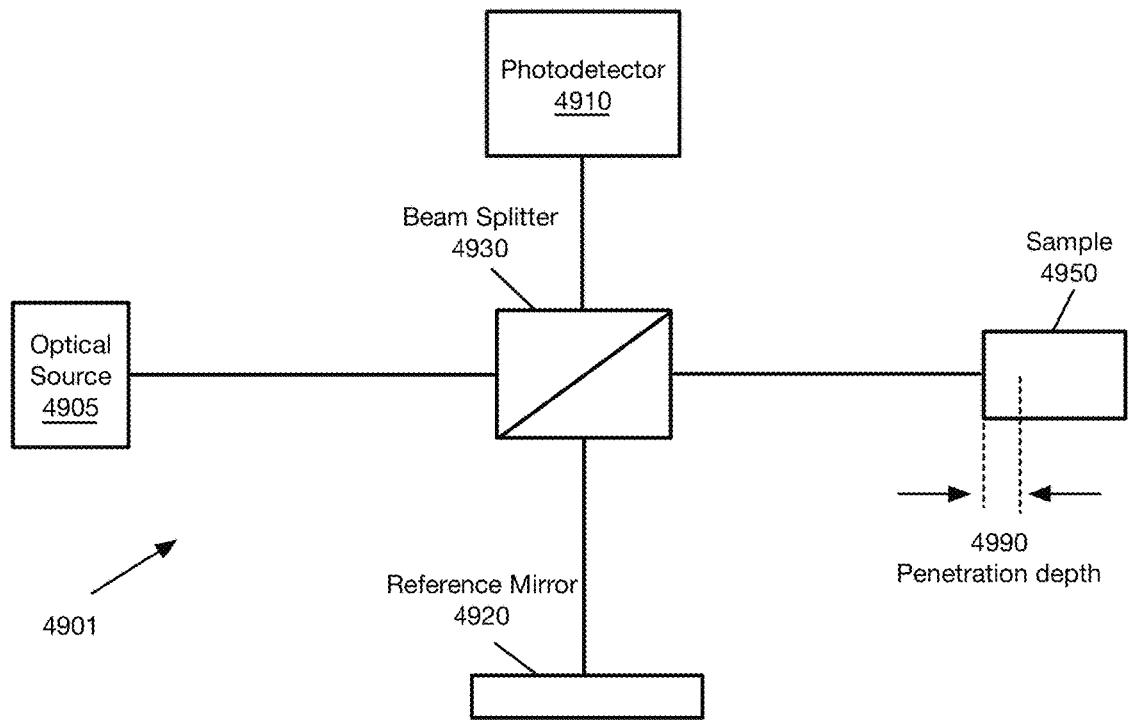
FIG. 49A is a functional diagram illustrating an optical coherence tomography (OCT) system based on a Michelson interferometer, according to prior art.

FIG. 49A is a functional diagram illustrating an OCT system based on a Michelson interferometer 4901, according to prior art. With reference to FIG. 49A, the OCT system 4901 may include an optical source 4905, a photodetector 4910, a beam splitter 4930, and a reference mirror 4920. The interferometer may be used to take an image of a sample 4950, which may be tissue or other target of interest.

In a typical configuration, OCT records a series of adjacent axial scans (A-scans) to construct a cross-sectional image of the object. Each of the A-scans contains the depth-dependent intensity of reflections or back-scattering in the sample along the beam's path that reaches a static detector that is usually coaxial with the source.

In OCT, one uses interference of the sample's signal with a reference optical signal to extract the time of flight (phase) of the signal returning from the sample. This may be implemented using a Michelson interferometer.

The light from the optical source 4905 may be directed onto the beam splitter 4930. The beam splitter 4930 may be partially reflective and may split the light in two beams. One of beams may be incident onto the sample 4950 and the other beam may be incident on the reference mirror. The backscattered light from the sample 4950 may be interfered with the light reflected from the reference mirror 4920. The path between the beam splitter 4930 and the sample 4950 is referred to as the sample arm and the path between the beam splitter 4930 and the reference mirror is referred to as the reference arm.

Both beams may recombine at the beam splitter 4930 to produce an interference pattern incident on the photodetector 4910. All information about the object may be obtained by analyzing the spectral content of the interference signal The photodetector 4910 may include a sensor for detecting the incident light. The photodetector 4910 may be, for example, and without limitations a CCD, a color camera, etc. If there is a slight angle between the two returning beams, then the photodetector 4910 may record a sinusoidal fringe pattern. The fringe pattern may be created when the interaction of the two beams on the photodetector's sensor alternates between constructive interference and destructive interference causing alternating lines of a dark and light pattern. When there is perfect spatial alignment between the returning beams, there may not be any such pattern but rather a constant intensity over the beam dependent on the difference between the two beams' path lengths.

If the optical source 4905 is coherent, such as a laser, the fringe pattern may be recorded as the relative path lengths are varied. If low coherence or short pulse light is used, the fringe pattern may only occur when the two path lengths match to within the coherence length of the light. At present, the most popular light source in OCT is the superluminescent diode (SLD). Since SLDs are implemented in waveguide structures, the space-coherence of the emitted radiation is generally high. The wavelength is determined by the material and its layering within the diode semiconductor. The coherence length of the light is the propagation distance over which a coherent electromagnetic wave maintains a specified degree of coherence. As an example, the multimode helium-neon lasers may have a coherence length of 20 cm and the coherence length of the single-mode lasers may exceed 100 m.

In order to make an image of the sample 4950, the light may be focused on the sample 4950 and an axial backscattering profile of the sample may be generated. The incident beam may then be scanned in the traverse direction to yield a two-dimensional date set that may represent the optical backscattering through a cross section of the sample. By performing multiple scans and moving the reference mirror 4920 between each scan, an entire three-dimensional image of the sample 4950 may be reconstructed.

The drawbacks of the system 4901 of FIG. 49A may include the shallow depth penetration 4990 of the light into the sample 4950, the need for a high-intensity optical source 4905, and the precise distancing of the optical components of the system 4901 from each other. Some of the present embodiments may include a $C^2AM$ probe in at least one of the light paths of the interferometer of FIG. 49A to increase the light's penetration depth into the sample 4950, to increase the image resolution, and/or to lower the intensity required for the optical source 4905.

Figure 49B:
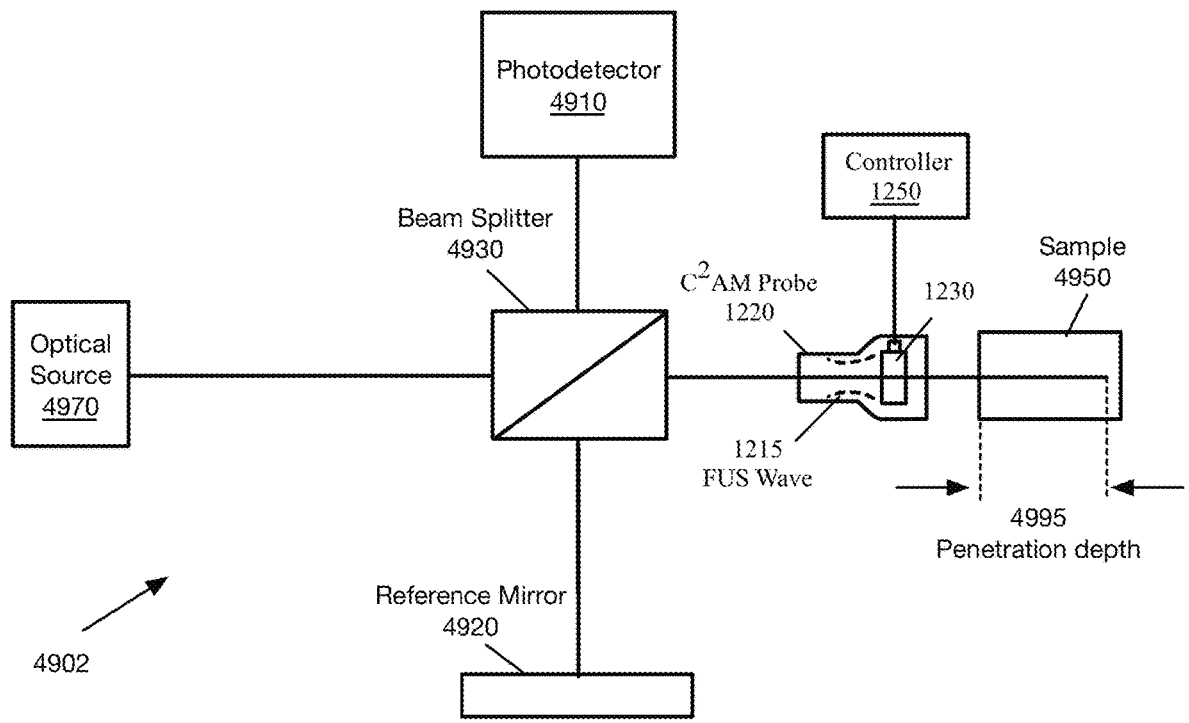
FIG. 49B is a functional diagram illustrating the addition of a coaxial acousto-optic modulator probe between the beam splitter and the sample in the OCT system based on the Michelson interferometer of FIG. 49A, according to various embodiments of the present disclosure.

FIG. 49B is a functional diagram illustrating the addition of a $C^2AM$ probe between the beam splitter and the sample in the OCT system based on the Michelson interferometer of FIG. 49A, according to various embodiments of the present disclosure. With reference to the system 4902 of FIG. 49B, a $C^2AM$ probe 1220 may be placed between the beam splitter 4930 and the sample 4950. The $C^2AM$ probe 1220 may have a counter propagating configuration (as shown) or may have a co-propagating configuration (e.g., as shown in FIG. 12B). It should be noted both counter propagating and co-propagating configurations of the $C^2AM$ probe 1220 provide similar modulated laser beam forming and dynamic focusing effects.

Since the $C^2AM$ probe 1220 intensifies the optical beam, the signal to noise ratio (SNR) of the laser may increase, resulting in a better resolution at the photodetector 4910. The $C^2AM$ probe 1220 may, therefore, make the OCT system suitable both for imaging deeper regions and with lower laser required power with higher optical resolution over an elongated depth of field. The $C^2AM$ probe 1220 may increase the focal length and therefore, the depth of penetration 4995 of laser into the sample 4950. The depth of penetration may be changed, for example, by changing the duty cycle and/or the voltage amplitude of the driving signal provided by the controller 1250. The OCT system 4902 may, therefore, provide better imaging of the sample 4950 and better diagnosis than the OCT system 4901.

The medium (e.g., and without limitations, water) inside the CAM probe 1220 may be different than the outside medium (e.g., and without limitations, air). The difference between the diffraction indexes of the two mediums may cause a change in the path travelled by the laser in the sample arm. This increase in the optical path, in some embodiments, may be compensated by adjusting the position of the reference mirror 4920. Furthermore, in the signal processing for the sample arm, the increase in the optical path may be considered and the OCT algorithm may be adjusted. The controller 1250 may not include a laser, as the optical source 4970 may be used as the source of laser.

Figure 49C:
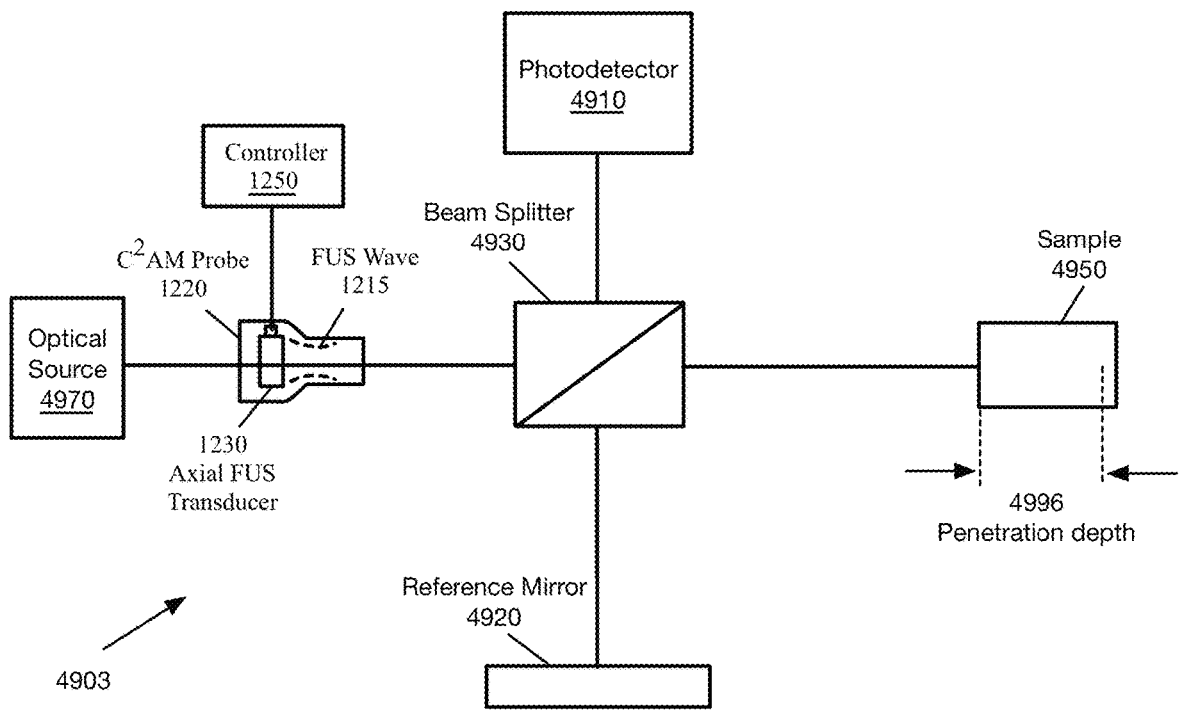
FIG. 49C is a functional diagram illustrating the addition of a coaxial acousto-optic modulator probe between the optical source and the beam splitter in the OCT system based on the Michelson interferometer of FIG. 49A, according to various embodiments of the present disclosure.

FIG. 49C is a functional diagram illustrating the addition of a $C^2AM$ probe between the optical source and the beam splitter in the OCT system based on the Michelson interferometer of FIG. 49A, according to various embodiments of the present disclosure. With reference to the system 4903 of FIG. 49C, a CAM probe 1220 may be placed between the optical source 4970 and the beam splitter 4930.

Since the coaxially travelling FUS wave 1215 focuses and increases the intensity of the laser beam, the use of the $C^2AM$ probe 1220 may result in using a weaker optical source 4970 than the optical source 4905 of FIG. 49A. The optical source 4970 may be, for example, and without limitations, a 10 W optical source 4905 may be replaced with less than a 0.1 W power source 4970 according to experimental results.

In the configuration of FIG. 49C, since there is no change in the reference arm or sample arm, the setup of the OCT system 4903 (e.g., the distance between the beam splitter 4930 and the photodetector 4910, the sample 4950, and/or the reference mirror 4920 may be similar to the configuration of the system 4901 of FIG. 49A. Despite the optical source 4970 being a weaker optical source than the optical source 4905 of FIG. 49A, the presence of the $C^2AM$ probe 1220 may still result in a higher penetration depth 4997 than the penetration depth 4990 of FIG. 49A. The modulated laser beam forming and the dynamic focusing capabilities of the $C^2AM$ probe 1220 may eliminate the need for a very tight tolerance and precise positioning of the optical source 4970 and the beam splitter 4930.

Figure 49D:
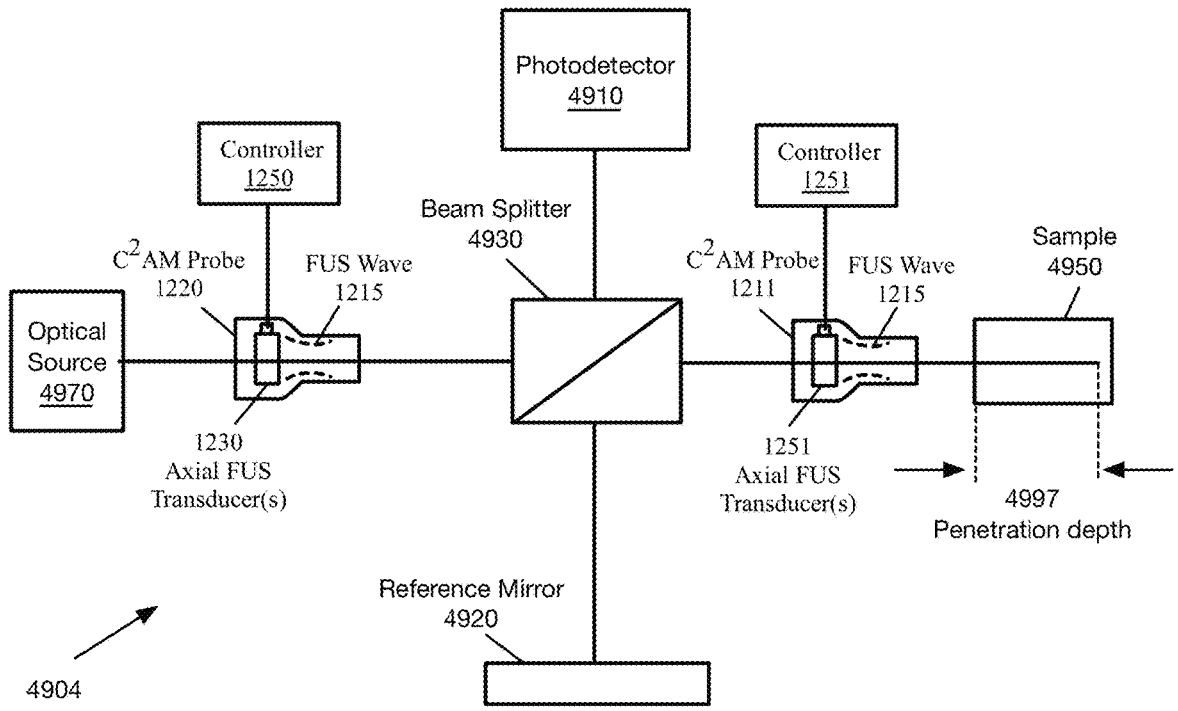
FIG. 49D is a functional diagram illustrating the addition of two coaxial acousto-optic modulator probes in the OCT system based on a Michelson interferometer of FIG. 49A, according to various embodiments of the present disclosure.

FIG. 49D is a functional diagram illustrating the addition of two CAM probes in the OCT system based on the Michelson interferometer of FIG. 49A, according to various embodiments of the present disclosure. With reference to the system 4904 of FIG. 49D, a CAM probe 1220 may be included between the optical source 4970 and the beam splitter 4930 and another CAM probe 1211 may be placed between the beam splitter 4930 and the sample 4950.

The controller 1251 may not include a laser, as the optical source 4970 may be used as the source of laser. Using the two CAM probes 1210-1211 in the system 4904 may combine the advantages provided by the systems 4902 and 4903, described above. With further reference to FIGS. 49B-49D, in addition to, or in lieu of the $C^2AM$ probes shown in FIGS. 49B-49D, one or more $C^2AM$ probes may be used in other light paths of the OCT system of FIG. 49A in order to increase the light intensity, to increase the resolution, to reduce the need for a high power optical source, and/or to provide for a more flexible positioning of the optical devices.

b. Using the $C^2AM$ in a Polarization Sensitive OCT

One of the functional extensions of the OCT is the polarization sensitive OCT (PS-OCT). While the standard OCT (e.g., the interferometer of FIG. 49A) is based only on the intensity of the light backscattered from the sample and the reference mirror, the PS-OCT also detects the polarization of the reflected light. The PS-OCT enhances the image contrast and may further reveal the microstructures within a target sample.

Figure 50A:
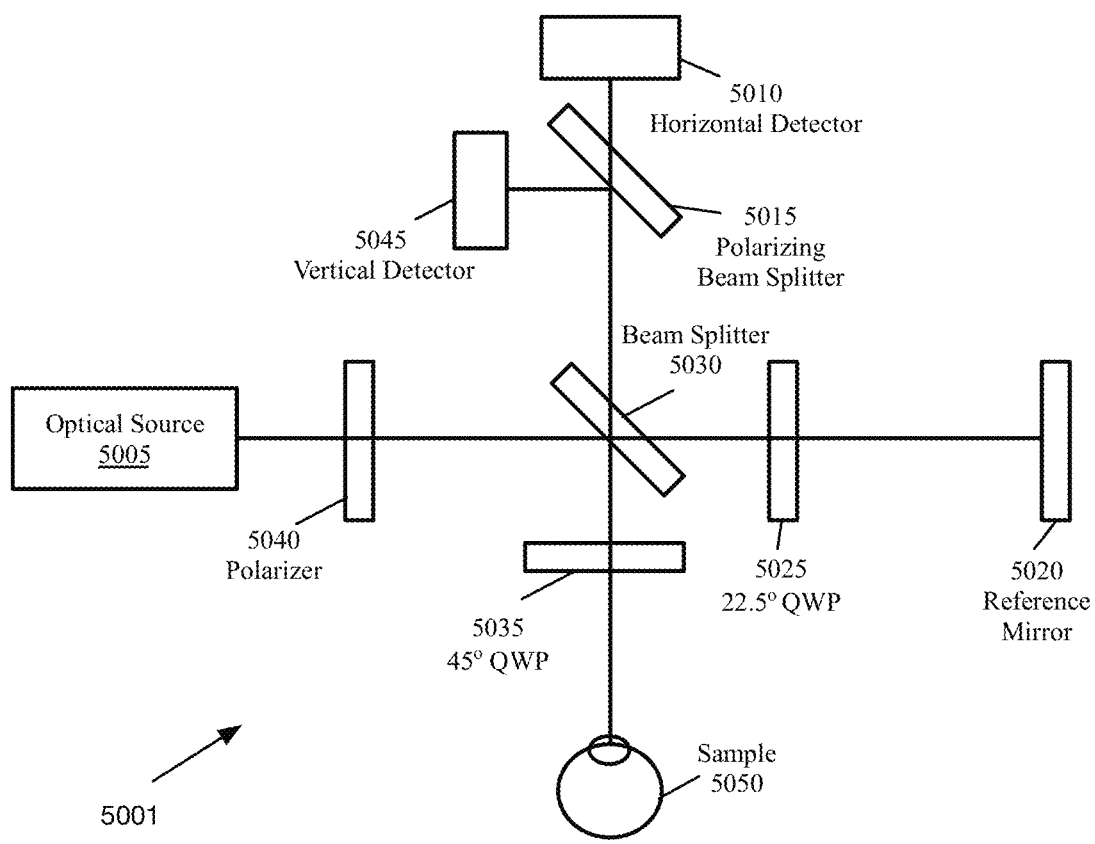
FIG. 50A is a functional diagram illustrating a polarization sensitive OCT system, according to prior art.

FIG. 50A is a functional diagram illustrating a PS-OCT system 4901, according to prior art. With reference to FIG. 50, the PS-OCT system may include an optical source 5005, a horizontal detector 5010, a polarizing beam splitter (PBS) 5015, a 22.5 degrees quarter waveplate (QWP) 5025, a beam splitter 5030, a 45 degrees QWP 5035, a polarizer 5040, and a vertical detector 5045. The optical source 5005 may be a tunable optical source such as, for example, a swept laser.

A quarter waveplate is an optical device that alters the polarization state of a light wave that travels through it by converting linearly polarized light into circularly polarized light and vice versa. The QWP 5035 may be oriented at 22.5 degrees. The QWP 5025 may be oriented at 45 degrees.

The light from the optical source 5005 may be polarized by the polarizer 5040. The polarized light may be split by the beam splitter 5030 into two beams. One beam may pass through the QWP 5035, which may linearly polarize the light after the light passes through the QWP 5035 once before being incident on the reference mirror 5020 and a second time after the light is reflected from the reference mirror 5020 back into the QWP 5025.

The light beam that is split by the beam splitter 5030 towards the sample 5050 may first enter the QWP 5035 and may be polarized by the QWP 5035. The polarized light may then be incident on the sample 5050. The beam splitter 5030 may then recombine the light reflected from the reference mirror 5020 and the light backscattered from the sample 5050.

The recombined light from the beam splitter 5030 may then be separated by the polarizing beam splitter 5015 into a horizontal beam and a vertical beam. The horizontal detector 5010 may record the amplitude and the phase of the horizontal beam and the vertical detector 5045 may record the amplitude and the phase of the vertical beam, which may be used to determine the polarization parameters.

The drawbacks of the PS-OCT system of FIG. 50A may include the shallow depth of penetration of the light into the sample 5050. Some of the present embodiments may include a CAM probe in at least one of the light paths of the PS-OCT system of FIG. 50A to increase the light's penetration depth into the sample 5050 and/or to lower the intensity required for the optical source 5005.

Figure 50B:
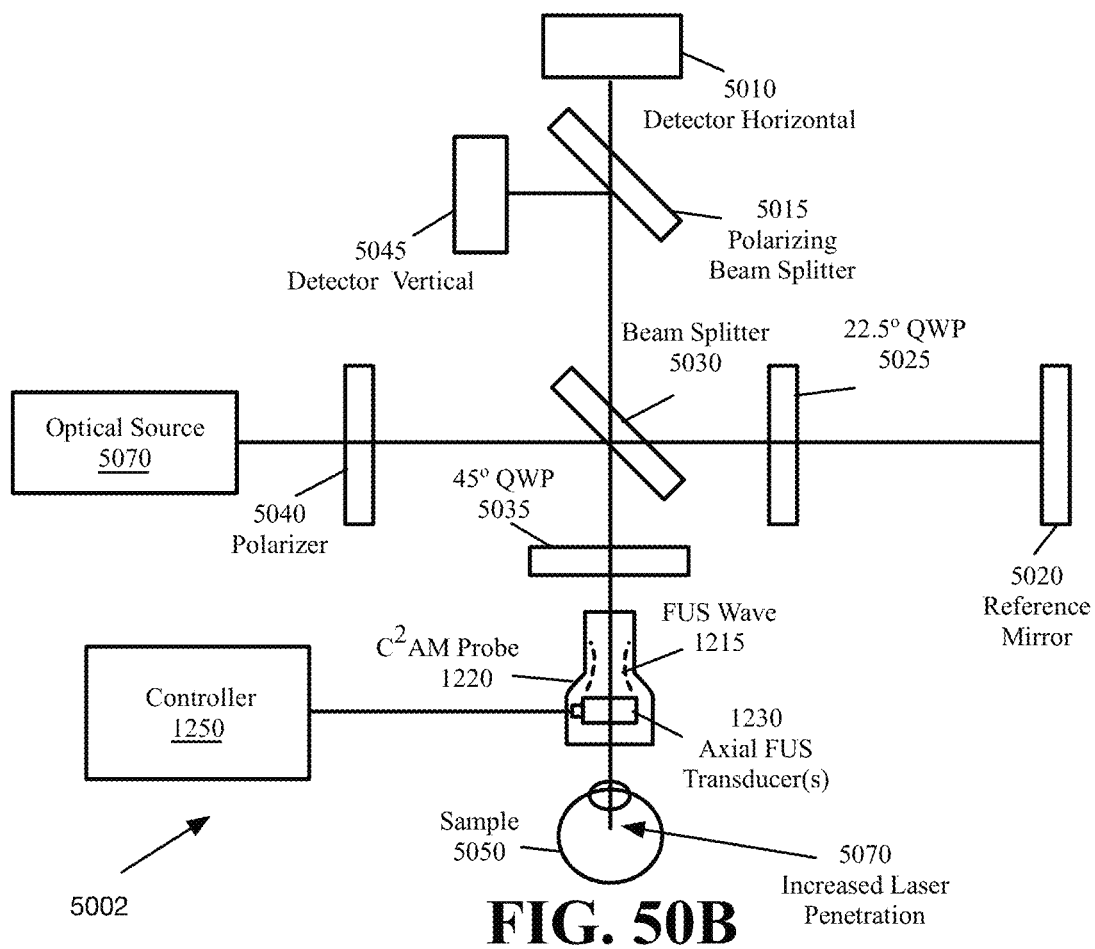
FIG. 50B is a functional diagram illustrating the addition of a coaxial acousto-optic modulator probe between the 45 degrees quarter waveplate and the sample in the polarization sensitive system of FIG. 50A, according to various embodiments of the present disclosure.

FIG. 50B is a functional diagram illustrating the addition of a CAM probe between the 45 degrees QWP and the sample in the PS-OCT system of FIG. 50A, according to various embodiments of the present disclosure. With reference to the system 5002 of FIG. 50B, a CAM probe 1220 may be placed between the QWP 5035 and the sample 5050. The $C^2AM$ probe 1220 may have a counter propagating configuration (as shown) or may have a co-propagating configuration (e.g., as shown in FIG. 12B).

Since the $C^2AM$ probe 1220 intensifies the optical beam, the signal to noise ratio (SNR) of the laser may increase, resulting in a better resolution at the detectors 5010 and 5045. The $C^2AM$ probe 1220 may, therefore, make the OCT system suitable for imaging. The $C^2AM$ probe 1220 may increase the focal length and therefore, the depth of penetration of laser into the sample 5050. The depth of penetration may be changed, for example, by changing the duty cycle and/or the voltage amplitude of the driving signal provided by the controller 1250. The OCT system 5002 may, therefore, provide better imaging of the sample 5050 and better diagnosis than the OCT system 5001.

With reference to FIG. 50B, in addition to, or in lieu of the $C^2AM$ probe 1220, a CAM probe may be added between the optical source 5070 and the beam splitter 5030 (either before or after the polarizer 5040). Similar to what described above with reference to FIGS. 49B and 49D, the coaxially travelling FUS wave 1215 focuses and increases the intensity of the laser beam and the use of the $C^2AM$ probe 1220 may result in using a weaker optical source 5070 than the optical source 5005 of FIG. 50A. The controller 1250 may not include a laser, as the optical source 5070 may be used as the source of laser.

With further reference to FIG. 50B, in addition to, or in lieu of the $C^2AM$ probe 1220, one or more $C^2AM$ probes may be used in other light paths of the PS-OCT system in order to increase the light intensity, to increase the resolution, and/or to reduce the need for a high power optical source.

c. Using the $C^2AM$ in a Full-Field Michelson Type OCT

Figure 51A:
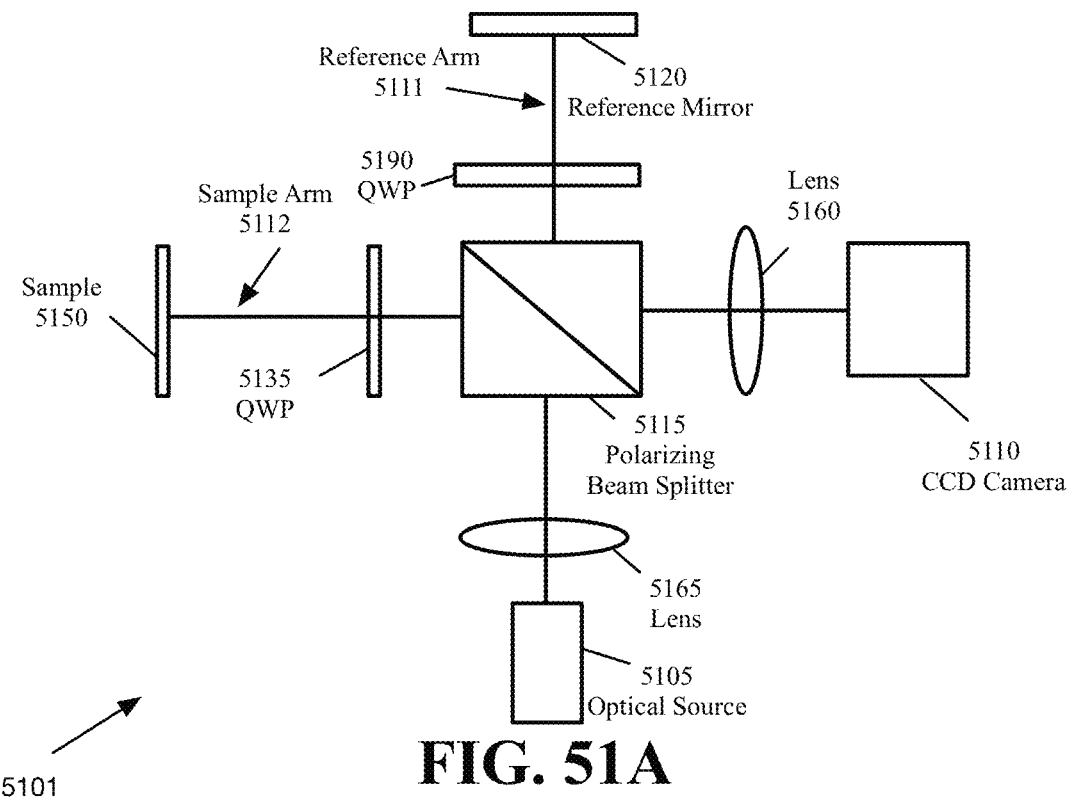
FIG. 51A is a functional diagram illustrating a full-filed OCT system, according to prior art.

Unlike other OCT techniques that acquire cross-sections of the sample, the images in the full-field OCT are taken en face (i.e., orthogonal to the light beam of illumination). FIG. 51A is a functional diagram illustrating a full-field OCT system 5101, according to prior art. The full-field OCT system 5101 may include an optical source 5105, a polarizing beam splitter 5115, two QWPs 5190 and 5195, two lenses 5160 and 5165, and a reference mirror 5120.

The lens 5165 may collimate the light from the optical source 5165. The collimated light may be split into two orthogonally polarized light beams by the polarizing beam splitter. The beam that goes through the reference arm 5111 may go through the QWP 5190 and be reflected from the reference mirror 5120. The beam that goes through the sample arm 5112 may go through the QWP 5135 and be scattered from the sample 5150.

After the round trip transmission through the corresponding QWPs 5190 and 5195, the polarizing states of light beams in the sample arm 5112 and the reference arms 5111 are exchanged. The polarizing beam splitter 5115 may recombine the two beams. The lens 5160 may receive the combined beams and may make them incident on the CCD camera 5110. The CCD camera 5110 may record and en face image of the sample 5150.

Figure 51B:
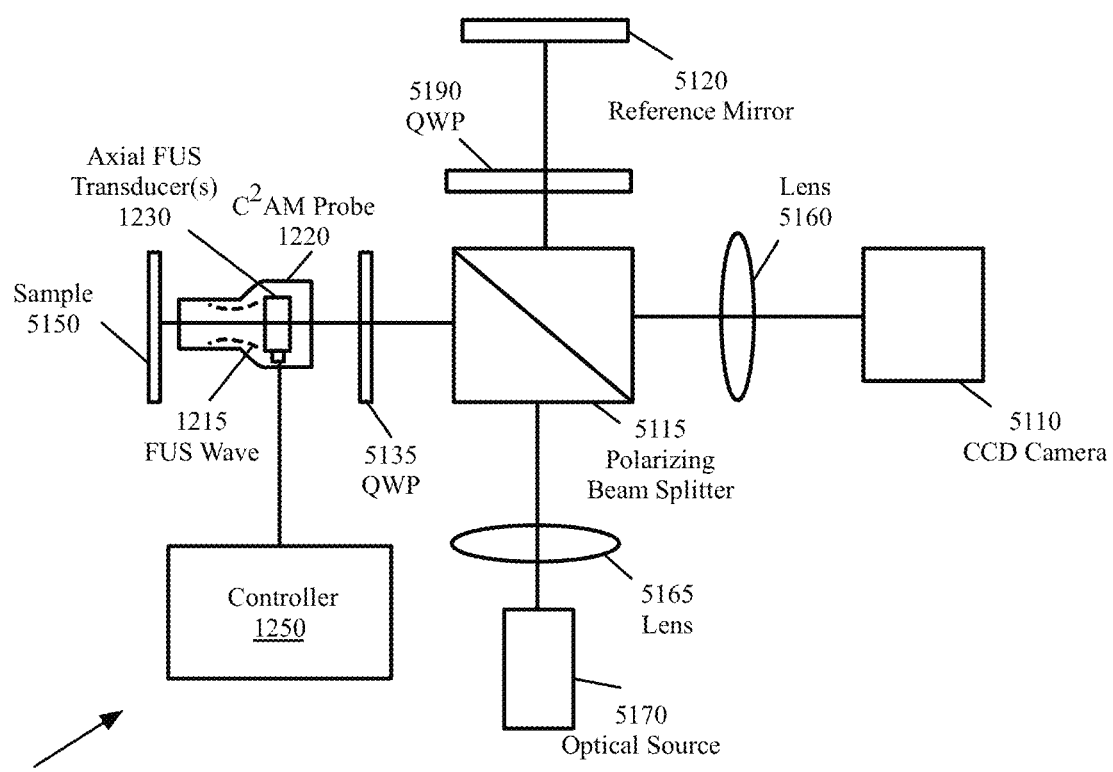
FIG. 51B is a functional diagram illustrating the addition of a coaxial acousto-optic modulator probe in the full-filed OCT system of FIG. 51B, according to various embodiments of the present disclosure.

FIG. 51B is a functional diagram illustrating the addition of a $C^2AM$ probe in the full-filed OCT system of FIG. 51A, according to various embodiments of the present disclosure. With reference to the system 5102 of FIG. 51B, a $C^2AM$ probe 1220 may be placed between the QWP 5135 and the sample 5150. The $C^2AM$ probe 1220 may have a counter propagating configuration (as shown) or may have a co-propagating configuration (e.g., as shown in FIG. 12B).

Since the $C^2AM$ probe 1220 intensifies the optical beam, the SNR of the laser may increase, resulting in a better resolution at the CCD camera 5110. The $C^2AM$ probe 1220 may, therefore, provide the OCT system 5102 with significant advantages for imaging. The $C^2AM$ probe 1220 may increase the focal length and, therefore, the depth of penetration of laser into the sample 5150. The depth of penetration may be changed, for example, by changing the duty cycle and/or the voltage amplitude of the driving signal provided by the controller 1250. The OCT system 5102 may, therefore, provide better imaging of the sample 5150 and better diagnosis than the OCT system 5101.

With reference to FIG. 51B, in addition to, or in lieu of the $C^2AM$ probe 1220, a $C^2AM$ probe may be added between the optical source 5170 and the polarizing beam splitter 5115 (either before or after the lens 5165). Similar to what described above with reference to FIGS. 49B and 49D, the coaxially travelling FUS wave 1215 focuses and increases the intensity of the laser beam and the use of the $C^2AM$ probe 1220 may result in using a weaker optical source 5170 than the optical source 5105 of FIG. 51A. The controller 1250 may not include a laser, as the optical source 5170 may be used as the source of laser.

With further reference to FIG. 51B, in addition to, or in lieu of the $C^2AM$ probe 1220, one or more $C^2AM$ probes may be used in other light paths of the OCT system 5102 in order to increase the light intensity, to increase the resolution, and/or to reduce the need for a high power optical source.

d. Using the $C^2AM$ in a Fourier Domain OCT

Figure 52A:
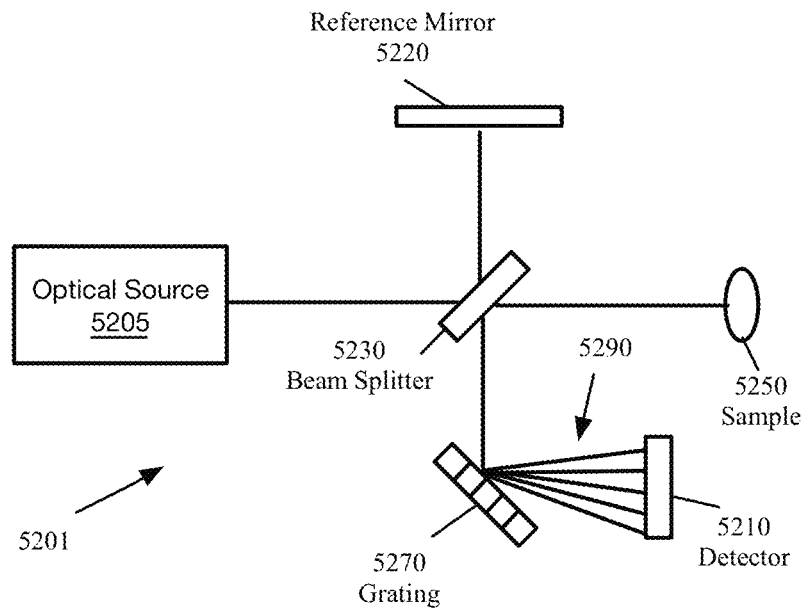
FIG. 52A is a functional diagram illustrating a Fourier domain OCT system, according to prior art.

FIG. 52A is a functional diagram illustrating a Fourier domain OCT (FD-OCT) system, according to prior art. The FD-OCT system 5201 may include an optical source 5205, a reference mirror 5220, a beam splitter 5230, a diffraction grating 5270, and a detector 5210. The optical source 5205 may be, for example, a broadband light source, which may produce light with a broad bandwidth.

Similar to the interferometer 4901 of FIG. 49A, the light from the optical source 5205 may be directed onto the beam splitter 5230. The beam splitter 5230 may be partially reflective and may split the light into two beams. One of beams may be incident onto the sample 5250 and the other beam may be incident on the reference mirror 5220.

The backscattered light from the sample 5250 may be interfered with the light reflected from the reference mirror 5220. Both beams may recombine at the beam splitter 5230 to produce an interference pattern incident on the diffraction grating 5270. The diffraction grating 5270 is an optical component with a periodic structure that splits light into several separate beams 5290 that travel in different directions.

The detector 5210 may be a linear detector array, which may detect the beams 5290. The Fourier transform may be applied to the detected beams to determine the depth of each scattered signal. The results may be used to generate an image of the sample 5250. Using the Fourier transform, the depth of scan may be immediately calculated from the acquired spectra, without movement of the reference mirror 5220. The FD-OCT systems typically have a better imaging speed comparing to other types of OCT. Separating the scattered light into separate beams 5290 at multiple wavelength ranges limits the scanning range.

The drawbacks of the FD-OCT system of FIG. 52A may include the shallow depth penetration of the light into the sample 5250 and the need for a high-intensity optical source 5205. Some of the present embodiments may include the $C^2AM$ probe in at least one of the light paths of the system of FIG. 52A to increase the light's penetration depth into the sample 5250, to increase the image resolution, and/or to lower the intensity required for the optical source 5205.

Figure 52B:
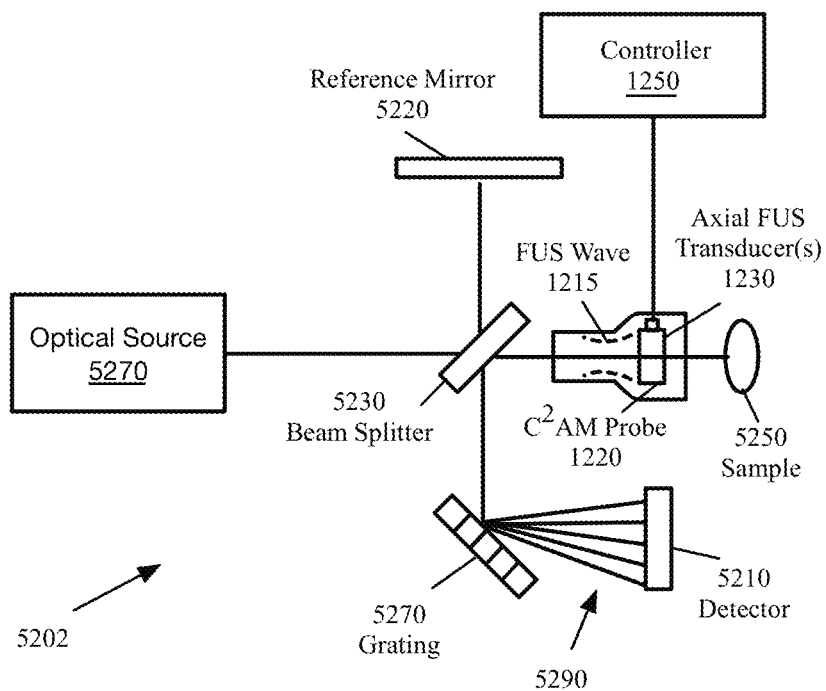
FIG. 52B is a functional diagram illustrating the addition of a coaxial acousto-optic modulator probe between the beam splitter and the sample in the Fourier domain OCT system of FIG. 52A, according to various embodiments of the present disclosure.

FIG. 52B is a functional diagram illustrating the addition of a $C^2AM$ probe between the beam splitter and the sample in the FD-OCT system of FIG. 52A, according to various embodiments of the present disclosure. With reference to the system 5202 of FIG. 52B, a $C^2AM$ probe 1220 may be placed between the beam splitter 5230 and the sample 5250. The $C^2AM$ probe 1220 may have a counter propagating configuration (as shown) or may have a co-propagating configuration (e.g., as shown in FIG. 12B).

Since the $C^2AM$ probe 1220 intensifies the optical beam, the SNR of the laser may increase, resulting in a better resolution of the beams 5290 at the detector 5210. The $C^2AM$ probe 1220 may, therefore, provide the OCT system a more powerful modality for imaging. The $C^2AM$ probe 1220 may increase the focal length and, therefore, the depth of penetration of laser into the sample 5250. The depth of penetration may be changed, for example, by changing the duty cycle and/or the voltage amplitude of the driving signal provided by the controller 1250. The OCT system 5202 may, therefore, provide better imaging of the sample 5250 and better diagnosis than the OCT system 5201.

With reference to FIG. 52B, in addition to, or in lieu of the $C^2AM$ probe 1220, a CAM probe may be added between the optical source 5270 and the beam splitter 5230. Similar to what described above with reference to FIGS. 49B and 49D, the coaxially travelling FUS wave 1215 focuses and increases the intensity of the laser beam and the use of the $C^2AM$ probe 1220 may result in using a weaker optical source 5270 than the optical source 5205 of FIG. 52A.

With further reference to FIG. 52B, in addition to, or in lieu of the $C^2AM$ probe 1220, one or more $C^2AM$ probes may be used in other light paths of the FD-OCT system in order to increase the light intensity, to increase the resolution, and/or to reduce the need for a high power optical source.

e. Using the $C^2AM$ in a Polarization Sensitive OCT

OCT typically uses light in the near-infrared spectral range, which has a penetration depth of several hundred microns in the tissue. The backscattered light is measured with an interferometric set-up to reconstruct the depth profile of the sample at the selected location. A scanning OCT beam allows for acquisition of cross-sectional images of the tissue structure.

Figure 53:
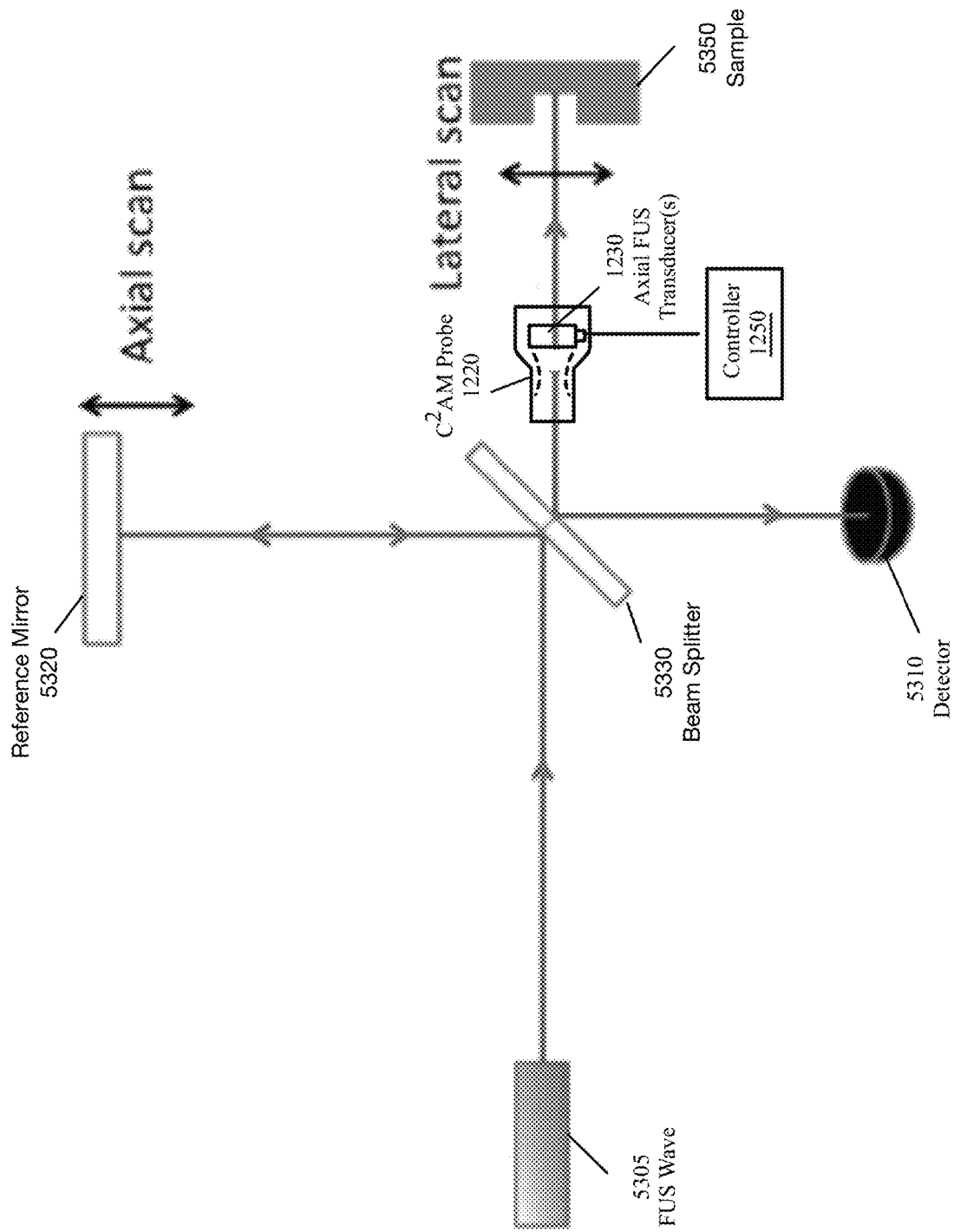
FIG. 53 is a functional diagram illustrating the addition of a CAM probe between the beam splitter and the sample in an OCT system of the uses a scanning beam, according to various embodiments of the present disclosure.

FIG. 53 is a functional diagram illustrating the addition of a C²AM probe between the beam splitter and the sample in an OCT system of the uses a scanning beam, according to various embodiments of the present disclosure. With reference to FIG. 53, the light source 5310 may be a broadband light source. The reference mirror 5320, the beam splitter 5330, and the detector may function similar as the corresponding components of FIG. 49B. The lateral scanning of the laser beam allows for acquisition of cross-sectional images of the tissue structure.

The CAM probe 1220 may be placed between the beam splitter 5330 and the sample 5350. The C²AM probe 1220 may have a counter propagating configuration (as shown) or may have a co-propagating configuration (e.g., as shown in FIG. 12B). The penetration depth limitation of optical coherence tomography is a clear challenge By using the CAM probe 1220 in sample arm after the beam splitter 5330, the resolution and penetration depth improve.

VI. USING THE C²AM IN A FABRY-PEROT INTERFEROMETER

Figure 54A:
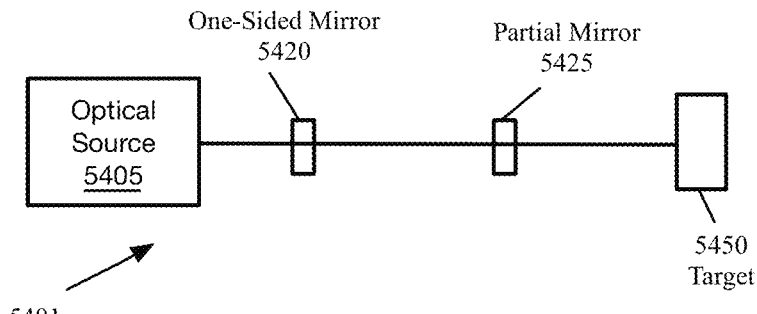
FIG. 54A is a functional diagram of a Fabry-Perot Interferometer, according to prior art.

FIG. 54A is a functional diagram of a Fabry-Perot Interferometer 5401, according to prior art. With reference to FIG. 54A, the Fabry-Perot Interferometer 5401 may include an optical source 5405, a one-sided mirror 5420, and a partial mirror 5425. The Fabry-Perot Interferometer 5401 may include other optical elements, such as, for example, optional collimating and/or focusing lenses (not shown).

The Fabry-Perot Interferometer 5401 may be used as a standalone optical device or may be incorporated in other optical devices, such as, for example, OCT systems, laser resonators, optical wavemeters, telecommunications, spectroscopy, etc., to control and measure the wavelengths of light. The target 5450 may, for example, be a sample tissue. As another example, in cases that the Fabry-Perot Interferometer is incorporated in another optical device, the target 5450 may be another optical component of the optical device.

With further reference to FIG. 54A, the two mirrors 5420 and 5425 may make an optical cavity. Optical waves may pass through the optical cavity only when they are in resonance with the cavity. The distance between the two mirrors may be fixed or changeable. In a typical Fabry-Perot Interferometer, the light that enters the one-sided mirror 5420 is collimated light. For example, a laser may be used as the optical source 5405. Alternatively, a diffused light source may be used as the optical source and the light from the optical source 5405 may pass through a collimating lens (not shown) before reaching the one-sided mirror 5420.

Figure 54B:
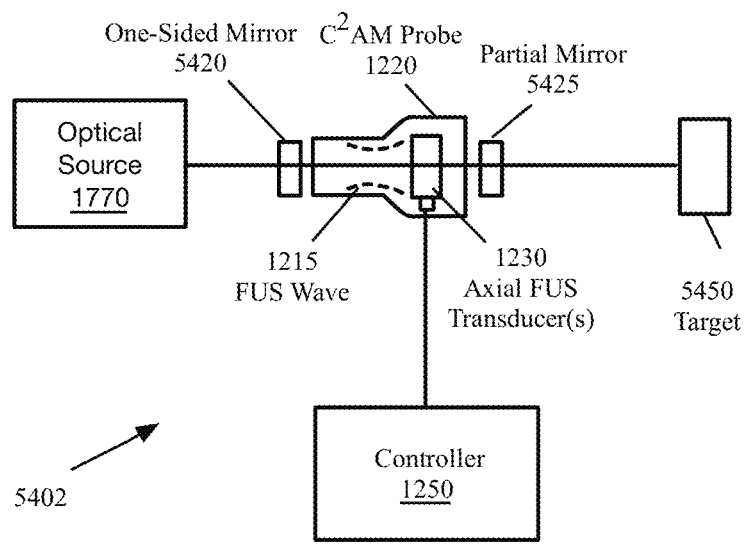
FIG. 54B is a functional diagram illustrating the addition of a coaxial acousto-optic modulator probe inside the cavity of the Fabry-Perot Interferometer of FIG. 54A, according to various embodiments of the present disclosure.

FIG. 54B is a functional diagram illustrating the addition of a CAM probe inside the cavity of the Fabry-Perot Interferometer of FIG. 54A, according to various embodiments of the present disclosure. With reference to the system 5402 of FIG. 54B, a C²AM probe 1220 may be placed inside the cavity of the Fabry-Perot Interferometer. The C²AM probe 1220 may have a counter propagating configuration (as shown) or may have a co-propagating configuration (e.g., as shown in FIG. 12B). The controller 1250 may not include a laser, as the optical source 5405 may be used as the source of laser.

The photons of the light wave resonating between the mirrors 5420 and 5425 may enter the CAM probe 1220. The axial FUS transducer(s) 1230 may generate the FUS wave 1215 that may travel coaxially (e.g., counter propagate as shown in FIG. 54B or co-propagate when a co-propagating C²AM probe is used) with the light wave.

One purpose of using the Fabry-Perot Interferometer is to intensify the light that passes through the interferometer's cavity. Adding the C²AM probe 1220 to the cavity may further intensify the optical beam by more than an order of magnitude. Adding the C²AM probe 1220 may also increase the resolution and/or reduce the need for a high power light source.

Figure 54C:
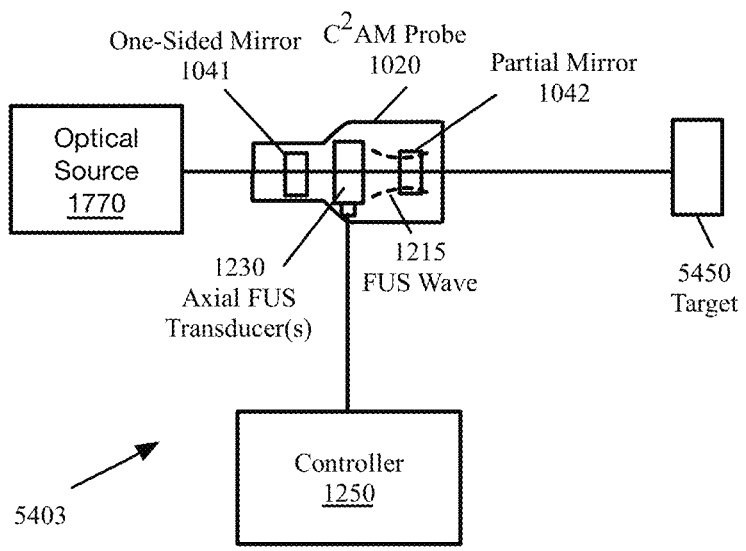
FIG. 54C is a functional diagram illustrating the use of a coaxial acousto-optic modulator probe as a Fabry-Perot Interferometer, according to various embodiments of the present disclosure.

In some of the present embodiments, the Fabry-Perot cavity may be inside the C²AM probe. FIG. 54C is a functional diagram illustrating the use of a C²AM probe as a Fabry-Perot Interferometer, according to various embodiments of the present disclosure.

In the system 5403 of FIG. 54C, the Fabry-Perot cavity is created between the one-sided mirror 1041 and the partially reflective mirror 1042, which are both inside the C²AM probe 1020. The C²AM probe 1020 may be similar to, and operate as, the C²AM probe 1020 described above with reference to FIGS. 10A and 10B. Adding the C²AM probe 1220 to the cavity in the system 5403 may further intensify the optical beam generated by the optical source 5470 by more than an order of magnitude. Adding the C²AM probe 1220 may also increase the resolution and/or reduce the need for a high power light source.

VII. USING THE C²AM IN GRIN LENS-BASED OPTICAL SYSTEM

A gradient-index (GRIN) lens may be made of material with a gradual variation of the refractive index. A GRIN lens may be produced with flat surfaces. FIG. 55A is a cross section of an OCT catheter 5501, according to prior art. With reference to FIG. 55A, the GRIN lens imaging probe 5501 may be used, for example, as an endoscopic OCT probe.

The GRIN lens imaging probe 5501 may include a GRIN lens 5520, a prism 5530, an optical fiber 5510, a spacer 5540 between the optical fiber 5510 and the GRIN lens 5520, and a tubing 5545. The spacer 5540 may include, for example, an optical adhesive and/or an air gap. The tubing 5545 may be, for example, transparent plastic or glass.

As shown, the radial refractive index profile of the GRIN lens 5520 causes the light in the GRIN lens 5520 to follow a continuous curved trajectory 5550. The light coming out of the GRIN lens 5520 may be incident on the prism 5530, which may deflect the light in a vertical direction (e.g. to focus the light on a vein's wall). The spacer 5540, the GRIN lens 5520, and the prism 5530 may be configured such that the focal point 5560 of the light may be at a fixed distance from the imaging probe's 5501 tubing 5545.

The drawbacks of the GRIN lens imaging probe 5501 may include lack of control over changing the focal point, insufficient depth of penetration, and/or difficulty in achieving desirable light intensity and image resolution. As an example, if the width of the light at the optical fiber 5510 is W, the best achievable focused width of the light may be 2 W at the focal point 5560 of FIG. 55A.

FIG. 55B is a cross section of an OCT catheter of FIG. 55A after a CAM probe is added inside the catheter, according to various embodiments of the present disclosure. With reference to the imaging probe 5502 of FIG. 55B, a CAM probe 1220 may be placed between the GRIN lens 5520 and the prism 5530. The CAM probe 1220 may have a counter propagating configuration (as shown) or may have a co-propagating configuration (e.g., as shown in FIG. 12B).

The light may enter the CAM probe 1220, for example, and without limitation thorough a transparent window, as described above with reference to FIGS. 1A-1D. The axial FUS transducer(s) 1230 may generate the FUS wave 1215 that may travel coaxially (e.g., counter propagate as shown in FIG. 49B or co-propagate when a co-propagating CAM probe is used) with the light wave. The FUS wave 1215 may enhance the light's focus. For example, the light beam diameter may decrease from 6.5 mm at the laser input 5560 of FIG. 55A to 0.3 mm at the optical focal point 5565 of FIG. 55B.

The controller 1250 may not include a laser, as the light may be provided through the optical fiber 5510. The values of duty cycle and the voltage amplitude generated by the controller 1250 may be changed, as described above with reference to FIGS. 4-7. For example, and without limitations, a table lookup may be made to select the values of duty cycle and the voltage amplitude in order to achieve a desired light intensity at a given distance. The focal point 5565 of the light and the depth of penetration of the light in FIG. 55B may, therefore, be controllable.

FIG. 55C is a cross section of the imaging probe of FIG. 55A after the GRIN lens is replaced by a CAM probe, according to various embodiments of the present disclosure. With reference to the imaging probe 5503 of FIG. 55C, a CAM probe 1220 may replace the GRIN lens 5520 of FIG. 55A.

Similar to what was described above with reference to FIG. 55B, the controller 1250 in FIG. 55C may not include a laser, as the light may be provided through the optical fiber 5510. The values of duty cycle and the voltage amplitude generated by the controller 1250 may be changed, as described above with reference to FIGS. 4-7. For example, and without limitations, a table lookup may be made to select the values of duty cycle and the voltage amplitude in order to achieve a desired light intensity at a given distance. The focal point 5565 of the light and the depth of penetration of the light in FIG. 55C may, therefore, be controllable.

Another advantage of replacing the GRIN lens 5520 of FIG. 55A with the CAM probe 1220 of FIG. 55C is the light in FIG. 55C may not have the curved trajectory 5550 of FIG. 55A. As a result, the beam width at the optical focal point 5565 may be narrower and the light may be more focused in the system of FIG. 55C than the systems of FIGS. 55A and 55B.

VIII. MICROIMAGING USING C²AM (COAXIAL FUS)

Figure 56:
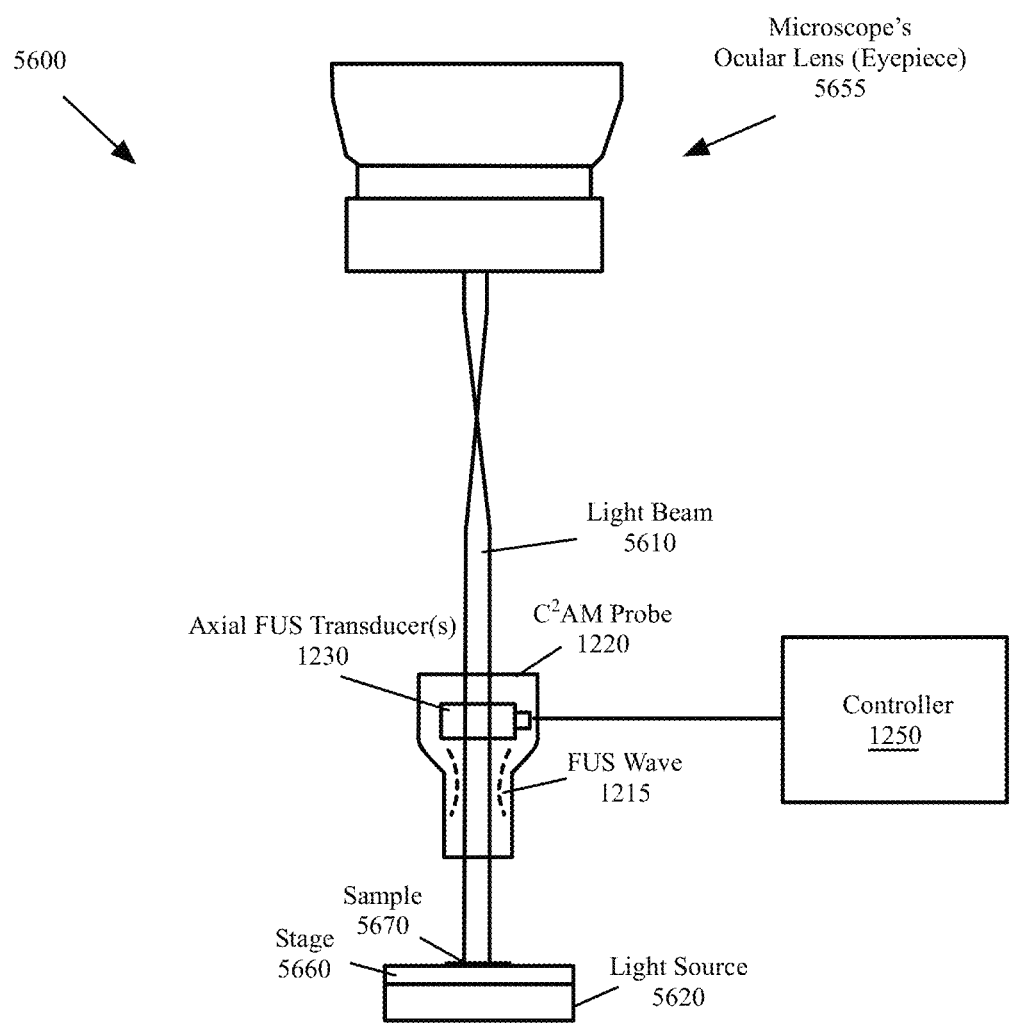
FIG. 56 is a functional diagram illustrating an embodiment of a microscope that uses axial US focusing, according to various aspects of the present disclosure.

Some embodiments may use axial FUS focusing to observe a micro sized target with a microscope. FIG. 56 is a functional diagram illustrating an embodiment of a microscope that uses axial US focusing, according to various aspects of the present disclosure. With reference to FIG. 56, the microscope 5600 may include an ocular lens (or eyepiece) 5655, a stage 5660, a C²AM probe 1220 (which may include the axial FUS transducer(s) 1230) and a controller 1250. Several other components of the microscope 5600, including the microscope's body and different adjustment controls are not shown for simplicity.

With reference to FIG. 56, a sample 5670 may be placed on the stage 5660. A light source 5620 (e.g., a florescence light source or a laser light source) may illuminate light at the sample 5670. The sample may allow the light to pass through. For example, the sample 5670 may be a micron size engraving with an image and/or letters. The sample may also be a thin transparent or semi-transparent object such as tissue, liquid, or any other material that is high responsive to light.

The C²AM probe 1220 may be positioned such that the visible light beam 5610 that is emanated from the light source 5620 may pass through the FUS transducer 1230. The C²AM probe 1220 may be adjusted by the controller 1250 such that the US wave 1220 generated by the C²AM probe 1220 may focus the visible light beam 5610 that is emanated from the light source 5620 and has passed through the sample 5670. The controller 1250, in some embodiments, may include components similar to the components of the C²AM controller 150. In some embodiments, the controller 1250 may not include the laser generator 170 of the C²AM controller 150. The light beam 5610 may be focused such that the image of the sample 5670 may be seen or may be recorded through the microscope's ocular lens 5655.

Some embodiments may include mechanical three-dimensional (3-D) control (not shown) to move the C²AM probe 1220 in different directions to adjust the position of the C²AM probe 1220 in the microscope. The mechanical control may make it possible to tilt and/or move the C²AM probe 1220 to make the FUS wave 1215 coaxial with the laser beam. The focus of the light beam 5610, in some embodiments, may be fine-tuned by a set of controls (not shown) on the controller 1250 that may, for example, change one or more of the frequency, the duty cycle, and/or the power of the FUS wave 1215.

Figure 57:
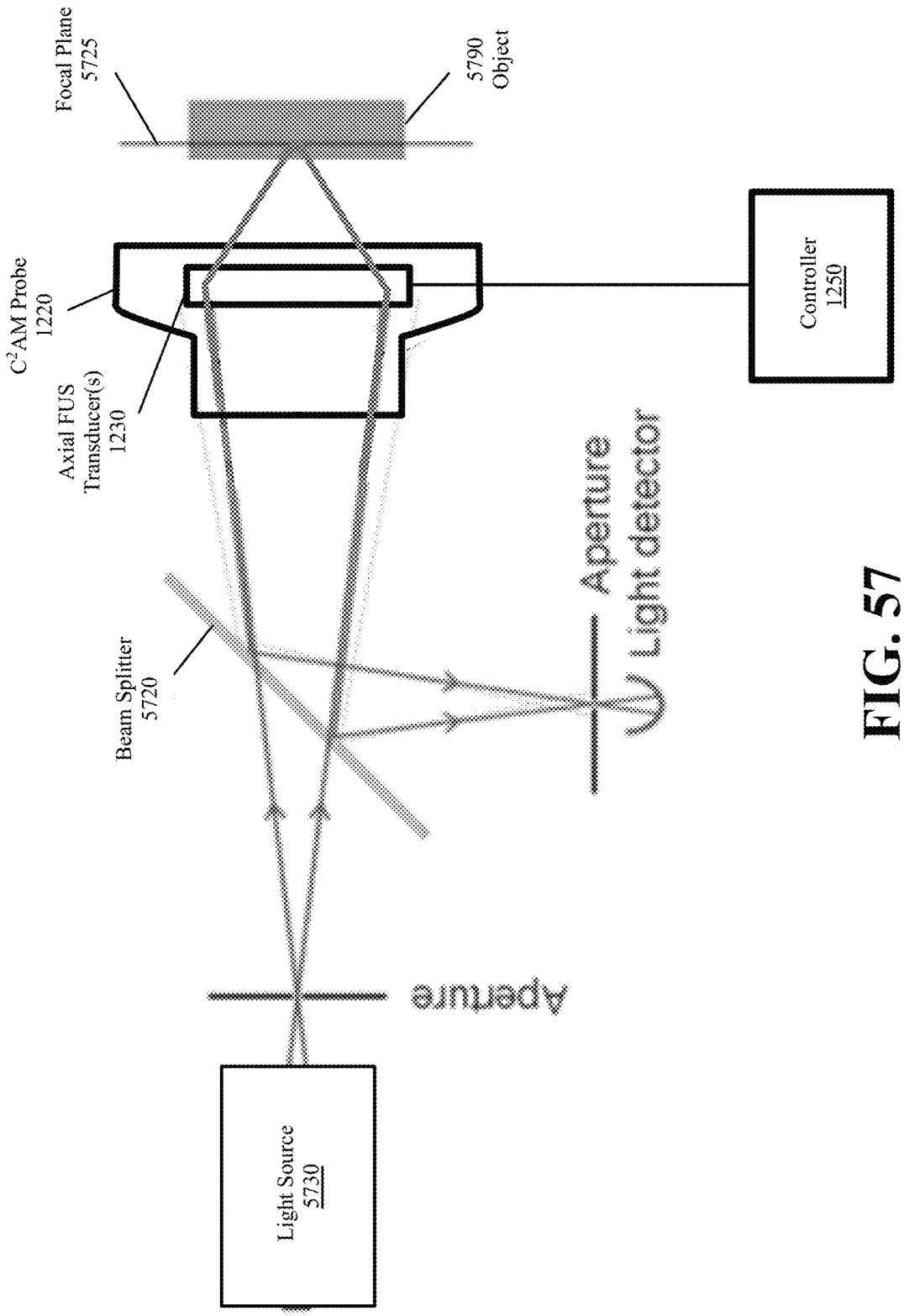
FIG. 57 is a functional diagram illustrating an example use of a coaxial acousto-optic modulator probe for microscopy, according to various aspects of the present disclosure.

FIG. 57 is a functional diagram illustrating an example use of a coaxial acousto-optic modulator probe for microscopy, according to various aspects of the present disclosure. A typical microscope may include three or four objective lenses in order to provide additional optical powers to a single stage or compound lens. Additionally, the microscope may include a condenser lens to focus light onto an item 5790.

By using the C²AM probe 1220 in the path of the laser beam 5710 (for example, in FIG. 57 the C²AM probe 1220 is placed after beam splitter 5720), a novel scheme is provided to shift the distance of the focal plane 5725 and light source 5730. The confocal imaging increases contrast by blocking out-of-focus light by means of pinholes, and, therefore, the resolution and penetration depth may improve.

IX. USING C²AM IN PHOTOACOUSTIC COMMUNICATION DEVICES

FIG. 58A is a functional diagram illustrating an apparatus used for photoacoustic communication, according to prior art. With reference to FIG. 58A, the system 5801 may be used for localized communication. The system 5801 may be used, for example, to precisely communicate with a person without any communication equipment and is located at a far distance that prevents direct person to person communication.

With further reference to FIG. 58A, the acousto-optic modulator (AOM) 5805 may provide amplitude modulation to the laser beam generated by the laser source 5810. The laser source 5810 may, for example, be a 1.9 micrometer thulium laser. The ambient water vapor 5820 may generate continuous-wave (CW) audible signals by absorption of the amplitude modulated laser light.

FIG. 58B shows the sound generated in the system of FIG. 58A as recorded by a microphone 5815, according to prior art. The figure shows the amplitude 5850 of the microphone's signal 5870 as a function of time 5855.

One disadvantage of the system 5801 is the requirement for a very specific distance between the laser AOM 5805 and the subject (e.g., a human or the microphone 5815). Any closer distance may result in the generated sound to be too high-pitched. Any farther distance may result in the frequency to drop below audibility.

FIG. 58C is a functional diagram illustrating the replacement of the acousto-optic modulator in the apparatus of FIG. 58A with a $C^2AM$ probe, according to various aspects of the present disclosure. With reference to FIG. 58C, the CAM probe may replace the AOM 5805 of FIG. 58A. The $C^2AM$ probe 1220 may have a counter propagating configuration (as shown) or may have a co-propagating configuration (e.g., as shown in FIG. 12B). The controller 1250 may not include a laser, as the optical source 5810 may be used as the source of laser.

The axial FUS transducer(s) 1230 may generate the FUS wave 1215 that may travel coaxially (e.g., counter propagate as shown in FIG. 58C or co-propagate when a co-propagating $C^2AM$ probe is used) with the light wave. The coaxially travelling FUS wave 1215 focuses and increases the intensity of the laser beam and the use of the $C^2AM$ probe 1220 may result in a better intensifying of the laser beam generated by the laser source 5890 and/or may allow using a laser source 5890 that has a lower intensity that the laser source 5810 of FIG. 58A.

The $C^2AM$ probe 1220 may allow the photoacoustic communication system 5802 to work with smaller amount of ambient water vapor 5820 than the system 5801 of FIG. 58A. In addition, the modulated laser beam forming and dynamic focusing of the $C^2AM$ probe 1220 may allow the focal point of the laser beam to be adjusted in an extended range to accommodate different distances between the recipient (e.g., a person or the microphone 5820) and the $C^2AM$ probe 1220. The use of the $C^2AM$ probe 1220 may, therefore, eliminate the requirement for a very specific distance between the laser transmitter and the subject.

FIG. 58D shows the sound generated in the system of FIG. 58C as recorded by a microphone 5815, according to various aspects of the present disclosure. The figure shows the amplitude 5850 of the microphone's signal 5875 as a function of time 5855. As shown, the amplitude 5850 of the signal 5875 may be higher than the amplitude 5850 of the signal 5870 of FIG. 58B.

Figure 59A:
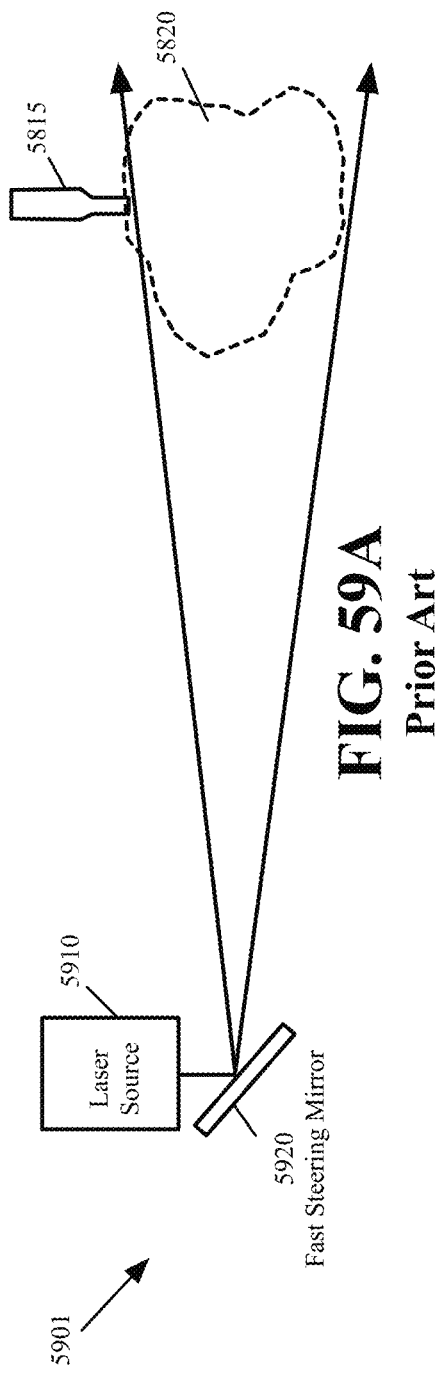
FIG. 59A is a functional diagram illustrating a photoacoustic communication apparatus that uses a fast steering mirror, according to prior art.

FIG. 59A is a functional diagram illustrating a photoacoustic communication apparatus that uses a fast steering mirror, according to prior art. With reference to FIG. 59A, the fast steering mirror 5920 may be used to sweep the laser beam such that the laser focal point travels at the speed of sound over an arch adjacent to the receiver (e.g., a human or the microphone 5815). The sweeping laser may result in coherent addition of acoustic waves that may result in an amplification of the acoustic signals.

Figure 59B:
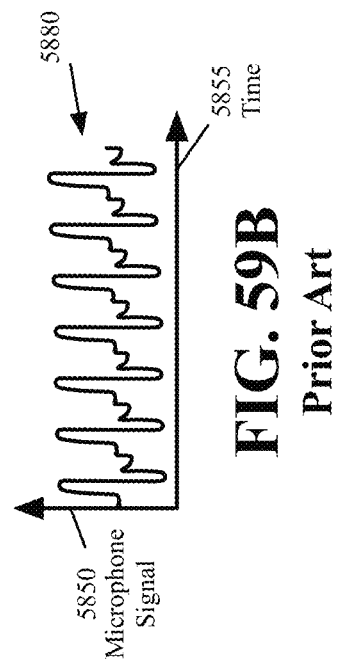
FIG. 59B shows the sound generated in the system of FIG. 59A as recorded by a microphone, according to prior art.

FIG. 59B shows the sound generated in the system of FIG. 59A as recorded by a microphone 5815, according to prior art. The figure shows the amplitude 5880 of the microphone's signal 5870 as a function of time 5855.

FIG. 59C is a functional diagram illustrating the replacement of the fast steering mirror in the acousto-optic modulator in the apparatus of FIG. 59A with a $C^2AM$ probe that includes a fast steering mirror, according to various aspects of the present disclosure. With reference to FIG. 59C, the $C^2AM$ probe 1120 may be similar to the $C^2AM$ probe 1120 of FIG. 11A or 11B. The built-in steering mirror 1140, inside the CAM probe 1120, may replace the fast steering mirror 5920 of FIG. 59A. In addition, the coaxially travelling FUS wave 1215 focuses and increases the intensity of the laser beam and the use of the $C^2AM$ probe 1120 may result in intensifying the laser beam generated by the laser source 5810 and/or may allow using a laser source 5890 that has a lower intensity that the laser source 5810 of FIG. 59A.

The $C^2AM$ probe 1120 may allow the photoacoustic communication system 5802 to work with smaller amount of ambient water vapor 5820 than the system 5901 of FIG. 59A. In addition, the modulated laser beam forming and dynamic focusing of the $C^2AM$ probe 1120 may allow the focal point of the laser beam to be adjusted to accommodate different distances between the recipient (e.g., a person or the microphone 5820) and the $C^2AM$ probe 1120.

FIG. 59D shows the sound generated in the system of FIG. 59C as recorded by a microphone 5815, according to various aspects of the present disclosure. The figure shows the amplitude 5850 of the microphone's signal 5885 as a function of time 5855. As shown, the amplitude 5850 of the signal 5885 may be higher than the amplitude 5850 of the signal 5880 of FIG. 59B.

X. USING THE $C^2AM$ FOR CELL MANIPULATION

Optical trapping has become a familiar tool for manipulating biological macro-molecules, cellular organelles and living cells under the microscope. Among the various techniques that come under the heading of 'optical trapping' are optical tweezers, which have become indispensable for nanometer-scale measurements of motor molecules and for analysis of the mechanical properties of DNA and microtubules.

Figure 60:
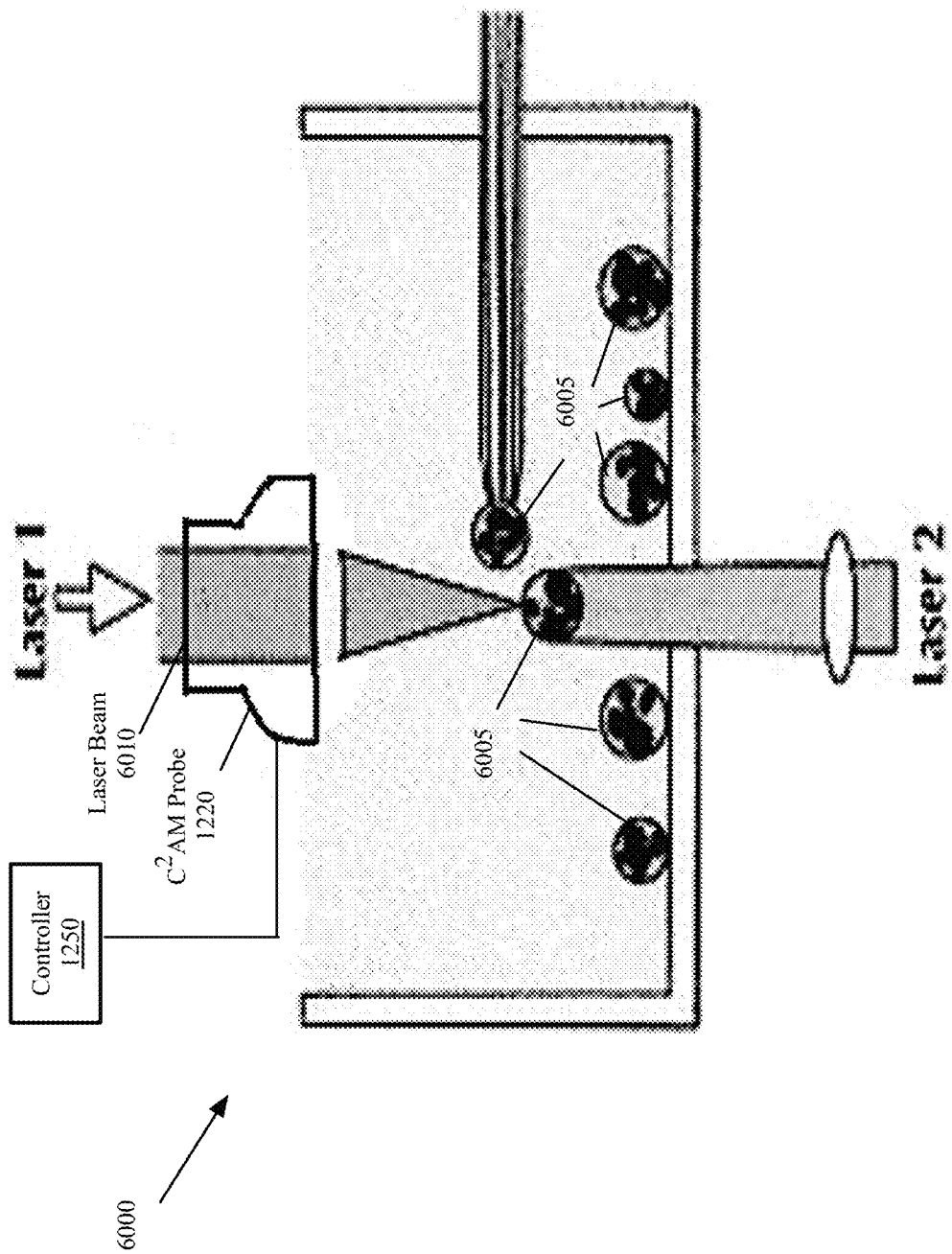
FIG. 60 is a functional diagram illustrating the addition of a coaxial acousto-optic modulator probe in the path of the laser beam for cell manipulation, according to various embodiments of the present disclosure.

FIG. 60 is a functional diagram illustrating the addition of a coaxial acousto-optic modulator probe in the path of the laser beam for cell manipulation, according to various embodiments of the present disclosure. The $C^2AM$ probe 1220 may have a counter propagating configuration or may have a co-propagating configuration. The axial FUS transducer of the CAM probe 1230 is not shown for simplicity.

With reference to FIG. 60, the optical tweezer 6000 may use highly focused laser beams to hold and move microscopic objects 6005, such as atoms, nanoparticles, droplets, cells, etc., in a manner similar to tweezers.

As shown, a CAM probe 1220 may be positioned on the path of a laser beam 6010. The addition of the CAM probe 1220 in front of laser source 6040, the laser beam 6010 may be focused deeply. The focal zone of the laser beam may be controlled by the controller 1250, for example, as described above with reference to FIGS. 1A-1D. The CAM probe 1220 may be used as a time stable reliable varifocal lensing device which may break the penetration depth limit.

XI. USING THE $C^2AM$ FOR LASER AMPLIFICATION

Figure 61:
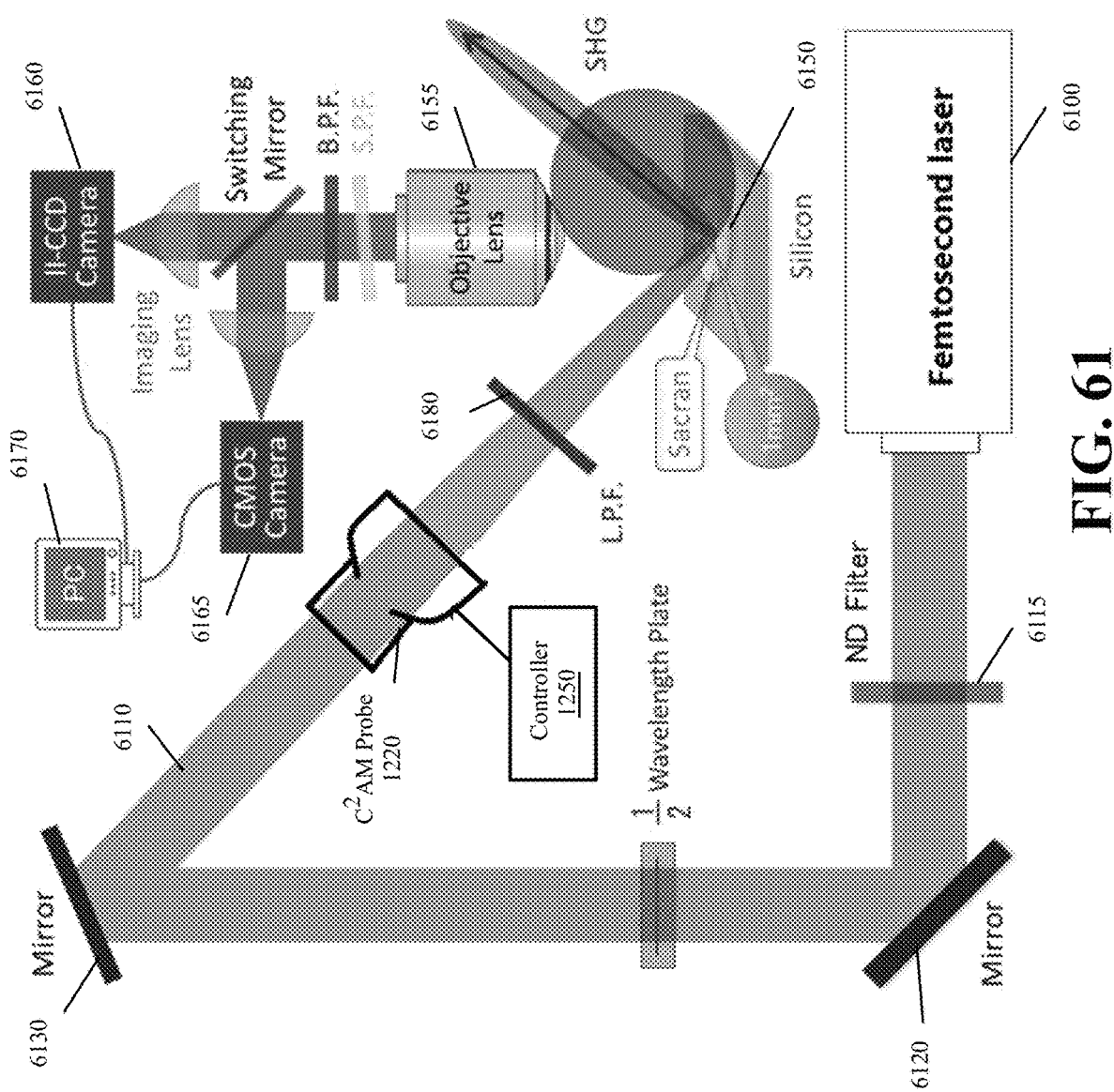
FIG. 61 is a functional diagram illustrating the addition of a coaxial acousto-optic modulator probe in the path of the laser beam of a femtosecond laser, according to various embodiments of the present disclosure.

A femtosecond laser is a laser that emits optical pulses with a duration of less than 1 picoseconds. One example, of such femtosecond laser is provided by Laser-Femto's proprietary technology. Femtosecond lasers may be used for applications such as material processing, bio-medicals, sensors, optical communications, and fiber-laser products. FIG. 61 is a functional diagram illustrating the addition of a coaxial acousto-optic modulator probe in the path of the laser beam of a femtosecond laser, according to various embodiments of the present disclosure. The CAM probe 1220 may have a counter propagating configuration or may have a co-propagating configuration. The axial FUS transducer of the CAM probe 1230 is not shown for simplicity.

With reference to FIG. 61, the laser beam 6110 from the femtosecond laser 6100 may be filtered by the neutral-density (ND) filter 6115, and may be deflected by the mirror 6120 and 6130 on an object 6150. The images formed by the objective lens 6155 may be captured by the CMOS camera 6165 and the CCD camera 6150. The images may be sent to the computing device 6170 for further manipulation and/or display.

By placing the $C^2AM$ probe 1220 on the path of laser beam 6110 (in the example of FIG. 61 the $C^2AM$ probe is placed after the mirror 6130 and before the low-pass filter 6180), the laser light focuses, and the optical focal zone and penetration depth of the laser may be controlled by the controller 1250, for example, as described above with reference to FIGS. 1A-1D.

XII. THE $C^2AM$ INTEGRATED INTO A FIBER OPTIC CABLE

Optical filters are the heart of optical networks. Without the wavelength selective device wavelength division multiplexing and dense wavelength division multiplexing, networks may not exist. As the networks are progressing towards closer wavelength spacing, performance requirement for filters are becoming more demanding. Currently, the popular filters include grafting, thin-film filters, and Fabry-Perot filters and acousto-optic tunable filters (AOTFs).

Acousto-optic (AO) effect in fibers has been studies to produce tunable filters, gain flatteners, modulators, frequency shifters, and optical switches reported. Most AO devices work on coupling from the fundamental mode (LP11) of light to higher order asymmetrical (LP12 . . . LP1n) modes. Acousto-optic is defined as the discipline devoted to the interactions between the acoustic waves and the light waves in a material medium. Acoustic (vibrational) waves may be made to modulate, deflect, and focus light waves by causing a variation in the refractive index. Acousto-optic tunable filters are a promising technology for dynamic gain equalization of optical fiber amplifiers.

Figure 62:
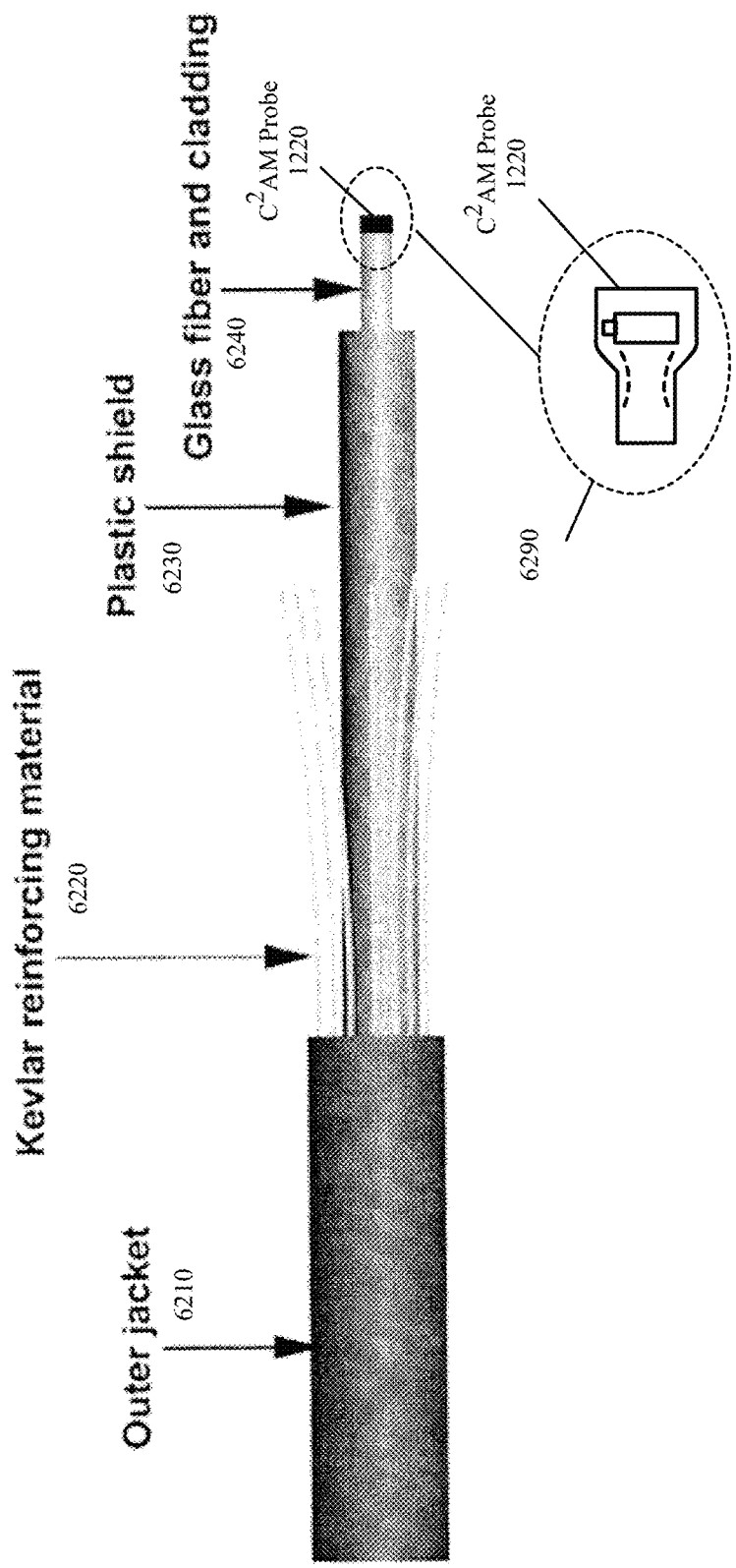
FIG. 62 is a functional diagram illustrating a CAM probe integrated into a fiber optic cable along a glass fiber, according to various aspects of the present disclosure.

FIG. 62 is a functional diagram illustrating a $C^2AM$ probe integrated into a fiber optic cable along a glass fiber, according to various aspects of the present disclosure. With reference to FIG. 62, the fiber optic cable may include an outer jacket 6210, kevlar reinforcing material 6220, a plastic shield 6230, and glass fiber and cladding 6240.

By using the $C^2AM$ probe 1220 (as shown by the expanded view 6290) and launching an acoustic wave directly on the fiber, the device combines the merits of fiber and AOTF devices namely the low insertion loss, low polarization dependence loss, wide tunability, fast tuning speed and ease of packaging. Furthermore, the CAM probe acts as a time-stable varifocal lens. Some embodiments may make a horn shape optical fiber and put the $C^2AM$ probe at the beginning of the optical fiber. Both co-propagating and counter propagating alignments of the FUS wave and the laser wave may be used.

XIII. USING THE $C^2AM$ FOR PHOTOTHERMAL AND THERAPEUTIC APPLICATIONS

Laser energy may be used to modify tissue structure, both in photochemical and in photothermal actions. Surgical procedures targeting removal of pathologic tissues extending on large tissue surfaces, occupying large tissue volumes, especially with bleeding tendency, may safely and quickly be removed with laser ablation. Using the beam focusing ability, the lasers may be used in applications, such as, making incision at a small size spot or tissue ablation at larger spot sizes. The laser beam creates deeper impact at a narrow diameter at surface when focused.

Figure 63:
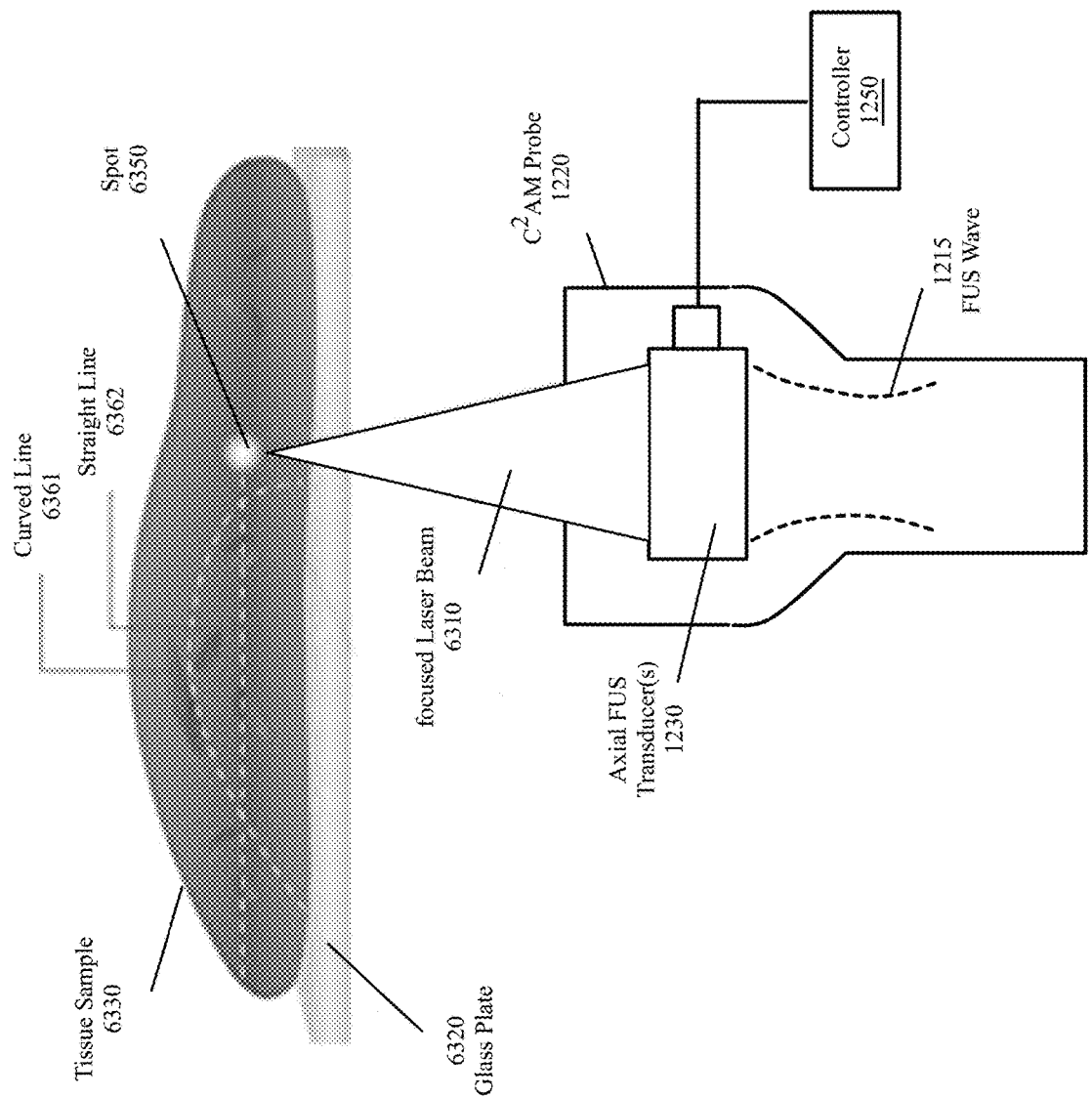
FIG. 63 is a functional diagram illustrating the use of a coaxial acousto-optic modulator probe as the source of a focused laser beam for making an incision in tissue, according to various embodiments of the present disclosure.
Figure 64:
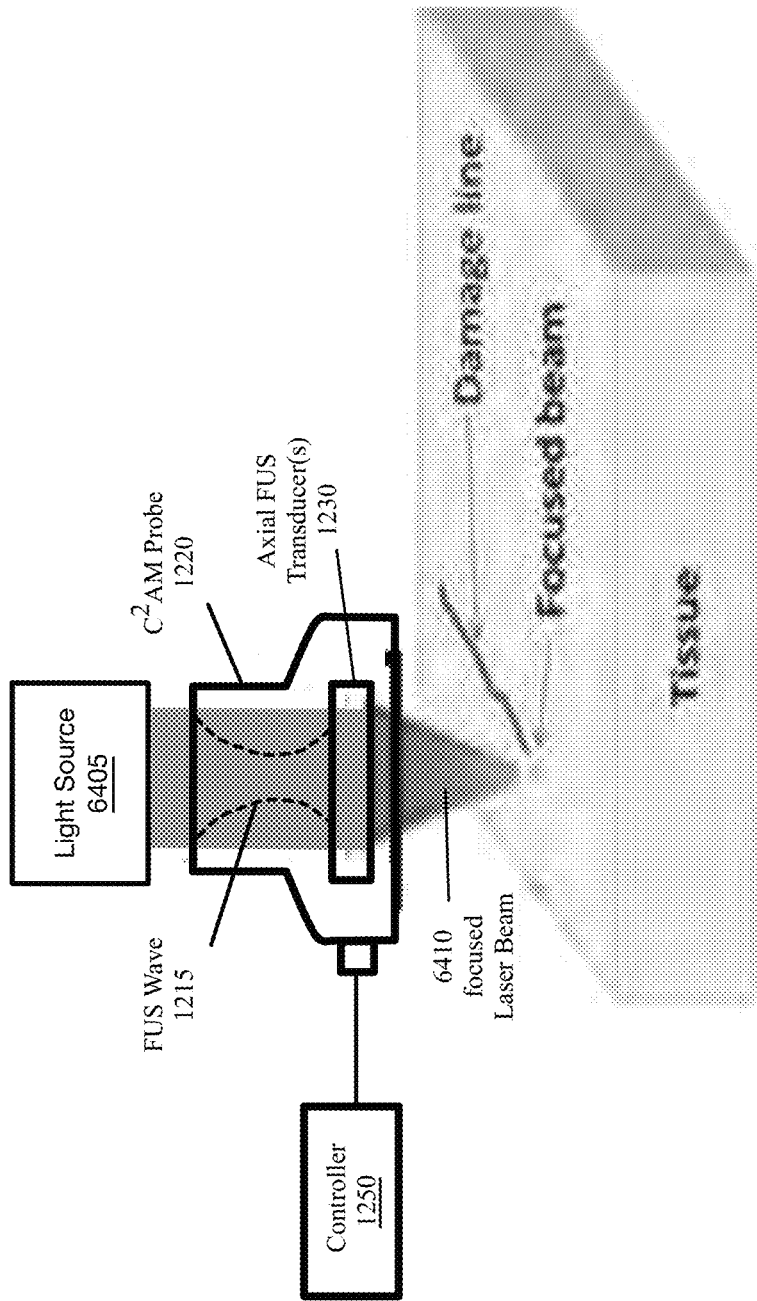
FIG. 64 is a functional diagram illustrating the addition of a coaxial acousto-optic modulator probe in the path of a laser beam for making tissue ablation, according to various embodiments of the present disclosure.

FIG. 63 is a functional diagram illustrating the use of a coaxial acousto-optic modulator probe as the source of a focused laser beam for making an incision in tissue, according to various embodiments of the present disclosure. FIG. 64 is a functional diagram illustrating the addition of a coaxial acousto-optic modulator probe in the path of a laser beam for making tissue ablation, according to various embodiments of the present disclosure.

The $C^2AM$ probe 1220, in FIGS. 63 and 64 may have a counter propagating configuration (as shown) or may have a co-propagating configuration (e.g., as shown in FIG. 12B). With reference to FIG. 63, the $C^2AM$ probe 1220 may be used as a laser source to project a focused laser beam 6310 on a spot 6350 on the tissue sample 6330 to make a curved line cut 6361 or a straight line cut 6362 in the tissue sample 6330 placed on the glass 6320. Alternatively, the $C^2AM$ probe 1220 may be placed on the path of a laser source, for example as shown in FIG. 64.

With reference to FIG. 64, the $C^2AM$ probe 1220 may be placed in the path of the light source 6405. Alternatively, the $C^2AM$ probe 1220 may be used as the light source, as shown in FIG. 63. By using the $C^2AM$ probe 1220 as the light source or placing the $C^2AM$ probe 1220 in front of the laser beam of a light source, the $C^2AM$ probe 1220 may be used a time stable varifocal lens and may universally and rapidly change the focal plane, for example by using the controller 1250 to change the signals that are applied to the axial FUS transducer 1230, as described above with reference to FIGS. 1A-1D.

XIV. USING THE $C^2AM$ FOR PHOTOACOUSTIC THERAPY

Photoacoustic treatment uses the photoacoustic effect of photoabsorbers to selectively destruct cancer cells. When the photoabsorbers are exposed to a pulsed laser beam, the light energy may be transformed into acoustic energy, and, therefore, acoustic waves may be generated. That is the so called photoacoustic effect. The magnitude of photoacoustic amplitudes may generate a strong shock wave, which may result in the death of the cell.

Figure 65:
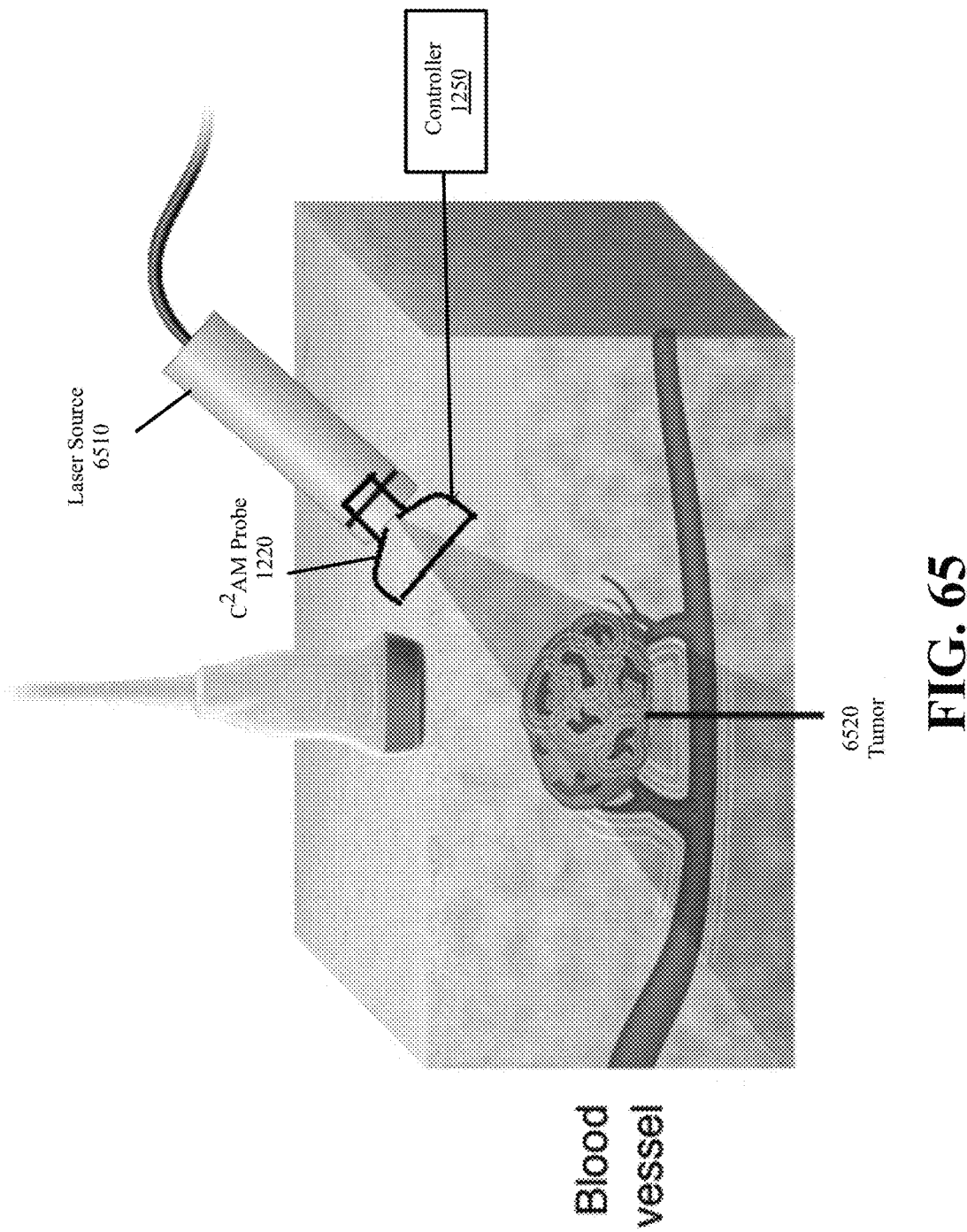
FIG. 65 is a functional diagram illustrating the use of a coaxial acousto-optic modulator probe in photoacoustic therapy, according to various embodiments of the present disclosure.

FIG. 65 is a functional diagram illustrating the use of a coaxial acousto-optic modulator probe in photoacoustic therapy, according to various embodiments of the present disclosure. The $C^2AM$ probe 1220 may have a counter propagating configuration or may have a co-propagating configuration. The axial FUS transducer of the $C^2AM$ probe 1230 is not shown for simplicity.

With reference to FIG. 65, the $C^2AM$ probe 1220 may be placed in front of the laser source 6510 to increase the laser intensity, which improves the efficacy of killing cancer cells in the tumor 6520 by shock wave. The penetration depth of the laser may be improved and the focal zone inside of the target may deeply and non-invasively be adjusted and controlled (e.g., by the controller 1230).

XV. USING THE $C^2AM$ FOR PHOTOACOUSTIC IMAGING

Figure 66:
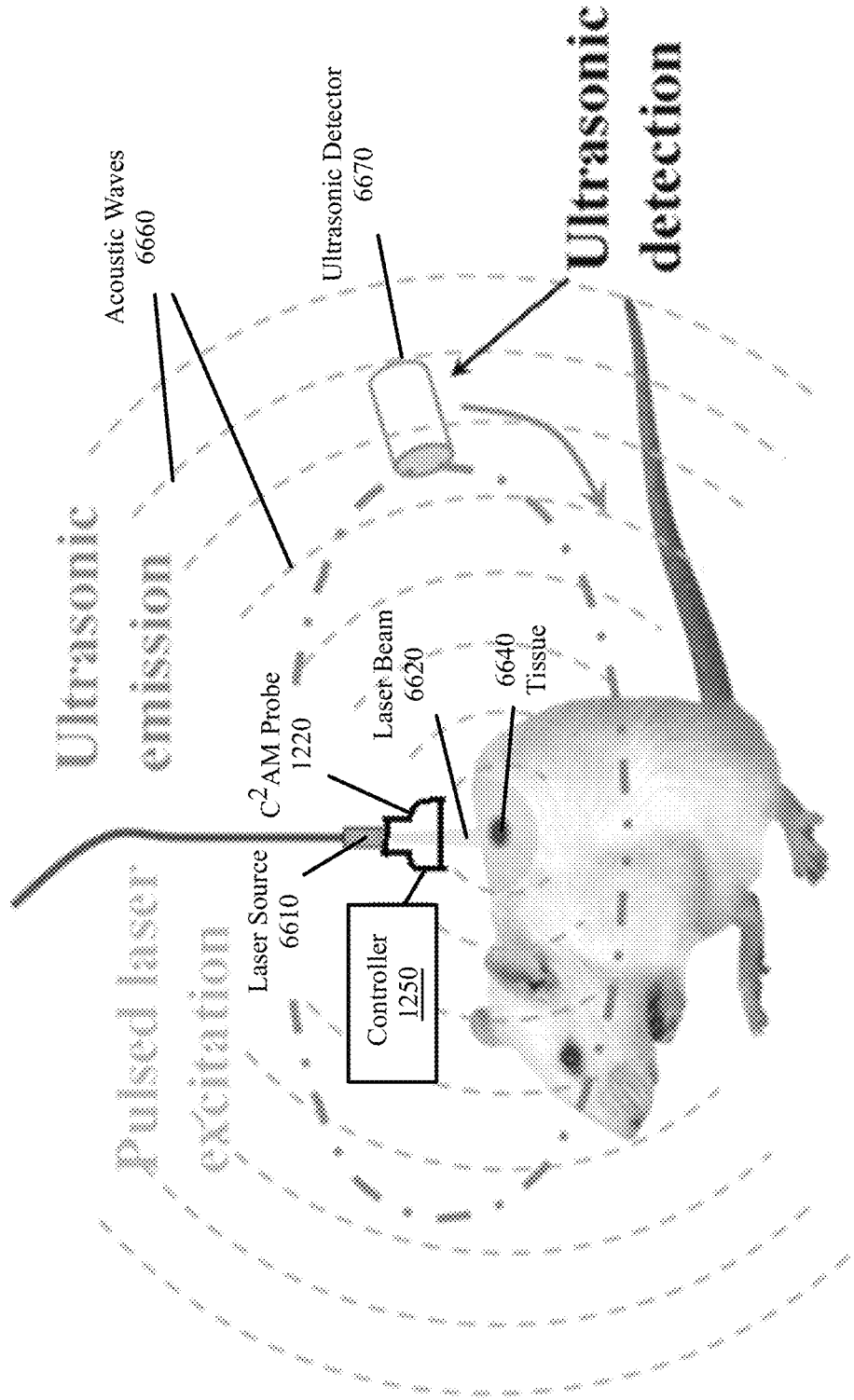
FIG. 66 is a functional diagram illustrating the use of a coaxial acousto-optic modulator probe in photoacoustic imaging, according to various embodiments of the present disclosure.

The principle of photoacoustic imaging is based on photoacoustic effect, in which electromagnetic radiation such as high energy pulse of applied laser light is converted to ultrasound waves. FIG. 66 is a functional diagram illustrating the use of a coaxial acousto-optic modulator probe in photoacoustic imaging, according to various embodiments of the present disclosure. The C²AM probe 1220 may have a counter propagating configuration or may have a co-propagating configuration. The axial FUS transducer of the C²AM probe 1230 is not shown for simplicity.

With reference to FIG. 66, the pulsed laser beam 6620 may be absorbed by the tissue 6640. The thermal expansion of the tissue may generate acoustic waves 6660. The ultrasonic detector 6670 may detect the acoustic waves 6660 and may form an image of the tissue 6640.

By placing the C²AM probe 1220 in front of the laser source 6610, the laser light 6620 focuses. Using the C²AM probe 1220 in this setup provides the technical advantage of improving the penetration depth of the laser beam 6620, improving the resolution, and controlling the focal zone by the controller 1250.

XVI. USING THE C²AM FOR PHOTODYNAMIC THERAPY

Photodynamic therapy (PDT) is a technique that uses laser energy to improve the appearance of the skin. This type of laser treatment creates changes in a layer of the skin called the dermis without causing an open wound in the skin.

Figure 67:
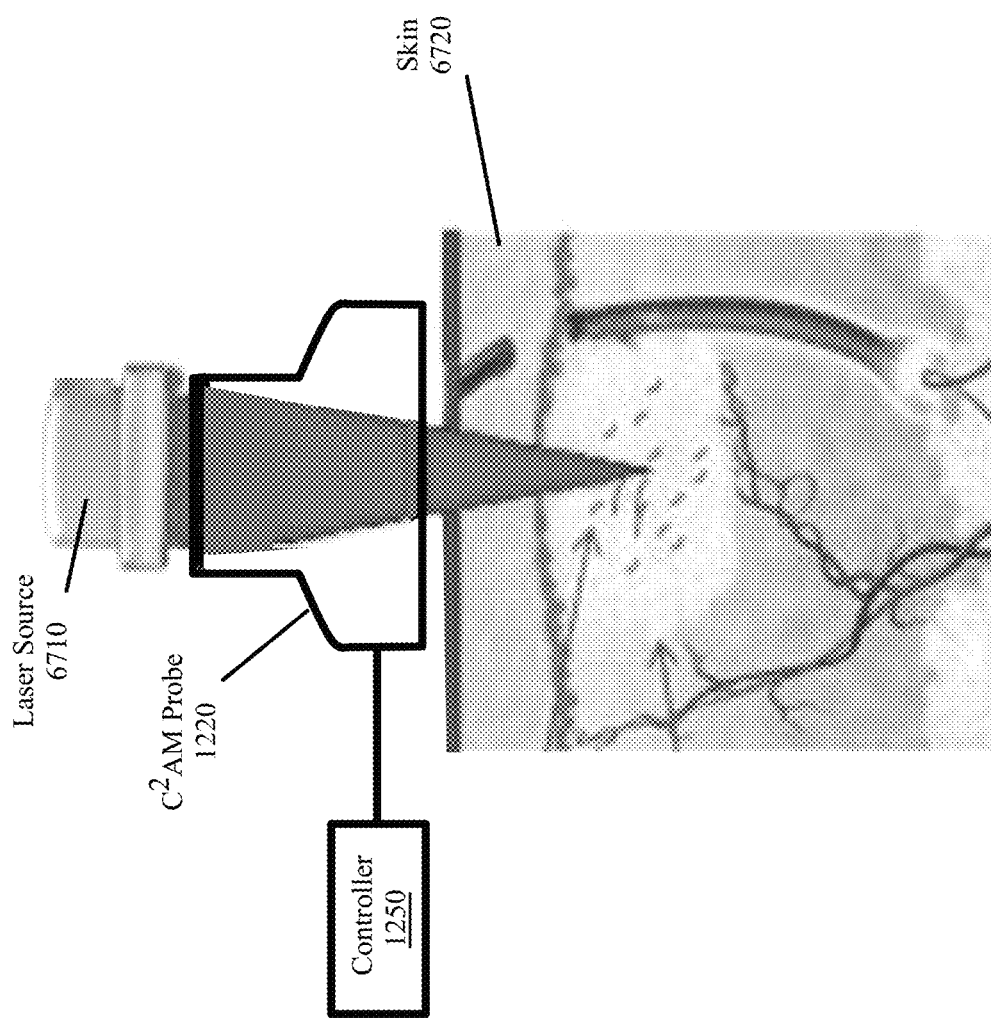
FIG. 67 is a functional diagram illustrating the use of a coaxial acousto-optic modulator probe in photodynamic therapy, according to various embodiments of the present disclosure.

FIG. 67 is a functional diagram illustrating the use of a coaxial acousto-optic modulator probe in photodynamic therapy, according to various embodiments of the present disclosure. The C²AM probe 1220 may have a counter propagating configuration or may have a co-propagating configuration. The axial FUS transducer of the C²AM probe 1230 is not shown for simplicity.

With reference to FIG. 67, the C²AM probe 1220 may be placed between laser source 6710 and the skin 6720 to provide dynamic focusing and enhance the focal length, power density, and depth of field. The C²AM probe 1220 has a dynamic control of the optical focusing to break the penetration depth limit. Therefore, by incorporating C²AM probe 1220, the efficiency of PDT improves greatly.

XVII. USING THE C²AM FOR PHOTOTHERMAL THERAPY

Photothermal therapy (PTT), based on the principle of converting light energy into heat energy, may lead to tumor necrosis. Compared with the traditional cancer therapies, such as surgery, radiotherapy, and chemotherapy, the PTT is a targeted and noninvasive therapeutic intervention for specific biological targets when combined with light excitation and photoinduced heating nanoparticles.

Figure 68:
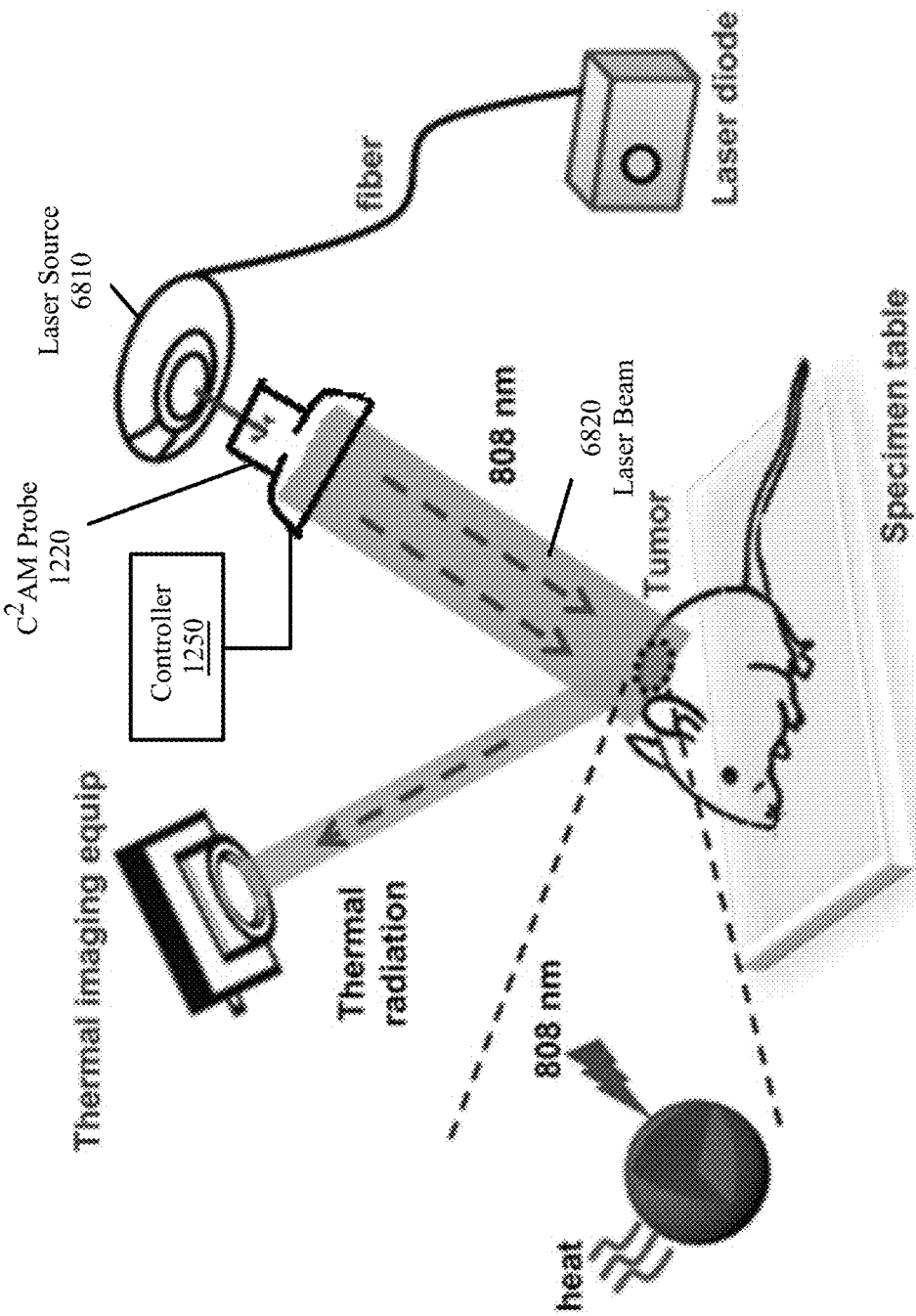
FIG. 68 is a functional diagram illustrating the use of a coaxial acousto-optic modulator probe in photothermal therapy, according to various embodiments of the present disclosure.

FIG. 68 is a functional diagram illustrating the use of a coaxial acousto-optic modulator probe in photothermal therapy, according to various embodiments of the present disclosure. The C²AM probe 1220 may have a counter propagating configuration or may have a co-propagating configuration. The axial FUS transducer of the C²AM probe 1230 is not shown for simplicity.

With reference to FIG. 68, by placing C²AM probe 1220 in front of the laser source 6810, the laser beam 6820 focuses and the focal zone and the depth of the laser beam penetration may be controlled by the controller 1250.

XVIII. USING THE C²AM IN ROBOTIC MANIPULATION

Figure 69A:
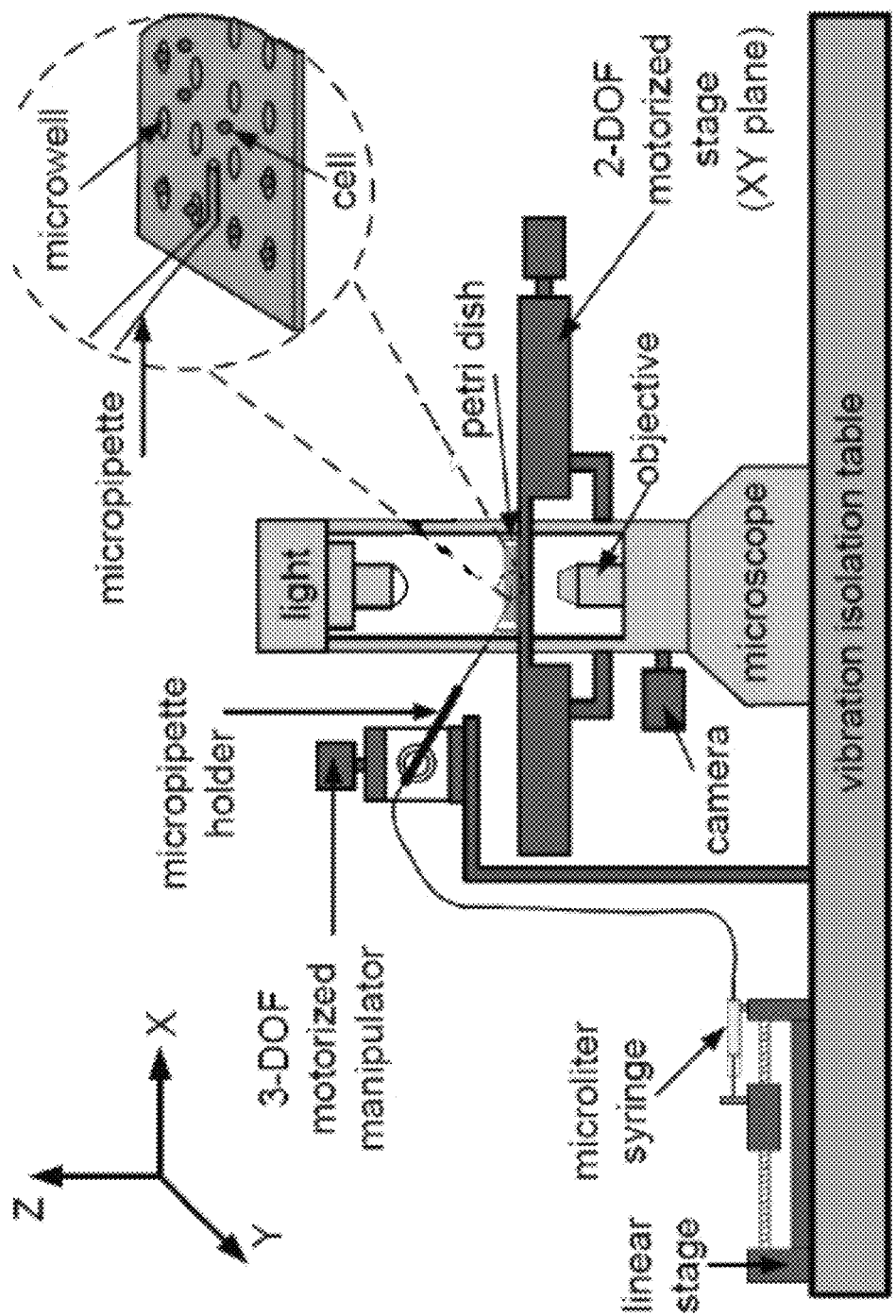
FIG. 69A is a functional diagram illustrating a robotic manipulation system for single cell deposition, according to prior art.

FIG. 69A is a functional diagram illustrating a robotic manipulation system for single cell deposition, according to prior art. Integrating single-cell manipulation techniques in traditional and emerging biological culture systems is challenging. In particular, microfabricated devices for single cell studies often require cells to be spatially positioned at specific culture sites on the device surface.

The setup of FIG. 69A shows a robotic micromanipulation system for pick-and-place positioning of single cells. By integrating computer vision and motion control algorithms, the system visually tracks a cell in real time and controls multiple positioning devices simultaneously to accurately pick up a single cell, transfer it to a desired substrate, and deposit it at a specified location.

Figure 69B:
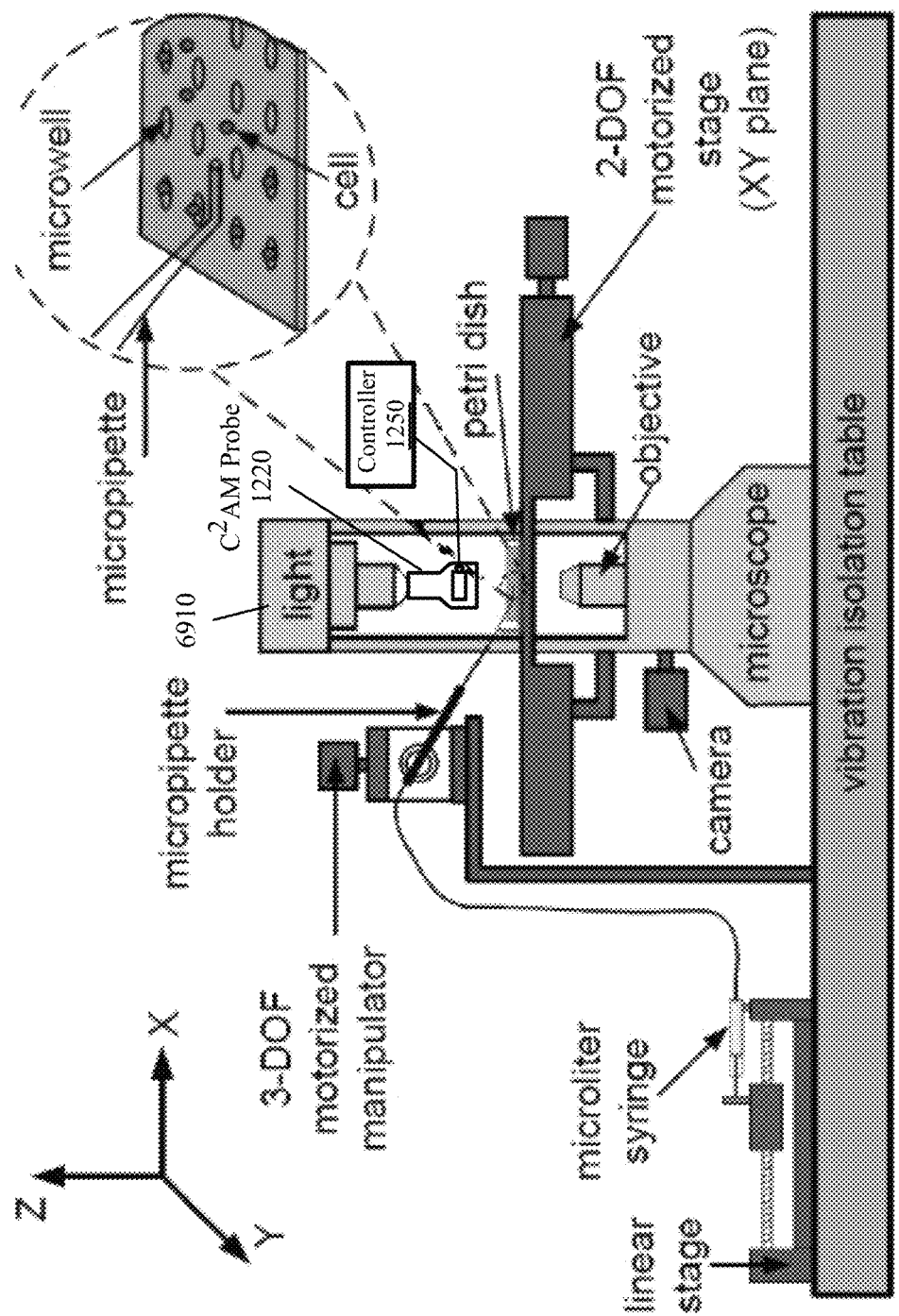
FIG. 69B is a functional diagram illustrating the addition of a coaxial acousto-optic modulator probe to the robotic manipulation system of FIG. 69A, according to various aspects of the present disclosure.

FIG. 69B is a functional diagram illustrating the addition of a coaxial acousto-optic modulator probe to the robotic manipulation system of FIG. 69A, according to various aspects of the present disclosure. The CAM probe 1220 may have a counter propagating configuration or may have a co-propagating configuration. The axial FUS transducer of the C²AM probe 1230 is not shown for simplicity. By using C²AM probe 1220 in front of the light source 6910, the C²AM probe 1220 may act as a time-stable varifocal lens which may improve the efficiency of the system.

XIX. USING THE C²AM IN NON-INVASIVE BRAIN THERAPY

Figure 70:
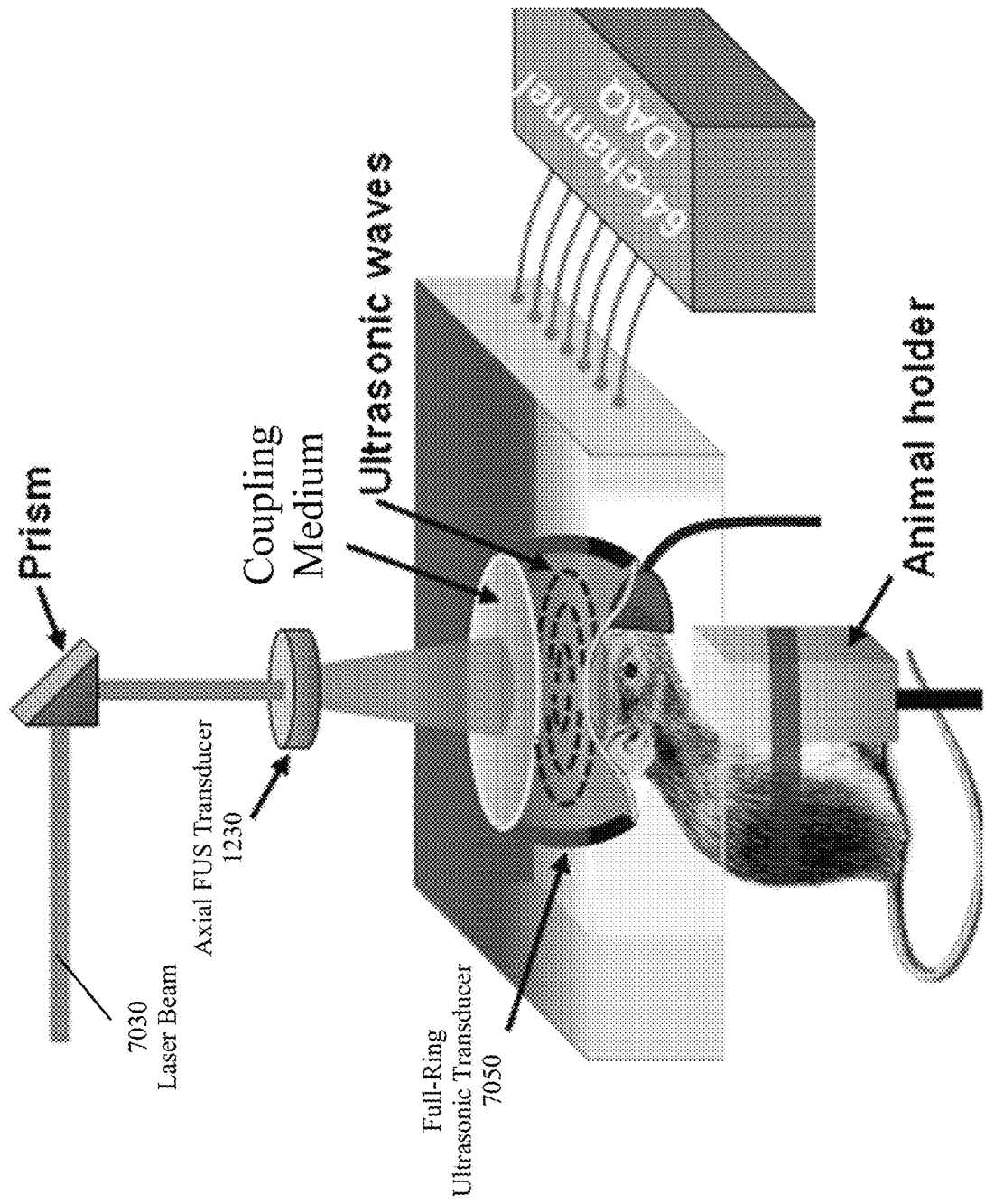
FIG. 70 is a functional diagram illustrating the use of a coaxial acousto-optic modulator probe in non-invasive brain therapy and sending modulated laser through skull for therapy and imaging, according to various aspects of the present disclosure.

FIG. 70 is a functional diagram illustrating the use of a coaxial acousto-optic modulator probe in non-invasive brain therapy and sending modulated laser through skull for therapy and imaging, according to various aspects of the present disclosure. The figure only shows the FUS transducer 1230. Other components of the C²AM probe 1220 and the controller 1250 are not shown for simplicity. The axial FUS transducer 1230 may be setup in either counter propagating or co-propagating alignments with the laser beam 7030.

With reference to FIG. 70, light may not pass the skull. The C²AM-photoacoustic tomography system is developed based on a full-ring ultrasonic transducer array 7050 to pass through the skull and provide the imaging of the brain. The CAM enhances the power density and intensity of the passing photons from the skull. The dynamic focusing and large depth of penetration and depth of field provided by the CAM significantly improved results for tomography of brain.

XX. COMPUTER SYSTEM

Many of the above-described features and applications may be implemented as software processes that are specified as a set of instructions recorded on a computer readable storage medium (also referred to as computer readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which may be read into memory for processing by a processor. Also, in some embodiments, multiple software inventions may be implemented as sub-parts of a larger program while remaining distinct software inventions. In some embodiments, multiple software inventions may also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 71:
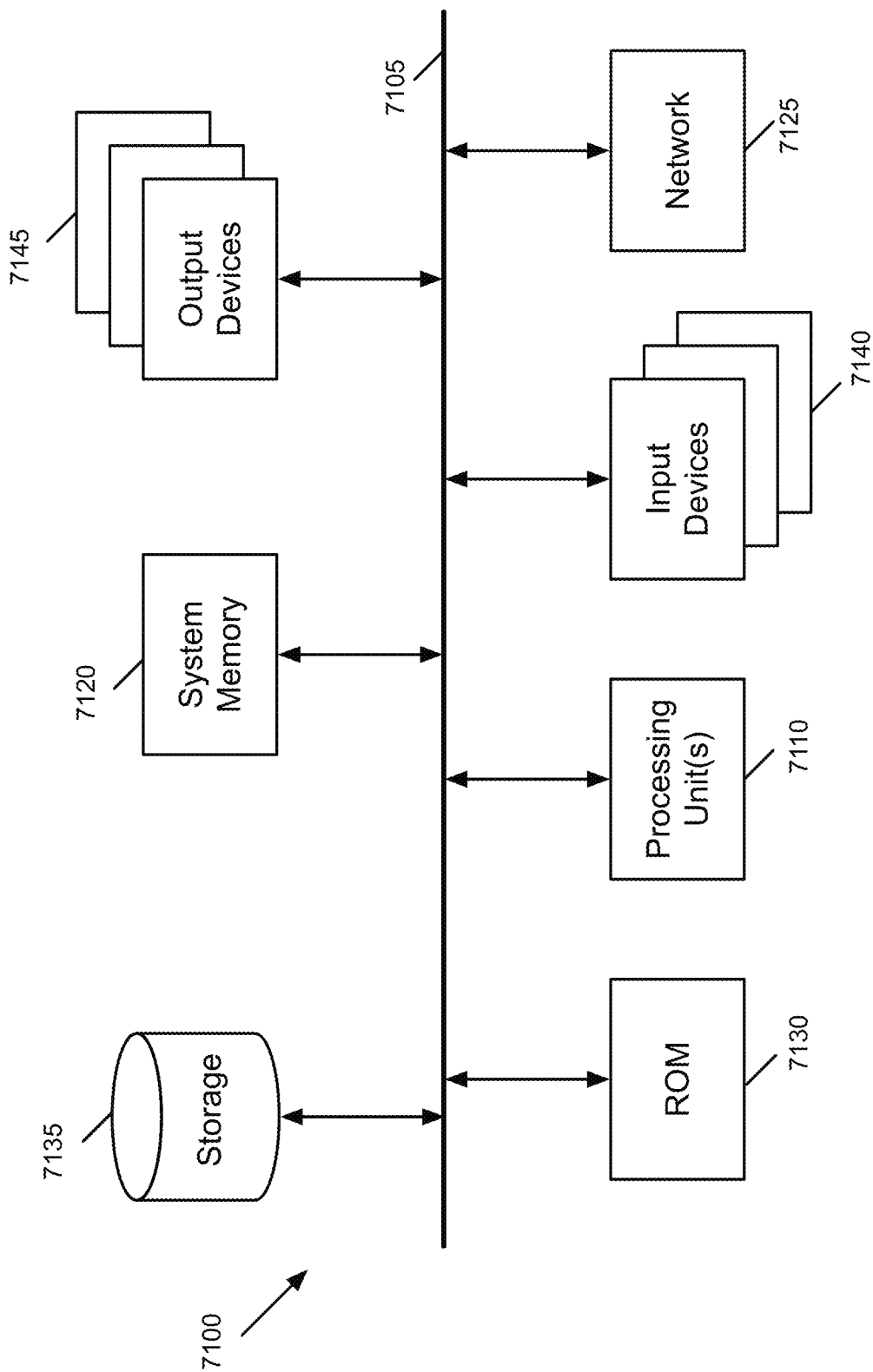
FIG. 71 is a functional block diagram illustrating an example electronic system, according to various aspects of the present disclosure.

FIG. 71 is a functional block diagram illustrating an example electronic system 7100, according to various aspects of the present disclosure. With reference to FIG. 71, some embodiments of the invention, such as for example, and without limitations, the controllers, mobile devices, etc., described above, may be implemented using the electronic system 7100. The electronic system 7100 may be used to execute any of the processes, methods, controls, or operating system applications described above. The electronic system 7100 may be a controller (e.g., the controller 150 of FIGS. 1A-1C), a computer (e.g., a desktop computer, personal computer, tablet computer, server computer, mainframe, a blade computer etc.), phone (e.g., a smartphone), a personal digital assistant (PDA), or any other sort of electronic device. Such an electronic system may include various types of computer readable media and interfaces for various other types of computer readable media. The electronic system 7100 may include a bus 7105, processing unit(s) 7110, a system memory 7120, a read-only memory (ROM) 7130, a permanent storage device 7135, input devices 7140, and output devices 7145.

The bus 7105 may collectively represent all system, peripheral, and chipset buses that communicatively connect the numerous internal devices of the electronic system 7100. For example, the bus 7105 may communicatively connect the processing unit(s) 7110 with the read-only memory 7130, the system memory 7120, and the permanent storage device 7135.

From these various memory units, the processing unit(s) 7110 may retrieve instructions to execute and data to process in order to execute the processes of the invention. The processing unit(s) may be a single processor or a multi-core processor in different embodiments.

The read-only-memory 7130 may store static data and instructions that are needed by the processing unit(s) 7110 and other modules of the electronic system. The permanent storage device 7135, on the other hand, may be a read-and-write memory device. This device is a non-volatile memory unit that may store instructions and data even when the electronic system 7100 is off. Some embodiments of the invention may use a mass-storage device (such as a magnetic or optical disk and its corresponding disk drive) as the permanent storage device 7135.

Other embodiments may use a removable storage device (such as a floppy disk, flash drive, etc.) as the permanent storage device. Like the permanent storage device 7135, the system memory 7120 may be a read-and-write memory device. However, unlike storage device 7135, the system memory may be a volatile read-and-write memory, such as random access memory. The system memory may store some of the instructions and data that the processor needs at runtime. In some embodiments, the invention's processes may be stored in the system memory 7120, the permanent storage device 7135, and/or the read-only memory 7130. From these various memory units, the processing unit(s) 7110 may retrieve instructions to execute and data to process in order to execute the processes of some embodiments.

The bus 7105 may also connect to the input and output devices 7140 and 7145. The input devices may enable the user to communicate information and select commands to the electronic system. The input devices 7140 may include alphanumeric keyboards and pointing devices (also called "cursor control devices"). The output devices 7145 may display images generated by the electronic system. The output devices may include printers and display devices, such as cathode ray tubes (CRT) or liquid crystal displays (LCD). Some embodiments may include devices such as a touchscreen that function as both input and output devices.

Finally, as shown in FIG. 71, the bus 7105 may also couple the electronic system 7100 to a network 7125 through a network adapter (not shown). In this manner, the computer may be a part of a network of computers (such as a local area network ("LAN"), a wide area network ("WAN"), an Intranet, or a network of networks, such as the Internet. Any or all components of the electronic system 7100 may be used in conjunction with the invention.

Some embodiments may include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra-density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some embodiments may be performed by one or more integrated circuits, such as application specific integrated circuits (ASICs) or field programmable gate arrays (FPGAs). In some embodiments, such integrated circuits may execute instructions that are stored on the circuit itself. Some of the present embodiments may include flexible circuit, also rereferred to as flexible printed circuit boards (PCBs). The flexible circuits may provide dynamic flexing and increased heat dissipation and may be used in the embodiments that require circuits with smaller footprint, increased package density, more tolerance to vibrations, and/or less weight.

As used in this specification, the terms "computer", "server", "processor", and "memory" all refer to electronic or other technological devices. These terms exclude people or groups of people. For the purposes of the specification, the terms display or displaying means displaying on an electronic device. As used in this specification, the terms "computer readable medium," "computer readable media," and "machine readable medium" are entirely restricted to tangible, physical objects that store information in a form that is readable by a computer. These terms exclude any wireless signals, wired download signals, and any other ephemeral or transitory signals.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented, and may be performed in any order(s).

Further, steps that have been presented as being performed separately may in alternative embodiments be performed concurrently. Likewise, steps that have been presented as being performed concurrently may in alternative embodiments be performed separately.

What is claimed is:

1. An acousto-optic modulator, comprising:
    an ultrasound transducer, comprising:
        a through-hole for allowing a laser beam to propagate along a propagation axis through the ultrasound transducer,
        the ultrasound transducer configured to generate ultrasound waves along the propagation axis of the laser beam in response to an electrical signal applied to the ultrasound transducer, the ultrasound waves to modulate the laser beam;
    a medium surrounding the ultrasound transducer, the medium comprising a fluid or a gel;
    a sealed enclosure enclosing the ultrasound transducer and the medium, the sealed enclosure comprising an optical input comprising one of a transparent window or an optical fiber, the sealed enclosure comprising an optical output comprising one of an optical fiber or a transparent window, wherein the optical input is for allowing the laser beam to enter the sealed enclosure, wherein the optical output is for allowing the laser beam modulated by the ultrasound waves to exit the sealed enclosure, and wherein the sealed enclosure and the ultrasound transducer through-hole are configured such that the ultrasound waves generated by the ultrasound transducer overlap the laser beam on at least a portion of the propagation axis of the laser beam; and
    a controller comprising:
        a pulse generator configured to generate a carrier wave signal;
        a function generator configured to modulate an electrical signal, with a frequency of the ultrasound waves, on the carrier wave signal; and
        a power amplifier configured to:
            receive the electrical signal from the function generator;
            amplify the electrical signal; and
            apply the amplified electrical signal to the ultrasound transducer; and
        a processor configured to:
            set a duty cycle of the carrier wave signal generated by the pulse generator, and set an amplification of the power amplifier, such that the ultrasound waves generated by the transducer focus the laser beam modulated by the ultrasound waves at a point along the propagation axis in an outside of the enclosure.

2. The acousto-optic modulator of claim 1, the processor configured to set the duty cycle of the carrier wave generated by the pulse generator and the amplification of the power amplifier, such that the ultrasound waves generated by the transducer increase a power density of the laser beam, decrease a width of the laser beam, and reduce a full width at half maximum (FWHM) of the laser beam.

3. The acousto-optic modulator of claim 2, wherein the reduced FWHM of the laser beam is preserved while the ultrasound transducer generates said ultrasound waves along the propagation axis of the laser beam.

4. The acousto-optic modulator of claim 2, wherein when the electrical signal applied to the ultrasound waves is turned off, the power density of the laser beam, the width of the laser beam, and the FWHM of the laser beam that is output by the acousto-optic modulator, respectively, return to the power density, the width, and the FWHM of the laser beam received by the acousto-optic modulator.

5. The acousto-optic modulator of claim 1, the processor configured to set the duty cycle of the carrier wave generated by the pulse generator and the amplification of the power amplifier, such that a lensing power of the laser beam, at a focal point of the laser beam, fluctuates by less than 10% while the amplified electrical signal is applied to the ultrasound transducer.

6. The acousto-optic modulator of claim 1, the processor configured to set the duty cycle of the carrier wave generated by the pulse generator and the amplification of the power amplifier, such that a lensing power of the laser beam, at a focal point of the laser beam, is time stable with a substantially constant positive value.

7. The acousto-optic modulator of claim 1, the processor configured to set the duty cycle of the carrier wave generated by the pulse generator and the amplification of the power amplifier, such that an optical depth of field of the modulated laser beam (DoFM) remains constant while the ultrasound transducer generates said ultrasound waves along the propagation axis of the laser beam.

8. The acousto-optic modulator of claim 1, the processor configured to set the duty cycle of the carrier wave generated by the pulse generator and the amplification of the power amplifier, such that a focal intensity of the modulated laser beam remains stable while the ultrasound transducer generates said ultrasound waves along the propagation axis of the laser beam.

9. The acousto-optic modulator of claim 1, the processor configured to set the duty cycle of the carrier wave generated by the pulse generator and the amplification of the power amplifier, such that a temperature of a medium at the focal point of the laser beam does not increase by more than 0.1 degree Fahrenheit.

10. The acousto-optic modulator of claim 1, the processor configured to set the duty cycle of the carrier wave generated by the pulse generator and the amplification of the power amplifier, such that no cavitation is generated in the medium surrounding the ultrasound transducer.

11. The acousto-optic modulator of claim 1, wherein the laser beam is generated by a laser device, the processor configured to set the duty cycle of the carrier wave generated by the pulse generator and the amplification of the power amplifier by looking up a table storing experimental values of laser beam intensity and voltage output values of the power amplifier to set an intensity of the laser beam at a predetermined distance.

12. The acousto-optic modulator of claim 1, wherein the laser beam and the ultrasound waves are counter propagated along the propagation axis.

13. The acousto-optic modulator of claim 1, wherein the laser beam and the ultrasound waves are co-propagated along the propagation axis.

14. The acousto-optic modulator of claim 1, wherein the medium surrounding the ultrasound transducer substantially comprises deionized purified water.

15. The acousto-optic modulator of claim 1, wherein the medium surrounding the ultrasound transducer substantially comprises one of water and an oil.

16. The acousto-optic modulator of claim 1, wherein a Gaussian profile of the laser beam is expanded and collimated with a beam expander prior to propagating the laser beam through the ultrasound transducer.

17. The acousto-optic modulator of claim 1, wherein the laser beam is generated by a laser device with an output power of less than 1 mW.

18. The acousto-optic modulator of claim 1, wherein the ultrasound transducer is fabricated using one of a piezoelectric material, a piezoelectric composite, a piezo polymer, and a single crystal as the active element of the ultrasound transducer.

19. The acousto-optic modulator of claim 1, wherein the ultrasound transducer is a capacitive micromachined ultrasonic transducer (CMUT).

* * * * *